US008409825B2

(12) United States Patent
Chiba et al.

(10) Patent No.: US 8,409,825 B2
(45) Date of Patent: Apr. 2, 2013

(54) METHOD FOR HIGH-LEVEL SECRETORY PRODUCTION OF PROTEIN

(75) Inventors: Yasunori Chiba, Tsukuba (JP); Yoshifumi Jigami, Tsukuba (JP); Yoshie Takahashi, Tsukuba (JP); Kosuke Kuroda, Takasaki (JP); Kazuo Kobayashi, Takasaki (JP); Kimihisa Ichikawa, Edogawa-ku (JP); Koichi Nonaka, Iwaki (JP); Takeshi Suzuki, Iwaki (JP); Minako Ono, Iwaki (JP)

(73) Assignees: National Institute of Advanced Industrial Science and Technology, Tokyo (JP); Kyowa Hakko Kirin Co., Ltd, Tokyo (JP); Daiichi Sankyo Company, Limited, Tokyo (JP)

( * ) Notice: Subject to any disclaimer, the term of this patent is extended or adjusted under 35 U.S.C. 154(b) by 199 days.

(21) Appl. No.: 12/740,995

(22) PCT Filed: Oct. 29, 2008

(86) PCT No.: PCT/JP2008/070155
§ 371 (c)(1),
(2), (4) Date: Apr. 30, 2010

(87) PCT Pub. No.: WO2009/057813
PCT Pub. Date: May 7, 2009

(65) Prior Publication Data
US 2011/0014651 A1 Jan. 20, 2011

(30) Foreign Application Priority Data

Oct. 31, 2007 (JP) .................................. 2007-283731
Nov. 6, 2007 (JP) .................................. 2007-288845

(51) Int. Cl.
| | |
|---|---|
| C12P 21/06 | (2006.01) |
| C07H 21/02 | (2006.01) |
| C12N 15/00 | (2006.01) |
| C12N 1/20 | (2006.01) |

(52) U.S. Cl. .................. 435/69.1; 536/23.1; 435/320.1; 435/252.3

(58) Field of Classification Search .................. None
See application file for complete search history.

(56) References Cited

U.S. PATENT DOCUMENTS

2006/0148039 A1* 7/2006 Kobayashi et al. ............. 435/85

FOREIGN PATENT DOCUMENTS

| EP | 0828004 A2 | 9/1997 |
|---|---|---|
| WO | 03/091431 A1 | 11/2003 |

OTHER PUBLICATIONS

Bacterial Gene Swapping in Nature, last viewed on Apr. 25, 2012.*
Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Sughrue Mion, PLLC

(57) ABSTRACT

This invention provides a means for high-level secretory production of a protein, and, in particular, a protein having a complicated structure such as an antibody, in a host cell such as a yeast cell. This invention provides a method for high-level secretory production of a foreign protein with the use of a transformed host cell having one or more types of chaperone protein genes and via suppression of O sugar chain inherent to a host cell such as a yeast cell.

27 Claims, 30 Drawing Sheets

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Borth et al., Effect of Increased Expression fo Protein Disulfide Isomerase and Heavy Chain binding Protein on Antibody Secretion in a Recombinant CHO Cell Line., Biotechnol. Prog. (2005), vol. 21, pp. 106-111.*

Kousuke Kuroda, et al., "Antibody expression in protease-deficient strains of the methylotrophic yeast Ogataea minuta", FEMS Yeast Res., Dec. 2007, pp. 1307-1316, vol. 7, No. 8.

Per Norgaard, et al., "Functional Differences in Yeast Protein Disulfide Isomerases", J. Cell Biol., Feb. 5, 2001, pp. 553-562, vol. 152, No. 3.

Joan Lin Cereghino, et al., "Heterologous protein expression in the methylotrophic yeast Pichia pastoris", FEMS Microbiology Reviews, 2000, pp. 45-66, vol. 24, No. 1.

Kousuke Kuroda, et al., "Efficient Antibody Production upon Suppression of O Mannosylation in the Yeast Ogataea minuta", Applied and Environmental Microbiology, Jan. 2008, pp. 446-453, vol. 74, No. 2.

Abdirashid Warsame, et al.; "Characterization of a Gene Encoding a *Pichia pastoris* Protein Disulfide Isomerase"; XP-002606999; Biochemical and Biophysical Research Communications; 2001; pp. 1176-1182; vol. 281, No. 5.

European Search Report dated Nov. 17, 2010 for European Application No. 08845087.9-2405.

* cited by examiner 1 ona02306 strain
2 ona02306 strain
  Add 100 µl of medium containing 20 µM 1c on day 3
3 ona02306 strain
  Add 100 µl of medium containing 20 µM 1c on day 2 and day 3

SEQUENCE LISTING

<160> NUMBER OF SEQ ID NOS: 171

<210> SEQ ID NO 1
<211> LENGTH: 1551
<212> TYPE: DNA
<213> ORGANISM: Ogataea minuta
<220> FEATURE:
<221> NAME/KEY: CDS
<222> LOCATION: (1)..(1551)

<400> SEQUENCE: 1

```
atg aag tta ttt gga ttg act aca ttg acc agc atc ctg gcc gcc ctc      48
Met Lys Leu Phe Gly Leu Thr Thr Leu Thr Ser Ile Leu Ala Ala Leu
1               5                   10                  15 aca gtg gtg agc gcc acc gaa gag cca gca gtt gcc tcg cca gac tcg      96
Thr Val Val Ser Ala Thr Glu Glu Pro Ala Val Ala Ser Pro Asp Ser
            20                  25                  30 gcg gtg gtg aag ctg acg gcc gac act ttc gag agc ttc atc aag gag     144
Ala Val Val Lys Leu Thr Ala Asp Thr Phe Glu Ser Phe Ile Lys Glu
        35                  40                  45 aac cca ttg gtt ctg gcg gag ttt ttt gcg cca tgg tgt ggc cac tgc     192
Asn Pro Leu Val Leu Ala Glu Phe Phe Ala Pro Trp Cys Gly His Cys
    50                  55                  60 aag aag ctg ggt cca gaa ttc agc gca gcc gca gac cag ctg gtg gag     240
Lys Lys Leu Gly Pro Glu Phe Ser Ala Ala Ala Asp Gln Leu Val Glu
65                  70                  75                  80 aag aac atc aag ctt gca cag atc gac tgt acc gag gaa aga gat ctg     288
Lys Asn Ile Lys Leu Ala Gln Ile Asp Cys Thr Glu Glu Arg Asp Leu
                85                  90                  95 tgt tcg tcg cac gga atc aga gga tac cca act ttg aag gtg ttc agg     336
Cys Ser Ser His Gly Ile Arg Gly Tyr Pro Thr Leu Lys Val Phe Arg
            100                 105                 110 ggc gct agt gag cct gct gac tac caa ggc gcc aga gaa cag gaa gct     384
Gly Ala Ser Glu Pro Ala Asp Tyr Gln Gly Ala Arg Glu Gln Glu Ala
        115                 120                 125 att gtc agt caa atg atc aag ctt tct tta cct gct gtt tcc gtc att     432
Ile Val Ser Gln Met Ile Lys Leu Ser Leu Pro Ala Val Ser Val Ile
    130                 135                 140 gag gat tct gcc gac ctg ttt gat acc att gca gaa gtc tcc gac gcc     480
Glu Asp Ser Ala Asp Leu Phe Asp Thr Ile Ala Glu Val Ser Asp Ala
145                 150                 155                 160 ctc att gtg caa gtg ttt cct gcg gga gct gct cag tct tcc aac gag     528
Leu Ile Val Gln Val Phe Pro Ala Gly Ala Ala Gln Ser Ser Asn Glu
                165                 170                 175 acg ttc tac gaa gtc gcc aac gaa ctg aga aac gac ttt gtt ttt gtc     576
Thr Phe Tyr Glu Val Ala Asn Glu Leu Arg Asn Asp Phe Val Phe Val
            180                 185                 190 tcc acc act aac gag ggg tac gtg aaa aag tac gcg aag gac tca aag     624
Ser Thr Thr Asn Glu Gly Tyr Val Lys Lys Tyr Ala Lys Asp Ser Lys
        195                 200                 205 tca cct gct tat gtc atc ttc agg caa gga gaa aag gtt gaa gat gcg     672
Ser Pro Ala Tyr Val Ile Phe Arg Gln Gly Glu Lys Val Glu Asp Ala
    210                 215                 220 tcc aca tac acc gga aag act gtt gac gac act cac ttg aag cag ttc     720
Ser Thr Tyr Thr Gly Lys Thr Val Asp Asp Thr His Leu Lys Gln Phe
225                 230                 235                 240
```

```
atc aat acc gaa acc aaa cct ctg ttt ggt gaa atc acc ggc aac act    768
Ile Asn Thr Glu Thr Lys Pro Leu Phe Gly Glu Ile Thr Gly Asn Thr
            245                 250                 255 ttc aag acc tac atg gag gcc gag ctt cct ttg gcg tac ttt ttc tgg    816
Phe Lys Thr Tyr Met Glu Ala Glu Leu Pro Leu Ala Tyr Phe Phe Trp
        260                 265                 270 gac gaa gag tct caa agg gcc gag gtc gct gac atc atc acc gag ctg    864
Asp Glu Glu Ser Gln Arg Ala Glu Val Ala Asp Ile Ile Thr Glu Leu
    275                 280                 285 gcc aag aag ttt aga gga gag atg aac ttt gtt ggt ttg gaa gcc aag    912
Ala Lys Lys Phe Arg Gly Glu Met Asn Phe Val Gly Leu Glu Ala Lys
290                 295                 300 aga tac ggt atg cat gcc aag aac ctc aac atg gag gaa aag ttc ccc    960
Arg Tyr Gly Met His Ala Lys Asn Leu Asn Met Glu Glu Lys Phe Pro
305                 310                 315                 320 ttg ttc gcc atc cac gat ttg acc gga aac ctc aag tac ggt att tct   1008
Leu Phe Ala Ile His Asp Leu Thr Gly Asn Leu Lys Tyr Gly Ile Ser
            325                 330                 335 caa gag tct gat ctt gac gtc aag gaa atc cct aag ttc gtt gag gat   1056
Gln Glu Ser Asp Leu Asp Val Lys Glu Ile Pro Lys Phe Val Glu Asp
        340                 345                 350 ttc aag aag ggc aag ttg caa gca att gtc aag tct gag cca att cca   1104
Phe Lys Lys Gly Lys Leu Gln Ala Ile Val Lys Ser Glu Pro Ile Pro
    355                 360                 365 gaa gtc caa gag gag tcc gtg tac cac ctg gtt gga cac gag cac gac   1152
Glu Val Gln Glu Glu Ser Val Tyr His Leu Val Gly His Glu His Asp
370                 375                 380 gcc atc acc aag cag aag aag gac gtt ttg gtt gag tac tac gcc cca   1200
Ala Ile Thr Lys Gln Lys Lys Asp Val Leu Val Glu Tyr Tyr Ala Pro
385                 390                 395                 400 tgg tgt gga cac tgc aag aag ctg gct cca act tac gaa att ttg gcc   1248
Trp Cys Gly His Cys Lys Lys Leu Ala Pro Thr Tyr Glu Ile Leu Ala
            405                 410                 415 agc atc tac cag aac gac act gat gcc aag gaa aag gtt gtg att gcc   1296
Ser Ile Tyr Gln Asn Asp Thr Asp Ala Lys Glu Lys Val Val Ile Ala
        420                 425                 430 aag att gac cac act gcc aac gat gtt gcc ggt gtc gac atc gcc ggt   1344
Lys Ile Asp His Thr Ala Asn Asp Val Ala Gly Val Asp Ile Ala Gly
    435                 440                 445 tat cca acc atc atc ttg tat cct ggt gac gaa tct gag ccg gtt gtg   1392
Tyr Pro Thr Ile Ile Leu Tyr Pro Gly Asp Glu Ser Glu Pro Val Val
450                 455                 460 tac gag ggt tct aga act cta gag gct ctc agt tca ttc atc aag gag   1440
Tyr Glu Gly Ser Arg Thr Leu Glu Ala Leu Ser Ser Phe Ile Lys Glu
465                 470                 475                 480 aag ggt tcg aac ggc gtt gac gct ttg tcc atc aag gaa tcg cgt gtt   1488
Lys Gly Ser Asn Gly Val Asp Ala Leu Ser Ile Lys Glu Ser Arg Val
            485                 490                 495 gaa aaa gaa gcc gat gct caa gcc gat gct cct gac gct ggc gtg gct   1536
Glu Lys Glu Ala Asp Ala Gln Ala Asp Ala Pro Asp Ala Gly Val Ala
        500                 505                 510 cac gac gag ttg taa                                                1551
His Asp Glu Leu
        515

<210> SEQ ID NO 2
<211> LENGTH: 516
<212> TYPE: PRT
<213> ORGANISM: Ogataea minuta
```

```
<400> SEQUENCE: 2

Met Lys Leu Phe Gly Leu Thr Thr Leu Thr Ser Ile Leu Ala Ala Leu
1               5                   10                  15

Thr Val Val Ser Ala Thr Glu Glu Pro Ala Val Ala Ser Pro Asp Ser
            20                  25                  30

Ala Val Val Lys Leu Thr Ala Asp Thr Phe Glu Ser Phe Ile Lys Glu
            35                  40                  45

Asn Pro Leu Val Leu Ala Glu Phe Phe Ala Pro Trp Cys Gly His Cys
    50                  55                  60

Lys Lys Leu Gly Pro Glu Phe Ser Ala Ala Asp Gln Leu Val Glu
65                  70                  75                  80

Lys Asn Ile Lys Leu Ala Gln Ile Asp Cys Thr Glu Arg Asp Leu
                85                  90                  95

Cys Ser Ser His Gly Ile Arg Gly Tyr Pro Thr Leu Lys Val Phe Arg
                100                 105                 110

Gly Ala Ser Glu Pro Ala Asp Tyr Gln Gly Ala Arg Glu Gln Glu Ala
            115                 120                 125

Ile Val Ser Gln Met Ile Lys Leu Ser Leu Pro Ala Val Ser Val Ile
130                 135                 140

Glu Asp Ser Ala Asp Leu Phe Asp Thr Ile Ala Glu Val Ser Asp Ala
145                 150                 155                 160

Leu Ile Val Gln Val Phe Pro Ala Gly Ala Gln Ser Ser Asn Glu
                165                 170                 175

Thr Phe Tyr Glu Val Ala Asn Glu Leu Arg Asn Asp Phe Val Phe Val
            180                 185                 190

Ser Thr Thr Asn Glu Gly Tyr Val Lys Lys Tyr Ala Lys Asp Ser Lys
            195                 200                 205

Ser Pro Ala Tyr Val Ile Phe Arg Gln Gly Glu Lys Val Glu Asp Ala
210                 215                 220

Ser Thr Tyr Thr Gly Lys Thr Val Asp Asp Thr His Leu Lys Gln Phe
225                 230                 235                 240

Ile Asn Thr Glu Thr Lys Pro Leu Phe Gly Glu Ile Thr Gly Asn Thr
                245                 250                 255

Phe Lys Thr Tyr Met Glu Ala Glu Leu Pro Leu Ala Tyr Phe Phe Trp
            260                 265                 270

Asp Glu Glu Ser Gln Arg Ala Glu Val Ala Asp Ile Thr Glu Leu
            275                 280                 285

Ala Lys Lys Phe Arg Gly Glu Met Asn Phe Val Gly Leu Glu Ala Lys
290                 295                 300

Arg Tyr Gly Met His Ala Lys Asn Leu Asn Met Glu Glu Lys Phe Pro
305                 310                 315                 320

Leu Phe Ala Ile His Asp Leu Thr Gly Asn Leu Lys Tyr Gly Ile Ser
                325                 330                 335

Gln Glu Ser Asp Leu Asp Val Lys Glu Ile Pro Lys Phe Val Glu Asp
            340                 345                 350

Phe Lys Lys Gly Lys Leu Gln Ala Ile Val Lys Ser Glu Pro Ile Pro
            355                 360                 365

Glu Val Gln Glu Glu Ser Val Tyr His Leu Val Gly His Glu His Asp
            370                 375                 380

Ala Ile Thr Lys Gln Lys Asp Val Leu Val Glu Tyr Tyr Ala Pro
385                 390                 395                 400

Trp Cys Gly His Cys Lys Lys Leu Ala Pro Thr Tyr Glu Ile Leu Ala
            405                 410                 415
```

```
Ser Ile Tyr Gln Asn Asp Thr Asp Ala Lys Glu Lys Val Val Ile Ala
        420                 425                 430

Lys Ile Asp His Thr Ala Asn Asp Val Ala Gly Val Asp Ile Ala Gly
                435                 440                 445

Tyr Pro Thr Ile Ile Leu Tyr Pro Gly Asp Glu Ser Glu Pro Val Val
        450                 455                 460

Tyr Glu Gly Ser Arg Thr Leu Glu Ala Leu Ser Ser Phe Ile Lys Glu
465                 470                 475                 480

Lys Gly Ser Asn Gly Val Asp Ala Leu Ser Ile Lys Glu Ser Arg Val
                485                 490                 495

Glu Lys Glu Ala Asp Ala Gln Ala Asp Ala Pro Asp Ala Gly Val Ala
                500                 505                 510

His Asp Glu Leu
        515

<210> SEQ ID NO 3
<211> LENGTH: 936
<212> TYPE: DNA
<213> ORGANISM: Ogataea minuta
<220> FEATURE:
<221> NAME/KEY: CDS
<222> LOCATION: (1)..(936)

<400> SEQUENCE: 3 atg aaa gtg gca agt ttg ata gca ttg gtc gtt acg ccg att att gct      48
Met Lys Val Ala Ser Leu Ile Ala Leu Val Val Thr Pro Ile Ile Ala
1               5                   10                  15 gcc act ggg gtg gta gca gat ccg cag cag cag gcc aaa aga cct ggt      96
Ala Thr Gly Val Val Ala Asp Pro Gln Gln Gln Ala Lys Arg Pro Gly
                20                  25                  30 ttt tac aag aat tca aag cat atc tac aat ctc act ccc cag aac ttt     144
Phe Tyr Lys Asn Ser Lys His Ile Tyr Asn Leu Thr Pro Gln Asn Phe
            35                  40                  45 gac gac gtc gtc ctg caa acc aac cat acg tct gtc gtg gag ttc tat     192
Asp Asp Val Val Leu Gln Thr Asn His Thr Ser Val Val Glu Phe Tyr
    50                  55                  60 gcg cca tgg tgt ggc tat tgc gca gag ttt gag agc cag tac cgc aaa     240
Ala Pro Trp Cys Gly Tyr Cys Ala Glu Phe Glu Ser Gln Tyr Arg Lys
65                  70                  75                  80 gca gca aag atc gga tcg gag ttc gtg aat ttt gcg gcc gtt aac tgc     288
Ala Ala Lys Ile Gly Ser Glu Phe Val Asn Phe Ala Ala Val Asn Cys
                85                  90                  95 gac gaa gac aag aac aaa cca ttg tgc aac aag tac cgc gtc gaa ggg     336
Asp Glu Asp Lys Asn Lys Pro Leu Cys Asn Lys Tyr Arg Val Glu Gly
            100                 105                 110 ttc ccg acg gtg atg gtt ttc cgt cca gcg aag gtc aac tcg gcg gga     384
Phe Pro Thr Val Met Val Phe Arg Pro Ala Lys Val Asn Ser Ala Gly
        115                 120                 125 tcc aac ggc aac agg cct cat tcc tcc gaa acg tat cgg ggc gag aga     432
Ser Asn Gly Asn Arg Pro His Ser Ser Glu Thr Tyr Arg Gly Glu Arg
    130                 135                 140 acg gcg gct aag ttg ctc gag cat gtc aag ggc cgt gtg gtg aat tac     480
Thr Ala Ala Lys Leu Leu Glu His Val Lys Gly Arg Val Val Asn Tyr
145                 150                 155                 160 gtg aag aga atc aag ctc aac aaa ctt gat gaa ttt ctc aaa ccg aat     528
Val Lys Arg Ile Lys Leu Asn Lys Leu Asp Glu Phe Leu Lys Pro Asn
                165                 170                 175 gaa aag agc aga gtc ttg ctg gtg act tca aaa agc act ctt tcg ccg     576
Glu Lys Ser Arg Val Leu Leu Val Thr Ser Lys Ser Thr Leu Ser Pro
            180                 185                 190
```

```
gtt ttc aag agc ctg tcg atc gat ttt ctc gac tca gtc acg ttg gca       624
Val Phe Lys Ser Leu Ser Ile Asp Phe Leu Asp Ser Val Thr Leu Ala
    195                 200                 205 tac ctc act ctg agc gaa aac gac tcc gaa ggt aga gac aaa ctg ctg       672
Tyr Leu Thr Leu Ser Glu Asn Asp Ser Glu Gly Arg Asp Lys Leu Leu
210                 215                 220 gaa aag att cct gcc ctc aaa gcg gac ttc aaa gtc ccg act tta ctc       720
Glu Lys Ile Pro Ala Leu Lys Ala Asp Phe Lys Val Pro Thr Leu Leu
225                 230                 235                 240 gcc atc gac aag gga acg aaa aat gtg acg gtt tat gat tcc gaa tcg       768
Ala Ile Asp Lys Gly Thr Lys Asn Val Thr Val Tyr Asp Ser Glu Ser
                245                 250                 255 atg tcg aaa aaa gag ctg acg aag ttc atg tct aag ttc ggc cag cca       816
Met Ser Lys Lys Glu Leu Thr Lys Phe Met Ser Lys Phe Gly Gln Pro
            260                 265                 270 caa gag ggg gca atg agc gaa aga ggg ggc atc ttg aaa gga atc aag       864
Gln Glu Gly Ala Met Ser Glu Arg Gly Gly Ile Leu Lys Gly Ile Lys
        275                 280                 285 aag ggt gct tac aag agc ttc aaa gat tac aaa aag aag atg caa caa       912
Lys Gly Ala Tyr Lys Ser Phe Lys Asp Tyr Lys Lys Lys Met Gln Gln
    290                 295                 300 gct ctt gaa aaa gat gag cta tga                                       936
Ala Leu Glu Lys Asp Glu Leu
305                 310
```

<210> SEQ ID NO 4
<211> LENGTH: 311
<212> TYPE: PRT
<213> ORGANISM: Ogataea minuta

<400> SEQUENCE: 4

```
Met Lys Val Ala Ser Leu Ile Ala Leu Val Val Thr Pro Ile Ile Ala
1               5                   10                  15

Ala Thr Gly Val Val Ala Asp Pro Gln Gln Gln Ala Lys Arg Pro Gly
            20                  25                  30

Phe Tyr Lys Asn Ser Lys His Ile Tyr Asn Leu Thr Pro Gln Asn Phe
        35                  40                  45

Asp Asp Val Val Leu Gln Thr Asn His Thr Ser Val Val Glu Phe Tyr
50                  55                  60

Ala Pro Trp Cys Gly Tyr Cys Ala Glu Phe Glu Ser Gln Tyr Arg Lys
65                  70                  75                  80

Ala Ala Lys Ile Gly Ser Glu Phe Val Asn Phe Ala Ala Val Asn Cys
                85                  90                  95

Asp Glu Asp Lys Asn Lys Pro Leu Cys Asn Lys Tyr Arg Val Glu Gly
            100                 105                 110

Phe Pro Thr Val Met Val Phe Arg Pro Ala Lys Val Asn Ser Ala Gly
        115                 120                 125

Ser Asn Gly Asn Arg Pro His Ser Ser Glu Thr Tyr Arg Gly Glu Arg
    130                 135                 140

Thr Ala Ala Lys Leu Leu Glu His Val Lys Gly Arg Val Val Asn Tyr
145                 150                 155                 160

Val Lys Arg Ile Lys Leu Asn Lys Leu Asp Glu Phe Leu Lys Pro Asn
                165                 170                 175

Glu Lys Ser Arg Val Leu Leu Val Thr Ser Lys Ser Thr Leu Ser Pro
            180                 185                 190

Val Phe Lys Ser Leu Ser Ile Asp Phe Leu Asp Ser Val Thr Leu Ala
        195                 200                 205

Tyr Leu Thr Leu Ser Glu Asn Asp Ser Glu Gly Arg Asp Lys Leu Leu
```

```
                  210                 215                 220
Glu Lys Ile Pro Ala Leu Lys Ala Asp Phe Lys Val Pro Thr Leu Leu
225                 230                 235                 240

Ala Ile Asp Lys Gly Thr Lys Asn Val Thr Val Tyr Asp Ser Glu Ser
                245                 250                 255

Met Ser Lys Lys Glu Leu Thr Lys Phe Met Ser Lys Phe Gly Gln Pro
            260                 265                 270

Gln Glu Gly Ala Met Ser Glu Arg Gly Gly Ile Leu Lys Gly Ile Lys
            275                 280                 285

Lys Gly Ala Tyr Lys Ser Phe Lys Asp Tyr Lys Lys Met Gln Gln
        290                 295                 300

Ala Leu Glu Lys Asp Glu Leu
305                 310

<210> SEQ ID NO 5
<211> LENGTH: 930
<212> TYPE: DNA
<213> ORGANISM: Ogataea minuta
<220> FEATURE:
<221> NAME/KEY: CDS
<222> LOCATION: (1)..(930)

<400> SEQUENCE: 5 atg ttt atg gag atc gga gag gcg tac gag gtg ctg atg gat tca gaa    48
Met Phe Met Glu Ile Gly Glu Ala Tyr Glu Val Leu Met Asp Ser Glu
1               5                   10                  15 aag aga tcc ata tat gac agg tac gga gag gaa ggc ttg aaa ggc ggt    96
Lys Arg Ser Ile Tyr Asp Arg Tyr Gly Glu Glu Gly Leu Lys Gly Gly
            20                  25                  30 gca ggg ggc gga gga gga gga caa cac cac gat ccg ttc gac atg ttt   144
Ala Gly Gly Gly Gly Gly Gly Gln His His Asp Pro Phe Asp Met Phe
        35                  40                  45 gcc aac ttt ttc ggc ggc gcc ggt ggg cgt caa caa gca cgg gga gtt   192
Ala Asn Phe Phe Gly Gly Ala Gly Gly Arg Gln Gln Ala Arg Gly Val
50                  55                  60 cca aga ggg tcg gac att gcc acg gag atg gag ttt acc ttg aaa gag   240
Pro Arg Gly Ser Asp Ile Ala Thr Glu Met Glu Phe Thr Leu Lys Glu
65                  70                  75                  80 ttt tac aac gga gtg aat agc gac ttt tca ctc gaa ctg caa gac atc   288
Phe Tyr Asn Gly Val Asn Ser Asp Phe Ser Leu Glu Leu Gln Asp Ile
                85                  90                  95 tgt gac cgt tgt gac gga agc ggg tcg cag gac ggg aaa gtg cac aag   336
Cys Asp Arg Cys Asp Gly Ser Gly Ser Gln Asp Gly Lys Val His Lys
            100                 105                 110 tgt tct cga tgc aat ggt cgt ggc cgg gtg tta gtg aag aga cag ttg   384
Cys Ser Arg Cys Asn Gly Arg Gly Arg Val Leu Val Lys Arg Gln Leu
        115                 120                 125 ggt cct ggc atg ttc cag cag atg gag tcg gcg tgt ccc gac tgt cgt   432
Gly Pro Gly Met Phe Gln Gln Met Glu Ser Ala Cys Pro Asp Cys Arg
130                 135                 140 gga gca gga aaa cag att act cac cat tgc aag aag tgt cgg ggt ggc   480
Gly Ala Gly Lys Gln Ile Thr His His Cys Lys Lys Cys Arg Gly Gly
145                 150                 155                 160 ggg gtt gtc cgt gga att cgc aac ttc aac atc cac ctt gag cca gga   528
Gly Val Val Arg Gly Ile Arg Asn Phe Asn Ile His Leu Glu Pro Gly
                165                 170                 175 act ccg cgc gac cac gtc gaa gtg tac gag ggt cag tcc gac agg tct   576
Thr Pro Arg Asp His Val Glu Val Tyr Glu Gly Gln Ser Asp Arg Ser
            180                 185                 190 ccg gag tgg gag gct ggt aac tta cgt ctg agc gtc aga gag aag aaa   624
Pro Glu Trp Glu Ala Gly Asn Leu Arg Leu Ser Val Arg Glu Lys Lys
```

```
                                                                                    -continued Pro Glu Trp Glu Ala Gly Asn Leu Arg Leu Ser Val Arg Glu Lys Lys
        195                 200                 205 agc gga aac ctt ggg tat cgt cgg atc gga aac aat ctg tac cgc aca      672
Ser Gly Asn Leu Gly Tyr Arg Arg Ile Gly Asn Asn Leu Tyr Arg Thr
210                 215                 220 gag atc ttg acg ctg agc gag tct ctg aag ggt ggt tgg gtc cgc gag      720
Glu Ile Leu Thr Leu Ser Glu Ser Leu Lys Gly Gly Trp Val Arg Glu
225                 230                 235                 240 atc ccg ttt ctg gac aac tac gac gcc gtc tta aag ctg gaa aga cca      768
Ile Pro Phe Leu Asp Asn Tyr Asp Ala Val Leu Lys Leu Glu Arg Pro
            245                 250                 255 ctc gga agt gtt gtt acc agc ggg gaa gtg cag gtg gtg aaa gga aag      816
Leu Gly Ser Val Val Thr Ser Gly Glu Val Gln Val Val Lys Gly Lys
        260                 265                 270 ggt atg ccg att gcc aac tcc gtg gat cag ttt ggc gat ctg tat gtg      864
Gly Met Pro Ile Ala Asn Ser Val Asp Gln Phe Gly Asp Leu Tyr Val
    275                 280                 285 gag tat gtg gtg ttg tat ccg gga gga agc ccg aag aag gtg agc aag      912
Glu Tyr Val Val Leu Tyr Pro Gly Gly Ser Pro Lys Lys Val Ser Lys
290                 295                 300 ttg cac gac gag ctg tga                                              930
Leu His Asp Glu Leu
305

<210> SEQ ID NO 6
<211> LENGTH: 309
<212> TYPE: PRT
<213> ORGANISM: Ogataea minuta

<400> SEQUENCE: 6

Met Phe Met Glu Ile Gly Glu Ala Tyr Glu Val Leu Met Asp Ser Glu
1               5                   10                  15

Lys Arg Ser Ile Tyr Asp Arg Tyr Gly Glu Glu Gly Leu Lys Gly Gly
            20                  25                  30

Ala Gly Gly Gly Gly Gly Gln His His Asp Pro Phe Asp Met Phe
        35                  40                  45

Ala Asn Phe Phe Gly Gly Ala Gly Gly Arg Gln Ala Arg Gly Val
    50                  55                  60

Pro Arg Gly Ser Asp Ile Ala Thr Glu Met Glu Phe Thr Leu Lys Glu
65                  70                  75                  80

Phe Tyr Asn Gly Val Asn Ser Asp Phe Ser Leu Glu Leu Gln Asp Ile
                85                  90                  95

Cys Asp Arg Cys Asp Gly Ser Gly Ser Gln Asp Gly Lys Val His Lys
            100                 105                 110

Cys Ser Arg Cys Asn Gly Arg Gly Arg Val Leu Val Lys Arg Gln Leu
        115                 120                 125

Gly Pro Gly Met Phe Gln Gln Met Glu Ser Ala Cys Pro Asp Cys Arg
    130                 135                 140

Gly Ala Gly Lys Gln Ile Thr His His Cys Lys Lys Cys Arg Gly Gly
145                 150                 155                 160

Gly Val Val Arg Gly Ile Arg Asn Phe Asn Ile His Leu Glu Pro Gly
                165                 170                 175

Thr Pro Arg Asp His Val Glu Val Tyr Glu Gly Gln Ser Asp Arg Ser
            180                 185                 190

Pro Glu Trp Glu Ala Gly Asn Leu Arg Leu Ser Val Arg Glu Lys Lys
        195                 200                 205

Ser Gly Asn Leu Gly Tyr Arg Arg Ile Gly Asn Asn Leu Tyr Arg Thr
    210                 215                 220
```

```
Glu Ile Leu Thr Leu Ser Glu Ser Leu Lys Gly Gly Trp Val Arg Glu
225                 230                 235                 240

Ile Pro Phe Leu Asp Asn Tyr Asp Ala Val Leu Lys Leu Glu Arg Pro
            245                 250                 255

Leu Gly Ser Val Val Thr Ser Gly Glu Val Gln Val Val Lys Gly Lys
            260                 265                 270

Gly Met Pro Ile Ala Asn Ser Val Asp Gln Phe Gly Asp Leu Tyr Val
        275                 280                 285

Glu Tyr Val Val Leu Tyr Pro Gly Gly Ser Pro Lys Lys Val Ser Lys
    290                 295                 300

Leu His Asp Glu Leu
305

<210> SEQ ID NO 7
<211> LENGTH: 1137
<212> TYPE: DNA
<213> ORGANISM: Ogataea minuta
<220> FEATURE:
<221> NAME/KEY: CDS
<222> LOCATION: (1)..(1137)

<400> SEQUENCE: 7 atg aaa gtc acg tct atc tgg caa gtc ctg ttt atg ttg atc gcc ggc      48
Met Lys Val Thr Ser Ile Trp Gln Val Leu Phe Met Leu Ile Ala Gly
1               5                   10                  15 gtt atg gcg tca gcg tcc aaa gtg atg gag ctg aac gac aag aac ttt     96
Val Met Ala Ser Ala Ser Lys Val Met Glu Leu Asn Asp Lys Asn Phe
            20                  25                  30 gac gag gtg gtt ctc aac tcc gga aag acc tcg cta gtg gaa ttc tac    144
Asp Glu Val Val Leu Asn Ser Gly Lys Thr Ser Leu Val Glu Phe Tyr
        35                  40                  45 gcg tcg tgg tgc agt cac tgc aag aag ttg gag cct act tgg gaa gag    192
Ala Ser Trp Cys Ser His Cys Lys Lys Leu Glu Pro Thr Trp Glu Glu
    50                  55                  60 ctg gcc tcg gcg tac gga aac aag aac gat atc cag atc gtc aag atc    240
Leu Ala Ser Ala Tyr Gly Asn Lys Asn Asp Ile Gln Ile Val Lys Ile
65                  70                  75                  80 gac gct gac gaa aac gga aac gtg gga aga aaa ttc gga atc aag gga    288
Asp Ala Asp Glu Asn Gly Asn Val Gly Arg Lys Phe Gly Ile Lys Gly
                85                  90                  95 ttt ccc acg ctg aaa ctg ttc aaa aaa gat gat ctc aac aac cca gtg    336
Phe Pro Thr Leu Lys Leu Phe Lys Lys Asp Asp Leu Asn Asn Pro Val
            100                 105                 110 gaa ttt gaa ggc tcc agg gac ttc cat tct ttc acc aac ttc att gct    384
Glu Phe Glu Gly Ser Arg Asp Phe His Ser Phe Thr Asn Phe Ile Ala
        115                 120                 125 gca cac acg ggt atc aag gct gcc aac gcg gtt ccc act gag ccg tcc    432
Ala His Thr Gly Ile Lys Ala Ala Asn Ala Val Pro Thr Glu Pro Ser
    130                 135                 140 aaa gtg gtg gaa ctg cac gat gga aat ttg gag gag ctt gtt aag gag    480
Lys Val Val Glu Leu His Asp Gly Asn Leu Glu Glu Leu Val Lys Glu
145                 150                 155                 160 cag gga aaa aat gct ctt ttt gca atc acc gca gag tgg tgt ggt tac    528
Gln Gly Lys Asn Ala Leu Phe Ala Ile Thr Ala Glu Trp Cys Gly Tyr
                165                 170                 175 tgc aag aag ctc aag cct aca tgg gag cag ctg gct gcc gtt ttc caa    576
Cys Lys Lys Leu Lys Pro Thr Trp Glu Gln Leu Ala Ala Val Phe Gln
            180                 185                 190 ggc gac gag gaa aac atc ttg att gga cag gtc caa acc acc ggc gat    624
Gly Asp Glu Glu Asn Ile Leu Ile Gly Gln Val Gln Thr Thr Gly Asp
```

```
                     195                 200                 205
aac cca aca gaa tgg atc cag gag aaa tac aac ctc cag tcg ttc ccc      672
Asn Pro Thr Glu Trp Ile Gln Glu Lys Tyr Asn Leu Gln Ser Phe Pro
210                 215                 220 aca ata gtc ttc atc gag aag ggc aac ctg gac gag cct gtg ttc tat      720
Thr Ile Val Phe Ile Glu Lys Gly Asn Leu Asp Glu Pro Val Phe Tyr
225                 230                 235                 240 ccg tac gga aga gag ctg gga gac ctg gtt gag ttc gtt aac acc cag      768
Pro Tyr Gly Arg Glu Leu Gly Asp Leu Val Glu Phe Val Asn Thr Gln
                245                 250                 255 gcc gga act cac cgg aac gag aaa ggc gag ctg gac tcc gag gcc ggg      816
Ala Gly Thr His Arg Asn Glu Lys Gly Glu Leu Asp Ser Glu Ala Gly
            260                 265                 270 ctg ata cac gca gtc gac gag ctg gtt gag cag ttt gtc ggt tcc tcg      864
Leu Ile His Ala Val Asp Glu Leu Val Glu Gln Phe Val Gly Ser Ser
        275                 280                 285 agc agc ggc aga aaa aat ctg gtt ccg aaa ttc ttg gaa gct ttg aaa      912
Ser Ser Gly Arg Lys Asn Leu Val Pro Lys Phe Leu Glu Ala Leu Lys
    290                 295                 300 tcg gct gac acc gac aat gca ttg tcg aaa gaa gtg aaa tac tac aac      960
Ser Ala Asp Thr Asp Asn Ala Leu Ser Lys Glu Val Lys Tyr Tyr Asn
305                 310                 315                 320 aag atc atc cat acg atg gtc aac ggt ccc ttt gac ttc gtc gcg aaa     1008
Lys Ile Ile His Thr Met Val Asn Gly Pro Phe Asp Phe Val Ala Lys
                325                 330                 335 gaa acc gct aga ctg gag tcg cta ctg aag tcg gat ctg tct tcc cga     1056
Glu Thr Ala Arg Leu Glu Ser Leu Leu Lys Ser Asp Leu Ser Ser Arg
            340                 345                 350 gcc aga gac tca gct tcc ttt aga ctc aac atc ctc aag ttt ttc agc     1104
Ala Arg Asp Ser Ala Ser Phe Arg Leu Asn Ile Leu Lys Phe Phe Ser
        355                 360                 365 gat cct gcc cct cca gcc aag gat gag ctg tga                         1137
Asp Pro Ala Pro Pro Ala Lys Asp Glu Leu
    370                 375

<210> SEQ ID NO 8
<211> LENGTH: 378
<212> TYPE: PRT
<213> ORGANISM: Ogataea minuta

<400> SEQUENCE: 8

Met Lys Val Thr Ser Ile Trp Gln Val Leu Phe Met Leu Ile Ala Gly
1               5                   10                  15

Val Met Ala Ser Ala Ser Lys Val Met Glu Leu Asn Asp Lys Asn Phe
            20                  25                  30

Asp Glu Val Val Leu Asn Ser Gly Lys Thr Ser Leu Val Glu Phe Tyr
        35                  40                  45

Ala Ser Trp Cys Ser His Cys Lys Lys Leu Glu Pro Thr Trp Glu Glu
    50                  55                  60

Leu Ala Ser Ala Tyr Gly Asn Lys Asn Asp Ile Gln Ile Val Lys Ile
65                  70                  75                  80

Asp Ala Asp Glu Asn Gly Asn Val Gly Arg Lys Phe Gly Ile Lys Gly
                85                  90                  95

Phe Pro Thr Leu Lys Leu Phe Lys Asp Asp Leu Asn Asn Pro Val
            100                 105                 110

Glu Phe Glu Gly Ser Arg Asp Phe His Ser Phe Thr Asn Phe Ile Ala
        115                 120                 125

Ala His Thr Gly Ile Lys Ala Ala Asn Ala Val Pro Thr Glu Pro Ser
    130                 135                 140
```

```
Lys Val Val Glu Leu His Asp Gly Asn Leu Glu Glu Leu Val Lys Glu
145                 150                 155                 160

Gln Gly Lys Asn Ala Leu Phe Ala Ile Thr Ala Glu Trp Cys Gly Tyr
            165                 170                 175

Cys Lys Lys Leu Lys Pro Thr Trp Glu Gln Leu Ala Ala Val Phe Gln
            180                 185                 190

Gly Asp Glu Glu Asn Ile Leu Ile Gly Gln Val Gln Thr Thr Gly Asp
                195                 200                 205

Asn Pro Thr Glu Trp Ile Gln Glu Lys Tyr Asn Leu Gln Ser Phe Pro
    210                 215                 220

Thr Ile Val Phe Ile Glu Lys Gly Asn Leu Asp Glu Pro Val Phe Tyr
225                 230                 235                 240

Pro Tyr Gly Arg Glu Leu Gly Asp Leu Val Glu Phe Val Asn Thr Gln
                245                 250                 255

Ala Gly Thr His Arg Asn Glu Lys Gly Glu Leu Asp Ser Glu Ala Gly
            260                 265                 270

Leu Ile His Ala Val Asp Glu Leu Val Glu Gln Phe Val Gly Ser Ser
            275                 280                 285

Ser Gly Arg Lys Asn Leu Val Pro Lys Phe Leu Glu Ala Leu Lys
290                 295                 300

Ser Ala Asp Thr Asp Asn Ala Leu Ser Lys Glu Val Lys Tyr Tyr Asn
305                 310                 315                 320

Lys Ile Ile His Thr Met Val Asn Gly Pro Phe Asp Phe Val Ala Lys
                325                 330                 335

Glu Thr Ala Arg Leu Glu Ser Leu Leu Lys Ser Asp Leu Ser Ser Arg
                340                 345                 350

Ala Arg Asp Ser Ala Ser Phe Arg Leu Asn Ile Leu Lys Phe Phe Ser
            355                 360                 365

Asp Pro Ala Pro Pro Ala Lys Asp Glu Leu
    370                 375

<210> SEQ ID NO 9
<211> LENGTH: 1728
<212> TYPE: DNA
<213> ORGANISM: Ogataea minuta
<220> FEATURE:
<221> NAME/KEY: CDS
<222> LOCATION: (1)..(1728)

<400> SEQUENCE: 9 atg aag cac gtg ata agt ggc cga tcc cgg gtg gcg ttg ggc tgg att      48
Met Lys His Val Ile Ser Gly Arg Ser Arg Val Ala Leu Gly Trp Ile
1               5                   10                  15 ctg acg tgg ttg atc tgt gcg att tgc gct gtt ccc gga gct ggg ttg      96
Leu Thr Trp Leu Ile Cys Ala Ile Cys Ala Val Pro Gly Ala Gly Leu
            20                  25                  30 cag gag att tcg tcc ttg gag agg aaa ccg gct tac ctg tcg ccg cag     144
Gln Glu Ile Ser Ser Leu Glu Arg Lys Pro Ala Tyr Leu Ser Pro Gln
        35                  40                  45 tat gag tac gac aac att cac gag ttt gag tcg acg cct ttc cgc gat     192
Tyr Glu Tyr Asp Asn Ile His Glu Phe Glu Ser Thr Pro Phe Arg Asp
    50                  55                  60 tac gag acg ttc acg ggg tcc aag gtg agt gag agt tcg aac gtg act     240
Tyr Glu Thr Phe Thr Gly Ser Lys Val Ser Glu Ser Ser Asn Val Thr
65                  70                  75                  80 ttt ggc cag atc aac gcg ctc aac aac gaa atc aga ccg gtt ttg cac     288
Phe Gly Gln Ile Asn Ala Leu Asn Asn Glu Ile Arg Pro Val Leu His
                85                  90                  95
```

-continued

| | |
|---|---|
| gat ctg att aac gag aac ttc ttc aaa atc ttt cga ctc aac ctg tac<br>Asp Leu Ile Asn Glu Asn Phe Phe Lys Ile Phe Arg Leu Asn Leu Tyr<br>               100                      105                 110 | 336 |
| aag gag tgt ccg ttc tgg tcg agt tcg gag gga ttt tgc atg cac aag<br>Lys Glu Cys Pro Phe Trp Ser Ser Ser Glu Gly Phe Cys Met His Lys<br>       115                     120                       125 | 384 |
| agc tgt gcc gtg gac acc att gac gac tgg aaa gat ctt ccg gag ata<br>Ser Cys Ala Val Asp Thr Ile Asp Asp Trp Lys Asp Leu Pro Glu Ile<br>130                       135                       140 | 432 |
| tgg cag ccc gag gct ctg ggt cgg atc gag tcg ttg acg cga gaa ccg<br>Trp Gln Pro Glu Ala Leu Gly Arg Ile Glu Ser Leu Thr Arg Glu Pro<br>145                   150                     155               160 | 480 |
| cct acg acg ata tct gac gcg gga aat ggc tcg tgt gtc gct gca ggc<br>Pro Thr Thr Ile Ser Asp Ala Gly Asn Gly Ser Cys Val Ala Ala Gly<br>               165                      170                   175 | 528 |
| gga cgg agc acg cgg gat tac tgc gaa ctg gac gag gtc aac gag gac<br>Gly Arg Ser Thr Arg Asp Tyr Cys Glu Leu Asp Glu Val Asn Glu Asp<br>             180                      185                   190 | 576 |
| tcg gta tac gtg aat ctg gtg gac aat ccc gag aga ttc acg ggg tac<br>Ser Val Tyr Val Asn Leu Val Asp Asn Pro Glu Arg Phe Thr Gly Tyr<br>      195                     200                      205 | 624 |
| gga gga gat cag tcg ttc caa att tgg cgc agc att tac aac gag aac<br>Gly Gly Asp Gln Ser Phe Gln Ile Trp Arg Ser Ile Tyr Asn Glu Asn<br>210                       215                      220 | 672 |
| tgt ttc aat ttg ggc tcg gat caa tgt ctc gag aag aac ttt ttc tac<br>Cys Phe Asn Leu Gly Ser Asp Gln Cys Leu Glu Lys Asn Phe Phe Tyr<br>225                   230                     235               240 | 720 |
| aag ttg atc agt gga atg cac tcg tcg atc tcg act cat ctg acc aac<br>Lys Leu Ile Ser Gly Met His Ser Ser Ile Ser Thr His Leu Thr Asn<br>                 245                     250               255 | 768 |
| gag tac ctg aac ttc aag acc aag cag tat gga cag gat ctc aag cag<br>Glu Tyr Leu Asn Phe Lys Thr Lys Gln Tyr Gly Gln Asp Leu Lys Gln<br>             260                      265                   270 | 816 |
| ttc atg atc cgg gtg ggg gac ttc cct gac cgg ttc gag aac ttg tat<br>Phe Met Ile Arg Val Gly Asp Phe Pro Asp Arg Phe Glu Asn Leu Tyr<br>      275                     280                      285 | 864 |
| ctg aac tac gtt ctg gtg gtg aag tcc ttg atc aag ctg gag cag tcg<br>Leu Asn Tyr Val Leu Val Val Lys Ser Leu Ile Lys Leu Glu Gln Ser<br>290                       295                     300 | 912 |
| ggt gtg ctg gac aac ctc cag ttc tgt gac gag gag gtg ttt cag acg<br>Gly Val Leu Asp Asn Leu Gln Phe Cys Asp Glu Glu Val Phe Gln Thr<br>305                       310                     315               320 | 960 |
| aag gag aag gag cta aaa cgc gag ctg aag gag atg att tct ccg ttc<br>Lys Glu Lys Glu Leu Lys Arg Glu Leu Lys Glu Met Ile Ser Pro Phe<br>                 325                     330                   335 | 1008 |
| tac cag ctg gcg gaa ggt ggg aaa gtg gac gag tgt ctg ttc aac gag<br>Tyr Gln Leu Ala Glu Gly Gly Lys Val Asp Glu Cys Leu Phe Asn Glu<br>             340                      345                  350 | 1056 |
| cac tcg ctg ttc cag agc gag gac tcg acg tat ctg aag gac gag ttc<br>His Ser Leu Phe Gln Ser Glu Asp Ser Thr Tyr Leu Lys Asp Glu Phe<br>      355                     360                      365 | 1104 |
| agt gag aac ttc agg aac gtg tcg cgg atc atg gat tgt gtc cac tgc<br>Ser Glu Asn Phe Arg Asn Val Ser Arg Ile Met Asp Cys Val His Cys<br>370                       375                     380 | 1152 |
| gac agg tgc aga ctg tgg ggg aag gtg cag acc acc ggg tac gga act<br>Asp Arg Cys Arg Leu Trp Gly Lys Val Gln Thr Thr Gly Tyr Gly Thr<br>385                       390                     395               400 | 1200 |
| gcg ctg aag att ttg ttt gag ctg gat gca agc gac agc cac gag ctg<br>Ala Leu Lys Ile Leu Phe Glu Leu Asp Ala Ser Asp Ser His Glu Leu<br>                 405                     410               415 | 1248 |

```
ggc aag aat ttc cag atc tcc aaa atc gag ctg gtc gcc ctg atc aac    1296
Gly Lys Asn Phe Gln Ile Ser Lys Ile Glu Leu Val Ala Leu Ile Asn
        420                 425                 430 acg ttt gac agg ctg tcc aag agc gtg cac gcc atc gga aac ttc aaa    1344
Thr Phe Asp Arg Leu Ser Lys Ser Val His Ala Ile Gly Asn Phe Lys
    435                 440                 445 caa ctg tac gat ctg aga atg aaa cag gag gaa gaa ggg ggg tcc atg    1392
Gln Leu Tyr Asp Leu Arg Met Lys Gln Glu Glu Glu Gly Gly Ser Met
450                 455                 460 att act gca gac acg ttt gac ttg gag caa ttg ctg ttg aca gac cag    1440
Ile Thr Ala Asp Thr Phe Asp Leu Glu Gln Leu Leu Leu Thr Asp Gln
465                 470                 475                 480 acg gtg gac gta ttc ggc cag agc act tct gag cca gaa acc ccg tcg    1488
Thr Val Asp Val Phe Gly Gln Ser Thr Ser Glu Pro Glu Thr Pro Ser
            485                 490                 495 gac gtt aga tat ccc gac aga aca cgg ggc tcg ctc gtt ccc gag ggg    1536
Asp Val Arg Tyr Pro Asp Arg Thr Arg Gly Ser Leu Val Pro Glu Gly
        500                 505                 510 ctc ggc gag gcg ttc aag aca gag ctg tac agc gtt tat cag gcg ttc    1584
Leu Gly Glu Ala Phe Lys Thr Glu Leu Tyr Ser Val Tyr Gln Ala Phe
    515                 520                 525 tac ttt gtc gtg acc agc tac acc atg ttc ccc aag ctg atc tac aac    1632
Tyr Phe Val Val Thr Ser Tyr Thr Met Phe Pro Lys Leu Ile Tyr Asn
530                 535                 540 tac ctg ctg atc cgg gtg gtg tac tgg tgg aac atc ttt gtg ggt cat    1680
Tyr Leu Leu Ile Arg Val Val Tyr Trp Trp Asn Ile Phe Val Gly His
545                 550                 555                 560 gta cac gag gac ttt gac gtg gat cgc ctg tat cgt ttg gag cta taa    1728
Val His Glu Asp Phe Asp Val Asp Arg Leu Tyr Arg Leu Glu Leu
            565                 570                 575

<210> SEQ ID NO 10
<211> LENGTH: 575
<212> TYPE: PRT
<213> ORGANISM: Ogataea minuta

<400> SEQUENCE: 10

Met Lys His Val Ile Ser Gly Arg Ser Arg Val Ala Leu Gly Trp Ile
1               5                   10                  15

Leu Thr Trp Leu Ile Cys Ala Ile Cys Ala Val Pro Gly Ala Gly Leu
            20                  25                  30

Gln Glu Ile Ser Ser Leu Glu Arg Lys Pro Ala Tyr Leu Ser Pro Gln
        35                  40                  45

Tyr Glu Tyr Asp Asn Ile His Glu Phe Glu Ser Thr Pro Phe Arg Asp
    50                  55                  60

Tyr Glu Thr Phe Thr Gly Ser Lys Val Ser Glu Ser Asn Val Thr
65                  70                  75                  80

Phe Gly Gln Ile Asn Ala Leu Asn Asn Glu Ile Arg Pro Val Leu His
                85                  90                  95

Asp Leu Ile Asn Glu Asn Phe Phe Lys Ile Phe Arg Leu Asn Leu Tyr
            100                 105                 110

Lys Glu Cys Pro Phe Trp Ser Ser Glu Gly Phe Cys Met His Lys
        115                 120                 125

Ser Cys Ala Val Asp Thr Ile Asp Asp Trp Lys Asp Leu Pro Glu Ile
    130                 135                 140

Trp Gln Pro Glu Ala Leu Gly Arg Ile Glu Ser Leu Thr Arg Glu Pro
145                 150                 155                 160

Pro Thr Thr Ile Ser Asp Ala Gly Asn Gly Ser Cys Val Ala Ala Gly
```

```
                    165                 170                 175
Gly Arg Ser Thr Arg Asp Tyr Cys Glu Leu Asp Glu Val Asn Glu Asp
                180                 185                 190

Ser Val Tyr Val Asn Leu Val Asp Asn Pro Glu Arg Phe Thr Gly Tyr
            195                 200                 205

Gly Gly Asp Gln Ser Phe Gln Ile Trp Arg Ser Ile Tyr Asn Glu Asn
        210                 215                 220

Cys Phe Asn Leu Gly Ser Asp Gln Cys Leu Lys Asn Phe Phe Tyr
225                 230                 235                 240

Lys Leu Ile Ser Gly Met His Ser Ser Ile Ser Thr His Leu Thr Asn
                245                 250                 255

Glu Tyr Leu Asn Phe Lys Thr Lys Gln Tyr Gly Gln Asp Leu Lys Gln
            260                 265                 270

Phe Met Ile Arg Val Gly Asp Phe Pro Asp Arg Phe Glu Asn Leu Tyr
        275                 280                 285

Leu Asn Tyr Val Leu Val Val Lys Ser Leu Ile Lys Leu Glu Gln Ser
    290                 295                 300

Gly Val Leu Asp Asn Leu Gln Phe Cys Asp Glu Val Phe Gln Thr
305                 310                 315                 320

Lys Glu Lys Glu Leu Lys Arg Glu Leu Lys Glu Met Ile Ser Pro Phe
                325                 330                 335

Tyr Gln Leu Ala Glu Gly Gly Lys Val Asp Glu Cys Leu Phe Asn Glu
            340                 345                 350

His Ser Leu Phe Gln Ser Glu Asp Ser Thr Tyr Leu Lys Asp Glu Phe
        355                 360                 365

Ser Glu Asn Phe Arg Asn Val Ser Arg Ile Met Asp Cys Val His Cys
    370                 375                 380

Asp Arg Cys Arg Leu Trp Gly Lys Val Gln Thr Thr Gly Tyr Gly Thr
385                 390                 395                 400

Ala Leu Lys Ile Leu Phe Glu Leu Asp Ala Ser Asp Ser His Glu Leu
                405                 410                 415

Gly Lys Asn Phe Gln Ile Ser Lys Ile Glu Leu Val Ala Leu Ile Asn
            420                 425                 430

Thr Phe Asp Arg Leu Ser Lys Ser Val His Ala Ile Gly Asn Phe Lys
        435                 440                 445

Gln Leu Tyr Asp Leu Arg Met Lys Gln Glu Glu Gly Gly Ser Met
    450                 455                 460

Ile Thr Ala Asp Thr Phe Asp Leu Glu Gln Leu Leu Thr Asp Gln
465                 470                 475                 480

Thr Val Asp Val Phe Gly Gln Ser Thr Ser Glu Pro Glu Thr Pro Ser
                485                 490                 495

Asp Val Arg Tyr Pro Asp Arg Thr Arg Gly Ser Leu Val Pro Glu Gly
            500                 505                 510

Leu Gly Glu Ala Phe Lys Thr Glu Leu Tyr Ser Val Tyr Gln Ala Phe
        515                 520                 525

Tyr Phe Val Val Thr Ser Tyr Thr Met Phe Pro Lys Leu Ile Tyr Asn
    530                 535                 540

Tyr Leu Leu Ile Arg Val Val Tyr Trp Trp Asn Ile Phe Val Gly His
545                 550                 555                 560

Val His Glu Asp Phe Asp Val Asp Arg Leu Tyr Arg Leu Glu Leu
                565                 570                 575

<210> SEQ ID NO 11
<211> LENGTH: 2700
```

```
<212> TYPE: DNA
<213> ORGANISM: Ogataea minuta
<220> FEATURE:
<221> NAME/KEY: CDS
<222> LOCATION: (1)..(2700)

<400> SEQUENCE: 11 atg gat tct acg caa ttt aca gac aga gct cta gac ata gtg acg acg      48
Met Asp Ser Thr Gln Phe Thr Asp Arg Ala Leu Asp Ile Val Thr Thr
1               5                  10                  15 gct cag aag cta tgt cag cag aac tca aac gca cag ata gtg cca ttg      96
Ala Gln Lys Leu Cys Gln Gln Asn Ser Asn Ala Gln Ile Val Pro Leu
            20                  25                  30 cac ttt ctg gcg gca atg act ccg acc tcc agt gag ggg gag gca atc     144
His Phe Leu Ala Ala Met Thr Pro Thr Ser Ser Glu Gly Glu Ala Ile
        35                  40                  45 tat ctc aag acg ttg att gag aga ggt cga ttt gac tgg act gct ttt     192
Tyr Leu Lys Thr Leu Ile Glu Arg Gly Arg Phe Asp Trp Thr Ala Phe
    50                  55                  60 gaa aga gcc gtt aat aaa gca gtg gtg cgg ctc cca agc gtg gcc ggt     240
Glu Arg Ala Val Asn Lys Ala Val Val Arg Leu Pro Ser Val Ala Gly
65                  70                  75                  80 tcc aac acc gag cca agc att tcc gcc tcc gcc gcc agc att atc acc     288
Ser Asn Thr Glu Pro Ser Ile Ser Ala Ser Ala Ala Ser Ile Ile Thr
                85                  90                  95 aac gca tcc aag atc aag gca cag cag aaa gac tcg tac atc ggc caa     336
Asn Ala Ser Lys Ile Lys Ala Gln Gln Lys Asp Ser Tyr Ile Gly Gln
            100                 105                 110 gac cac att ctc tcg gcc ctt ttg gac gat tct agt atc cag gct gtg     384
Asp His Ile Leu Ser Ala Leu Leu Asp Asp Ser Ser Ile Gln Ala Val
        115                 120                 125 ctg aag gaa gcg aac gtc aag ccc gac gca ttg aag aca cag atc gtt     432
Leu Lys Glu Ala Asn Val Lys Pro Asp Ala Leu Lys Thr Gln Ile Val
    130                 135                 140 gaa ctc aga ggc aat cag aga att gat tct cgt caa gct gat tcg tct     480
Glu Leu Arg Gly Asn Gln Arg Ile Asp Ser Arg Gln Ala Asp Ser Ser
145                 150                 155                 160 cag aag ttt gag ttt ctg tcc aag tac gcc ctt gat ctt acc gag cag     528
Gln Lys Phe Glu Phe Leu Ser Lys Tyr Ala Leu Asp Leu Thr Glu Gln
                165                 170                 175 gcg ttg cag ggt aag att gac cct gta ata ggc aga gag gag gag atc     576
Ala Leu Gln Gly Lys Ile Asp Pro Val Ile Gly Arg Glu Glu Glu Ile
            180                 185                 190 aga agg gcc att cgg gtt ctt tcg aga cgg gcc aag tcg aac ccg tgt     624
Arg Arg Ala Ile Arg Val Leu Ser Arg Arg Ala Lys Ser Asn Pro Cys
        195                 200                 205 ctg att gga gat cct ggt gtt ggt aag act agt att gtt gag gga gtc     672
Leu Ile Gly Asp Pro Gly Val Gly Lys Thr Ser Ile Val Glu Gly Val
    210                 215                 220 gca cag agg ata gtg gac aac gat gtt cct acc gtt tta cag ggg tgc     720
Ala Gln Arg Ile Val Asp Asn Asp Val Pro Thr Val Leu Gln Gly Cys
225                 230                 235                 240 aag ctg tac tcg ctg gac ttg ggt gcg ttg aaa gcg gga gcc aag tac     768
Lys Leu Tyr Ser Leu Asp Leu Gly Ala Leu Lys Ala Gly Ala Lys Tyr
                245                 250                 255 cag ggt gag ttc gag gaa aga ttg aag gga gtt ttg agc gac atc gaa     816
Gln Gly Glu Phe Glu Glu Arg Leu Lys Gly Val Leu Ser Asp Ile Glu
            260                 265                 270 agc tcg aac tcg atg atc atc ttg ttc atc gac gag atc cac atg ttg     864
Ser Ser Asn Ser Met Ile Ile Leu Phe Ile Asp Glu Ile His Met Leu
        275                 280                 285
```

```
atg ggc gat gga aag tcg gac gct gcc aac ttg ctg aag cct gct ctg      912
Met Gly Asp Gly Lys Ser Asp Ala Ala Asn Leu Leu Lys Pro Ala Leu
290                 295                 300 gcg aga ggt cag ttc cac tgc atc ggt gcg act acc gtg acc gag tac      960
Ala Arg Gly Gln Phe His Cys Ile Gly Ala Thr Thr Val Thr Glu Tyr
305                 310                 315                 320 aga aag cac atc gag aag gac ggt gct ttc gag aga aga ttt cag aga     1008
Arg Lys His Ile Glu Lys Asp Gly Ala Phe Glu Arg Arg Phe Gln Arg
                325                 330                 335 atc gac gtg aga gag ccg acc atc aga gaa acc gtt gcc att ctc aga     1056
Ile Asp Val Arg Glu Pro Thr Ile Arg Glu Thr Val Ala Ile Leu Arg
            340                 345                 350 gga ctg cag cca agg tac gag atc cac cac ggt gtc cga atc ctg gac     1104
Gly Leu Gln Pro Arg Tyr Glu Ile His His Gly Val Arg Ile Leu Asp
        355                 360                 365 agt gcc ctg gtg acg gct gct caa ctg gcc tcc aga tac ctc acc tac     1152
Ser Ala Leu Val Thr Ala Ala Gln Leu Ala Ser Arg Tyr Leu Thr Tyr
    370                 375                 380 aga aag ctt ccg gac tct gca gtg gat ctg att gac gag tcc gcc gcg     1200
Arg Lys Leu Pro Asp Ser Ala Val Asp Leu Ile Asp Glu Ser Ala Ala
385                 390                 395                 400 gga gtc gct gtt gcc agg gac tcc aag ccg gag gag ctg gac tcc aag     1248
Gly Val Ala Val Ala Arg Asp Ser Lys Pro Glu Glu Leu Asp Ser Lys
                405                 410                 415 gag aga cag cta cag ctg atc gag gtt gag atc aat gct ctg gaa aga     1296
Glu Arg Gln Leu Gln Leu Ile Glu Val Glu Ile Asn Ala Leu Glu Arg
            420                 425                 430 gac cag gac gcc gac acg tcc acc aag gag aga ctg gag cag gcc aga     1344
Asp Gln Asp Ala Asp Thr Ser Thr Lys Glu Arg Leu Glu Gln Ala Arg
        435                 440                 445 cag aga aga cag aac ctg gag gaa gag ctg gct cca ttg agg gag aag     1392
Gln Arg Arg Gln Asn Leu Glu Glu Glu Leu Ala Pro Leu Arg Glu Lys
    450                 455                 460 tac cag cag gaa aga gcg ggc cac gag gag ctg act gct gcc aag aga     1440
Tyr Gln Gln Glu Arg Ala Gly His Glu Glu Leu Thr Ala Ala Lys Arg
465                 470                 475                 480 aag tta gac gac ctc gaa gtt aag gcg caa gat gcg gag aga aga cac     1488
Lys Leu Asp Asp Leu Glu Val Lys Ala Gln Asp Ala Glu Arg Arg His
                485                 490                 495 gac tct cag acc att gcg gac ctg cgg atg ttt gcc att ccg gac gtg     1536
Asp Ser Gln Thr Ile Ala Asp Leu Arg Met Phe Ala Ile Pro Asp Val
            500                 505                 510 aaa cgc aga att gag gag ttg gaa cag aaa gtg gtt gaa gaa gag gcc     1584
Lys Arg Arg Ile Glu Glu Leu Glu Gln Lys Val Val Glu Glu Glu Ala
        515                 520                 525 act tct gaa gat ttc atg gtg aag aac gtt gtt ggt tcg gag caa gtt     1632
Thr Ser Glu Asp Phe Met Val Lys Asn Val Val Gly Ser Glu Gln Val
    530                 535                 540 tcc gag acc gcg gcc agg ttg acc ggt att ccg gtc agc aag ctg acg     1680
Ser Glu Thr Ala Ala Arg Leu Thr Gly Ile Pro Val Ser Lys Leu Thr
545                 550                 555                 560 cag gca gaa aat gct aag ctg atc acc atg gag aag gag ctg tcc gct     1728
Gln Ala Glu Asn Ala Lys Leu Ile Thr Met Glu Lys Glu Leu Ser Ala
                565                 570                 575 gcc gtt gtc gga cag ggc gag gct gtc aag gct gtt tcg aac tcg atc     1776
Ala Val Val Gly Gln Gly Glu Ala Val Lys Ala Val Ser Asn Ser Ile
            580                 585                 590 aga ttg tcg aga tct ggt ctg gcc aat cct aac cag ccg gcc tcg ttc     1824
Arg Leu Ser Arg Ser Gly Leu Ala Asn Pro Asn Gln Pro Ala Ser Phe
        595                 600                 605
```

```
ctg ttc ctg gga ctc tcg ggt tcc ggt aag acg gag ctg gcc aaa aag      1872
Leu Phe Leu Gly Leu Ser Gly Ser Gly Lys Thr Glu Leu Ala Lys Lys
    610             615                 620 ctg gca ggg ttc ctg ttc tcg gat gag aag gcc atg atc aga atc gac      1920
Leu Ala Gly Phe Leu Phe Ser Asp Glu Lys Ala Met Ile Arg Ile Asp
625             630                 635                 640 tgt tca gaa ctg atg gag aag tac tcg gtt tcc aag ctg ctg ggc tcc      1968
Cys Ser Glu Leu Met Glu Lys Tyr Ser Val Ser Lys Leu Leu Gly Ser
                645                 650                 655 acc gcc ggt tac gtt ggc tac gag gag ggt ggt atg ttg acc aac cag      2016
Thr Ala Gly Tyr Val Gly Tyr Glu Glu Gly Gly Met Leu Thr Asn Gln
            660                 665                 670 ctt ttg aga aga ccg tac tct gtg gtg ttg ttc gac gag gtc gag aag      2064
Leu Leu Arg Arg Pro Tyr Ser Val Val Leu Phe Asp Glu Val Glu Lys
        675                 680                 685 gcc gct ccc gag gtg ctg aac att ctc ctg cag atg ttg gac gac gga      2112
Ala Ala Pro Glu Val Leu Asn Ile Leu Leu Gln Met Leu Asp Asp Gly
690                 695                 700 aga atc acc gcc gcc aac ggt act ctc gtc aac tgc tcg aac gct atc      2160
Arg Ile Thr Ala Ala Asn Gly Thr Leu Val Asn Cys Ser Asn Ala Ile
705                 710                 715                 720 gtg atc atg acg tcc aac ctc ggc gcg gag tac atc aac gca tca aag      2208
Val Ile Met Thr Ser Asn Leu Gly Ala Glu Tyr Ile Asn Ala Ser Lys
                725                 730                 735 gga acg aag gtg acc gac gag gtc aga agc ctg gtg atg aac act gtc      2256
Gly Thr Lys Val Thr Asp Glu Val Arg Ser Leu Val Met Asn Thr Val
            740                 745                 750 aag gga cat ttc aga ccg gag ttc ctc aac aga atc tcg gcc acc gtg      2304
Lys Gly His Phe Arg Pro Glu Phe Leu Asn Arg Ile Ser Ala Thr Val
        755                 760                 765 gtg ttc aac aga ctc tcc aga cat gcc atc gcc aag atc gtg cgg ctg      2352
Val Phe Asn Arg Leu Ser Arg His Ala Ile Ala Lys Ile Val Arg Leu
770                 775                 780 aga ctg aag gaa atc gaa gag agg ttc gag gcc aac ggc aag tcg atc      2400
Arg Leu Lys Glu Ile Glu Glu Arg Phe Glu Ala Asn Gly Lys Ser Ile
785                 790                 795                 800 aaa ctg aac gtg gac gat ggg gca ctc gag tac ctg tgc aaa aag gga      2448
Lys Leu Asn Val Asp Asp Gly Ala Leu Glu Tyr Leu Cys Lys Lys Gly
                805                 810                 815 tac tct ccc gac ttg ggc gct aga ccg ctg aac aga ctg atc cag agt      2496
Tyr Ser Pro Asp Leu Gly Ala Arg Pro Leu Asn Arg Leu Ile Gln Ser
            820                 825                 830 gaa atc ctg aac cat ctg gcg gtg atg gtg ttg aac gga cag gtg ttg      2544
Glu Ile Leu Asn His Leu Ala Val Met Val Leu Asn Gly Gln Val Leu
        835                 840                 845 gac aaa gag gaa gtt cag att acg acg ggc agc aag gga ctg tct gtg      2592
Asp Lys Glu Glu Val Gln Ile Thr Thr Gly Ser Lys Gly Leu Ser Val
850                 855                 860 gtt cct aac cat gac atc gag gac gaa gct atg gac gtg gac gtg gac      2640
Val Pro Asn His Asp Ile Glu Asp Glu Ala Met Asp Val Asp Val Asp
865                 870                 875                 880 gag tgg acc gac gcc gcc gac gac gac gac tcg ggc tac ggc agt cct      2688
Glu Trp Thr Asp Ala Ala Asp Asp Asp Asp Ser Gly Tyr Gly Ser Pro
                885                 890                 895 gat ctc gat taa                                                      2700
Asp Leu Asp <210> SEQ ID NO 12
<211> LENGTH: 899
<212> TYPE: PRT
<213> ORGANISM: Ogataea minuta
```

<400> SEQUENCE: 12

```
Met Asp Ser Thr Gln Phe Thr Asp Arg Ala Leu Asp Ile Val Thr Thr
1               5                   10                  15

Ala Gln Lys Leu Cys Gln Gln Asn Ser Asn Ala Gln Ile Val Pro Leu
            20                  25                  30

His Phe Leu Ala Ala Met Thr Pro Thr Ser Ser Glu Gly Glu Ala Ile
        35                  40                  45

Tyr Leu Lys Thr Leu Ile Glu Arg Gly Arg Phe Asp Trp Thr Ala Phe
    50                  55                  60

Glu Arg Ala Val Asn Lys Ala Val Val Arg Leu Pro Ser Val Ala Gly
65                  70                  75                  80

Ser Asn Thr Glu Pro Ser Ile Ser Ala Ser Ala Ser Ile Ile Thr
                85                  90                  95

Asn Ala Ser Lys Ile Lys Ala Gln Gln Lys Asp Ser Tyr Ile Gly Gln
                100                 105                 110

Asp His Ile Leu Ser Ala Leu Leu Asp Asp Ser Ser Ile Gln Ala Val
            115                 120                 125

Leu Lys Glu Ala Asn Val Lys Pro Asp Ala Leu Lys Thr Gln Ile Val
    130                 135                 140

Glu Leu Arg Gly Asn Gln Arg Ile Asp Ser Arg Gln Ala Asp Ser Ser
145                 150                 155                 160

Gln Lys Phe Glu Phe Leu Ser Lys Tyr Ala Leu Asp Leu Thr Glu Gln
                165                 170                 175

Ala Leu Gln Gly Lys Ile Asp Pro Val Ile Gly Arg Glu Glu Glu Ile
            180                 185                 190

Arg Arg Ala Ile Arg Val Leu Ser Arg Arg Ala Lys Ser Asn Pro Cys
    195                 200                 205

Leu Ile Gly Asp Pro Gly Val Gly Lys Thr Ser Ile Val Glu Gly Val
210                 215                 220

Ala Gln Arg Ile Val Asp Asn Asp Val Pro Thr Val Leu Gln Gly Cys
225                 230                 235                 240

Lys Leu Tyr Ser Leu Asp Leu Gly Ala Leu Lys Ala Gly Ala Lys Tyr
                245                 250                 255

Gln Gly Glu Phe Glu Glu Arg Leu Lys Gly Val Leu Ser Asp Ile Glu
            260                 265                 270

Ser Ser Asn Ser Met Ile Ile Leu Phe Ile Asp Glu Ile His Met Leu
    275                 280                 285

Met Gly Asp Gly Lys Ser Asp Ala Ala Asn Leu Leu Lys Pro Ala Leu
290                 295                 300

Ala Arg Gly Gln Phe His Cys Ile Gly Ala Thr Thr Val Thr Glu Tyr
305                 310                 315                 320

Arg Lys His Ile Glu Lys Asp Gly Ala Phe Glu Arg Arg Phe Gln Arg
                325                 330                 335

Ile Asp Val Arg Glu Pro Thr Ile Arg Glu Thr Val Ala Ile Leu Arg
            340                 345                 350

Gly Leu Gln Pro Arg Tyr Glu Ile His His Gly Val Arg Ile Leu Asp
    355                 360                 365

Ser Ala Leu Val Thr Ala Ala Gln Leu Ala Ser Arg Tyr Leu Thr Tyr
370                 375                 380

Arg Lys Leu Pro Asp Ser Ala Val Asp Leu Ile Asp Glu Ser Ala Ala
385                 390                 395                 400

Gly Val Ala Val Ala Arg Asp Ser Lys Pro Glu Glu Leu Asp Ser Lys
                405                 410                 415
```

```
Glu Arg Gln Leu Gln Leu Ile Glu Val Glu Ile Asn Ala Leu Glu Arg
                420                 425                 430

Asp Gln Asp Ala Asp Thr Ser Thr Lys Glu Arg Leu Glu Gln Ala Arg
            435                 440                 445

Gln Arg Arg Gln Asn Leu Glu Glu Leu Ala Pro Leu Arg Glu Lys
450                 455                 460

Tyr Gln Gln Glu Arg Ala Gly His Glu Leu Thr Ala Ala Lys Arg
465                 470                 475                 480

Lys Leu Asp Asp Leu Glu Val Lys Ala Gln Asp Ala Glu Arg Arg His
                485                 490                 495

Asp Ser Gln Thr Ile Ala Asp Leu Arg Met Phe Ala Ile Pro Asp Val
            500                 505                 510

Lys Arg Arg Ile Glu Glu Leu Glu Gln Lys Val Val Glu Glu Ala
            515                 520                 525

Thr Ser Glu Asp Phe Met Val Lys Asn Val Val Gly Ser Glu Gln Val
            530                 535                 540

Ser Glu Thr Ala Ala Arg Leu Thr Gly Ile Pro Val Ser Lys Leu Thr
545                 550                 555                 560

Gln Ala Glu Asn Ala Lys Leu Ile Thr Met Glu Lys Glu Leu Ser Ala
                565                 570                 575

Ala Val Val Gly Gln Gly Glu Ala Val Lys Ala Val Ser Asn Ser Ile
            580                 585                 590

Arg Leu Ser Arg Ser Gly Leu Ala Asn Pro Asn Gln Pro Ala Ser Phe
            595                 600                 605

Leu Phe Leu Gly Leu Ser Gly Ser Gly Lys Thr Glu Leu Ala Lys Lys
            610                 615                 620

Leu Ala Gly Phe Leu Phe Ser Asp Glu Lys Ala Met Ile Arg Ile Asp
625                 630                 635                 640

Cys Ser Glu Leu Met Glu Lys Tyr Ser Val Ser Lys Leu Leu Gly Ser
                645                 650                 655

Thr Ala Gly Tyr Val Gly Tyr Glu Glu Gly Gly Met Leu Thr Asn Gln
            660                 665                 670

Leu Leu Arg Arg Pro Tyr Ser Val Leu Phe Asp Glu Val Glu Lys
            675                 680                 685

Ala Ala Pro Glu Val Leu Asn Ile Leu Leu Gln Met Leu Asp Asp Gly
            690                 695                 700

Arg Ile Thr Ala Ala Asn Gly Thr Leu Val Asn Cys Ser Asn Ala Ile
705                 710                 715                 720

Val Ile Met Thr Ser Asn Leu Gly Ala Glu Tyr Ile Asn Ala Ser Lys
                725                 730                 735

Gly Thr Lys Val Thr Asp Glu Val Arg Ser Leu Val Met Asn Thr Val
            740                 745                 750

Lys Gly His Phe Arg Pro Glu Phe Leu Asn Arg Ile Ser Ala Thr Val
            755                 760                 765

Val Phe Asn Arg Leu Ser Arg His Ala Ile Ala Lys Ile Val Arg Leu
            770                 775                 780

Arg Leu Lys Glu Ile Glu Glu Arg Phe Glu Ala Asn Gly Lys Ser Ile
785                 790                 795                 800

Lys Leu Asn Val Asp Asp Gly Ala Leu Glu Tyr Leu Cys Lys Lys Gly
                805                 810                 815

Tyr Ser Pro Asp Leu Gly Ala Arg Pro Leu Asn Arg Leu Ile Gln Ser
            820                 825                 830

Glu Ile Leu Asn His Leu Ala Val Met Val Leu Asn Gly Gln Val Leu
```

```
                    835                 840                 845
Asp Lys Glu Glu Val Gln Ile Thr Thr Gly Ser Lys Gly Leu Ser Val
    850                 855                 860

Val Pro Asn His Asp Ile Glu Asp Glu Ala Met Asp Val Asp Val Asp
865                 870                 875                 880

Glu Trp Thr Asp Ala Ala Asp Asp Asp Ser Gly Tyr Gly Ser Pro
                885                 890                 895

Asp Leu Asp

<210> SEQ ID NO 13
<211> LENGTH: 1998
<212> TYPE: DNA
<213> ORGANISM: Ogataea minuta
<220> FEATURE:
<221> NAME/KEY: CDS
<222> LOCATION: (1)..(1998)

<400> SEQUENCE: 13 atg ttt aag ttc aac cgc tct gtg cta tct ata gct acg ata ctg tat       48
Met Phe Lys Phe Asn Arg Ser Val Leu Ser Ile Ala Thr Ile Leu Tyr
1               5                   10                  15 gca gtg ctg ttg gta gtc cta cct ttg gct tca caa caa ttc gtg gaa       96
Ala Val Leu Leu Val Val Leu Pro Leu Ala Ser Gln Gln Phe Val Glu
                20                  25                  30 gca gag gcg aac gac aac tat ggt act gtt atc ggt atc gat ttg gga      144
Ala Glu Ala Asn Asp Asn Tyr Gly Thr Val Ile Gly Ile Asp Leu Gly
            35                  40                  45 acc act tac tca tgt gtg ggt gtg atg aaa gct ggt aga gtt gag atc      192
Thr Thr Tyr Ser Cys Val Gly Val Met Lys Ala Gly Arg Val Glu Ile
        50                  55                  60 ctt gcc aat gac cag ggt aac aga att act cca tct tat gtg gca ttt      240
Leu Ala Asn Asp Gln Gly Asn Arg Ile Thr Pro Ser Tyr Val Ala Phe
65                  70                  75                  80 act gat gaa gag aga ctt gtc gga gat gcc gca aag aac cag att gcc      288
Thr Asp Glu Glu Arg Leu Val Gly Asp Ala Ala Lys Asn Gln Ile Ala
                85                  90                  95 tcc aac cca agc aac aca atc ttc gat atc aag aga ctc ata gga cac      336
Ser Asn Pro Ser Asn Thr Ile Phe Asp Ile Lys Arg Leu Ile Gly His
            100                 105                 110 aga ttt gac gat aag gtt gtg caa aaa gag att gca cac ctc cct tac      384
Arg Phe Asp Asp Lys Val Val Gln Lys Glu Ile Ala His Leu Pro Tyr
        115                 120                 125 aag atc aga aac caa gag ggc aga ccg gtc gtt gag gcc act gtc aat      432
Lys Ile Arg Asn Gln Glu Gly Arg Pro Val Val Glu Ala Thr Val Asn
130                 135                 140 gga gag gtg acc acg ttc acg gcc gaa gaa gtt tcg gcc atg atc ttg      480
Gly Glu Val Thr Thr Phe Thr Ala Glu Glu Val Ser Ala Met Ile Leu
                150                 155                 160
145 gga aag atg aag caa att gct gaa gat tat ctc gga aag aag gtt acc      528
Gly Lys Met Lys Gln Ile Ala Glu Asp Tyr Leu Gly Lys Lys Val Thr
            165                 170                 175 cat gct gtt gtc acg gtt cct gca tac ttt aac gac gcc caa aga cag      576
His Ala Val Val Thr Val Pro Ala Tyr Phe Asn Asp Ala Gln Arg Gln
        180                 185                 190 gcc act aag gat gct ggt acc att gcc ggt ctg gaa gtt ttg aga att      624
Ala Thr Lys Asp Ala Gly Thr Ile Ala Gly Leu Glu Val Leu Arg Ile
195                 200                 205 gtt aac gag cct act gcc gct gca att gct tac ggt ctc gac aag acg      672
Val Asn Glu Pro Thr Ala Ala Ala Ile Ala Tyr Gly Leu Asp Lys Thr
                210                 215                 220
```

```
gac gaa gag aag cat atc att gtt tac gat ttg ggt gga gga act ttt      720
Asp Glu Glu Lys His Ile Ile Val Tyr Asp Leu Gly Gly Gly Thr Phe
225                 230                 235                 240 gat gtt tct ctg ttg aca att gca ggt gga gct ttc gag gtt cgt gcc      768
Asp Val Ser Leu Leu Thr Ile Ala Gly Gly Ala Phe Glu Val Arg Ala
                245                 250                 255 acc gct ggt gat acc cat ctt ggt ggt gag gac ttt gat tac aga gtt      816
Thr Ala Gly Asp Thr His Leu Gly Gly Glu Asp Phe Asp Tyr Arg Val
            260                 265                 270 gtc aga cat ttc atc aag gtg ttt aag aag aag cat ggc att gat atc      864
Val Arg His Phe Ile Lys Val Phe Lys Lys Lys His Gly Ile Asp Ile
        275                 280                 285 agt gat aat cca aag gct ctt gct aaa ttg aag aga gaa gtt gaa aaa      912
Ser Asp Asn Pro Lys Ala Leu Ala Lys Leu Lys Arg Glu Val Glu Lys
    290                 295                 300 gct aag aga acc ttg tct tct caa atg tcc acc aga att gag att gac      960
Ala Lys Arg Thr Leu Ser Ser Gln Met Ser Thr Arg Ile Glu Ile Asp
305                 310                 315                 320 tcg ttc gct gac ggt att gac ttc tcc gag tcc tta tcc agg gcc aag     1008
Ser Phe Ala Asp Gly Ile Asp Phe Ser Glu Ser Leu Ser Arg Ala Lys
                325                 330                 335 ttc gag gaa ttg aac att gag ttg ttc aaa aag acc ttg aag cct gtt     1056
Phe Glu Glu Leu Asn Ile Glu Leu Phe Lys Lys Thr Leu Lys Pro Val
            340                 345                 350 caa cgt gtt ctt gaa gac gcc aaa ttc aag gtt tca gaa att gat gac     1104
Gln Arg Val Leu Glu Asp Ala Lys Phe Lys Val Ser Glu Ile Asp Asp
        355                 360                 365 att gtc ttg gtt ggt ggt tcc acg aga att cca aag gtg caa gag ttg     1152
Ile Val Leu Val Gly Gly Ser Thr Arg Ile Pro Lys Val Gln Glu Leu
    370                 375                 380 ctg gaa agt tac ttc aac ggc aag caa gtg tcc aag gga att aac cca     1200
Leu Glu Ser Tyr Phe Asn Gly Lys Gln Val Ser Lys Gly Ile Asn Pro
385                 390                 395                 400 gat gaa gct gtt gct tac ggt gcg gct gtt caa gct ggt gtc ctc tct     1248
Asp Glu Ala Val Ala Tyr Gly Ala Ala Val Gln Ala Gly Val Leu Ser
                405                 410                 415 ggt gaa gaa ggc gtt gaa gac att gtt ttg att gat gtg aat cca tta     1296
Gly Glu Glu Gly Val Glu Asp Ile Val Leu Ile Asp Val Asn Pro Leu
            420                 425                 430 act ttg ggt atc gag acc tcc ggc ggt gtc atg acc act ttg att aag     1344
Thr Leu Gly Ile Glu Thr Ser Gly Gly Val Met Thr Thr Leu Ile Lys
        435                 440                 445 aga aac act gca att cca acc aag aag tct caa att ttc tct act gct     1392
Arg Asn Thr Ala Ile Pro Thr Lys Lys Ser Gln Ile Phe Ser Thr Ala
    450                 455                 460 gct gac aat caa cct gtt gtc ttg atc caa gtc tat gaa ggt gag aga     1440
Ala Asp Asn Gln Pro Val Val Leu Ile Gln Val Tyr Glu Gly Glu Arg
465                 470                 475                 480 gcc atg gca aag gat aac aat ttg cta gga aag ttc gag ttg aag gat     1488
Ala Met Ala Lys Asp Asn Asn Leu Leu Gly Lys Phe Glu Leu Lys Asp
                485                 490                 495 att cct cca gcc cca aga ggt acc cca caa att gag gtg act ttc act     1536
Ile Pro Pro Ala Pro Arg Gly Thr Pro Gln Ile Glu Val Thr Phe Thr
            500                 505                 510 ctg gac tcc aac gga atc ctg aag gtt gct gcc act gat aaa ggt act     1584
Leu Asp Ser Asn Gly Ile Leu Lys Val Ala Ala Thr Asp Lys Gly Thr
        515                 520                 525 ggt aag tct aac tct atc aca atc aca aac gac aag ggt aga ctt tcg     1632
Gly Lys Ser Asn Ser Ile Thr Ile Thr Asn Asp Lys Gly Arg Leu Ser
    530                 535                 540
```

-continued

```
aag gag gag att gag aag aag gtt gag gag gcc gaa cag tat gct caa    1680
Lys Glu Glu Ile Glu Lys Lys Val Glu Glu Ala Glu Gln Tyr Ala Gln
545                 550                 555                 560 caa gat aag gag gtc aga gag aag atc gag agc aga aac gga ctt gag    1728
Gln Asp Lys Glu Val Arg Glu Lys Ile Glu Ser Arg Asn Gly Leu Glu
                565                 570                 575 aac tac gcc cac tcg ttg aaa aac caa gtg aac gat gag acc gga ttc    1776
Asn Tyr Ala His Ser Leu Lys Asn Gln Val Asn Asp Glu Thr Gly Phe
            580                 585                 590 ggc tcc aag ctt gat gag gat gac aag gaa act ttg ttg gat gcc atc    1824
Gly Ser Lys Leu Asp Glu Asp Asp Lys Glu Thr Leu Leu Asp Ala Ile
        595                 600                 605 aac gag gca ttg gag tac ttg gac gac aac ttt gag acc gca aca aag    1872
Asn Glu Ala Leu Glu Tyr Leu Asp Asp Asn Phe Glu Thr Ala Thr Lys
    610                 615                 620 caa gac ttt gag gat cag aag gaa aaa ttg agt aag gtt gct tac cca    1920
Gln Asp Phe Glu Asp Gln Lys Glu Lys Leu Ser Lys Val Ala Tyr Pro
625                 630                 635                 640 att act tca aag ttg tat gat acg cca cct act agt gac gaa gat gat    1968
Ile Thr Ser Lys Leu Tyr Asp Thr Pro Pro Thr Ser Asp Glu Asp Asp
                645                 650                 655 gag gat gac tgg gat cat gat gag ctg tga                            1998
Glu Asp Asp Trp Asp His Asp Glu Leu
            660                 665
```

<210> SEQ ID NO 14
<211> LENGTH: 665
<212> TYPE: PRT
<213> ORGANISM: Ogataea minuta

<400> SEQUENCE: 14

```
Met Phe Lys Phe Asn Arg Ser Val Leu Ser Ile Ala Thr Ile Leu Tyr
1               5                   10                  15

Ala Val Leu Leu Val Val Leu Pro Leu Ala Ser Gln Gln Phe Val Glu
            20                  25                  30

Ala Glu Ala Asn Asp Asn Tyr Gly Thr Val Ile Gly Ile Asp Leu Gly
        35                  40                  45

Thr Thr Tyr Ser Cys Val Gly Val Met Lys Ala Gly Arg Val Glu Ile
    50                  55                  60

Leu Ala Asn Asp Gln Gly Asn Arg Ile Thr Pro Ser Tyr Val Ala Phe
65                  70                  75                  80

Thr Asp Glu Glu Arg Leu Val Gly Asp Ala Ala Lys Asn Gln Ile Ala
                85                  90                  95

Ser Asn Pro Ser Asn Thr Ile Phe Asp Ile Lys Arg Leu Ile Gly His
            100                 105                 110

Arg Phe Asp Asp Lys Val Val Gln Lys Glu Ile Ala His Leu Pro Tyr
        115                 120                 125

Lys Ile Arg Asn Gln Glu Gly Arg Pro Val Val Glu Ala Thr Val Asn
    130                 135                 140

Gly Glu Val Thr Thr Phe Thr Ala Glu Val Ser Ala Met Ile Leu
145                 150                 155                 160

Gly Lys Met Lys Gln Ile Ala Glu Asp Tyr Leu Gly Lys Lys Val Thr
                165                 170                 175

His Ala Val Val Thr Val Pro Ala Tyr Phe Asn Asp Ala Gln Arg Gln
            180                 185                 190

Ala Thr Lys Asp Ala Gly Thr Ile Ala Gly Leu Glu Val Leu Arg Ile
        195                 200                 205

Val Asn Glu Pro Thr Ala Ala Ala Ile Ala Tyr Gly Leu Asp Lys Thr
```

-continued

```
              210                 215                 220
Asp Glu Glu Lys His Ile Ile Val Tyr Asp Leu Gly Gly Gly Thr Phe
225                 230                 235                 240

Asp Val Ser Leu Leu Thr Ile Ala Gly Gly Ala Phe Glu Val Arg Ala
                245                 250                 255

Thr Ala Gly Asp Thr His Leu Gly Gly Glu Asp Phe Asp Tyr Arg Val
                260                 265                 270

Val Arg His Phe Ile Lys Val Phe Lys Lys His Gly Ile Asp Ile
                275                 280                 285

Ser Asp Asn Pro Lys Ala Leu Ala Lys Leu Arg Glu Val Glu Lys
290                 295                 300

Ala Lys Arg Thr Leu Ser Ser Gln Met Ser Thr Arg Ile Glu Ile Asp
305                 310                 315                 320

Ser Phe Ala Asp Gly Ile Asp Phe Ser Glu Ser Leu Ser Arg Ala Lys
                325                 330                 335

Phe Glu Glu Leu Asn Ile Glu Leu Phe Lys Lys Thr Leu Lys Pro Val
                340                 345                 350

Gln Arg Val Leu Glu Asp Ala Lys Phe Lys Val Ser Glu Ile Asp Asp
                355                 360                 365

Ile Val Leu Val Gly Gly Ser Thr Arg Ile Pro Lys Val Gln Glu Leu
370                 375                 380

Leu Glu Ser Tyr Phe Asn Gly Lys Gln Val Ser Lys Gly Ile Asn Pro
385                 390                 395                 400

Asp Glu Ala Val Ala Tyr Gly Ala Ala Val Gln Ala Gly Val Leu Ser
                405                 410                 415

Gly Glu Glu Gly Val Glu Asp Ile Val Leu Ile Asp Val Asn Pro Leu
                420                 425                 430

Thr Leu Gly Ile Glu Thr Ser Gly Gly Val Met Thr Thr Leu Ile Lys
                435                 440                 445

Arg Asn Thr Ala Ile Pro Thr Lys Lys Ser Gln Ile Phe Ser Thr Ala
450                 455                 460

Ala Asp Asn Gln Pro Val Val Leu Ile Gln Val Tyr Glu Gly Glu Arg
465                 470                 475                 480

Ala Met Ala Lys Asp Asn Asn Leu Leu Gly Lys Phe Glu Leu Lys Asp
                485                 490                 495

Ile Pro Pro Ala Pro Arg Gly Thr Pro Gln Ile Glu Val Thr Phe Thr
                500                 505                 510

Leu Asp Ser Asn Gly Ile Leu Lys Val Ala Ala Thr Asp Lys Gly Thr
                515                 520                 525

Gly Lys Ser Asn Ser Ile Thr Ile Thr Asn Asp Lys Gly Arg Leu Ser
530                 535                 540

Lys Glu Glu Ile Glu Lys Val Glu Glu Ala Glu Gln Tyr Ala Gln
545                 550                 555                 560

Gln Asp Lys Glu Val Arg Glu Lys Ile Glu Ser Arg Asn Gly Leu Glu
                565                 570                 575

Asn Tyr Ala His Ser Leu Lys Asn Gln Val Asn Asp Glu Thr Gly Phe
                580                 585                 590

Gly Ser Lys Leu Asp Glu Asp Lys Glu Thr Leu Leu Asp Ala Ile
                595                 600                 605

Asn Glu Ala Leu Glu Tyr Leu Asp Asp Asn Phe Glu Thr Ala Thr Lys
                610                 615                 620

Gln Asp Phe Glu Asp Gln Lys Glu Lys Leu Ser Lys Val Ala Tyr Pro
625                 630                 635                 640
```

Ile Thr Ser Lys Leu Tyr Asp Thr Pro Pro Thr Ser Asp Glu Asp Asp
            645                 650                 655

Glu Asp Asp Trp Asp His Asp Glu Leu
            660                 665

<210> SEQ ID NO 15
<211> LENGTH: 1929
<212> TYPE: DNA
<213> ORGANISM: Artificial Sequence
<220> FEATURE:
<223> OTHER INFORMATION: Synthetic DNA

<400> SEQUENCE: 15

| | | | | | |
|---|---|---|---|---|---|
| ggtacccgat | cccccacaca | ccatagcttc | aaaatgtttc | tactcctttt | ttactcttcc | 60 |
| agattttctc | ggactccgcg | catcgccgta | ccacttcaaa | acacccaagc | acagcatact | 120 |
| aaattttccc | tctttcttcc | tctagggtgt | cgttaattac | ccgtactaaa | ggtttggaaa | 180 |
| agaaaaaaga | gaccgcctcg | tttcttttc | ttcgtcgaaa | aaggcaataa | aaatttttat | 240 |
| cacgtttctt | tttcttgaaa | tttttttttt | tagttttttt | ctctttcagt | gacctccatt | 300 |
| gatatttaag | ttaataaacg | gtcttcaatt | tctcaagttt | cagtttcatt | tttcttgttc | 360 |
| tattacaact | ttttttactt | cttgttcatt | agaaagaaag | catagcaatc | taatctaagg | 420 |
| ggcggtgttg | acaattaatc | atcggcatag | tatatcggca | tagtataata | cgacaaggtg | 480 |
| aggaactaaa | ccatggccaa | gttgaccagt | gccgttccgg | tgctcaccgc | gcgcgacgtc | 540 |
| gccgagcgg | tcgagttctg | gaccgaccgg | ctcgggttct | cccgggactt | cgtggaggac | 600 |
| gacttcgccg | gtgtggtccg | ggacgacgtg | accctgttca | tcagcgcggt | ccaggaccag | 660 |
| gtggtgccgg | acaacaccct | ggcctgggtg | tgggtgcgcg | gcctggacga | gctgtacgcc | 720 |
| gagtggtcgg | aggtcgtgtc | cacgaacttc | cgggacgcct | ccgggccggc | catgaccgag | 780 |
| atcggcgagc | agccgtgggg | gcgggagttc | gccctgcgcg | accggccgg | caactgcgtg | 840 |
| cacttcgtgg | ccgaggagca | ggactgacac | gtccgacggc | ggcccacggg | tcccaggcct | 900 |
| cggagatccg | tccccctttt | cctttgtcga | tatcatgtaa | ttagttatgt | cacgcttaca | 960 |
| ttcacgccct | ccccccacat | ccgctctaac | cgaaaaggaa | ggagttagac | aacctgaagt | 1020 |
| ctaggtccct | atttattttt | ttatagttat | gttagtatta | agaacgttat | ttatatttca | 1080 |
| aatttttctt | ttttttctgt | acagacgcgt | gtacgcatgt | aacattatac | tgaaaacctt | 1140 |
| gcttgagaag | gttttgggac | gctcgaaggc | tttaatttgc | aagctggaga | ccaacatgtg | 1200 |
| agcaaaaggc | cagcaaaagg | ccaggaaccg | taaaaaggcc | gcgttgctgg | cgtttttcca | 1260 |
| taggctccgc | ccccctgacg | agcatcacaa | aaatcgacgc | tcaagtcaga | ggtggcgaaa | 1320 |
| cccgacagga | ctataaagat | accaggcgtt | tccccctgga | agctccctcg | tgcgctctcc | 1380 |
| tgttccgacc | ctgccgctta | ccggatacct | gtccgccttt | ctcccttcgg | gaagcgtggc | 1440 |
| gctttctcaa | tgctcacgct | gtaggtatct | cagttcggtg | taggtcgttc | gctccaagct | 1500 |
| gggctgtgtg | cacgaacccc | ccgttcagcc | cgaccgctgc | gccttatccg | gtaactatcg | 1560 |
| tcttgagtcc | aacccggtaa | gacacgactt | atcgccactg | gcagcagcca | ctggtaacag | 1620 |
| gattagcaga | gcgaggtatg | taggcggtgc | tacagagttc | ttgaagtggt | ggcctaacta | 1680 |
| cggctacact | agaaggacag | tatttggtat | ctgcgctctg | ctgaagccag | ttaccttcgg | 1740 |
| aaaaagagtt | ggtagctctt | gatccggcaa | acaaaccacc | gctggtagcg | gtggtttttt | 1800 |
| tgtttgcaag | cagcagatta | cgcgcagaaa | aaaaggatct | caagaagatc | ctttgatctt | 1860 |
| ttctacgggg | tctgacgctc | agtggaacga | aaactcacgt | taagggattt | tggtcatgag | 1920 |

-continued atcaagctt                                                              1929

<210> SEQ ID NO 16
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 16
ggagctcaaa aagctagcac caagggtcca tccgttttcc                              40

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 17
cagatcttta cttacctggg gacaaggaca ag                                     32

<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 18
gactagtaaa aacgtacggt tgctgctcca tccgttttca tc                           42

<210> SEQ ID NO 19
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 19
cagatcttta gcactcacct ctgttgaagg ac                                     32

<210> SEQ ID NO 20
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 20
ggagctcatg tttaagttca accgctc                                           27

<210> SEQ ID NO 21
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 21
caacgagttg aacctccgcc tctgcttcca cg                                     32

<210> SEQ ID NO 22
<211> LENGTH: 32
<212> TYPE: DNA
<213> ORGANISM: Artificial Sequence
<220> FEATURE:

-continued

<223> OTHER INFORMATION: Synthetic oligonucleotide primer

<400> SEQUENCE: 22
cgtggaagca gaggcggagg ttcaactcgt tg                                32

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 23
ggctagcgga ggaaacggta ac                                          22

<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 24
gactagtatg tttaagttca accgctc                                     27

<210> SEQ ID NO 25
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 25
gggtcatctg gatgtccgcc tctgcttcca cg                               32

<210> SEQ ID NO 26
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 26
cgtggaagca gaggcggaca tccagatgac cc                               32

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 27
gcgtacgctt gatctcaacc                                             20

<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 28
ggtcgacatg aagttatttg gattgac                                     27

<210> SEQ ID NO 29

```
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 29
gatgcattta caactcgtcg tgagccac                                          28

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 30
gagatacggt atgcacgcca agaac                                             25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 31
gttcttggcg tgcataccgt atctc                                             25

<210> SEQ ID NO 32
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 32
gttgccggtg ttgacatcgc cgg                                               23

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 33
ccggcgatgt caacaccggc aac                                               23

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 34
ggtcgacatg aaagtggcaa gtttg                                             25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 35
```
gatgcattca tagctcatct ttttc                                          25

<210> SEQ ID NO 36
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 36
ggtcgacatg tttatggaga tcggag                                         26

<210> SEQ ID NO 37
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 37
gatgcattca cagctcgtcg tgcaac                                         26

<210> SEQ ID NO 38
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 38
ggtcgacatg aaagtcacgt ctatctgg                                       28

<210> SEQ ID NO 39
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 39
gatgcattca cagctcatcc ttggctgg                                       28

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 40
gatacacgca gttgacgagc tg                                             22

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 41
cagctcgtca actgcgtgta tc                                             22

<210> SEQ ID NO 42
<211> LENGTH: 22
<212> TYPE: DNA
<213> ORGANISM: Artificial Sequence
<220> FEATURE:

<223> OTHER INFORMATION: Synthetic oligonucleotide primer

<400> SEQUENCE: 42
gacaacgcat tgtcgaaaga ag                                            22

<210> SEQ ID NO 43
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 43
cttctttcga caatgcgttg tc                                            22

<210> SEQ ID NO 44
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 44
ggtcgacatg aagcacgtga taagtggc                                      28

<210> SEQ ID NO 45
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 45
gatgcattta tagctccaaa cgatacag                                      28

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 46
gagtttgagt ccacgccttt ccgcg                                         25

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 47
cgcggaaagg cgtggactca aactc                                         25

<210> SEQ ID NO 48
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 48
ggtcgacatg gattctacgc aatttac                                       27

<210> SEQ ID NO 49

```
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 49
gatgcattta atcgagatca ggactgc                                        27

<210> SEQ ID NO 50
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 50
ggtcgacatg tttaagttca accgctctg                                      29

<210> SEQ ID NO 51
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 51
gatgcattca cagctcatca tgatcccag                                      29

<210> SEQ ID NO 52
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 52
cactaaggat gctggaacca ttgccggtct ggaag                               35

<210> SEQ ID NO 53
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 53
cttccagacc ggcaatggtt ccagcatcct tagtg                               35

<210> SEQ ID NO 54
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 54
ccagccccaa gaggaacccc acaaattgag gtgac                               35

<210> SEQ ID NO 55
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 55
```

```
gtcacctcaa tttgtggggt tcctcttggg gctgg                                  35

<210> SEQ ID NO 56
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 56
cggattcggc tccaaacttg atgaggatga caagg                                  35

<210> SEQ ID NO 57
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 57
ccttgtcatc ctcatcaagt ttggagccga atccg                                  35

<210> SEQ ID NO 58
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 58
ggtcgacatg aagttttctg ctggtg                                            26

<210> SEQ ID NO 59
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 59
gatgcattta caattcatcg tgaatg                                            26

<210> SEQ ID NO 60
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 60
ggtcgacatg ctgcgccgcg ctctgc                                            26

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 61
gatgcattta cagttcatct ttcacag                                           27

<210> SEQ ID NO 62
<211> LENGTH: 22
<212> TYPE: DNA
<213> ORGANISM: Artificial Sequence
<220> FEATURE:
```

```
<223> OTHER INFORMATION: Synthetic oligonucleotide primer

<400> SEQUENCE: 62
gcagggccct actggttcaa gg                                           22

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 63
gcagggcccg ctcgaatcga c                                            21

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 64
gngtngaytt yaaygtnccn ttrga                                        25

<210> SEQ ID NO 65
<211> LENGTH: 26
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 65
gynacdccng gyaaytcytt dccytc                                       26

<210> SEQ ID NO 66
<211> LENGTH: 9046
<212> TYPE: DNA
<213> ORGANISM: Ogataea minuta
<220> FEATURE:
<221> NAME/KEY: CDS
<222> LOCATION: (4766)..(6016)

<400> SEQUENCE: 66
ggatcccgcc ctcgacggtt gttggtgcgg gataatgttc gttgatgagc caacttcgat    60
ttttgctgaa acgactgaga cagatccgac agacgaggtg tagttgcgga tcagattttg   120
```

```
catcactctg ctgtttcttt tgatgtgtct ttcgtcgtcc tggaaccccc aactcgatag      180
cagcgaaagg actttgtcgt ctcgctccac aagcgatagt tttggacgag ctagatatgg      240
attgacgtag cttcttgtcg aggtggcgga ctcttttttg atgtgggttt cggtaacgga      300
ttccgacttg gcatgtgatt caatcactcc ctcgtagtgg gacgacacca cgctcatgtt      360
gtcgtcgtcc tgttgtccgc tgaagtcaaa cggattgctt tttctgtcaa cggtgtcgac      420
gacagcgtca acgctcaaca gatctgagtc cacagtctcg acgctggaga cgtccgactc      480
atgaacagga tacctgaaat tcatctgggt cccaagaaac gtgtctgtgt gtgtctttct      540
gtgctgtctt ttcgtcattg cttgatattc cccctaaata gttatcacgt acggaactct      600
ggtaaaaaaa cctgatccgt ttcagatcaa ctacatttaa aatcaggttg ttcctccagc      660
cccggcggaa gctaaagatg gctggttttt tcaatcagat ggtgaaatat taattttttt      720
gagccgcaac ccagccccag atccgaggct gtgcagcaga ttcggtcgat aaatgtacaa      780
cgactatgct aaatagggag tgaaaagcag caaaaaaaat gtcttagagg tagtaccttg      840
gttcttcaaa gacatggaat ttgtggtctc tgaccccatc tccatagaac atcgatggga      900
atcggaggtc tggatcaacg gtttcctcgt ctatccgctg ttgcgagtag ctttcgtcgt      960
agtctccatt ggagggtatg ataaatttac ccacctgaac ctcagtgtcg gtgatggacc     1020
cacgactgat ccgagcatac ccggttcttt tgagtttctt gtacaagatg tactcgcacc     1080
aacgatcgtc atcagtagcg tcgatatcgt gcattcctga cttgtcgctc acgtaggtgt     1140
tgtaattccc cttgaggggt tcggtcacca agtagctcaa caggatcatt ggcctttctg     1200
aactgcccat aatttcggaa acaccgagag attgtaaacg gcggtcctca acgtcctctt     1260
cttgtcccga atggaaaacg acaacgtcca cgagctctcc gtaacagtcc agagtagcgt     1320
ggatggcagg agccaattcg cccacaggag acggaagcaa gtgatgcgtg gaattgatga     1380
tcggaaactt ggacaaaagg gccgcacccc aggtatgttt cgttgggttc ggaccgaaat     1440
cggcgtacat gccgagttct tcggcaattc tttgggtgag atctctgttt cccatgatga     1500
ttctttgagt gtccgattct aataaaccca caacgtccaa ctccaggtct ttgatcaggt     1560
ctctcattct gtgctcagat gcccacatgt cgttatcgag accaaagtga atggtccaaa     1620
taccagccgt gacaagtctg gactggggat ggtagggtct tggttttttcg aactggaatc     1680 tgttgaaagc gataaatccc gagagcagtg taaagaaaat gaggtaattt gtgattttttt     1740 tcaacgacga cttcagtcgc tttgaatgcg aaacttcaga ctgcttgtag ttgaaaacaa     1800
gaccgcaaat catcagaact gaaacagaca ggatgatatc tgttctttct ctcaacaatg     1860
gtccaccggg aacaaaggca tatgcgacaa cccagacgtg agccaaagag agcactatgt     1920
caaacaggaa cgaaagacca aacactagag ccacgccgtc cactttggaa acctgatcaa     1980
aacaaacagg agtgatgaaa cacagccaga aagcgtatgc cagcccacca gcgtaactga     2040
tccagccgtt gaaatagtac aggaacaaag ctccgagaac tcccgcataa gtgacagact     2100
tgtaggaact ggaccggtag aatccgaaaa aggctcctag acacatgaaa atcaccgtca     2160
ccgcaccgtg gggaacaggg atcggcccgt tgataggata gccctcccat gtccacagaa     2220
caatggtaga agagtcggta agcatggcac taatcgagaa aatcagagat ccaaaaccca     2280
tggctgacag cataagagaa ggcttttgag tcttaagtgg gcctttctca gatacagtcc     2340
cctgtggtag cttttgtgaaa gctgcagctg tcaatccgac aactagaccg gtgaggttcc     2400
acccaccggt gtcgctgttc atgatgggcc aaataggatt attggtccag aacgcaaact     2460
tggcgagact ggacagaatg agccccattg taaacgaggt tgcaaacgtt ttcgtagcca     2520
```

```
gttgatcatt cagtttgcca atggcagcca cttcggtact taaggcaatg gttgcgaacg    2580
aaacagccgc gccaataacc atcaatctgc aggcagggtc taccaccaag taagccccca    2640
caccgaacaa acaggtgagc gttctagcga cttgaggacg ttttgtgaaa acagcttca     2700 cctttggaac tgccaagaca aacggagtca atagaaggac acagactgcc tcgtatcccg    2760
agattcccat gtaccacagc gggaagtacc agatacagag gaacaatgag gagtagacag    2820
accagaaaac gaaccaattg atggtgtcga cagtgagttg ccagaaagag ctgctgaact    2880
gagtcgactt cggtaatagc ttcccgctgg aggttgggc cgaggaactt gaagtgccgt     2940
ttattctgtc ttgaatgagc ttgatgtcga aattggcact gaaaaattcg tctcttgttg    3000
ctgaaggtct gagctcgatg atcaggtctt tgaagtccaa gatggaccag gcatcaaagc    3060
caacatcaag aaagatcaac gcccattcgc agtatgcgta gtaagaataa gctcccttga    3120
cgtgatgaac cttgtgctgg ataaaaagat acaccagagg gacaagtgca ccaaaaaatg    3180
tccatgcggt gtacttcctg gctcttctga tcctggaccg tggtgggac agcttggtga     3240 tagcgaggtc ccacgggata gtcaggacaa tgtaggagat cataaacaca tcgtgcgcgt    3300
cgtgatcatc cgtagaagta atataaaccc agcctccaca cgtgatggtt ctgatgaagc    3360
ccgatatcag ggcaagttta gggtacactg aattggcctt gtgcagacga acatacgtta    3420
gtagcagtag taagaaccga ggaccagctg taagcgcgat caaaatctgg aagattgacc    3480
gttcaggata tctgtcacca atggtggccg agacactcgg gaaccactcg tctggatacc    3540
cataatactc gttctcaacg attttgtaaa aatggagcca gcacccaaca gccaaggcag    3600
ctaaaaaggc agagagcgag cacacagagt gtgcgatcgc aatggcctgt gagttcaacc    3660
gcactagagg ctgcgagttg ggcccgtctg gaactgccat gatgataaat tgcgagcaaa    3720
ttgggtgaac atcagcacta aagcgacttg ttcccatcag aatctttaaa aacaacacct    3780
gaaatggacg ttttcagaga tcaggtgtaa gggtgtttgc ttggaaaaac acgaggaaaa    3840
gagcttgggc tgggaacacc cgtacaccgg atctagctcc tggctgcggg atctggattt    3900
aggaaaaaaa caaaacgcac gaatgagctt tgtcgccttt agcagagggt agaggtgata    3960
cactagacag caagagattg gaaaatggcg ggtaagtcgg ctgttgatga aatcttgatg    4020
acaactactg acatggaaca gaaatcaaag agaaacctga atttagaaag tcgccagacg    4080
tttcgttcga cgagattgat tacagagacc cgcttgctct aaaaaaggca caggagtcga    4140
tgctgagaga gcagttcatc agaattgagg ttctgaaggt ggtgagaaaa gcgctagaga    4200
attgctggag ggtgaacggg cccaacggac acgaagagtg ccgggacctg gccgacaagt    4260
acctagacat gctgccaaac tcccgggccc agggatacat gggataccaa agaaacgacc    4320
cgtccaaata ggctggctgc ggctggctgc ggctggctgc agaccgaccg caaaccaact    4380
gcaggcttgt tgtaggctga ttatttattg actatttatt gaatatttat tgcaccactt    4440
gtgtgttccc cttgaccatg cgtcgatcga cgcgcgaggc ttaggaagcc cggagcgggg    4500
aattcacgtg gtgtacgggt gtggaggtct agcacccgag ttttcggaga ggcagatgat    4560
gcatctccgg ggagtgtcag gcaaggagga atgggcagat cgacgaaga aagggatata    4620 aaatgttata tttgcacttg ttttttgtgaa tatcagcacc caaacaaaat aagacaactt    4680
atcagtttct taagtattac aagtgagtaa ttgtcaacca gcacagctgt cgtagtgtaa    4740
acactaacgc cgcatagaac tagca atg tcg tta tcc agc aag ctg tca gtt     4792
                               Met Ser Leu Ser Ser Lys Leu Ser Val
                                1               5 aag gac ttg gac gtc tcg ggc aag aga gtg ttc ata aga gtg gac ttc      4840
```

-continued

| | | |
|---|---|---|
| Lys Asp Leu Asp Val Ser Gly Lys Arg Val Phe Ile Arg Val Asp Phe<br>10                    15                      20                      25 | |
| aat gtt cca ttg gac gga gac aag atc acc aac aac caa aga att gtc<br>Asn Val Pro Leu Asp Gly Asp Lys Ile Thr Asn Asn Gln Arg Ile Val<br>                      30                      35                      40 | 4888 |
| gct gct ttg cca acc att cag tac gtt ctt gag aac aag cca aag gtg<br>Ala Ala Leu Pro Thr Ile Gln Tyr Val Leu Glu Asn Lys Pro Lys Val<br>                          45                      50                      55 | 4936 |
| gtt gtt ttg gcc tcc cac ttg ggc aga ccc aac gga gag aag aac ctc<br>Val Val Leu Ala Ser His Leu Gly Arg Pro Asn Gly Glu Lys Asn Leu<br>           60                      65                      70 | 4984 |
| aag tac aca ttg aag cct gtc gcc aag gaa ctg gag act ctt ttg ggc<br>Lys Tyr Thr Leu Lys Pro Val Ala Lys Glu Leu Glu Thr Leu Leu Gly<br>75                    80                      85 | 5032 |
| cag aaa gtg acc ttc ttg gac gac tgt gtt ggt tct gag gtc gaa tct<br>Gln Lys Val Thr Phe Leu Asp Asp Cys Val Gly Ser Glu Val Glu Ser<br>90                      95                    100                 105 | 5080 |
| acc gtc aac tct gcc cct gct ggc tcg gtg att ttg cta gaa aat ttg<br>Thr Val Asn Ser Ala Pro Ala Gly Ser Val Ile Leu Leu Glu Asn Leu<br>                      110                     115                     120 | 5128 |
| aga ttc cac att gag gag gaa ggc tcg aaa aag act tca gag gga aaa<br>Arg Phe His Ile Glu Glu Glu Gly Ser Lys Lys Thr Ser Glu Gly Lys<br>               125                     130                     135 | 5176 |
| gtt aag gct tcc aaa gag gac gtt gaa aaa ttc aga aag caa ctc act<br>Val Lys Ala Ser Lys Glu Asp Val Glu Lys Phe Arg Lys Gln Leu Thr<br>         140                     145                     150 | 5224 |
| gct ctg gct gat gtc tac gtt aac gac gct ttc ggt act gct cac aga<br>Ala Leu Ala Asp Val Tyr Val Asn Asp Ala Phe Gly Thr Ala His Arg<br>155                    160                     165 | 5272 |
| gcc cac tcc tcc atg gtc ggt ttc gag ctc gag gac aga gct gct ggc<br>Ala His Ser Ser Met Val Gly Phe Glu Leu Glu Asp Arg Ala Ala Gly<br>170                    175                     180                     185 | 5320 |
| ttc ctg atg gcc aag gag ctg gag tac ttc tcc aag gct ctg gag aac<br>Phe Leu Met Ala Lys Glu Leu Glu Tyr Phe Ser Lys Ala Leu Glu Asn<br>               190                     195                     200 | 5368 |
| ccg gtg aga ccg ttt ttg gct atc ctt ggt ggt gca aag gtg tct gac<br>Pro Val Arg Pro Phe Leu Ala Ile Leu Gly Gly Ala Lys Val Ser Asp<br>         205                     210                     215 | 5416 |
| aaa att cag ctg att gac aat ttg ctc gac aag gtc gat ctc ttg att<br>Lys Ile Gln Leu Ile Asp Asn Leu Leu Asp Lys Val Asp Leu Leu Ile<br>220                    225                     230 | 5464 |
| gtc ggt gga gga atg gcc ttc act ttc aac aag gtg ttg aac gac atg<br>Val Gly Gly Gly Met Ala Phe Thr Phe Asn Lys Val Leu Asn Asp Met<br>         235                     240                     245 | 5512 |
| aag atc ggt aag tct ttg ttc gac gag act gga gct gag att gtt cca<br>Lys Ile Gly Lys Ser Leu Phe Asp Glu Thr Gly Ala Glu Ile Val Pro<br>250                    255                     260                     265 | 5560 |
| aag ctc gtg gag aag gcc aag aag aac ggc gtc aag atc gtt ttg cca<br>Lys Leu Val Glu Lys Ala Lys Lys Asn Gly Val Lys Ile Val Leu Pro<br>         270                     275                     280 | 5608 |
| gtg gac ttt gtc act gcc gat gcg ttc tcg cca gat gcc aag gtt ggc<br>Val Asp Phe Val Thr Ala Asp Ala Phe Ser Pro Asp Ala Lys Val Gly<br>         285                     290                     295 | 5656 |
| tac gcc acc ctt gag gag ggt att gcc gac gat ttg caa ggt ctg gac<br>Tyr Ala Thr Leu Glu Glu Gly Ile Ala Asp Asp Leu Gln Gly Leu Asp<br>300                    305                     310 | 5704 |
| ggt ggt gaa aag acc cgt aag ctg ttt gcc gac acc atc gcg cag gcc<br>Gly Gly Glu Lys Thr Arg Lys Leu Phe Ala Asp Thr Ile Ala Gln Ala<br>         315                     320                     325 | 5752 |
| aag acc atc gtc tgg aac ggt cca cct ggt gtg ttt gag ttc gag agc | 5800 |

```
Lys Thr Ile Val Trp Asn Gly Pro Pro Gly Val Phe Glu Phe Glu Ser
330             335             340             345 ttt gcc agc ggt acc aag tcg atg ttg caa gct tgt gtc gag tct gcc    5848
Phe Ala Ser Gly Thr Lys Ser Met Leu Gln Ala Cys Val Glu Ser Ala
                350             355             360 cag gcc gga aac acc gtt att atc ggt ggt gga gac act gcc acc gtg    5896
Gln Ala Gly Asn Thr Val Ile Ile Gly Gly Gly Asp Thr Ala Thr Val
            365             370             375 gca aag aag ttt ggc ggt gcc gac aag ctg tcc cac gtt tcc act gga    5944
Ala Lys Lys Phe Gly Gly Ala Asp Lys Leu Ser His Val Ser Thr Gly
        380             385             390 gga ggt gct tcc ctg gaa ttg ttg gag ggt aag gag ctt cct ggt gtt    5992
Gly Gly Ala Ser Leu Glu Leu Leu Glu Gly Lys Glu Leu Pro Gly Val
    395             400             405 gct gct ttg aag agc aag act gct taggtgggat ttgcgtgatc tacgtagtgg   6046
Ala Ala Leu Lys Ser Lys Thr Ala
410             415
```
ttatttttgt agttagtttg actgtctaga aatactcttt gcacagcccc aaataaatta 6106
cactgccgtg aaattcatga gaaaaagta ccaaagataa acaggggaga agtgatcgg 6166
gtgttccctc ttgtgtgatc cagtcgtgaa cagtactgat caccaccca gatgactaaa 6226
cacaggcgca aaacattcc actgacttac atcacacaga gcctagacaa ttccaggacc 6286
aatcagggtt cttcgtttga taaggctcta gtgaacaaac acaacaaca cagatcaaag 6346
actcacaatt ctgtcaaatt ggccagtcta accaagtctt acttgtctgc aagccggtc 6406
caggcaacaa agagcccaac agttgacaaa atcaccaaaa ggatcaaccg aaagtcccac 6466
tcgaccaaga aaatcgaccc tgtcgcctct ttctcagggc cctgggggct tcttaccggc 6526
caacttaacg actatttaac gtcgattcgc tcaatgaact ctgttttgga ttacgaccag 6586
ccccttgacca cggctcagaa gtcgtcgtcg tcgattttgg acatcaaacc gatttcagac 6646
catttgaacg tggtcaggtt cgcagagctc gatagcgtga tgctgggctc gttccaaaac 6706
cacccagtca gactcaaggc tggcgaccaa attcacattg gagacgatta ctacaatgtt 6766
ccgtacaacg gaaagtatct cagatgttac tatcgatgct ttaaagtgat atgaggtata 6826
tacaggatgc cgactagacg gtgaactgtt cgcgcagttg agagtactgg ctggaacggt 6886
ccggatcaca cttttccaac agttgcgaca caaatggtcc gtgcacagtt ttttccagag 6946
tgtttgaaat actcaacaaa ggcatgtact cgtccaggaa ctccttgcac atggtggcat 7006
cgcctttcac tgccaggaat tgaagagcaa ccagcgacgg ggtcaaatct tcccgtttca 7066
atgcaccgtc aaggactttc ttcatgtaca cccagttgtt gcggttggca aaaatggtga 7126
ggaaaacaac atccaatctg gaacgaaatt gggcagcagc caggtcgtgt tcgaacattc 7186
gggtggacag ttggtacagc ttgtgaacca ttggagagta cttgaagctg taattagggt 7246
ctgcagttag cgaaccgatc gtaaggaagt tttcgttatc gatctgcgag cccgagatga 7306
ctaatagagg tattagtttt tgaacgtcct ccgttgacaa aacagggtta taagtgttga 7366
gaatccggaa gatacgtgcg tatctcttgt tgaacacctc cgcctctgtc tctactgatt 7426
tgtgaaattc agacgactgt agcacgagat caatatatct gaacacctcg tcaacagtaa 7486
cgggttttccc gttggcttgc atggctttga aatggttctc gatcttgttc agagggtaag 7546
tggctgggtc cttcaaatgc agtgttttta aagcctcaaa tcgctggttg tagttctccg 7606
aggttaagag ttccggtcta aaagcgctcg agctcgcttg ggtggtgtag agatgtagcc 7666
ggttcagctc caaaatagtt tgaagattcg agatcctcgg ccgggcagtg tgatagtatc 7726
tgatcccggc aaagatatcg tcgttgtagc cacggtcact tctggctgga tactttgtct 7786

```
tctctttcga ccacaggttc tccaagcaca tgacttctct tctctccgcg gtcagaaagt   7846
ggacgtaaat gttatcgatt ttgcagtcca tcatcatcca ggtatttgct gaggccccgt   7906
aatcattgct ggcgtacgaa ggggctctct tacccttttt caacagtctt ctgtgatact   7966
tggctagctg gccactgctc agaagacctt ctgccagagg gatggttttc agagtgtgtt   8026
tgatgaaaag attgagctcc gccgtagctt tctggagatg cttcgaactc tttcctgttc   8086
caatgatcat gaagtcggcg atctcttggg ctccttcgtt gacctctgcc ccggtgctat   8146
cgcgcaagtc gaacagggcc agatcggtca ttcccagctt ctccgcgata aactcgagaa   8206
ctggctgcaa gctggccgga gagttgggcg aagatccgg aatctgaatc tgtctaggct   8266
gcgaggccaa atccgcagac tcttcagctc tcatgtacca cgggagagct gccgttttga   8326
cttcttggtg gctgactgga actgacgaga agtcggcgac cagttgctgg aactggcag   8386 cgttgtgagg gaagaagccg ctccgaaggg cgcggggcac aggacgcgac accggacaca   8446
accgacaccg tctccacatt atggctgtat ttggaaaaga ttgagtagtc gatagtttct   8506
gcaaaagctt tagcaaacaa caaacacgcg acgtttgaag acagttttt ggcagcttcg    8566 atctgtcgat agttcagtgg tgatctcagt ggtcgtttcg tctaccttga atctctcacc   8626
ccagatgttg tctctgtgtg aagtttttgt gaatttttca tctttctttt tactcgattt   8686
tttcctcttc cacgtcgata gtcgcgagac gccttgcgac gcgccgtttt aatttcccaa   8746
aatttgcaca acaaaagat aaaaacagga ctgtcgattt gggttttgtg ggaacagaaa    8806
agaggaaccg tttgaacaat aaagcaacgg tcctccaaaa tcatcctcta ccactcattc   8866
tcaacacgtg accatcggga acaagttctg gagctctctt caaaccgcga ctcaacatag   8926
tgttttgtgc caggcccgta ttttactata aaggtgccct caagaaccat tagttcgtgc   8986
tacttgcctc cgatttgtgc ttcctaacgg tgtttcaaca atcatgacag gccgggatcc   9046
```

<210> SEQ ID NO 67  
<211> LENGTH: 417  
<212> TYPE: PRT  
<213> ORGANISM: Ogataea minuta

<400> SEQUENCE: 67

```
Met Ser Leu Ser Ser Lys Leu Ser Val Lys Asp Leu Asp Val Ser Gly
 1               5                  10                  15

Lys Arg Val Phe Ile Arg Val Asp Phe Asn Val Pro Leu Asp Gly Asp
            20                  25                  30

Lys Ile Thr Asn Asn Gln Arg Ile Val Ala Ala Leu Pro Thr Ile Gln
        35                  40                  45

Tyr Val Leu Glu Asn Lys Pro Lys Val Val Leu Ala Ser His Leu
    50                  55                  60

Gly Arg Pro Asn Gly Glu Lys Asn Leu Lys Tyr Thr Leu Lys Pro Val
 65                 70                  75                  80

Ala Lys Glu Leu Glu Thr Leu Leu Gly Gln Lys Val Thr Phe Leu Asp
                85                  90                  95

Asp Cys Val Gly Ser Glu Val Glu Ser Thr Val Asn Ser Ala Pro Ala
           100                 105                 110

Gly Ser Val Ile Leu Leu Glu Asn Leu Arg Phe His Ile Glu Glu Glu
       115                 120                 125

Gly Ser Lys Lys Thr Ser Glu Gly Lys Val Ala Ser Lys Glu Asp
   130                 135                 140

Val Glu Lys Phe Arg Lys Gln Leu Thr Ala Leu Ala Asp Val Tyr Val
145                 150                 155                 160
```

```
Asn Asp Ala Phe Gly Thr Ala His Arg Ala His Ser Ser Met Val Gly
                165                 170                 175

Phe Glu Leu Glu Asp Arg Ala Ala Gly Phe Leu Met Ala Lys Glu Leu
            180                 185                 190

Glu Tyr Phe Ser Lys Ala Leu Glu Asn Pro Val Arg Pro Phe Leu Ala
        195                 200                 205

Ile Leu Gly Gly Ala Lys Val Ser Asp Lys Ile Gln Leu Ile Asp Asn
    210                 215                 220

Leu Leu Asp Lys Val Asp Leu Leu Ile Val Gly Gly Met Ala Phe
225                 230                 235                 240

Thr Phe Asn Lys Val Leu Asn Asp Met Lys Ile Gly Lys Ser Leu Phe
                245                 250                 255

Asp Glu Thr Gly Ala Glu Ile Val Pro Lys Leu Val Glu Lys Ala Lys
            260                 265                 270

Lys Asn Gly Val Lys Ile Val Leu Pro Val Asp Phe Val Thr Ala Asp
        275                 280                 285

Ala Phe Ser Pro Asp Ala Lys Val Gly Tyr Ala Thr Leu Glu Glu Gly
    290                 295                 300

Ile Ala Asp Asp Leu Gln Gly Leu Asp Gly Gly Glu Lys Thr Arg Lys
305                 310                 315                 320

Leu Phe Ala Asp Thr Ile Ala Gln Ala Lys Thr Ile Val Trp Asn Gly
                325                 330                 335

Pro Pro Gly Val Phe Glu Phe Glu Ser Phe Ala Ser Gly Thr Lys Ser
            340                 345                 350

Met Leu Gln Ala Cys Val Glu Ser Ala Gln Ala Gly Asn Thr Val Ile
        355                 360                 365

Ile Gly Gly Gly Asp Thr Ala Thr Val Ala Lys Lys Phe Gly Gly Ala
    370                 375                 380

Asp Lys Leu Ser His Val Ser Thr Gly Gly Gly Ala Ser Leu Glu Leu
385                 390                 395                 400

Leu Glu Gly Lys Glu Leu Pro Gly Val Ala Ala Leu Lys Ser Lys Thr
                405                 410                 415

Ala

<210> SEQ ID NO 68
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 68
aagcttgaca atgtaggaga tcataaacac atcgtgcgcg tc                          42

<210> SEQ ID NO 69
<211> LENGTH: 65
<212> TYPE: DNA
<213> ORGANISM: Artificial Sequence
<220> FEATURE:
<223> OTHER INFORMATION: Synthetic oligonucleotide primer

<400> SEQUENCE: 69
ggatccagat ctcatatgac tagttgctag ttctatgcgg cgttagtgtt tacactacga      60
cagct                                                                 65

<210> SEQ ID NO 70
<211> LENGTH: 40
```

```
<212> TYPE: DNA
<213> ORGANISM: Artificial Sequence
<220> FEATURE:
<223> OTHER INFORMATION: Synthetic oligonucleotide primer

<400> SEQUENCE: 70
ggatccgtgg gatttgcgtg atctacgtag tggttatttt                                40

<210> SEQ ID NO 71
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 71
ggtaccgcag tgaaaggcga tgccaccatg tgcaaggagt tc                             42

<210> SEQ ID NO 72
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 72
ggaagcttga caatgtagga gatcataaac a                                         31

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 73
ggtcgactgc tagttctatg cggc                                                 24

<210> SEQ ID NO 74
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 74
ggatgcatgt gggatttgcg tgatctac                                             28

<210> SEQ ID NO 75
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 75
gggtaccagg gtcgattttc ttggtcg                                              27

<210> SEQ ID NO 76
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 76
gatctcaggc cgagtcaaga c                                                    21
```

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 77
taacgccgca tagaactagc                                              20

<210> SEQ ID NO 78
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 78
gatgcattta caactcgtcc ttaac                                         25

<210> SEQ ID NO 79
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 79
atgtcctcga ctaagacata cgc                                           23

<210> SEQ ID NO 80
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 80
tcatgcgaca cgactcaaat aag                                           23

<210> SEQ ID NO 81
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 81
gtctagatgt ttttcaacag actaag                                        26

<210> SEQ ID NO 82
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 82
gactccacca gctgtacttc agttccgtag ttttctacat c                       41

<210> SEQ ID NO 83
<211> LENGTH: 41
<212> TYPE: DNA
<213> ORGANISM: Artificial Sequence
<220> FEATURE:
<223> OTHER INFORMATION: Synthetic oligonucleotide primer

```
<400> SEQUENCE: 83
gatgtagaaa actacggaac tgaagtacag ctggtggagt c                           41

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 84
ggtcgactca tttacccggg gacag                                             25

<210> SEQ ID NO 85
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 85
gtctagatgt ttttcaacag actaag                                            26

<210> SEQ ID NO 86
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 86
gattgggtca tctgaatgtc agttccgtag ttttctacat c                           41

<210> SEQ ID NO 87
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 87
gatgtagaaa actacggaac tgacattcag atgacccaat c                           41

<210> SEQ ID NO 88
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 88
ggtcgaccta acactctccc ctgt                                              24

<210> SEQ ID NO 89
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 89
caaaatgaag cacagatgc                                                    19

<210> SEQ ID NO 90
<211> LENGTH: 26
```

```
<212> TYPE: DNA
<213> ORGANISM: Artificial Sequence
<220> FEATURE:
<223> OTHER INFORMATION: Synthetic oligonucleotide primer

<400> SEQUENCE: 90
cgagctcatg aagttttctg ctggtg                                           26

<210> SEQ ID NO 91
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 91
gcccgggtta caattcatcg tgaatg                                           26

<210> SEQ ID NO 92
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 92
cgagctcatg ttatttctta atattattaa g                                     31

<210> SEQ ID NO 93
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 93
gcccgggcta caattcgtcg tgcttgtttc c                                     31

<210> SEQ ID NO 94
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 94
cgagctcatg attccaaaat tatatatac                                        29

<210> SEQ ID NO 95
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 95
gcccgggcta caactcatct ttgagc                                           26

<210> SEQ ID NO 96
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 96
cgagctcatg agattaagaa ccgccattg                                        29
```

<210> SEQ ID NO 97
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 97
gcccgggtta ttgtatatct agcttatag                              29

<210> SEQ ID NO 98
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 98
cgagctcatg atgtttaata tttacc                                 26

<210> SEQ ID NO 99
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 99
gcccgggcta ggcggctgat ttcacg                                 26

<210> SEQ ID NO 100
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 100
cgagctcatg atactgatct cgggatactg tc                          32

<210> SEQ ID NO 101
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 101
gcccgggtca aagcccaaaa ttcattttaa ag                          32

<210> SEQ ID NO 102
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 102
cgagctcatg cgaaacgttt taaggcttt                              29

<210> SEQ ID NO 103
<211> LENGTH: 29
<212> TYPE: DNA
<213> ORGANISM: Artificial Sequence
<220> FEATURE:
<223> OTHER INFORMATION: Synthetic oligonucleotide primer -continued

<400> SEQUENCE: 103
gcccgggcta taattcatca tgcaaaatg    29

<210> SEQ ID NO 104
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 104
cgagctcatg aaattgcacg gctttttatt ttc    33

<210> SEQ ID NO 105
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 105
gcccgggtca aagctcgtca tgactactgg    30

<210> SEQ ID NO 106
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 106
cgagctcatg aacggttact ggaaac    26

<210> SEQ ID NO 107
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 107
gcccgggtca tttacgtgaa tagatc    26

<210> SEQ ID NO 108
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 108
cgagctcatg caagtgacca caagatt    27

<210> SEQ ID NO 109
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 109
gcccgggtta taattcatca tgtacgg    27

<210> SEQ ID NO 110
<211> LENGTH: 35

```
<212> TYPE: DNA
<213> ORGANISM: Artificial Sequence
<220> FEATURE:
<223> OTHER INFORMATION: Synthetic oligonucleotide primer

<400> SEQUENCE: 110
atcatcatca tgcccgggcc gactacaaag accat                              35

<210> SEQ ID NO 111
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 111
gcaccgtctc ggatcccttg tcatcgtcat cctt                               34

<210> SEQ ID NO 112
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 112
gatgacgatg acaagggatc caactactcc cacaccatgg                         40

<210> SEQ ID NO 113
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 113
gcaccgtctc ggatcctcat ctccccttga agatccggat                         40

<210> SEQ ID NO 114
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 114
accctcgaga tgaagttccc tatggtgg                                      28

<210> SEQ ID NO 115
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 115
accgcggccg cctacaactc atc                                           23

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 116
accctcgaga tgctgagccg ttctc                                         25
```

<210> SEQ ID NO 117
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 117
accgcggccg cctacaattc gtcctttac                                      29

<210> SEQ ID NO 118
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 118
accctcgaga tgagccaagg g                                              21

<210> SEQ ID NO 119
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 119
accctcgagt tacctactgt gttgtaataa gac                                 33

<210> SEQ ID NO 120
<211> LENGTH: 1569
<212> TYPE: DNA
<213> ORGANISM: Saccharomyces cerevisiae
<220> FEATURE:
<221> NAME/KEY: CDS
<222> LOCATION: (1)..(1569)

<400> SEQUENCE: 120

```
atg aag ttt tct gct ggt gcc gtc ctg tca tgg tcc tcc ctg ctg ctc    48
Met Lys Phe Ser Ala Gly Ala Val Leu Ser Trp Ser Ser Leu Leu Leu
1               5                   10                  15 gcc tcc tct gtt ttc gcc caa caa gag gct gtg gcc cct gaa gac tcc    96
Ala Ser Ser Val Phe Ala Gln Gln Glu Ala Val Ala Pro Glu Asp Ser
                20                  25                  30 gct gtc gtt aag ttg gcc acc gac tcc ttc aat gag tac att cag tcg   144
Ala Val Val Lys Leu Ala Thr Asp Ser Phe Asn Glu Tyr Ile Gln Ser
            35                  40                  45 cac gac ttg gtg ctt gcg gag ttt ttt gct cca tgg tgt ggc cac tgt   192
His Asp Leu Val Leu Ala Glu Phe Phe Ala Pro Trp Cys Gly His Cys
        50                  55                  60 aag aac atg gct cct gaa tac gtt aaa gcc gcc gag act tta gtt gag   240
Lys Asn Met Ala Pro Glu Tyr Val Lys Ala Ala Glu Thr Leu Val Glu
65                  70                  75                  80 aaa aac att acc ttg gcc cag atc gac tgt act gaa aac cag gat ctg   288
Lys Asn Ile Thr Leu Ala Gln Ile Asp Cys Thr Glu Asn Gln Asp Leu
                85                  90                  95 tgt atg gaa cac aac att cca ggg ttc cca agc ttg aag att ttc aaa   336
Cys Met Glu His Asn Ile Pro Gly Phe Pro Ser Leu Lys Ile Phe Lys
                100                 105                 110 aac agc gat gtt aac aac tcg atc gat tac gag gga cct aga act gcc   384
Asn Ser Asp Val Asn Asn Ser Ile Asp Tyr Glu Gly Pro Arg Thr Ala
            115                 120                 125
```

```
gag gcc att gtc caa ttc atg atc aag caa agc caa ccg gct gtc gcc      432
Glu Ala Ile Val Gln Phe Met Ile Lys Gln Ser Gln Pro Ala Val Ala
130                 135                 140 gtt gtt gct gat cta cca gct tac ctt gct aac gag act ttt gtc act      480
Val Val Ala Asp Leu Pro Ala Tyr Leu Ala Asn Glu Thr Phe Val Thr
145                 150                 155                 160 cca gtt atc gtc caa tcc ggt aag att gac gcc gac ttc aac gcc acc      528
Pro Val Ile Val Gln Ser Gly Lys Ile Asp Ala Asp Phe Asn Ala Thr
                165                 170                 175 ttt tac tcc atg gcc aac aaa cac ttc aac gac tac gac ttt gtc tcc      576
Phe Tyr Ser Met Ala Asn Lys His Phe Asn Asp Tyr Asp Phe Val Ser
            180                 185                 190 gct gaa aac gca gac gat gat ttc aag ctt tct att tac ttg ccc tcc      624
Ala Glu Asn Ala Asp Asp Asp Phe Lys Leu Ser Ile Tyr Leu Pro Ser
        195                 200                 205 gcc atg gac gag cct gta gta tac aac ggt aag aaa gcc gat atc gct      672
Ala Met Asp Glu Pro Val Val Tyr Asn Gly Lys Lys Ala Asp Ile Ala
    210                 215                 220 gac gct gat gtt ttt gaa aaa tgg ttg caa gtg gaa gcc ttg ccc tac      720
Asp Ala Asp Val Phe Glu Lys Trp Leu Gln Val Glu Ala Leu Pro Tyr
225                 230                 235                 240 ttt ggt gaa atc gac ggt tcc gtt ttc gcc caa tac gtc gaa agc ggt      768
Phe Gly Glu Ile Asp Gly Ser Val Phe Ala Gln Tyr Val Glu Ser Gly
                245                 250                 255 ttg cct ttg ggt tac tta ttc tac aat gac gag gaa gaa ttg gaa gaa      816
Leu Pro Leu Gly Tyr Leu Phe Tyr Asn Asp Glu Glu Glu Leu Glu Glu
            260                 265                 270 tac aag cct ctc ttt acc gag ttg gcc aaa aag aac aga ggt cta atg      864
Tyr Lys Pro Leu Phe Thr Glu Leu Ala Lys Lys Asn Arg Gly Leu Met
        275                 280                 285 aac ttt gtt agc atc gat gcc aga aaa ttc ggc aga cac gcc ggc aac      912
Asn Phe Val Ser Ile Asp Ala Arg Lys Phe Gly Arg His Ala Gly Asn
    290                 295                 300 ttg aac atg aag gaa caa ttc cct cta ttt gcc atc cac gac atg act      960
Leu Asn Met Lys Glu Gln Phe Pro Leu Phe Ala Ile His Asp Met Thr
305                 310                 315                 320 gaa gac ttg aag tac ggt ttg cct caa ctc tct gaa gag gcg ttt gac     1008
Glu Asp Leu Lys Tyr Gly Leu Pro Gln Leu Ser Glu Glu Ala Phe Asp
                325                 330                 335 gaa ttg agc gac aag atc gtg ttg gag tct aag gct att gaa tct ttg     1056
Glu Leu Ser Asp Lys Ile Val Leu Glu Ser Lys Ala Ile Glu Ser Leu
            340                 345                 350 gtt aag gac ttc ttg aaa ggt gat gcc tcc cca atc gtg aag tcc caa     1104
Val Lys Asp Phe Leu Lys Gly Asp Ala Ser Pro Ile Val Lys Ser Gln
        355                 360                 365 gag atc ttc gag aac caa gat tcc tct gtc ttc caa ttg gtc ggt aag     1152
Glu Ile Phe Glu Asn Gln Asp Ser Ser Val Phe Gln Leu Val Gly Lys
    370                 375                 380 aac cat gac gaa atc gtc aac gac cca aag aag gac gtt ctt gtt ttg     1200
Asn His Asp Glu Ile Val Asn Asp Pro Lys Lys Asp Val Leu Val Leu
385                 390                 395                 400 tac tat gcc cca tgg tgt ggt cac tgt aag aga ttg gcc cca act tac     1248
Tyr Tyr Ala Pro Trp Cys Gly His Cys Lys Arg Leu Ala Pro Thr Tyr
                405                 410                 415 caa gaa cta gct gat acc tac gcc aac gcc aca tcc gac gtt ttg att     1296
Gln Glu Leu Ala Asp Thr Tyr Ala Asn Ala Thr Ser Asp Val Leu Ile
            420                 425                 430 gct aaa cta gac cac act gaa aac gat gtc aga ggc gtc gta att gaa     1344
Ala Lys Leu Asp His Thr Glu Asn Asp Val Arg Gly Val Val Ile Glu
        435                 440                 445
```

```
ggt tac cca aca atc gtc tta tac cca ggt ggt aag aag tcc gaa tct    1392
Gly Tyr Pro Thr Ile Val Leu Tyr Pro Gly Gly Lys Lys Ser Glu Ser
450                 455                 460 gtt gtg tac caa ggt tca aga tcc ttg gac tct tta ttc gac ttc atc    1440
Val Val Tyr Gln Gly Ser Arg Ser Leu Asp Ser Leu Phe Asp Phe Ile
465                 470                 475                 480 aag gaa aac ggt cac ttc gac gtc gac ggt aag gcc ttg tac gaa gaa    1488
Lys Glu Asn Gly His Phe Asp Val Asp Gly Lys Ala Leu Tyr Glu Glu
                485                 490                 495 gcc cag gaa aaa gct gct gag gaa gcc gat gct gac gct gaa ttg gct    1536
Ala Gln Glu Lys Ala Ala Glu Glu Ala Asp Ala Asp Ala Glu Leu Ala
            500                 505                 510 gac gaa gaa gat gcc att cac gat gaa ttg taa                        1569
Asp Glu Glu Asp Ala Ile His Asp Glu Leu
        515                 520

<210> SEQ ID NO 121
<211> LENGTH: 522
<212> TYPE: PRT
<213> ORGANISM: Saccharomyces cerevisiae

<400> SEQUENCE: 121

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
        35                  40                  45

His Asp Leu Val Leu Ala Glu Phe Phe Ala Pro Trp Cys Gly His Cys
    50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
            100                 105                 110

Asn Ser Asp Val Asn Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
    210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Glu Leu Glu Glu
            260                 265                 270

Tyr Lys Pro Leu Phe Thr Glu Leu Ala Lys Lys Asn Arg Gly Leu Met
```

```
                275                 280                 285
Asn Phe Val Ser Ile Asp Ala Arg Lys Phe Gly Arg His Ala Gly Asn
    290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Ala Phe Asp
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
            355                 360                 365

Glu Ile Phe Glu Asn Gln Asp Ser Ser Val Phe Gln Leu Val Gly Lys
        370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
            435                 440                 445

Gly Tyr Pro Thr Ile Val Leu Tyr Pro Gly Gly Lys Lys Ser Glu Ser
        450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Ala Asp Ala Asp Ala Glu Leu Ala
            500                 505                 510

Asp Glu Glu Asp Ala Ile His Asp Glu Leu
            515                 520

<210> SEQ ID NO 122
<211> LENGTH: 957
<212> TYPE: DNA
<213> ORGANISM: Saccharomyces cerevisiae
<220> FEATURE:
<221> NAME/KEY: CDS
<222> LOCATION: (1)..(957)

<400> SEQUENCE: 122 atg tta ttt ctt aat att att aag ctc ctt ttg gga ctt ttt att atg      48
Met Leu Phe Leu Asn Ile Ile Lys Leu Leu Leu Gly Leu Phe Ile Met
1               5                   10                  15 aat gaa gta aag gcg caa aac ttt tac gat tcc gat cct cat ata tca      96
Asn Glu Val Lys Ala Gln Asn Phe Tyr Asp Ser Asp Pro His Ile Ser
            20                  25                  30 gag tta acg cca aaa agc ttc gat aaa gcg atc cat aac aca aat tac     144
Glu Leu Thr Pro Lys Ser Phe Asp Lys Ala Ile His Asn Thr Asn Tyr
        35                  40                  45 aca tca tta gtg gaa ttt tat gct ccg tgg tgc ggc cat tgt aag aag     192
Thr Ser Leu Val Glu Phe Tyr Ala Pro Trp Cys Gly His Cys Lys Lys
    50                  55                  60 ctc tct agt acg ttc cgc aag gca gca aaa aga ttg gat ggt gta gtc     240
Leu Ser Ser Thr Phe Arg Lys Ala Ala Lys Arg Leu Asp Gly Val Val
65                  70                  75                  80 caa gtt gct gct gta aac tgt gac ctt aac aag aat aag gct ttg tgt     288
Gln Val Ala Ala Val Asn Cys Asp Leu Asn Lys Asn Lys Ala Leu Cys
```

```
                      85                  90                  95
gct aaa tac gac gta aac gga ttt ccc acg tta atg gta ttt agg ccc    336
Ala Lys Tyr Asp Val Asn Gly Phe Pro Thr Leu Met Val Phe Arg Pro
            100                 105                 110 cca aaa att gac cta tct aag cca ata gat aac gcc aaa aaa agt ttc    384
Pro Lys Ile Asp Leu Ser Lys Pro Ile Asp Asn Ala Lys Lys Ser Phe
        115                 120                 125 agc gct cat gcc aat gaa gtg tac tca ggt gca aga act ctc gcg cct    432
Ser Ala His Ala Asn Glu Val Tyr Ser Gly Ala Arg Thr Leu Ala Pro
    130                 135                 140 att gtt gat ttt tct ctt tca aga ata agg tca tat gtc aaa aag ttt    480
Ile Val Asp Phe Ser Leu Ser Arg Ile Arg Ser Tyr Val Lys Lys Phe
145                 150                 155                 160 gtc cgt ata gat aca ctt ggc tct tta ctt aga aag tca ccc aaa ctt    528
Val Arg Ile Asp Thr Leu Gly Ser Leu Leu Arg Lys Ser Pro Lys Leu
                165                 170                 175 tcc gtg gtg ttg ttt tcc aaa caa gac aaa att tca ccg gtt tat aaa    576
Ser Val Val Leu Phe Ser Lys Gln Asp Lys Ile Ser Pro Val Tyr Lys
            180                 185                 190 agc att gcc ctt gat tgg tta gga aag ttc gat ttt tat tca att tca    624
Ser Ile Ala Leu Asp Trp Leu Gly Lys Phe Asp Phe Tyr Ser Ile Ser
        195                 200                 205 aac aaa aaa ctc aag caa cta acc gat atg aac cca aca tat gaa aaa    672
Asn Lys Lys Leu Lys Gln Leu Thr Asp Met Asn Pro Thr Tyr Glu Lys
    210                 215                 220 act cct gag att ttc aaa tat ttg cag aag gtc att cct gaa cag cga    720
Thr Pro Glu Ile Phe Lys Tyr Leu Gln Lys Val Ile Pro Glu Gln Arg
225                 230                 235                 240 cag agc gat aaa agt aag ctt gtc gtt ttt gat gca gac aaa gat aaa    768
Gln Ser Asp Lys Ser Lys Leu Val Val Phe Asp Ala Asp Lys Asp Lys
                245                 250                 255 ttt tgg gag tat gaa ggg aac tca atc aac aaa aat gac att tcc aaa    816
Phe Trp Glu Tyr Glu Gly Asn Ser Ile Asn Lys Asn Asp Ile Ser Lys
            260                 265                 270 ttt ctg cgg gac act ttt agt att acc ccc aat gag ggt cct ttt agt    864
Phe Leu Arg Asp Thr Phe Ser Ile Thr Pro Asn Glu Gly Pro Phe Ser
        275                 280                 285 aga cgt tct gaa tat att gct tac tta aaa act ggc aag aag cca att    912
Arg Arg Ser Glu Tyr Ile Ala Tyr Leu Lys Thr Gly Lys Lys Pro Ile
    290                 295                 300 aaa aag aac cat tcc tcc tca gga aac aag cac gac gaa ttg tag        957
Lys Lys Asn His Ser Ser Ser Gly Asn Lys His Asp Glu Leu
305                 310                 315

<210> SEQ ID NO 123
<211> LENGTH: 318
<212> TYPE: PRT
<213> ORGANISM: Saccharomyces cerevisiae

<400> SEQUENCE: 123

Met Leu Phe Leu Asn Ile Ile Lys Leu Leu Leu Gly Leu Phe Ile Met
1               5                   10                  15

Asn Glu Val Lys Ala Gln Asn Phe Tyr Asp Ser Asp Pro His Ile Ser
            20                  25                  30

Glu Leu Thr Pro Lys Ser Phe Asp Lys Ala Ile His Asn Thr Asn Tyr
        35                  40                  45

Thr Ser Leu Val Glu Phe Tyr Ala Pro Trp Cys Gly His Cys Lys Lys
    50                  55                  60

Leu Ser Ser Thr Phe Arg Lys Ala Ala Lys Arg Leu Asp Gly Val Val
65                  70                  75                  80
```

```
Gln Val Ala Ala Val Asn Cys Asp Leu Asn Lys Asn Lys Ala Leu Cys
                 85                  90                  95

Ala Lys Tyr Asp Val Asn Gly Phe Pro Thr Leu Met Val Phe Arg Pro
            100                 105                 110

Pro Lys Ile Asp Leu Ser Lys Pro Ile Asp Asn Ala Lys Lys Ser Phe
            115                 120                 125

Ser Ala His Ala Asn Glu Val Tyr Ser Gly Ala Arg Thr Leu Ala Pro
            130                 135                 140

Ile Val Asp Phe Ser Leu Ser Arg Ile Arg Ser Tyr Val Lys Lys Phe
145                 150                 155                 160

Val Arg Ile Asp Thr Leu Gly Ser Leu Leu Arg Lys Ser Pro Lys Leu
                165                 170                 175

Ser Val Val Leu Phe Ser Lys Gln Asp Lys Ile Ser Pro Val Tyr Lys
            180                 185                 190

Ser Ile Ala Leu Asp Trp Leu Gly Lys Phe Asp Phe Tyr Ser Ile Ser
            195                 200                 205

Asn Lys Lys Leu Lys Gln Leu Thr Asp Met Asn Pro Thr Tyr Glu Lys
            210                 215                 220

Thr Pro Glu Ile Phe Lys Tyr Leu Gln Lys Val Ile Pro Glu Gln Arg
225                 230                 235                 240

Gln Ser Asp Lys Ser Lys Leu Val Val Phe Ala Asp Lys Asp Lys
                245                 250                 255

Phe Trp Glu Tyr Glu Gly Asn Ser Ile Asn Lys Asn Asp Ile Ser Lys
            260                 265                 270

Phe Leu Arg Asp Thr Phe Ser Ile Thr Pro Asn Glu Gly Pro Phe Ser
                275                 280                 285

Arg Arg Ser Glu Tyr Ile Ala Tyr Leu Lys Thr Gly Lys Pro Ile
            290                 295                 300

Lys Lys Asn His Ser Ser Ser Gly Asn Lys His Asp Glu Leu
305                 310                 315

<210> SEQ ID NO 124
<211> LENGTH: 1134
<212> TYPE: DNA
<213> ORGANISM: Saccharomyces cerevisiae
<220> FEATURE:
<221> NAME/KEY: CDS
<222> LOCATION: (1)..(1134)

<400> SEQUENCE: 124 atg att cca aaa tta tat ata cat ttg ata cta tct tta ttg ttg ttg      48
Met Ile Pro Lys Leu Tyr Ile His Leu Ile Leu Ser Leu Leu Leu Leu
1               5                   10                  15 ccg cta att ttg gcg cag gat tat tat gca ata cta gag ata gac aaa      96
Pro Leu Ile Leu Ala Gln Asp Tyr Tyr Ala Ile Leu Glu Ile Asp Lys
            20                  25                  30 gat gcc act gag aag gaa atc aaa tca gcg tac aga caa ttg tct aag     144
Asp Ala Thr Glu Lys Glu Ile Lys Ser Ala Tyr Arg Gln Leu Ser Lys
        35                  40                  45 aag tac cat ccg gat aaa aat gct ggg agc gaa gaa gcc cat caa aaa     192
Lys Tyr His Pro Asp Lys Asn Ala Gly Ser Glu Glu Ala His Gln Lys
    50                  55                  60 ttc att gaa gtc ggc gag gca tac gat gta ttg agc gat cct gaa aag     240
Phe Ile Glu Val Gly Glu Ala Tyr Asp Val Leu Ser Asp Pro Glu Lys
65                  70                  75                  80 aaa aag att tat gac cag ttt ggt gca gat gct gta aag aat ggc ggt     288
Lys Lys Ile Tyr Asp Gln Phe Gly Ala Asp Ala Val Lys Asn Gly Gly
                85                  90                  95
```

| | | |
|---|---|---|
| ggc ggt ggc ggt cca gga ggc cct ggc gca ggt gga ttc cac gat ccg<br>Gly Gly Gly Gly Pro Gly Gly Pro Gly Ala Gly Gly Phe His Asp Pro<br>           100                 105               110 | | 336 |
| ttt gac ata ttc gaa cgg atg ttt caa gga ggt cat gga ggt cct ggc<br>Phe Asp Ile Phe Glu Arg Met Phe Gln Gly Gly His Gly Gly Pro Gly<br>        115                 120               125 | | 384 |
| ggc gga ttt ggc cag aga cag agg cag cgt ggt cca atg atc aag gtc<br>Gly Gly Phe Gly Gln Arg Gln Arg Gln Arg Gly Pro Met Ile Lys Val<br>130               135               140 | | 432 |
| cag gaa aaa cta tct tta aag cag ttt tat tcc ggg tcc tcg ata gaa<br>Gln Glu Lys Leu Ser Leu Lys Gln Phe Tyr Ser Gly Ser Ser Ile Glu<br>145               150               155               160 | | 480 |
| ttt act tta aac cta aac gat gaa tgt gat gca tgc cat ggt agt ggc<br>Phe Thr Leu Asn Leu Asn Asp Glu Cys Asp Ala Cys His Gly Ser Gly<br>                 165               170               175 | | 528 |
| tct gca gat ggt aag ctg gcc caa tgt ccc gat tgt caa ggt cgt ggg<br>Ser Ala Asp Gly Lys Leu Ala Gln Cys Pro Asp Cys Gln Gly Arg Gly<br>           180                 185               190 | | 576 |
| gtt ata ata caa gtg ctg cgc atg ggt att atg acg cag cag att caa<br>Val Ile Ile Gln Val Leu Arg Met Gly Ile Met Thr Gln Gln Ile Gln<br>                 195               200               205 | | 624 |
| cag atg tgt ggt agg tgt ggt ggt acg gga caa att atc aaa aat gaa<br>Gln Met Cys Gly Arg Cys Gly Gly Thr Gly Gln Ile Ile Lys Asn Glu<br>210               215               220 | | 672 |
| tgc aaa aca tgt cac ggc aaa aaa gtt acc aaa aag aac aag ttc ttc<br>Cys Lys Thr Cys His Gly Lys Lys Val Thr Lys Lys Asn Lys Phe Phe<br>225               230               235               240 | | 720 |
| cac gtt gac gtt cca cca ggc gca cca aga aac tac atg gac aca aga<br>His Val Asp Val Pro Pro Gly Ala Pro Arg Asn Tyr Met Asp Thr Arg<br>                 245               250               255 | | 768 |
| gtc ggc gag gct gaa aaa ggg cct gac ttt gac gcc ggt gac ttg gtc<br>Val Gly Glu Ala Glu Lys Gly Pro Asp Phe Asp Ala Gly Asp Leu Val<br>           260                 265               270 | | 816 |
| ata gaa ttc aag gaa aag gat act gag aac atg ggt tac aga aga aga<br>Ile Glu Phe Lys Glu Lys Asp Thr Glu Asn Met Gly Tyr Arg Arg Arg<br>                 275               280               285 | | 864 |
| ggc gac aat ctg tac aga aca gaa gtt ctt tct gct gcg gaa gcg cta<br>Gly Asp Asn Leu Tyr Arg Thr Glu Val Leu Ser Ala Ala Glu Ala Leu<br>290               295               300 | | 912 |
| tac ggc gga tgg caa aga acg ata gaa ttc ctt gat gag aac aag ccc<br>Tyr Gly Gly Trp Gln Arg Thr Ile Glu Phe Leu Asp Glu Asn Lys Pro<br>305               310               315               320 | | 960 |
| gtt aag tta tct aga ccc gct cat gta gtt gtc tcc aat ggc gaa gtt<br>Val Lys Leu Ser Arg Pro Ala His Val Val Val Ser Asn Gly Glu Val<br>                 325               330               335 | | 1008 |
| gaa gtc gtg aag gga ttc ggc atg ccc aag ggt agc aag ggt tac ggt<br>Glu Val Val Lys Gly Phe Gly Met Pro Lys Gly Ser Lys Gly Tyr Gly<br>           340                 345               350 | | 1056 |
| gat ttg tac ata gac tac gtc gtt gtc atg cca aag act ttc aaa tct<br>Asp Leu Tyr Ile Asp Tyr Val Val Val Met Pro Lys Thr Phe Lys Ser<br>                 355               360               365 | | 1104 |
| ggg caa aat atg ctc aaa gat gag ttg tag<br>Gly Gln Asn Met Leu Lys Asp Glu Leu<br>           370                 375 | | 1134 |

<210> SEQ ID NO 125
<211> LENGTH: 377
<212> TYPE: PRT
<213> ORGANISM: Saccharomyces cerevisiae

<400> SEQUENCE: 125

```
Met Ile Pro Lys Leu Tyr Ile His Leu Ile Leu Ser Leu Leu Leu Leu
1               5                   10                  15

Pro Leu Ile Leu Ala Gln Asp Tyr Tyr Ala Ile Leu Glu Ile Asp Lys
            20                  25                  30

Asp Ala Thr Glu Lys Glu Ile Lys Ser Ala Tyr Arg Gln Leu Ser Lys
        35                  40                  45

Lys Tyr His Pro Asp Lys Asn Ala Gly Ser Glu Glu Ala His Gln Lys
    50                  55                  60

Phe Ile Glu Val Gly Glu Ala Tyr Asp Val Leu Ser Asp Pro Glu Lys
65                  70                  75                  80

Lys Lys Ile Tyr Asp Gln Phe Gly Ala Asp Ala Val Lys Asn Gly Gly
                85                  90                  95

Gly Gly Gly Gly Pro Gly Gly Pro Gly Ala Gly Phe His Asp Pro
                100                 105                 110

Phe Asp Ile Phe Glu Arg Met Phe Gln Gly His Gly Gly Pro Gly
            115                 120                 125

Gly Gly Phe Gly Gln Arg Gln Arg Gln Arg Gly Pro Met Ile Lys Val
        130                 135                 140

Gln Glu Lys Leu Ser Leu Lys Gln Phe Tyr Ser Gly Ser Ser Ile Glu
145                 150                 155                 160

Phe Thr Leu Asn Leu Asn Asp Glu Cys Asp Ala Cys His Gly Ser Gly
                165                 170                 175

Ser Ala Asp Gly Lys Leu Ala Gln Cys Pro Asp Cys Gln Gly Arg Gly
            180                 185                 190

Val Ile Ile Gln Val Leu Arg Met Gly Ile Met Thr Gln Gln Ile Gln
        195                 200                 205

Gln Met Cys Gly Arg Cys Gly Gly Thr Gly Gln Ile Ile Lys Asn Glu
    210                 215                 220

Cys Lys Thr Cys His Gly Lys Lys Val Thr Lys Asn Lys Phe Phe
225                 230                 235                 240

His Val Asp Val Pro Pro Gly Ala Pro Arg Asn Tyr Met Asp Thr Arg
                245                 250                 255

Val Gly Glu Ala Glu Lys Gly Pro Asp Phe Asp Ala Gly Asp Leu Val
            260                 265                 270

Ile Glu Phe Lys Glu Lys Asp Thr Glu Asn Met Gly Tyr Arg Arg Arg
        275                 280                 285

Gly Asp Asn Leu Tyr Arg Thr Glu Val Leu Ser Ala Ala Glu Ala Leu
    290                 295                 300

Tyr Gly Gly Trp Gln Arg Thr Ile Glu Phe Leu Asp Glu Asn Lys Pro
305                 310                 315                 320

Val Lys Leu Ser Arg Pro Ala His Val Val Ser Asn Gly Glu Val
                325                 330                 335

Glu Val Val Lys Gly Phe Gly Met Pro Lys Gly Ser Lys Gly Tyr Gly
            340                 345                 350

Asp Leu Tyr Ile Asp Tyr Val Val Met Pro Lys Thr Phe Lys Ser
        355                 360                 365

Gly Gln Asn Met Leu Lys Asp Glu Leu
    370                 375

<210> SEQ ID NO 126
<211> LENGTH: 1692
<212> TYPE: DNA
<213> ORGANISM: Saccharomyces cerevisiae
<220> FEATURE:
<221> NAME/KEY: CDS
```

<222> LOCATION: (1)..(1692)

<400> SEQUENCE: 126

| | | | | | | | | | | | | | | | | |
|---|---|---|---|---|---|---|---|---|---|---|---|---|---|---|---|---|
| atg | aga | tta | aga | acc | gcc | att | gcc | aca | ctg | tgc | ctc | acg | gct | ttt | aca | 48 |
| Met | Arg | Leu | Arg | Thr | Ala | Ile | Ala | Thr | Leu | Cys | Leu | Thr | Ala | Phe | Thr | |
| 1 | | | | 5 | | | | | 10 | | | | | 15 | | |

| tct | gca | act | tca | aac | aat | agc | tac | atc | gcc | acc | gac | caa | aca | caa | aat | 96 |
|---|---|---|---|---|---|---|---|---|---|---|---|---|---|---|---|---|
| Ser | Ala | Thr | Ser | Asn | Asn | Ser | Tyr | Ile | Ala | Thr | Asp | Gln | Thr | Gln | Asn | |
| | | | 20 | | | | | 25 | | | | | 30 | | | |

| gcc | ttt | aat | gac | act | cac | ttt | tgt | aag | gtc | gac | agg | aat | gat | cac | gtt | 144 |
|---|---|---|---|---|---|---|---|---|---|---|---|---|---|---|---|---|
| Ala | Phe | Asn | Asp | Thr | His | Phe | Cys | Lys | Val | Asp | Arg | Asn | Asp | His | Val | |
| | | 35 | | | | | 40 | | | | | 45 | | | | |

| agt | ccc | agt | tgt | aac | gta | aca | ttc | aat | gaa | tta | aat | gcc | ata | aat | gaa | 192 |
|---|---|---|---|---|---|---|---|---|---|---|---|---|---|---|---|---|
| Ser | Pro | Ser | Cys | Asn | Val | Thr | Phe | Asn | Glu | Leu | Asn | Ala | Ile | Asn | Glu | |
| 50 | | | | | 55 | | | | | 60 | | | | | | |

| aac | att | aga | gat | gat | ctt | tcg | gcg | tta | tta | aaa | tct | gat | ttc | ttc | aaa | 240 |
|---|---|---|---|---|---|---|---|---|---|---|---|---|---|---|---|---|
| Asn | Ile | Arg | Asp | Asp | Leu | Ser | Ala | Leu | Leu | Lys | Ser | Asp | Phe | Phe | Lys | |
| 65 | | | | 70 | | | | | 75 | | | | | 80 | | |

| tac | ttt | cgg | ctg | gat | tta | tac | aag | caa | tgt | tca | ttt | tgg | gac | gcc | aac | 288 |
|---|---|---|---|---|---|---|---|---|---|---|---|---|---|---|---|---|
| Tyr | Phe | Arg | Leu | Asp | Leu | Tyr | Lys | Gln | Cys | Ser | Phe | Trp | Asp | Ala | Asn | |
| | | | | 85 | | | | | 90 | | | | | 95 | | |

| gat | ggt | ctg | tgc | tta | aac | cgc | gct | tgc | tct | gtt | gat | gtc | gta | gag | gac | 336 |
|---|---|---|---|---|---|---|---|---|---|---|---|---|---|---|---|---|
| Asp | Gly | Leu | Cys | Leu | Asn | Arg | Ala | Cys | Ser | Val | Asp | Val | Val | Glu | Asp | |
| | | 100 | | | | | 105 | | | | | 110 | | | | |

| tgg | gat | aca | ctg | cct | gag | tac | tgg | cag | cct | gag | atc | ttg | ggt | agt | ttc | 384 |
|---|---|---|---|---|---|---|---|---|---|---|---|---|---|---|---|---|
| Trp | Asp | Thr | Leu | Pro | Glu | Tyr | Trp | Gln | Pro | Glu | Ile | Leu | Gly | Ser | Phe | |
| | | 115 | | | | | 120 | | | | | 125 | | | | |

| aat | aat | gat | aca | atg | aag | gaa | gcg | gat | gat | agc | gat | gac | gaa | tgt | aag | 432 |
|---|---|---|---|---|---|---|---|---|---|---|---|---|---|---|---|---|
| Asn | Asn | Asp | Thr | Met | Lys | Glu | Ala | Asp | Asp | Ser | Asp | Asp | Glu | Cys | Lys | |
| 130 | | | | | 135 | | | | | 140 | | | | | | |

| ttc | tta | gat | caa | cta | tgt | caa | acc | agt | aaa | aaa | cct | gta | gat | atc | gaa | 480 |
|---|---|---|---|---|---|---|---|---|---|---|---|---|---|---|---|---|
| Phe | Leu | Asp | Gln | Leu | Cys | Gln | Thr | Ser | Lys | Lys | Pro | Val | Asp | Ile | Glu | |
| 145 | | | | 150 | | | | | 155 | | | | | 160 | | |

| gac | acc | atc | aac | tac | tgt | gat | gta | aat | gac | ttt | aac | ggt | aaa | aac | gcc | 528 |
|---|---|---|---|---|---|---|---|---|---|---|---|---|---|---|---|---|
| Asp | Thr | Ile | Asn | Tyr | Cys | Asp | Val | Asn | Asp | Phe | Asn | Gly | Lys | Asn | Ala | |
| | | | | 165 | | | | | 170 | | | | | 175 | | |

| gtt | ctg | att | gat | tta | aca | gca | aat | ccg | gaa | cga | ttt | aca | ggt | tat | ggt | 576 |
|---|---|---|---|---|---|---|---|---|---|---|---|---|---|---|---|---|
| Val | Leu | Ile | Asp | Leu | Thr | Ala | Asn | Pro | Glu | Arg | Phe | Thr | Gly | Tyr | Gly | |
| | | | 180 | | | | | 185 | | | | | 190 | | | |

| ggt | aag | caa | gct | ggt | caa | att | tgg | tct | act | atc | tac | caa | gac | aac | tgt | 624 |
|---|---|---|---|---|---|---|---|---|---|---|---|---|---|---|---|---|
| Gly | Lys | Gln | Ala | Gly | Gln | Ile | Trp | Ser | Thr | Ile | Tyr | Gln | Asp | Asn | Cys | |
| | 195 | | | | | 200 | | | | | 205 | | | | | |

| ttt | aca | att | ggc | gaa | act | ggt | gaa | tca | ttg | gcc | aaa | gat | gca | ttt | tat | 672 |
|---|---|---|---|---|---|---|---|---|---|---|---|---|---|---|---|---|
| Phe | Thr | Ile | Gly | Glu | Thr | Gly | Glu | Ser | Leu | Ala | Lys | Asp | Ala | Phe | Tyr | |
| 210 | | | | | 215 | | | | | 220 | | | | | | |

| aga | ctt | gta | tcc | ggt | ttc | cat | gcc | tct | atc | ggt | act | cac | tta | tca | aag | 720 |
|---|---|---|---|---|---|---|---|---|---|---|---|---|---|---|---|---|
| Arg | Leu | Val | Ser | Gly | Phe | His | Ala | Ser | Ile | Gly | Thr | His | Leu | Ser | Lys | |
| 225 | | | | 230 | | | | | 235 | | | | | 240 | | |

| gaa | tat | ttg | aac | acg | aaa | act | ggt | aaa | tgg | gag | ccc | aat | ctg | gat | ttg | 768 |
|---|---|---|---|---|---|---|---|---|---|---|---|---|---|---|---|---|
| Glu | Tyr | Leu | Asn | Thr | Lys | Thr | Gly | Lys | Trp | Glu | Pro | Asn | Leu | Asp | Leu | |
| | | | 245 | | | | | 250 | | | | | 255 | | | |

| ttt | atg | gca | aga | atc | ggg | aac | ttt | cct | gat | aga | gtg | aca | aac | atg | tat | 816 |
|---|---|---|---|---|---|---|---|---|---|---|---|---|---|---|---|---|
| Phe | Met | Ala | Arg | Ile | Gly | Asn | Phe | Pro | Asp | Arg | Val | Thr | Asn | Met | Tyr | |
| | | 260 | | | | | 265 | | | | | 270 | | | | |

| ttc | aat | tat | gct | gtt | gta | gct | aag | gct | ctc | tgg | aaa | att | caa | cca | tat | 864 |
|---|---|---|---|---|---|---|---|---|---|---|---|---|---|---|---|---|
| Phe | Asn | Tyr | Ala | Val | Val | Ala | Lys | Ala | Leu | Trp | Lys | Ile | Gln | Pro | Tyr | |
| | | 275 | | | | | 280 | | | | | 285 | | | | |

| tta | cca | gaa | ttt | tca | ttc | tgt | gat | cta | gtc | aat | aaa | gaa | atc | aaa | aac | 912 |
|---|---|---|---|---|---|---|---|---|---|---|---|---|---|---|---|---|
| Leu | Pro | Glu | Phe | Ser | Phe | Cys | Asp | Leu | Val | Asn | Lys | Glu | Ile | Lys | Asn | |
| 290 | | | | | 295 | | | | | 300 | | | | | | |

```
                                                                                -continued aaa atg gat aac gtt att tcc cag ctg gac aca aaa att ttt aac gaa      960
Lys Met Asp Asn Val Ile Ser Gln Leu Asp Thr Lys Ile Phe Asn Glu
305                 310                 315                 320 gac tta gtt ttt gcc aac gac cta agt ttg act ttg aag gac gaa ttc     1008
Asp Leu Val Phe Ala Asn Asp Leu Ser Leu Thr Leu Lys Asp Glu Phe
                325                 330                 335 aga tct cgc ttc aag aat gtc acg aag att atg gat tgt gtg caa tgt     1056
Arg Ser Arg Phe Lys Asn Val Thr Lys Ile Met Asp Cys Val Gln Cys
            340                 345                 350 gat aga tgt aga ttg tgg ggc aaa att caa act acc ggt tac gca act     1104
Asp Arg Cys Arg Leu Trp Gly Lys Ile Gln Thr Thr Gly Tyr Ala Thr
        355                 360                 365 gcc ttg aaa att ttg ttt gaa atc aac gac gct gat gaa ttc acc aaa     1152
Ala Leu Lys Ile Leu Phe Glu Ile Asn Asp Ala Asp Glu Phe Thr Lys
    370                 375                 380 caa cat att gtt ggt aag tta acc aaa tat gag ttg att gca cta tta     1200
Gln His Ile Val Gly Lys Leu Thr Lys Tyr Glu Leu Ile Ala Leu Leu
385                 390                 395                 400 cag act ttc ggt aga tta tct gaa tct att gaa tct gtt aac atg ttc     1248
Gln Thr Phe Gly Arg Leu Ser Glu Ser Ile Glu Ser Val Asn Met Phe
                405                 410                 415 gaa aaa atg tac ggg aaa agg tta aac ggt tct gaa aac agg tta agc     1296
Glu Lys Met Tyr Gly Lys Arg Leu Asn Gly Ser Glu Asn Arg Leu Ser
            420                 425                 430 tca ttc ttc caa aat aac ttc ttc aac att ttg aag gag gca ggc aaa     1344
Ser Phe Phe Gln Asn Asn Phe Phe Asn Ile Leu Lys Glu Ala Gly Lys
        435                 440                 445 tcg att cgt tac acc ata gag aac atc aat tcc act aaa gaa gga aag     1392
Ser Ile Arg Tyr Thr Ile Glu Asn Ile Asn Ser Thr Lys Glu Gly Lys
    450                 455                 460 aaa aag act aac aat tct caa tca cat gta ttt gat gat tta aaa atg     1440
Lys Lys Thr Asn Asn Ser Gln Ser His Val Phe Asp Asp Leu Lys Met
465                 470                 475                 480 ccc aaa gca gaa ata gtt cca agg ccc tct aac ggt aca gta aat aaa     1488
Pro Lys Ala Glu Ile Val Pro Arg Pro Ser Asn Gly Thr Val Asn Lys
                485                 490                 495 tgg aag aaa gct tgg aat act gaa gtt aac aac gtt tta gaa gca ttc     1536
Trp Lys Lys Ala Trp Asn Thr Glu Val Asn Asn Val Leu Glu Ala Phe
            500                 505                 510 aga ttt att tat aga agc tat ttg gat tta ccc agg aac atc tgg gaa     1584
Arg Phe Ile Tyr Arg Ser Tyr Leu Asp Leu Pro Arg Asn Ile Trp Glu
        515                 520                 525 tta tct ttg atg aag gta tac aaa ttt tgg aat aaa ttc atc ggt gtt     1632
Leu Ser Leu Met Lys Val Tyr Lys Phe Trp Asn Lys Phe Ile Gly Val
    530                 535                 540 gct gat tac gtt agt gag gag aca cga gag cct att tcc tat aag cta     1680
Ala Asp Tyr Val Ser Glu Glu Thr Arg Glu Pro Ile Ser Tyr Lys Leu
545                 550                 555                 560 gat ata caa taa                                                      1692
Asp Ile Gln <210> SEQ ID NO 127
<211> LENGTH: 563
<212> TYPE: PRT
<213> ORGANISM: Saccharomyces cerevisiae

<400> SEQUENCE: 127

Met Arg Leu Arg Thr Ala Ile Ala Thr Leu Cys Leu Thr Ala Phe Thr
1               5                   10                  15

Ser Ala Thr Ser Asn Asn Ser Tyr Ile Ala Thr Asp Gln Thr Gln Asn
                20                  25                  30
```

```
Ala Phe Asn Asp Thr His Phe Cys Lys Val Asp Arg Asn Asp His Val
        35                  40                  45

Ser Pro Ser Cys Asn Val Thr Phe Asn Glu Leu Asn Ala Ile Asn Glu
 50                  55                  60

Asn Ile Arg Asp Asp Leu Ser Ala Leu Leu Lys Ser Asp Phe Phe Lys
 65                  70                  75                  80

Tyr Phe Arg Leu Asp Leu Tyr Lys Gln Cys Ser Phe Trp Asp Ala Asn
                 85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Asp Ser Asp Asp Glu Cys Lys
        130                 135                 140

Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
                165                 170                 175

Val Leu Ile Asp Leu Thr Ala Asn Pro Glu Arg Phe Thr Gly Tyr Gly
            180                 185                 190

Gly Lys Gln Ala Gly Gln Ile Trp Ser Thr Ile Tyr Gln Asp Asn Cys
        195                 200                 205

Phe Thr Ile Gly Glu Thr Gly Glu Ser Leu Ala Lys Asp Ala Phe Tyr
        210                 215                 220

Arg Leu Val Ser Gly Phe His Ala Ser Ile Gly Thr His Leu Ser Lys
225                 230                 235                 240

Glu Tyr Leu Asn Thr Lys Thr Gly Lys Trp Glu Pro Asn Leu Asp Leu
                245                 250                 255

Phe Met Ala Arg Ile Gly Asn Phe Pro Asp Arg Val Thr Asn Met Tyr
            260                 265                 270

Phe Asn Tyr Ala Val Val Ala Lys Ala Leu Trp Lys Ile Gln Pro Tyr
        275                 280                 285

Leu Pro Glu Phe Ser Phe Cys Asp Leu Val Asn Lys Glu Ile Lys Asn
        290                 295                 300

Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
                325                 330                 335

Arg Ser Arg Phe Lys Asn Val Thr Lys Ile Met Asp Cys Val Gln Cys
            340                 345                 350

Asp Arg Cys Arg Leu Trp Gly Lys Ile Gln Thr Thr Gly Tyr Ala Thr
        355                 360                 365

Ala Leu Lys Ile Leu Phe Glu Ile Asn Asp Ala Asp Glu Phe Thr Lys
        370                 375                 380

Gln His Ile Val Gly Lys Leu Thr Lys Tyr Glu Leu Ile Ala Leu Leu
385                 390                 395                 400

Gln Thr Phe Gly Arg Leu Ser Glu Ser Ile Glu Ser Val Asn Met Phe
                405                 410                 415

Glu Lys Met Tyr Gly Lys Arg Leu Asn Gly Ser Glu Asn Arg Leu Ser
            420                 425                 430

Ser Phe Phe Gln Asn Asn Phe Phe Asn Ile Leu Lys Glu Ala Gly Lys
        435                 440                 445

Ser Ile Arg Tyr Thr Ile Glu Asn Ile Asn Ser Thr Lys Glu Gly Lys
```

```
                  450                 455                 460
Lys Lys Thr Asn Asn Ser Gln Ser His Val Phe Asp Asp Leu Lys Met
465                 470                 475                 480

Pro Lys Ala Glu Ile Val Pro Arg Pro Ser Asn Gly Thr Val Asn Lys
                485                 490                 495

Trp Lys Lys Ala Trp Asn Thr Glu Val Asn Asn Val Leu Glu Ala Phe
                    500                 505                 510

Arg Phe Ile Tyr Arg Ser Tyr Leu Asp Leu Pro Arg Asn Ile Trp Glu
                515                 520                 525

Leu Ser Leu Met Lys Val Tyr Lys Phe Trp Asn Lys Phe Ile Gly Val
            530                 535                 540

Ala Asp Tyr Val Ser Glu Glu Thr Arg Glu Pro Ile Ser Tyr Lys Leu
545                 550                 555                 560

Asp Ile Gln

<210> SEQ ID NO 128
<211> LENGTH: 408
<212> TYPE: DNA
<213> ORGANISM: Saccharomyces cerevisiae
<220> FEATURE:
<221> NAME/KEY: CDS
<222> LOCATION: (1)..(408)

<400> SEQUENCE: 128 atg atg ttt aat att tac ctt ttc gtc act ttt ttt tcc acc att ctt      48
Met Met Phe Asn Ile Tyr Leu Phe Val Thr Phe Phe Ser Thr Ile Leu
1               5                   10                  15 gca ggt tcc ctg tca gat ttg gaa atc ggt att atc aag aga ata ccg      96
Ala Gly Ser Leu Ser Asp Leu Glu Ile Gly Ile Ile Lys Arg Ile Pro
            20                  25                  30 gta gaa gat tgc tta att aag gca atg cca ggt gat aaa gtt aag gtt     144
Val Glu Asp Cys Leu Ile Lys Ala Met Pro Gly Asp Lys Val Lys Val
        35                  40                  45 cat tat aca gga tct tta tta gaa tcg gga act gta ttt gac tca agt     192
His Tyr Thr Gly Ser Leu Leu Glu Ser Gly Thr Val Phe Asp Ser Ser
    50                  55                  60 tat tca aga ggc tct cct atc gct ttt gaa ctt ggc gtt ggc aga gta     240
Tyr Ser Arg Gly Ser Pro Ile Ala Phe Glu Leu Gly Val Gly Arg Val
65                  70                  75                  80 att aaa ggt tgg gat caa ggt gtt gcc ggc atg tgc gtt ggc gaa aaa     288
Ile Lys Gly Trp Asp Gln Gly Val Ala Gly Met Cys Val Gly Glu Lys
                85                  90                  95 aga aag ctg caa att cca agt tct ttg gcc tac gga gaa aga ggt gtc     336
Arg Lys Leu Gln Ile Pro Ser Ser Leu Ala Tyr Gly Glu Arg Gly Val
            100                 105                 110 cca ggc gtc att cct cca agt gct gat ttg gtg ttt gat gtc gaa ttg     384
Pro Gly Val Ile Pro Pro Ser Ala Asp Leu Val Phe Asp Val Glu Leu
        115                 120                 125 gta gac gtg aaa tca gcc gcc tag                                     408
Val Asp Val Lys Ser Ala Ala
    130             135

<210> SEQ ID NO 129
<211> LENGTH: 135
<212> TYPE: PRT
<213> ORGANISM: Saccharomyces cerevisiae

<400> SEQUENCE: 129

Met Met Phe Asn Ile Tyr Leu Phe Val Thr Phe Phe Ser Thr Ile Leu
1               5                   10                  15
```

-continued

```
Ala Gly Ser Leu Ser Asp Leu Glu Ile Gly Ile Ile Lys Arg Ile Pro
         20                  25                  30

Val Glu Asp Cys Leu Ile Lys Ala Met Pro Gly Asp Lys Val Lys Val
     35                  40                  45

His Tyr Thr Gly Ser Leu Leu Glu Ser Gly Thr Val Phe Asp Ser Ser
 50                  55                  60

Tyr Ser Arg Gly Ser Pro Ile Ala Phe Glu Leu Gly Val Gly Arg Val
 65                  70                  75                  80

Ile Lys Gly Trp Asp Gln Gly Val Ala Gly Met Cys Val Gly Glu Lys
                 85                  90                  95

Arg Lys Leu Gln Ile Pro Ser Ser Leu Ala Tyr Gly Glu Arg Gly Val
             100                 105                 110

Pro Gly Val Ile Pro Pro Ser Ala Asp Leu Val Phe Asp Val Glu Leu
         115                 120                 125

Val Asp Val Lys Ser Ala Ala
         130                 135

<210> SEQ ID NO 130
<211> LENGTH: 1938
<212> TYPE: DNA
<213> ORGANISM: Saccharomyces cerevisiae
<220> FEATURE:
<221> NAME/KEY: CDS
<222> LOCATION: (1)..(1938)

<400> SEQUENCE: 130
```

| | | | | | | | | | | | | | | | | |
|---|---|---|---|---|---|---|---|---|---|---|---|---|---|---|---|---|
| atg | ata | ctg | atc | tcg | gga | tac | tgt | ctt | tta | gtg | tat | agc | gtt | att | ttg | 48 |
| Met | Ile | Leu | Ile | Ser | Gly | Tyr | Cys | Leu | Leu | Val | Tyr | Ser | Val | Ile | Leu | |
| 1 | | | | 5 | | | | | 10 | | | | | 15 | | |
| cca | gta | ctg | ata | tcg | gct | tct | aag | tta | tgt | gat | ttg | gct | gag | tta | caa | 96 |
| Pro | Val | Leu | Ile | Ser | Ala | Ser | Lys | Leu | Cys | Asp | Leu | Ala | Glu | Leu | Gln | |
| | | | 20 | | | | | 25 | | | | | 30 | | | |
| cga | ttg | aac | aag | aat | tta | aaa | gta | gac | act | gaa | tcc | ttg | cca | aaa | tac | 144 |
| Arg | Leu | Asn | Lys | Asn | Leu | Lys | Val | Asp | Thr | Glu | Ser | Leu | Pro | Lys | Tyr | |
| | | 35 | | | | | 40 | | | | | 45 | | | | |
| caa | tgg | atc | gct | ggg | cag | ttg | gaa | caa | aac | tgc | atg | act | gcg | gat | cca | 192 |
| Gln | Trp | Ile | Ala | Gly | Gln | Leu | Glu | Gln | Asn | Cys | Met | Thr | Ala | Asp | Pro | |
| | 50 | | | | | 55 | | | | | 60 | | | | | |
| gca | agt | gaa | aat | atg | tca | gac | gta | att | caa | cta | gcc | aat | caa | ata | tac | 240 |
| Ala | Ser | Glu | Asn | Met | Ser | Asp | Val | Ile | Gln | Leu | Ala | Asn | Gln | Ile | Tyr | |
| 65 | | | | | 70 | | | | | 75 | | | | | 80 | |
| tac | aaa | att | ggg | ctg | atc | caa | tta | tcc | aac | gat | caa | cat | cta | aga | gct | 288 |
| Tyr | Lys | Ile | Gly | Leu | Ile | Gln | Leu | Ser | Asn | Asp | Gln | His | Leu | Arg | Ala | |
| | | | | 85 | | | | | 90 | | | | | 95 | | |
| att | aac | aca | ttt | gaa | aaa | atc | gtt | ttt | aat | gaa | act | tac | aaa | ggt | tct | 336 |
| Ile | Asn | Thr | Phe | Glu | Lys | Ile | Val | Phe | Asn | Glu | Thr | Tyr | Lys | Gly | Ser | |
| | | | | 100 | | | | | 105 | | | | | 110 | | |
| ttt | ggg | aag | ctg | gcg | gaa | aag | agg | cta | caa | gag | ctg | tat | gtc | gat | ttt | 384 |
| Phe | Gly | Lys | Leu | Ala | Glu | Lys | Arg | Leu | Gln | Glu | Leu | Tyr | Val | Asp | Phe | |
| | | | 115 | | | | | 120 | | | | | 125 | | | |
| ggg | atg | tgg | gac | aag | gtg | cat | cag | aag | gat | gat | cag | tat | gcg | aaa | tat | 432 |
| Gly | Met | Trp | Asp | Lys | Val | His | Gln | Lys | Asp | Asp | Gln | Tyr | Ala | Lys | Tyr | |
| | 130 | | | | | 135 | | | | | 140 | | | | | |
| ctg | tcc | ttg | aat | gaa | acc | atc | aga | aac | aaa | ata | tca | tcc | aaa | gac | gtt | 480 |
| Leu | Ser | Leu | Asn | Glu | Thr | Ile | Arg | Asn | Lys | Ile | Ser | Ser | Lys | Asp | Val | |
| 145 | | | | | 150 | | | | | 155 | | | | | 160 | |
| tct | gtg | gag | gaa | gat | att | tct | gag | ctg | cta | cgc | ata | acg | ccg | tac | gat | 528 |
| Ser | Val | Glu | Glu | Asp | Ile | Ser | Glu | Leu | Leu | Arg | Ile | Thr | Pro | Tyr | Asp | |
| | | | | 165 | | | | | 170 | | | | | 175 | | |
| gtt | aac | gtc | ctc | tcc | acg | cac | atc | gat | gtt | ctt | ttt | cac | aaa | cta | gct | 576 |

```
Val Asn Val Leu Ser Thr His Ile Asp Val Leu Phe His Lys Leu Ala
            180                 185                 190 gaa gaa att gac gtt tcg tta gct gct gct atc att ttg gat tac gaa         624
Glu Glu Ile Asp Val Ser Leu Ala Ala Ala Ile Ile Leu Asp Tyr Glu
        195                 200                 205 aca atc ctc gac aag cat ttg gct agc tta agc ata gat aca aga ctt         672
Thr Ile Leu Asp Lys His Leu Ala Ser Leu Ser Ile Asp Thr Arg Leu
    210                 215                 220 tcg att cat tat gtc ata tct gtt tta cag acc ttt gta ctt aac tca         720
Ser Ile His Tyr Val Ile Ser Val Leu Gln Thr Phe Val Leu Asn Ser
225                 230                 235                 240 gat gcg tcg ttc aat ata aga aaa tgc ctt tcc att gat atg gac tat         768
Asp Ala Ser Phe Asn Ile Arg Lys Cys Leu Ser Ile Asp Met Asp Tyr
                245                 250                 255 gat aaa tgt aaa aaa cta agc ctg act att tcc aaa ttg aac aag gtg         816
Asp Lys Cys Lys Lys Leu Ser Leu Thr Ile Ser Lys Leu Asn Lys Val
            260                 265                 270 aat cca tca aaa aga cag atc ctg gat cca gca aca tat gca ttt gag         864
Asn Pro Ser Lys Arg Gln Ile Leu Asp Pro Ala Thr Tyr Ala Phe Glu
        275                 280                 285 aac aaa aag ttt aga agt tgg gat aga att att gaa ttt tat ttg aag         912
Asn Lys Lys Phe Arg Ser Trp Asp Arg Ile Ile Glu Phe Tyr Leu Lys
    290                 295                 300 gat aag aag cca ttt att aca cca atg aaa att ctt aac aaa gat aca         960
Asp Lys Lys Pro Phe Ile Thr Pro Met Lys Ile Leu Asn Lys Asp Thr
305                 310                 315                 320 aac ttt aaa aac aac tac ttc ttt tta gag gaa att atc aaa caa ttg        1008
Asn Phe Lys Asn Asn Tyr Phe Phe Leu Glu Glu Ile Ile Lys Gln Leu
                325                 330                 335 ata gaa gac gtt caa ctg tcg aga cct ttg gca aaa aat tta ttc gaa        1056
Ile Glu Asp Val Gln Leu Ser Arg Pro Leu Ala Lys Asn Leu Phe Glu
            340                 345                 350 gat ccc cca ata acc gat ggt ttt gtc aaa cca aaa tca tac tat cat        1104
Asp Pro Pro Ile Thr Asp Gly Phe Val Lys Pro Lys Ser Tyr Tyr His
        355                 360                 365 acc gat tat cta gta tac att gat tcc att ctt tgt cag gct tct agc        1152
Thr Asp Tyr Leu Val Tyr Ile Asp Ser Ile Leu Cys Gln Ala Ser Ser
    370                 375                 380 atg agt ccg gac gtc aag aga gct aaa ctg gct gcg ccg ttc tgt aaa        1200
Met Ser Pro Asp Val Lys Arg Ala Lys Leu Ala Ala Pro Phe Cys Lys
385                 390                 395                 400 aag agt ttg agg cat tca cta aca cta gaa aca tgg aaa cac tat cag        1248
Lys Ser Leu Arg His Ser Leu Thr Leu Glu Thr Trp Lys His Tyr Gln
                405                 410                 415 gat gct aag tcc gag caa aaa cct tta cct gag acg gta ttg agt gat        1296
Asp Ala Lys Ser Glu Gln Lys Pro Leu Pro Glu Thr Val Leu Ser Asp
            420                 425                 430 gta tgg aat tcc aat cct cat ttg ctg atg tat atg gta aac tca ata        1344
Val Trp Asn Ser Asn Pro His Leu Leu Met Tyr Met Val Asn Ser Ile
        435                 440                 445 ctt aat aaa agt agg tct aaa cct cat tca cag ttc aaa aag caa tta        1392
Leu Asn Lys Ser Arg Ser Lys Pro His Ser Gln Phe Lys Lys Gln Leu
    450                 455                 460 tat gac cag ata aac aaa ttt ttc caa gat aac ggc ctc tca gag tcg        1440
Tyr Asp Gln Ile Asn Lys Phe Phe Gln Asp Asn Gly Leu Ser Glu Ser
465                 470                 475                 480 acc aat cca tac gtg atg aag aac ttc cga tta tta cag aaa caa tta        1488
Thr Asn Pro Tyr Val Met Lys Asn Phe Arg Leu Leu Gln Lys Gln Leu
                485                 490                 495 caa acc tat aaa gag cat aaa cat cgg aat ttc aac cag caa tat ttc        1536
```

```
Gln Thr Tyr Lys Glu His Lys His Arg Asn Phe Asn Gln Gln Tyr Phe
                500                 505                 510 caa caa caa caa cag cag caa caa cac caa cga cat caa gca ccc cca        1584
Gln Gln Gln Gln Gln Gln Gln Gln His Gln Arg His Gln Ala Pro Pro
            515                 520                 525 gca gcg cct aac tac gac cca aaa aag gac tat tat aaa att ctt gga        1632
Ala Ala Pro Asn Tyr Asp Pro Lys Lys Asp Tyr Tyr Lys Ile Leu Gly
        530                 535                 540 gta tcg cct agt gct agt tcg aaa gaa ata agg aaa gca tat tta aat        1680
Val Ser Pro Ser Ala Ser Ser Lys Glu Ile Arg Lys Ala Tyr Leu Asn
545                 550                 555                 560 tta acc aaa aaa tac cac cca gac aaa ata aag gcc aac cat aac gac        1728
Leu Thr Lys Lys Tyr His Pro Asp Lys Ile Lys Ala Asn His Asn Asp
                565                 570                 575 aaa caa gaa tca att cac gaa act atg tca caa atc aat gaa gcg tac        1776
Lys Gln Glu Ser Ile His Glu Thr Met Ser Gln Ile Asn Glu Ala Tyr
            580                 585                 590 gaa aca tta agt gat gac gat aaa agg aag gaa tac gat ctt tcc aga        1824
Glu Thr Leu Ser Asp Asp Asp Lys Arg Lys Glu Tyr Asp Leu Ser Arg
        595                 600                 605 tca aac ccc cgc cgc aac act ttt cct cag ggg cct agg caa aat aac        1872
Ser Asn Pro Arg Arg Asn Thr Phe Pro Gln Gly Pro Arg Gln Asn Asn
610                 615                 620 atg ttc aaa aat cca gga agt ggc ttc cca ttc gga aat ggc ttt aaa        1920
Met Phe Lys Asn Pro Gly Ser Gly Phe Pro Phe Gly Asn Gly Phe Lys
625                 630                 635                 640 atg aat ttt ggg ctt tga                                                1938
Met Asn Phe Gly Leu
                645

<210> SEQ ID NO 131
<211> LENGTH: 645
<212> TYPE: PRT
<213> ORGANISM: Saccharomyces cerevisiae

<400> SEQUENCE: 131

Met Ile Leu Ile Ser Gly Tyr Cys Leu Leu Val Tyr Ser Val Ile Leu
1               5                   10                  15

Pro Val Leu Ile Ser Ala Ser Lys Leu Cys Asp Leu Ala Glu Leu Gln
                20                  25                  30

Arg Leu Asn Lys Asn Leu Lys Val Asp Thr Glu Ser Leu Pro Lys Tyr
            35                  40                  45

Gln Trp Ile Ala Gly Leu Glu Gln Asn Cys Met Thr Ala Asp Pro
        50                  55                  60

Ala Ser Glu Asn Met Ser Asp Val Ile Gln Leu Ala Asn Gln Ile Tyr
65                  70                  75                  80

Tyr Lys Ile Gly Leu Ile Gln Leu Ser Asn Asp Gln His Leu Arg Ala
                85                  90                  95

Ile Asn Thr Phe Glu Lys Ile Val Phe Asn Glu Thr Tyr Lys Gly Ser
            100                 105                 110

Phe Gly Lys Leu Ala Glu Lys Arg Leu Gln Glu Leu Tyr Val Asp Phe
        115                 120                 125

Gly Met Trp Asp Lys Val His Gln Lys Asp Asp Gln Tyr Ala Lys Tyr
    130                 135                 140

Leu Ser Leu Asn Glu Thr Ile Arg Asn Lys Ile Ser Ser Lys Asp Val
145                 150                 155                 160

Ser Val Glu Glu Asp Ile Ser Glu Leu Leu Arg Ile Thr Pro Tyr Asp
                165                 170                 175
```

```
Val Asn Val Leu Ser Thr His Ile Asp Val Leu Phe His Lys Leu Ala
            180                 185                 190
Glu Glu Ile Asp Val Ser Leu Ala Ala Ile Ile Leu Asp Tyr Glu
        195                 200                 205
Thr Ile Leu Asp Lys His Leu Ala Ser Leu Ser Ile Asp Thr Arg Leu
    210                 215                 220
Ser Ile His Tyr Val Ile Ser Val Leu Gln Thr Phe Val Leu Asn Ser
225                 230                 235                 240
Asp Ala Ser Phe Asn Ile Arg Lys Cys Leu Ser Ile Asp Met Asp Tyr
                245                 250                 255
Asp Lys Cys Lys Lys Leu Ser Leu Thr Ile Ser Lys Leu Asn Lys Val
            260                 265                 270
Asn Pro Ser Lys Arg Gln Ile Leu Asp Pro Ala Thr Tyr Ala Phe Glu
        275                 280                 285
Asn Lys Lys Phe Arg Ser Trp Asp Arg Ile Ile Glu Phe Tyr Leu Lys
    290                 295                 300
Asp Lys Lys Pro Phe Ile Thr Pro Met Lys Ile Leu Asn Lys Asp Thr
305                 310                 315                 320
Asn Phe Lys Asn Asn Tyr Phe Phe Leu Glu Glu Ile Ile Lys Gln Leu
                325                 330                 335
Ile Glu Asp Val Gln Leu Ser Arg Pro Leu Ala Lys Asn Leu Phe Glu
            340                 345                 350
Asp Pro Pro Ile Thr Asp Gly Phe Val Lys Pro Lys Ser Tyr Tyr His
        355                 360                 365
Thr Asp Tyr Leu Val Tyr Ile Asp Ser Ile Leu Cys Gln Ala Ser Ser
    370                 375                 380
Met Ser Pro Asp Val Lys Arg Ala Lys Leu Ala Ala Pro Phe Cys Lys
385                 390                 395                 400
Lys Ser Leu Arg His Ser Leu Thr Leu Glu Thr Trp Lys His Tyr Gln
                405                 410                 415
Asp Ala Lys Ser Glu Gln Lys Pro Leu Pro Glu Thr Val Leu Ser Asp
            420                 425                 430
Val Trp Asn Ser Asn Pro His Leu Leu Met Tyr Met Val Asn Ser Ile
        435                 440                 445
Leu Asn Lys Ser Arg Ser Lys Pro His Ser Gln Phe Lys Lys Gln Leu
    450                 455                 460
Tyr Asp Gln Ile Asn Lys Phe Phe Gln Asp Asn Gly Leu Ser Glu Ser
465                 470                 475                 480
Thr Asn Pro Tyr Val Met Lys Asn Phe Arg Leu Leu Gln Lys Gln Leu
                485                 490                 495
Gln Thr Tyr Lys Glu His Lys His Arg Asn Phe Asn Gln Gln Tyr Phe
            500                 505                 510
Gln Gln Gln Gln Gln Gln Gln His Gln Arg His Gln Ala Pro Pro
        515                 520                 525
Ala Ala Pro Asn Tyr Asp Pro Lys Lys Asp Tyr Tyr Lys Ile Leu Gly
    530                 535                 540
Val Ser Pro Ser Ala Ser Ser Lys Glu Ile Arg Lys Ala Tyr Leu Asn
545                 550                 555                 560
Leu Thr Lys Lys Tyr His Pro Asp Lys Ile Lys Ala Asn His Asn Asp
                565                 570                 575
Lys Gln Glu Ser Ile His Glu Thr Met Ser Gln Ile Asn Glu Ala Tyr
            580                 585                 590
Glu Thr Leu Ser Asp Asp Asp Lys Arg Lys Glu Tyr Asp Leu Ser Arg
        595                 600                 605
```

```
Ser Asn Pro Arg Arg Asn Thr Phe Pro Gln Gly Pro Arg Gln Asn Asn
        610                 615                 620

Met Phe Lys Asn Pro Gly Ser Gly Phe Pro Phe Gly Asn Gly Phe Lys
625                 630                 635                 640

Met Asn Phe Gly Leu
                645

<210> SEQ ID NO 132
<211> LENGTH: 2646
<212> TYPE: DNA
<213> ORGANISM: Saccharomyces cerevisiae
<220> FEATURE:
<221> NAME/KEY: CDS
<222> LOCATION: (1)..(2646)

<400> SEQUENCE: 132 atg cga aac gtt tta agg ctt tta ttt tta aca gct ttt gtt gct ata      48
Met Arg Asn Val Leu Arg Leu Leu Phe Leu Thr Ala Phe Val Ala Ile
1               5                   10                  15 ggg tct tta gca gcc gtt tta ggt gtt gat tac ggt cag caa aat atc     96
Gly Ser Leu Ala Ala Val Leu Gly Val Asp Tyr Gly Gln Gln Asn Ile
            20                  25                  30 aag gcc att gtg gtt tct ccg caa gcc cca tta gaa ctt gtg ctc aca     144
Lys Ala Ile Val Val Ser Pro Gln Ala Pro Leu Glu Leu Val Leu Thr
        35                  40                  45 cca gag gca aaa cgg aag gag ata tct ggt ctt tcg ata aaa aga tta     192
Pro Glu Ala Lys Arg Lys Glu Ile Ser Gly Leu Ser Ile Lys Arg Leu
    50                  55                  60 cca ggt tat gga aag gat gat ccg aat ggg att gaa aga atc tac ggt     240
Pro Gly Tyr Gly Lys Asp Asp Pro Asn Gly Ile Glu Arg Ile Tyr Gly
65                  70                  75                  80 tcc gct gtt ggc agt tta gca aca agg ttt ccc caa aac aca ttg ttg     288
Ser Ala Val Gly Ser Leu Ala Thr Arg Phe Pro Gln Asn Thr Leu Leu
                85                  90                  95 cat ttg aaa ccg cta ctt ggg aaa tca cta gaa gat gaa acc act gta     336
His Leu Lys Pro Leu Leu Gly Lys Ser Leu Glu Asp Glu Thr Thr Val
            100                 105                 110 act ttg tat tca aaa caa cac ccc ggt tta gaa atg gta tca aca aat     384
Thr Leu Tyr Ser Lys Gln His Pro Gly Leu Glu Met Val Ser Thr Asn
        115                 120                 125 aga agt acc ata gcc ttt tta gtt gat aat gtg gaa tat cca ttg gaa     432
Arg Ser Thr Ile Ala Phe Leu Val Asp Asn Val Glu Tyr Pro Leu Glu
    130                 135                 140 gag tta gtg gca atg aat gtc caa gag att gcc aat aga gcc aat tca     480
Glu Leu Val Ala Met Asn Val Gln Glu Ile Ala Asn Arg Ala Asn Ser
145                 150                 155                 160 ctg ttg aag gat aga gat gca aga act gag gac ttt gta aac aag atg     528
Leu Leu Lys Asp Arg Asp Ala Arg Thr Glu Asp Phe Val Asn Lys Met
                165                 170                 175 agt ttt aca att cct gac ttt ttt gac caa cat caa agg aaa gca ctt     576
Ser Phe Thr Ile Pro Asp Phe Phe Asp Gln His Gln Arg Lys Ala Leu
            180                 185                 190 tta gat gcc agt tca ata acc aca gga atc gaa gag aca tat ctg gtt     624
Leu Asp Ala Ser Ser Ile Thr Thr Gly Ile Glu Glu Thr Tyr Leu Val
        195                 200                 205 agt gaa ggg atg tct gtt gca gtt aac ttt gta tta aag cag cgc caa     672
Ser Glu Gly Met Ser Val Ala Val Asn Phe Val Leu Lys Gln Arg Gln
    210                 215                 220 ttt cca cca ggt gaa cag cag cat tat atc gta tat gac atg ggg agc     720
Phe Pro Pro Gly Glu Gln Gln His Tyr Ile Val Tyr Asp Met Gly Ser
225                 230                 235                 240
```

-continued

| | | |
|---|---|---|
| ggt tct att aag gcc tca atg ttc tct ata ttg cag ccg gag gac act<br>Gly Ser Ile Lys Ala Ser Met Phe Ser Ile Leu Gln Pro Glu Asp Thr<br>245 250 255 | 768 | |
| act cag ccc gtt aca ata gaa ttt gaa gga tat ggg tat aat cca cat<br>Thr Gln Pro Val Thr Ile Glu Phe Glu Gly Tyr Gly Tyr Asn Pro His<br>260 265 270 | 816 | |
| cta ggt ggt gca aag ttt aca atg gat att ggc agt ttg ata gag aat<br>Leu Gly Gly Ala Lys Phe Thr Met Asp Ile Gly Ser Leu Ile Glu Asn<br>275 280 285 | 864 | |
| aag ttt ttg gaa aca cac cca gcc ata aga act gat gaa ttg cac gct<br>Lys Phe Leu Glu Thr His Pro Ala Ile Arg Thr Asp Glu Leu His Ala<br>290 295 300 | 912 | |
| aat ccc aag gcc tta gca aaa atc aac caa gca gca gag aag gca aag<br>Asn Pro Lys Ala Leu Ala Lys Ile Asn Gln Ala Ala Glu Lys Ala Lys<br>305 310 315 320 | 960 | |
| tta att tta agc gcc aat tct gag gca agt att aac ata gaa tca ctg<br>Leu Ile Leu Ser Ala Asn Ser Glu Ala Ser Ile Asn Ile Glu Ser Leu<br>325 330 335 | 1008 | |
| atc aac gat att gat ttc cgt act tct ata act aga cag gaa ttc gaa<br>Ile Asn Asp Ile Asp Phe Arg Thr Ser Ile Thr Arg Gln Glu Phe Glu<br>340 345 350 | 1056 | |
| gaa ttt att gca gac tcg tta ttg gac att gtc aaa ccc ata aat gac<br>Glu Phe Ile Ala Asp Ser Leu Leu Asp Ile Val Lys Pro Ile Asn Asp<br>355 360 365 | 1104 | |
| gct gtt aca aaa caa ttc ggt ggc tat gga aca aat tta cct gag ata<br>Ala Val Thr Lys Gln Phe Gly Gly Tyr Gly Thr Asn Leu Pro Glu Ile<br>370 375 380 | 1152 | |
| aat ggg gtc att ttg gcg gga ggc tct tcc cga att ccc att gtg cag<br>Asn Gly Val Ile Leu Ala Gly Gly Ser Ser Arg Ile Pro Ile Val Gln<br>385 390 395 400 | 1200 | |
| gat caa tta atc aaa ctc gta tcc gaa gaa aaa gtg ttg aga aat gtc<br>Asp Gln Leu Ile Lys Leu Val Ser Glu Glu Lys Val Leu Arg Asn Val<br>405 410 415 | 1248 | |
| aat gct gat gaa tca gct gtg aat ggt gtt gtt atg aga ggg atc aag<br>Asn Ala Asp Glu Ser Ala Val Asn Gly Val Val Met Arg Gly Ile Lys<br>420 425 430 | 1296 | |
| tta tct aat tcg ttt aag acc aag ccg tta aat gtt gtt gac cgt tct<br>Leu Ser Asn Ser Phe Lys Thr Lys Pro Leu Asn Val Val Asp Arg Ser<br>435 440 445 | 1344 | |
| gta aat act tat tca ttc aaa tta tca aac gaa tct gaa ctg tat gat<br>Val Asn Thr Tyr Ser Phe Lys Leu Ser Asn Glu Ser Glu Leu Tyr Asp<br>450 455 460 | 1392 | |
| gtg ttc acg cgc gga agt gct tat cca aac aaa aca tct att ttg aca<br>Val Phe Thr Arg Gly Ser Ala Tyr Pro Asn Lys Thr Ser Ile Leu Thr<br>465 470 475 480 | 1440 | |
| aac acg act gat tcg att cct aat aat ttt acc att gac tta ttt gag<br>Asn Thr Thr Asp Ser Ile Pro Asn Asn Phe Thr Ile Asp Leu Phe Glu<br>485 490 495 | 1488 | |
| aat ggt aaa ttg ttc gaa act atc aca gtt aat tca gga gct ata aag<br>Asn Gly Lys Leu Phe Glu Thr Ile Thr Val Asn Ser Gly Ala Ile Lys<br>500 505 510 | 1536 | |
| aat tca tat tcc tct gat aag tgc tcg tca gga gtt gcg tat aac att<br>Asn Ser Tyr Ser Ser Asp Lys Cys Ser Ser Gly Val Ala Tyr Asn Ile<br>515 520 525 | 1584 | |
| act ttc gac ttg tcc agt gat aga tta ttc tct att caa gag gtt aac<br>Thr Phe Asp Leu Ser Ser Asp Arg Leu Phe Ser Ile Gln Glu Val Asn<br>530 535 540 | 1632 | |
| tgc att tgt cag agc gaa aat gac ata ggt aac tcc aag caa att aag<br>Cys Ile Cys Gln Ser Glu Asn Asp Ile Gly Asn Ser Lys Gln Ile Lys<br>545 550 555 560 | 1680 | |

```
aac aaa ggc agc cgt ttg gct ttt act tct gag gat gtt gag atc aaa    1728
Asn Lys Gly Ser Arg Leu Ala Phe Thr Ser Glu Asp Val Glu Ile Lys
            565                 570                 575 agg ctt tct cct tca gaa cgt tcg cgt ttg cat gag cat atc aag ttg    1776
Arg Leu Ser Pro Ser Glu Arg Ser Arg Leu His Glu His Ile Lys Leu
        580                 585                 590 ctc gat aaa cag gat aag gaa aga ttt caa ttc caa gaa aat tta aac    1824
Leu Asp Lys Gln Asp Lys Glu Arg Phe Gln Phe Gln Glu Asn Leu Asn
    595                 600                 605 gtt ctt gaa agt aac ttg tat gat gct aga aac ctg cta atg gat gat    1872
Val Leu Glu Ser Asn Leu Tyr Asp Ala Arg Asn Leu Leu Met Asp Asp
610                 615                 620 gaa gtt atg caa aat gga cca aaa tcc caa gta gaa gag tta tcg gag    1920
Glu Val Met Gln Asn Gly Pro Lys Ser Gln Val Glu Glu Leu Ser Glu
625                 630                 635                 640 atg gtt aaa gta tat ttg gat tgg ctc gaa gat gca tcc ttt gat act    1968
Met Val Lys Val Tyr Leu Asp Trp Leu Glu Asp Ala Ser Phe Asp Thr
                645                 650                 655 gac cct gag gat ata gtt agc aga att aga gaa att gga ata tta aaa    2016
Asp Pro Glu Asp Ile Val Ser Arg Ile Arg Glu Ile Gly Ile Leu Lys
            660                 665                 670 aag aaa ata gaa ctt tac atg gat tct gca aag gaa cct ttg aac tct    2064
Lys Lys Ile Glu Leu Tyr Met Asp Ser Ala Lys Glu Pro Leu Asn Ser
        675                 680                 685 caa caa ttt aaa gga atg ctt gaa gaa ggc cat aag tta ctt cag gct    2112
Gln Gln Phe Lys Gly Met Leu Glu Glu Gly His Lys Leu Leu Gln Ala
    690                 695                 700 ata gaa acc cat aag aat acc gtt gaa gaa ttt ttg agt caa ttt gaa    2160
Ile Glu Thr His Lys Asn Thr Val Glu Glu Phe Leu Ser Gln Phe Glu
705                 710                 715                 720 acc gag ttt gcg gat acc ata gat aat gtt aga gaa gaa ttt aaa aag    2208
Thr Glu Phe Ala Asp Thr Ile Asp Asn Val Arg Glu Glu Phe Lys Lys
                725                 730                 735 att aag caa cca gcg tat gtg tcg aag gcg tta tct aca tgg gag gaa    2256
Ile Lys Gln Pro Ala Tyr Val Ser Lys Ala Leu Ser Thr Trp Glu Glu
            740                 745                 750 acc tta acc tct ttt aaa aat tcc att agc gaa ata gag aag ttc ctg    2304
Thr Leu Thr Ser Phe Lys Asn Ser Ile Ser Glu Ile Glu Lys Phe Leu
        755                 760                 765 gca aaa aac cta ttt ggc gaa gac ctt cgt gaa cat tta ttt gaa atc    2352
Ala Lys Asn Leu Phe Gly Glu Asp Leu Arg Glu His Leu Phe Glu Ile
    770                 775                 780 aaa tta caa ttt gat atg tat cgt acg aaa cta gag gaa aaa ctg cgt    2400
Lys Leu Gln Phe Asp Met Tyr Arg Thr Lys Leu Glu Glu Lys Leu Arg
785                 790                 795                 800 tta ata aaa agc ggt gat gaa agt cgc tta aat gaa ata aag aag tta    2448
Leu Ile Lys Ser Gly Asp Glu Ser Arg Leu Asn Glu Ile Lys Lys Leu
                805                 810                 815 cat tta aga aac ttc cgc cta caa aag aga aag gag gaa aag ttg aaa    2496
His Leu Arg Asn Phe Arg Leu Gln Lys Arg Lys Glu Glu Lys Leu Lys
            820                 825                 830 aga aag ctt gaa cag gaa aaa agc aga aac aac aat gaa aca gaa tcg    2544
Arg Lys Leu Glu Gln Glu Lys Ser Arg Asn Asn Asn Glu Thr Glu Ser
        835                 840                 845 aca gta atc aac tcg gct gac gat aaa act act att gtc aat gac aag    2592
Thr Val Ile Asn Ser Ala Asp Asp Lys Thr Thr Ile Val Asn Asp Lys
    850                 855                 860 acc acc gag tcg aat cca agt tct gag gaa gac att ttg cat gat gaa    2640
Thr Thr Glu Ser Asn Pro Ser Ser Glu Glu Asp Ile Leu His Asp Glu
865                 870                 875                 880
```

```
tta tag                                                          2646
Leu

<210> SEQ ID NO 133
<211> LENGTH: 881
<212> TYPE: PRT
<213> ORGANISM: Saccharomyces cerevisiae

<400> SEQUENCE: 133

Met Arg Asn Val Leu Arg Leu Leu Phe Leu Thr Ala Phe Val Ala Ile
 1               5                  10                  15

Gly Ser Leu Ala Ala Val Leu Gly Val Asp Tyr Gly Gln Gln Asn Ile
            20                  25                  30

Lys Ala Ile Val Val Ser Pro Gln Ala Pro Leu Glu Leu Val Leu Thr
        35                  40                  45

Pro Glu Ala Lys Arg Lys Glu Ile Ser Gly Leu Ser Ile Lys Arg Leu
 50                  55                  60

Pro Gly Tyr Gly Lys Asp Asp Pro Asn Gly Ile Glu Arg Ile Tyr Gly
 65                  70                  75                  80

Ser Ala Val Gly Ser Leu Ala Thr Arg Phe Pro Gln Asn Thr Leu Leu
                85                  90                  95

His Leu Lys Pro Leu Leu Gly Lys Ser Leu Glu Asp Glu Thr Thr Val
            100                 105                 110

Thr Leu Tyr Ser Lys Gln His Pro Gly Leu Glu Met Val Ser Thr Asn
        115                 120                 125

Arg Ser Thr Ile Ala Phe Leu Val Asp Asn Val Glu Tyr Pro Leu Glu
130                 135                 140

Glu Leu Val Ala Met Asn Val Gln Glu Ile Ala Asn Arg Ala Asn Ser
145                 150                 155                 160

Leu Leu Lys Asp Arg Asp Ala Arg Thr Glu Asp Phe Val Asn Lys Met
                165                 170                 175

Ser Phe Thr Ile Pro Asp Phe Phe Asp Gln His Gln Arg Lys Ala Leu
            180                 185                 190

Leu Asp Ala Ser Ser Ile Thr Thr Gly Ile Glu Glu Thr Tyr Leu Val
        195                 200                 205

Ser Glu Gly Met Ser Val Ala Val Asn Phe Val Leu Lys Gln Arg Gln
    210                 215                 220

Phe Pro Pro Gly Glu Gln Gln His Tyr Ile Val Tyr Asp Met Gly Ser
225                 230                 235                 240

Gly Ser Ile Lys Ala Ser Met Phe Ser Ile Leu Gln Pro Glu Asp Thr
                245                 250                 255

Thr Gln Pro Val Thr Ile Glu Phe Glu Gly Tyr Gly Tyr Asn Pro His
            260                 265                 270

Leu Gly Gly Ala Lys Phe Thr Met Asp Ile Gly Ser Leu Ile Glu Asn
        275                 280                 285

Lys Phe Leu Glu Thr His Pro Ala Ile Arg Thr Asp Glu Leu His Ala
    290                 295                 300

Asn Pro Lys Ala Leu Ala Lys Ile Asn Gln Ala Ala Glu Lys Ala Lys
305                 310                 315                 320

Leu Ile Leu Ser Ala Asn Ser Glu Ala Ser Ile Asn Ile Glu Ser Leu
                325                 330                 335

Ile Asn Asp Ile Asp Phe Arg Thr Ser Ile Thr Arg Gln Glu Phe Glu
            340                 345                 350

Glu Phe Ile Ala Asp Ser Leu Leu Asp Ile Val Lys Pro Ile Asn Asp
        355                 360                 365
```

```
Ala Val Thr Lys Gln Phe Gly Gly Tyr Gly Thr Asn Leu Pro Glu Ile
    370                 375                 380

Asn Gly Val Ile Leu Ala Gly Gly Ser Ser Arg Ile Pro Ile Val Gln
385                 390                 395                 400

Asp Gln Leu Ile Lys Leu Val Ser Glu Glu Lys Val Leu Arg Asn Val
                405                 410                 415

Asn Ala Asp Glu Ser Ala Val Asn Gly Val Val Met Arg Gly Ile Lys
            420                 425                 430

Leu Ser Asn Ser Phe Lys Thr Lys Pro Leu Asn Val Val Asp Arg Ser
        435                 440                 445

Val Asn Thr Tyr Ser Phe Lys Leu Ser Asn Glu Ser Glu Leu Tyr Asp
    450                 455                 460

Val Phe Thr Arg Gly Ser Ala Tyr Pro Asn Lys Thr Ser Ile Leu Thr
465                 470                 475                 480

Asn Thr Thr Asp Ser Ile Pro Asn Asn Phe Thr Ile Asp Leu Phe Glu
                485                 490                 495

Asn Gly Lys Leu Phe Glu Thr Ile Thr Val Asn Ser Gly Ala Ile Lys
            500                 505                 510

Asn Ser Tyr Ser Ser Asp Lys Cys Ser Ser Gly Val Ala Tyr Asn Ile
        515                 520                 525

Thr Phe Asp Leu Ser Ser Asp Arg Leu Phe Ser Ile Gln Glu Val Asn
    530                 535                 540

Cys Ile Cys Gln Ser Glu Asn Asp Ile Gly Asn Ser Lys Gln Ile Lys
545                 550                 555                 560

Asn Lys Gly Ser Arg Leu Ala Phe Thr Ser Glu Asp Val Glu Ile Lys
                565                 570                 575

Arg Leu Ser Pro Ser Glu Arg Ser Arg Leu His Glu His Ile Lys Leu
            580                 585                 590

Leu Asp Lys Gln Asp Lys Glu Arg Phe Gln Phe Gln Glu Asn Leu Asn
        595                 600                 605

Val Leu Glu Ser Asn Leu Tyr Asp Ala Arg Asn Leu Leu Met Asp Asp
    610                 615                 620

Glu Val Met Gln Asn Gly Pro Lys Ser Gln Val Glu Glu Leu Ser Glu
625                 630                 635                 640

Met Val Lys Val Tyr Leu Asp Trp Leu Glu Asp Ala Ser Phe Asp Thr
                645                 650                 655

Asp Pro Glu Asp Ile Val Ser Arg Ile Arg Glu Ile Gly Ile Leu Lys
            660                 665                 670

Lys Lys Ile Glu Leu Tyr Met Asp Ser Ala Lys Glu Pro Leu Asn Ser
        675                 680                 685

Gln Gln Phe Lys Gly Met Leu Glu Glu Gly His Lys Leu Leu Gln Ala
    690                 695                 700

Ile Glu Thr His Lys Asn Thr Val Glu Glu Phe Leu Ser Gln Phe Glu
705                 710                 715                 720

Thr Glu Phe Ala Asp Thr Ile Asp Asn Val Arg Glu Glu Phe Lys Lys
                725                 730                 735

Ile Lys Gln Pro Ala Tyr Val Ser Lys Ala Leu Ser Thr Trp Glu Glu
            740                 745                 750

Thr Leu Thr Ser Phe Lys Asn Ser Ile Ser Glu Ile Glu Lys Phe Leu
        755                 760                 765

Ala Lys Asn Leu Phe Gly Glu Asp Leu Arg Glu His Leu Phe Glu Ile
    770                 775                 780

Lys Leu Gln Phe Asp Met Tyr Arg Thr Lys Leu Glu Glu Lys Leu Arg
```

```
               785                 790                 795                 800
Leu Ile Lys Ser Gly Asp Glu Ser Arg Leu Asn Glu Ile Lys Lys Leu
                805                 810                 815

His Leu Arg Asn Phe Arg Leu Gln Lys Arg Lys Glu Lys Leu Lys
                820                 825                 830

Arg Lys Leu Glu Gln Glu Lys Ser Arg Asn Asn Asn Glu Thr Glu Ser
            835                 840                 845

Thr Val Ile Asn Ser Ala Asp Asp Lys Thr Thr Ile Val Asn Asp Lys
            850                 855                 860

Thr Thr Glu Ser Asn Pro Ser Ser Glu Glu Asp Ile Leu His Asp Glu
865                 870                 875                 880

Leu

<210> SEQ ID NO 134
<211> LENGTH: 834
<212> TYPE: DNA
<213> ORGANISM: Saccharomyces cerevisiae
<220> FEATURE:
<221> NAME/KEY: CDS
<222> LOCATION: (1)..(834)

<400> SEQUENCE: 134 atg aaa ttg cac ggc ttt tta ttt tcc gta tta tca aca tgc gtc gtc        48
Met Lys Leu His Gly Phe Leu Phe Ser Val Leu Ser Thr Cys Val Val
1               5                   10                  15 att tta cca gcg ttg gcc tac agt gaa gct gtc acg atg gtc aag tcg        96
Ile Leu Pro Ala Leu Ala Tyr Ser Glu Ala Val Thr Met Val Lys Ser
                20                  25                  30 att gag cag tac ttc gat atc tgc aat agg aat gat tct tac aca atg       144
Ile Glu Gln Tyr Phe Asp Ile Cys Asn Arg Asn Asp Ser Tyr Thr Met
            35                  40                  45 ata aaa tac tac act tct tgg tgc caa cat tgt aaa act ctg gcc cca       192
Ile Lys Tyr Tyr Thr Ser Trp Cys Gln His Cys Lys Thr Leu Ala Pro
        50                  55                  60 gta tac gaa gag ctt ggt gag cta tac gcc aaa aaa gct aat aaa gat       240
Val Tyr Glu Glu Leu Gly Glu Leu Tyr Ala Lys Lys Ala Asn Lys Asp
65                  70                  75                  80 gat acc cca att aac ttc ctt gaa gtt aac tgt gaa ttc ttc ggg cca       288
Asp Thr Pro Ile Asn Phe Leu Glu Val Asn Cys Glu Phe Phe Gly Pro
                85                  90                  95 act tta tgt acc gac ttg cct gga ttt cca ata att gaa ctg gtc aaa       336
Thr Leu Cys Thr Asp Leu Pro Gly Phe Pro Ile Ile Glu Leu Val Lys
                100                 105                 110 cct cgt act aag ccc tta gtt ctt ccg aag ctc gat tgg tcg tct atg       384
Pro Arg Thr Lys Pro Leu Val Leu Pro Lys Leu Asp Trp Ser Ser Met
            115                 120                 125 aaa ttt cat gaa aga cta tgg caa aga atc aag acg tgg ttc aac aat       432
Lys Phe His Glu Arg Leu Trp Gln Arg Ile Lys Thr Trp Phe Asn Asn
        130                 135                 140 cct aag tac caa ctg gat acg tct agg gtt gtt cgt ttt gaa ggg agt       480
Pro Lys Tyr Gln Leu Asp Thr Ser Arg Val Val Arg Phe Glu Gly Ser
145                 150                 155                 160 agg aac cta aag agt tta agc aac ttt atc gat act gta aga agt aaa       528
Arg Asn Leu Lys Ser Leu Ser Asn Phe Ile Asp Thr Val Arg Ser Lys
                165                 170                 175 gat aca gaa gaa aga ttc ata gaa cat att ttc gat gat tct agg aat       576
Asp Thr Glu Glu Arg Phe Ile Glu His Ile Phe Asp Asp Ser Arg Asn
            180                 185                 190 tgc aat gaa gaa tta cgt tct caa cag ctt ctg tgt aaa gct ggt aaa       624
Cys Asn Glu Glu Leu Arg Ser Gln Gln Leu Leu Cys Lys Ala Gly Lys
```

```
              195                 200                 205
gaa tac tac tct gat act tta tct aaa tta tac ggt gac gtg aat ggg        672
Glu Tyr Tyr Ser Asp Thr Leu Ser Lys Leu Tyr Gly Asp Val Asn Gly
    210                 215                 220 ctg gaa aag gaa agg cga aga cta gaa gct tta att aag caa aat gga        720
Leu Glu Lys Glu Arg Arg Arg Leu Glu Ala Leu Ile Lys Gln Asn Gly
225                 230                 235                 240 gat gac ttg agt aaa gaa gtt aaa gaa aaa ctg aaa atc att cgt cta        768
Asp Asp Leu Ser Lys Glu Val Lys Glu Lys Leu Lys Ile Ile Arg Leu
                245                 250                 255 caa ttg agc cta tta tca cac ata gaa gac cag tta gaa gat acc agt        816
Gln Leu Ser Leu Leu Ser His Ile Glu Asp Gln Leu Glu Asp Thr Ser
            260                 265                 270 agt cat gac gag ctt tga                                                834
Ser His Asp Glu Leu
            275

<210> SEQ ID NO 135
<211> LENGTH: 277
<212> TYPE: PRT
<213> ORGANISM: Saccharomyces cerevisiae

<400> SEQUENCE: 135

Met Lys Leu His Gly Phe Leu Phe Ser Val Leu Ser Thr Cys Val Val
1               5                   10                  15

Ile Leu Pro Ala Leu Ala Tyr Ser Glu Ala Val Thr Met Val Lys Ser
            20                  25                  30

Ile Glu Gln Tyr Phe Asp Ile Cys Asn Arg Asn Asp Ser Tyr Thr Met
        35                  40                  45

Ile Lys Tyr Tyr Thr Ser Trp Cys Gln His Cys Lys Thr Leu Ala Pro
    50                  55                  60

Val Tyr Glu Glu Leu Gly Glu Leu Tyr Ala Lys Lys Ala Asn Lys Asp
65                  70                  75                  80

Asp Thr Pro Ile Asn Phe Leu Glu Val Asn Cys Glu Phe Phe Gly Pro
                85                  90                  95

Thr Leu Cys Thr Asp Leu Pro Gly Phe Pro Ile Ile Glu Leu Val Lys
            100                 105                 110

Pro Arg Thr Lys Pro Leu Val Leu Pro Lys Leu Asp Trp Ser Ser Met
        115                 120                 125

Lys Phe His Glu Arg Leu Trp Gln Arg Ile Lys Thr Trp Phe Asn Asn
    130                 135                 140

Pro Lys Tyr Gln Leu Asp Thr Ser Arg Val Val Arg Phe Glu Gly Ser
145                 150                 155                 160

Arg Asn Leu Lys Ser Leu Ser Asn Phe Ile Asp Thr Val Arg Ser Lys
                165                 170                 175

Asp Thr Glu Glu Arg Phe Ile Glu His Ile Phe Asp Asp Ser Arg Asn
            180                 185                 190

Cys Asn Glu Glu Leu Arg Ser Gln Gln Leu Leu Cys Lys Ala Gly Lys
        195                 200                 205

Glu Tyr Tyr Ser Asp Thr Leu Ser Lys Leu Tyr Gly Asp Val Asn Gly
    210                 215                 220

Leu Glu Lys Glu Arg Arg Arg Leu Glu Ala Leu Ile Lys Gln Asn Gly
225                 230                 235                 240

Asp Asp Leu Ser Lys Glu Val Lys Glu Lys Leu Lys Ile Ile Arg Leu
                245                 250                 255

Gln Leu Ser Leu Leu Ser His Ile Glu Asp Gln Leu Glu Asp Thr Ser
            260                 265                 270
```

Ser His Asp Glu Leu
        275

<210> SEQ ID NO 136
<211> LENGTH: 888
<212> TYPE: DNA
<213> ORGANISM: Saccharomyces cerevisiae
<220> FEATURE:
<221> NAME/KEY: CDS
<222> LOCATION: (1)..(888)

<400> SEQUENCE: 136

| | | | | | | | | | | | | | | | | |
|---|---|---|---|---|---|---|---|---|---|---|---|---|---|---|---|---|
| atg | aac | ggt | tac | tgg | aaa | cct | gcg | ttg | gtt | gtc | ctg | gga | ttg | gta | tct | 48 |
| Met | Asn | Gly | Tyr | Trp | Lys | Pro | Ala | Leu | Val | Val | Leu | Gly | Leu | Val | Ser | |
| 1 | | | | 5 | | | | | 10 | | | | | 15 | | |
| cta | tca | tat | gct | ttt | acc | acc | att | gaa | aca | gaa | att | ttc | caa | tta | caa | 96 |
| Leu | Ser | Tyr | Ala | Phe | Thr | Thr | Ile | Glu | Thr | Glu | Ile | Phe | Gln | Leu | Gln | |
| | | | 20 | | | | | 25 | | | | | 30 | | | |
| aat | gaa | ata | agt | acg | aaa | tat | ggc | cca | gat | atg | aac | ttc | tac | aag | ttc | 144 |
| Asn | Glu | Ile | Ser | Thr | Lys | Tyr | Gly | Pro | Asp | Met | Asn | Phe | Tyr | Lys | Phe | |
| | | 35 | | | | | 40 | | | | | 45 | | | | |
| ttg | aag | tta | cct | aaa | ctg | cag | aat | tct | agt | aca | aag | gag | att | aca | aaa | 192 |
| Leu | Lys | Leu | Pro | Lys | Leu | Gln | Asn | Ser | Ser | Thr | Lys | Glu | Ile | Thr | Lys | |
| 50 | | | | | 55 | | | | | 60 | | | | | | |
| aac | tta | aga | aag | cta | tcc | aag | aag | tac | cat | ccg | gat | aag | aac | cct | aaa | 240 |
| Asn | Leu | Arg | Lys | Leu | Ser | Lys | Lys | Tyr | His | Pro | Asp | Lys | Asn | Pro | Lys | |
| 65 | | | | | 70 | | | | | 75 | | | | | 80 | |
| tac | cgt | aaa | ttg | tat | gaa | agg | tta | aac | ctc | gct | act | caa | att | ctt | tca | 288 |
| Tyr | Arg | Lys | Leu | Tyr | Glu | Arg | Leu | Asn | Leu | Ala | Thr | Gln | Ile | Leu | Ser | |
| | | | | 85 | | | | | 90 | | | | | 95 | | |
| aac | agc | tct | aat | cgt | aag | att | tat | gat | tat | tat | cta | cag | aat | ggc | ttt | 336 |
| Asn | Ser | Ser | Asn | Arg | Lys | Ile | Tyr | Asp | Tyr | Tyr | Leu | Gln | Asn | Gly | Phe | |
| | | | 100 | | | | | 105 | | | | | 110 | | | |
| cca | aac | tat | gat | ttc | cat | aag | ggt | ggt | ttt | tat | ttt | tcc | aga | atg | aag | 384 |
| Pro | Asn | Tyr | Asp | Phe | His | Lys | Gly | Gly | Phe | Tyr | Phe | Ser | Arg | Met | Lys | |
| | | 115 | | | | | 120 | | | | | 125 | | | | |
| cct | aag | act | tgg | ttc | ctg | ctg | gcc | ttt | att | tgg | ata | gtc | gtt | aat | att | 432 |
| Pro | Lys | Thr | Trp | Phe | Leu | Leu | Ala | Phe | Ile | Trp | Ile | Val | Val | Asn | Ile | |
| | 130 | | | | | 135 | | | | | 140 | | | | | |
| ggg | cag | tat | atc | att | tct | att | att | caa | tat | cgt | tct | caa | aga | tca | aga | 480 |
| Gly | Gln | Tyr | Ile | Ile | Ser | Ile | Ile | Gln | Tyr | Arg | Ser | Gln | Arg | Ser | Arg | |
| 145 | | | | | 150 | | | | | 155 | | | | | 160 | |
| att | gaa | aac | ttc | atc | agt | cag | tgt | aaa | caa | cag | gat | gat | acc | aat | gga | 528 |
| Ile | Glu | Asn | Phe | Ile | Ser | Gln | Cys | Lys | Gln | Gln | Asp | Asp | Thr | Asn | Gly | |
| | | | | 165 | | | | | 170 | | | | | 175 | | |
| cta | ggc | gta | aaa | caa | cta | acg | ttt | aaa | caa | cat | gaa | aag | gat | gag | ggt | 576 |
| Leu | Gly | Val | Lys | Gln | Leu | Thr | Phe | Lys | Gln | His | Glu | Lys | Asp | Glu | Gly | |
| | | | 180 | | | | | 185 | | | | | 190 | | | |
| aaa | agt | ttg | gtt | gta | agg | ttt | agc | gat | gtc | tat | gtt | gta | gag | cct | gat | 624 |
| Lys | Ser | Leu | Val | Val | Arg | Phe | Ser | Asp | Val | Tyr | Val | Val | Glu | Pro | Asp | |
| | | 195 | | | | | 200 | | | | | 205 | | | | |
| gga | agt | gaa | aca | cta | att | tcg | cca | gat | acc | ttg | gat | aaa | cct | tca | gta | 672 |
| Gly | Ser | Glu | Thr | Leu | Ile | Ser | Pro | Asp | Thr | Leu | Asp | Lys | Pro | Ser | Val | |
| | 210 | | | | | 215 | | | | | 220 | | | | | |
| aag | aac | tgt | ttg | ttt | tgg | aga | ata | cct | gct | tcg | gtt | tgg | aac | atg | acg | 720 |
| Lys | Asn | Cys | Leu | Phe | Trp | Arg | Ile | Pro | Ala | Ser | Val | Trp | Asn | Met | Thr | |
| 225 | | | | | 230 | | | | | 235 | | | | | 240 | |
| ttt | ggc | aaa | tct | gtt | ggt | agc | gca | gga | aaa | gaa | gaa | ata | ata | acg | gat | 768 |
| Phe | Gly | Lys | Ser | Val | Gly | Ser | Ala | Gly | Lys | Glu | Glu | Ile | Ile | Thr | Asp | |
| | | | | 245 | | | | | 250 | | | | | 255 | | |
| agt | aaa | aag | tat | gat | ggt | aac | caa | aca | aaa | aag | ggg | aac | aaa | gta | aaa | 816 |

```
Ser Lys Lys Tyr Asp Gly Asn Gln Thr Lys Lys Gly Asn Lys Val Lys
            260                 265                 270 aag ggt tct gca aag aaa ggc caa aag aaa atg gaa ttg cct aac ggt        864
Lys Gly Ser Ala Lys Lys Gly Gln Lys Lys Met Glu Leu Pro Asn Gly
        275                 280                 285 aaa gtg atc tat tca cgt aaa tga                                        888
Lys Val Ile Tyr Ser Arg Lys
290                 295
```

<210> SEQ ID NO 137
<211> LENGTH: 295
<212> TYPE: PRT
<213> ORGANISM: Saccharomyces cerevisiae

<400> SEQUENCE: 137

```
Met Asn Gly Tyr Trp Lys Pro Ala Leu Val Val Gly Leu Val Ser
1               5                   10                  15

Leu Ser Tyr Ala Phe Thr Thr Ile Glu Thr Glu Ile Phe Gln Leu Gln
            20                  25                  30

Asn Glu Ile Ser Thr Lys Tyr Gly Pro Asp Met Asn Phe Tyr Lys Phe
        35                  40                  45

Leu Lys Leu Pro Lys Leu Gln Asn Ser Ser Thr Lys Glu Ile Thr Lys
50                  55                  60

Asn Leu Arg Lys Leu Ser Lys Lys Tyr His Pro Asp Lys Asn Pro Lys
65                  70                  75                  80

Tyr Arg Lys Leu Tyr Glu Arg Leu Asn Leu Ala Thr Gln Ile Leu Ser
                85                  90                  95

Asn Ser Ser Asn Arg Lys Ile Tyr Asp Tyr Tyr Leu Gln Asn Gly Phe
            100                 105                 110

Pro Asn Tyr Asp Phe His Lys Gly Gly Phe Tyr Phe Ser Arg Met Lys
        115                 120                 125

Pro Lys Thr Trp Phe Leu Leu Ala Phe Ile Trp Ile Val Val Asn Ile
130                 135                 140

Gly Gln Tyr Ile Ile Ser Ile Ile Gln Tyr Arg Ser Gln Arg Ser Arg
145                 150                 155                 160

Ile Glu Asn Phe Ile Ser Gln Cys Lys Gln Gln Asp Asp Thr Asn Gly
                165                 170                 175

Leu Gly Val Lys Gln Leu Thr Phe Lys Gln His Glu Lys Asp Glu Gly
            180                 185                 190

Lys Ser Leu Val Val Arg Phe Ser Asp Val Tyr Val Glu Pro Asp
        195                 200                 205

Gly Ser Glu Thr Leu Ile Ser Pro Asp Thr Leu Asp Lys Pro Ser Val
210                 215                 220

Lys Asn Cys Leu Phe Trp Arg Ile Pro Ala Ser Val Trp Asn Met Thr
225                 230                 235                 240

Phe Gly Lys Ser Val Gly Ser Ala Gly Lys Glu Glu Ile Ile Thr Asp
                245                 250                 255

Ser Lys Lys Tyr Asp Gly Asn Gln Thr Lys Lys Gly Asn Lys Val Lys
            260                 265                 270

Lys Gly Ser Ala Lys Lys Gly Gln Lys Lys Met Glu Leu Pro Asn Gly
        275                 280                 285

Lys Val Ile Tyr Ser Arg Lys
290                 295
```

<210> SEQ ID NO 138
<211> LENGTH: 1554
<212> TYPE: DNA

<213> ORGANISM: Saccharomyces cerevisiae
<220> FEATURE:
<221> NAME/KEY: CDS
<222> LOCATION: (1)..(1554)

<400> SEQUENCE: 138

```
atg caa gtg acc aca aga ttt ata tct gcg ata gtc tcg ttt tgc ctg      48
Met Gln Val Thr Thr Arg Phe Ile Ser Ala Ile Val Ser Phe Cys Leu
1               5                   10                  15 ttt gct tct ttc acg ttg gct gaa aac agc gca aga gct acg ccg gga      96
Phe Ala Ser Phe Thr Leu Ala Glu Asn Ser Ala Arg Ala Thr Pro Gly
            20                  25                  30 tca gat tta ctc gtt cta aca gag aag aaa ttt aaa tca ttc atc gaa     144
Ser Asp Leu Leu Val Leu Thr Glu Lys Lys Phe Lys Ser Phe Ile Glu
        35                  40                  45 tct cat ccg tta gtc ctc gtc gag ttt ttt gct cca tgg tgt ttg cat     192
Ser His Pro Leu Val Leu Val Glu Phe Phe Ala Pro Trp Cys Leu His
    50                  55                  60 tct cag atc tta cgc cct cac tta gaa gag gcc gcc tct att tta aag     240
Ser Gln Ile Leu Arg Pro His Leu Glu Glu Ala Ala Ser Ile Leu Lys
65                  70                  75                  80 gag cat aac gtc cca gtt gtt caa att gat tgt gag gct aac agt atg     288
Glu His Asn Val Pro Val Val Gln Ile Asp Cys Glu Ala Asn Ser Met
                85                  90                  95 gtt tgc ctg caa caa act ata aat acc tac cca acc ttg aaa atc ttt     336
Val Cys Leu Gln Gln Thr Ile Asn Thr Tyr Pro Thr Leu Lys Ile Phe
            100                 105                 110 aaa aat ggt cgt att ttt gat ggt caa gtc tat cgc ggt gtc aag atc     384
Lys Asn Gly Arg Ile Phe Asp Gly Gln Val Tyr Arg Gly Val Lys Ile
        115                 120                 125 acc gat gaa atc act cag tac atg att cag cta tac gag gct tct gtc     432
Thr Asp Glu Ile Thr Gln Tyr Met Ile Gln Leu Tyr Glu Ala Ser Val
    130                 135                 140 att tat tta aat tcc gaa gat gaa atc caa cca tac ttg gaa aat gca     480
Ile Tyr Leu Asn Ser Glu Asp Glu Ile Gln Pro Tyr Leu Glu Asn Ala
145                 150                 155                 160 act tta cca gta gta ata aac aga ggc ttg aca ggc ttg aat gaa acg     528
Thr Leu Pro Val Val Ile Asn Arg Gly Leu Thr Gly Leu Asn Glu Thr
                165                 170                 175 tat caa gaa gtc gca ctg gac ctt gct gag gat tac gtc ttt tta tcc     576
Tyr Gln Glu Val Ala Leu Asp Leu Ala Glu Asp Tyr Val Phe Leu Ser
            180                 185                 190 ctt cta gat tca gaa gat aag tca tta tca atc cac ttg cca aac act     624
Leu Leu Asp Ser Glu Asp Lys Ser Leu Ser Ile His Leu Pro Asn Thr
        195                 200                 205 aca gaa cca att ctg ttt gat gga aat gta gac tct ttg gtc gga aat     672
Thr Glu Pro Ile Leu Phe Asp Gly Asn Val Asp Ser Leu Val Gly Asn
    210                 215                 220 tcc gtt gct cta act cag tgg tta aaa gtg gta att tta cct tac ttt     720
Ser Val Ala Leu Thr Gln Trp Leu Lys Val Val Ile Leu Pro Tyr Phe
225                 230                 235                 240 acc gac atc gaa cct gat ctc ttc ccc aag tac att tct agc aat ttg     768
Thr Asp Ile Glu Pro Asp Leu Phe Pro Lys Tyr Ile Ser Ser Asn Leu
                245                 250                 255 ccg ttg gct tac ttc ttt tat act tct gag gaa gaa ttg gaa gat tac     816
Pro Leu Ala Tyr Phe Phe Tyr Thr Ser Glu Glu Glu Leu Glu Asp Tyr
            260                 265                 270 act gat ctt ttc acg cag tta ggt aag gaa aat cgt ggc caa ata aat     864
Thr Asp Leu Phe Thr Gln Leu Gly Lys Glu Asn Arg Gly Gln Ile Asn
        275                 280                 285 ttc att gca tta aac tct aca atg ttc cca cac cac gtt aga ttc cta     912
```

```
        Phe Ile Ala Leu Asn Ser Thr Met Phe Pro His His Val Arg Phe Leu
            290                 295                 300 aat atg aga gaa cag ttc cca tta ttt gct atc cat aat atg atc aat        960
Asn Met Arg Glu Gln Phe Pro Leu Phe Ala Ile His Asn Met Ile Asn
305                 310                 315                 320 aat ctg aaa tat ggt tta cca caa cta cca gaa gaa gag tac gcg aaa       1008
Asn Leu Lys Tyr Gly Leu Pro Gln Leu Pro Glu Glu Glu Tyr Ala Lys
                325                 330                 335 tta gaa aaa cca caa cca cta gac aga gat atg atc gtt cag ttg gta       1056
Leu Glu Lys Pro Gln Pro Leu Asp Arg Asp Met Ile Val Gln Leu Val
            340                 345                 350 aaa gat tac cgt gaa ggt act gcc aag cca att gtt aag tca gaa gag       1104
Lys Asp Tyr Arg Glu Gly Thr Ala Lys Pro Ile Val Lys Ser Glu Glu
        355                 360                 365 att cca aaa gaa caa aag tcc aat gtt tat aaa ata gtt ggg aag aca       1152
Ile Pro Lys Glu Gln Lys Ser Asn Val Tyr Lys Ile Val Gly Lys Thr
370                 375                 380 cat gac gac att gtt cat gat gat gac aag gat gtc ctt gtc aaa tat       1200
His Asp Asp Ile Val His Asp Asp Asp Lys Asp Val Leu Val Lys Tyr
385                 390                 395                 400 tac gcg aca tgg tgt att cat agt aaa agg ttt gcg cct att tac gaa       1248
Tyr Ala Thr Trp Cys Ile His Ser Lys Arg Phe Ala Pro Ile Tyr Glu
                405                 410                 415 gaa att gca aat gtc tta gca tct gat gaa tct gtt cgc gat aaa atc       1296
Glu Ile Ala Asn Val Leu Ala Ser Asp Glu Ser Val Arg Asp Lys Ile
            420                 425                 430 ttg atc gcc gaa gta gat tca ggg gca aat gat atc tta agt ttt cct       1344
Leu Ile Ala Glu Val Asp Ser Gly Ala Asn Asp Ile Leu Ser Phe Pro
        435                 440                 445 gtg aca gga tat cca acc att gct ttg tat cct gcc gga aat aac tct       1392
Val Thr Gly Tyr Pro Thr Ile Ala Leu Tyr Pro Ala Gly Asn Asn Ser
450                 455                 460 aag cct att atc ttc aat aaa att aga aat ttg gaa gat gtt ttc gaa       1440
Lys Pro Ile Ile Phe Asn Lys Ile Arg Asn Leu Glu Asp Val Phe Glu
465                 470                 475                 480 ttt atc aag gaa tca ggt aca cat cac att gac ggc cag gca att tat       1488
Phe Ile Lys Glu Ser Gly Thr His His Ile Asp Gly Gln Ala Ile Tyr
                485                 490                 495 gat aaa ttg cac cag gcc aag gat tct gaa gtg tct act gaa gat acc       1536
Asp Lys Leu His Gln Ala Lys Asp Ser Glu Val Ser Thr Glu Asp Thr
            500                 505                 510 gta cat gat gaa tta taa                                               1554
Val His Asp Glu Leu
        515

<210> SEQ ID NO 139
<211> LENGTH: 517
<212> TYPE: PRT
<213> ORGANISM: Saccharomyces cerevisiae

<400> SEQUENCE: 139

Met Gln Val Thr Thr Arg Phe Ile Ser Ala Ile Val Ser Phe Cys Leu
1               5                   10                  15

Phe Ala Ser Phe Thr Leu Ala Glu Asn Ser Ala Arg Ala Thr Pro Gly
                20                  25                  30

Ser Asp Leu Leu Val Leu Thr Glu Lys Lys Phe Lys Ser Phe Ile Glu
            35                  40                  45

Ser His Pro Leu Val Leu Glu Phe Phe Ala Pro Trp Cys Leu His
        50                  55                  60

Ser Gln Ile Leu Arg Pro His Leu Glu Glu Ala Ala Ser Ile Leu Lys
```

```
                65                  70                  75                  80
Glu His Asn Val Pro Val Gln Ile Asp Cys Glu Ala Asn Ser Met
                        85                  90                  95
Val Cys Leu Gln Gln Thr Ile Asn Thr Tyr Pro Thr Leu Lys Ile Phe
                100                 105                 110

Lys Asn Gly Arg Ile Phe Asp Gly Gln Val Tyr Arg Gly Val Lys Ile
                115                 120                 125

Thr Asp Glu Ile Thr Gln Tyr Met Ile Gln Leu Tyr Glu Ala Ser Val
            130                 135                 140

Ile Tyr Leu Asn Ser Glu Asp Glu Ile Gln Pro Tyr Leu Glu Asn Ala
145                 150                 155                 160

Thr Leu Pro Val Val Ile Asn Arg Gly Leu Thr Gly Leu Asn Glu Thr
                    165                 170                 175

Tyr Gln Glu Val Ala Leu Asp Leu Ala Glu Asp Tyr Val Phe Leu Ser
                180                 185                 190

Leu Leu Asp Ser Glu Asp Lys Ser Leu Ser Ile His Leu Pro Asn Thr
                195                 200                 205

Thr Glu Pro Ile Leu Phe Asp Gly Asn Val Asp Ser Leu Val Gly Asn
            210                 215                 220

Ser Val Ala Leu Thr Gln Trp Leu Lys Val Val Ile Leu Pro Tyr Phe
225                 230                 235                 240

Thr Asp Ile Glu Pro Asp Leu Phe Pro Lys Tyr Ile Ser Ser Asn Leu
                    245                 250                 255

Pro Leu Ala Tyr Phe Phe Tyr Thr Ser Glu Glu Glu Leu Glu Asp Tyr
                260                 265                 270

Thr Asp Leu Phe Thr Gln Leu Gly Lys Glu Asn Arg Gly Gln Ile Asn
                275                 280                 285

Phe Ile Ala Leu Asn Ser Thr Met Phe Pro His His Val Arg Phe Leu
            290                 295                 300

Asn Met Arg Glu Gln Phe Pro Leu Phe Ala Ile His Asn Met Ile Asn
305                 310                 315                 320

Asn Leu Lys Tyr Gly Leu Pro Gln Leu Pro Glu Glu Tyr Ala Lys
                    325                 330                 335

Leu Glu Lys Pro Gln Pro Leu Asp Arg Asp Met Ile Val Gln Leu Val
                340                 345                 350

Lys Asp Tyr Arg Glu Gly Thr Ala Lys Pro Ile Val Lys Ser Glu Glu
                355                 360                 365

Ile Pro Lys Glu Gln Lys Ser Asn Val Tyr Lys Ile Val Gly Lys Thr
            370                 375                 380

His Asp Asp Ile Val His Asp Asp Lys Asp Val Leu Val Lys Tyr
385                 390                 395                 400

Tyr Ala Thr Trp Cys Ile His Ser Lys Arg Phe Ala Pro Ile Tyr Glu
                    405                 410                 415

Glu Ile Ala Asn Val Leu Ala Ser Asp Glu Ser Val Arg Asp Lys Ile
                420                 425                 430

Leu Ile Ala Glu Val Asp Ser Gly Ala Asn Asp Ile Leu Ser Phe Pro
                435                 440                 445

Val Thr Gly Tyr Pro Thr Ile Ala Leu Tyr Pro Ala Gly Asn Asn Ser
            450                 455                 460

Lys Pro Ile Ile Phe Asn Lys Ile Arg Asn Leu Glu Asp Val Phe Glu
465                 470                 475                 480

Phe Ile Lys Glu Ser Gly Thr His Ile Asp Gly Gln Ala Ile Tyr
                    485                 490                 495
```

```
                        Asp Lys Leu His Gln Ala Lys Asp Ser Glu Val Ser Thr Glu Asp Thr
                                        500                 505                 510

Val His Asp Glu Leu
                                515

<210> SEQ ID NO 140
<211> LENGTH: 1527
<212> TYPE: DNA
<213> ORGANISM: Homo sapiens
<220> FEATURE:
<221> NAME/KEY: CDS
<222> LOCATION: (1)..(1527)

<400> SEQUENCE: 140 atg ctg cgc cgc gct ctg ctg tgc ctg gcc gtg gcc gcc ctg gtg cgc       48
Met Leu Arg Arg Ala Leu Leu Cys Leu Ala Val Ala Ala Leu Val Arg
1               5                   10                  15 gcc gac gcc ccc gag gag gag gac cac gtc ctg gtg ctg cgg aaa agc       96
Ala Asp Ala Pro Glu Glu Glu Asp His Val Leu Val Leu Arg Lys Ser
            20                  25                  30 aac ttc gcg gag gcg ctg gcg gcc cac aag tac ctg ctg gtg gag ttc      144
Asn Phe Ala Glu Ala Leu Ala Ala His Lys Tyr Leu Leu Val Glu Phe
        35                  40                  45 tat gcc cct tgg tgt ggc cac tgc aag gct ctg gcc cct gag tat gcc      192
Tyr Ala Pro Trp Cys Gly His Cys Lys Ala Leu Ala Pro Glu Tyr Ala
    50                  55                  60 aaa gcc gct ggg aag ctg aag gca gaa ggt tcc gag atc agg ttg gcc      240
Lys Ala Ala Gly Lys Leu Lys Ala Glu Gly Ser Glu Ile Arg Leu Ala
65                  70                  75                  80 aag gtg gac gcc acg gag gag tct gac ctg gcc cag cag tac ggc gtg      288
Lys Val Asp Ala Thr Glu Glu Ser Asp Leu Ala Gln Gln Tyr Gly Val
                85                  90                  95 cgc ggc tat ccc acc atc aag ttc ttc agg aat gga gac acg gct tcc      336
Arg Gly Tyr Pro Thr Ile Lys Phe Phe Arg Asn Gly Asp Thr Ala Ser
            100                 105                 110 ccc aag gaa tat aca gct ggc aga gag gct gat gac atc gtg aac tgg      384
Pro Lys Glu Tyr Thr Ala Gly Arg Glu Ala Asp Asp Ile Val Asn Trp
        115                 120                 125 ctg aag aag cgc acg ggc ccg gct gcc acc acc ctg cct gac ggc gca      432
Leu Lys Lys Arg Thr Gly Pro Ala Ala Thr Thr Leu Pro Asp Gly Ala
    130                 135                 140 gct gca gag tcc ttg gtg gag tcc agc gag gtg gct gtc atc ggc ttc      480
Ala Ala Glu Ser Leu Val Glu Ser Ser Glu Val Ala Val Ile Gly Phe
145                 150                 155                 160 ttc aag gac gtg gag tcg gac tct gcc aag cag ttt ttg cag gca gca      528
Phe Lys Asp Val Glu Ser Asp Ser Ala Lys Gln Phe Leu Gln Ala Ala
                165                 170                 175 gag gcc atc gat gac ata cca ttt ggg atc act tcc aac agt gac gtg      576
Glu Ala Ile Asp Asp Ile Pro Phe Gly Ile Thr Ser Asn Ser Asp Val
            180                 185                 190 ttc tcc aaa tac cag ctc gac aaa gat ggg gtt gtc ctc ttt aag aag      624
Phe Ser Lys Tyr Gln Leu Asp Lys Asp Gly Val Val Leu Phe Lys Lys
        195                 200                 205 ttt gat gaa ggc cgg aac aac ttt gaa ggg gag gtc acc aag gag aac      672
Phe Asp Glu Gly Arg Asn Asn Phe Glu Gly Glu Val Thr Lys Glu Asn
    210                 215                 220 ctg ctg gac ttt atc aaa cac aac cag ctg ccc ctt gtc atc gag ttc      720
Leu Leu Asp Phe Ile Lys His Asn Gln Leu Pro Leu Val Ile Glu Phe
225                 230                 235                 240 acc gag cag aca gcc ccg aag att ttt gga ggt gaa atc aag act cac      768
Thr Glu Gln Thr Ala Pro Lys Ile Phe Gly Gly Glu Ile Lys Thr His
                245                 250                 255
```

| | | | | | | | | | | | | | | | | |
|---|---|---|---|---|---|---|---|---|---|---|---|---|---|---|---|---|
| atc | ctg | ctg | ttc | ttg | ccc | aag | agt | gtg | tct | gac | tat | gac | ggc | aaa | ctg | 816 |
| Ile | Leu | Leu | Phe | Leu | Pro | Lys | Ser | Val | Ser | Asp | Tyr | Asp | Gly | Lys | Leu | |
| | | | | 260 | | | | | 265 | | | | | 270 | | |
| agc | aac | ttc | aaa | aca | gca | gcc | gag | agc | ttc | aag | ggc | aag | atc | ctg | ttc | 864 |
| Ser | Asn | Phe | Lys | Thr | Ala | Ala | Glu | Ser | Phe | Lys | Gly | Lys | Ile | Leu | Phe | |
| | | | 275 | | | | | 280 | | | | | 285 | | | |
| atc | ttc | atc | gac | agc | gac | cac | acc | gac | aac | cag | cgc | atc | ctc | gag | ttc | 912 |
| Ile | Phe | Ile | Asp | Ser | Asp | His | Thr | Asp | Asn | Gln | Arg | Ile | Leu | Glu | Phe | |
| | 290 | | | | | 295 | | | | | 300 | | | | | |
| ttt | ggc | ctg | aag | aag | gaa | gag | tgc | ccg | gcc | gtg | cgc | ctc | atc | acc | ctg | 960 |
| Phe | Gly | Leu | Lys | Lys | Glu | Glu | Cys | Pro | Ala | Val | Arg | Leu | Ile | Thr | Leu | |
| 305 | | | | | 310 | | | | | 315 | | | | | 320 | |
| gag | gag | gag | atg | acc | aag | tac | aag | ccc | gaa | tcg | gag | gag | ctg | acg | gca | 1008 |
| Glu | Glu | Glu | Met | Thr | Lys | Tyr | Lys | Pro | Glu | Ser | Glu | Glu | Leu | Thr | Ala | |
| | | | | 325 | | | | | 330 | | | | | 335 | | |
| gag | agg | atc | aca | gag | ttc | tgc | cac | cgc | ttc | ctg | gag | ggc | aaa | atc | aag | 1056 |
| Glu | Arg | Ile | Thr | Glu | Phe | Cys | His | Arg | Phe | Leu | Glu | Gly | Lys | Ile | Lys | |
| | | | 340 | | | | | 345 | | | | | 350 | | | |
| ccc | cac | ctg | atg | agc | cag | gag | ctg | ccg | gag | gac | tgg | gac | aag | cag | cct | 1104 |
| Pro | His | Leu | Met | Ser | Gln | Glu | Leu | Pro | Glu | Asp | Trp | Asp | Lys | Gln | Pro | |
| | 355 | | | | | 360 | | | | | 365 | | | | | |
| gtc | aag | gtg | ctt | gtt | ggg | aag | aac | ttt | gaa | gac | gtg | gct | ttt | gat | gag | 1152 |
| Val | Lys | Val | Leu | Val | Gly | Lys | Asn | Phe | Glu | Asp | Val | Ala | Phe | Asp | Glu | |
| 370 | | | | | 375 | | | | | 380 | | | | | | |
| aaa | aaa | aac | gtc | ttt | gtg | gag | ttc | tat | gcc | cca | tgg | tgt | ggt | cac | tgc | 1200 |
| Lys | Lys | Asn | Val | Phe | Val | Glu | Phe | Tyr | Ala | Pro | Trp | Cys | Gly | His | Cys | |
| 385 | | | | | 390 | | | | | 395 | | | | | 400 | |
| aaa | cag | ttg | gct | ccc | att | tgg | gat | aaa | ctg | gga | gag | acg | tac | aag | gac | 1248 |
| Lys | Gln | Leu | Ala | Pro | Ile | Trp | Asp | Lys | Leu | Gly | Glu | Thr | Tyr | Lys | Asp | |
| | | | | 405 | | | | | 410 | | | | | 415 | | |
| cat | gag | aac | atc | gtc | atc | gcc | aag | atg | gac | tcg | act | gcc | aac | gag | gtg | 1296 |
| His | Glu | Asn | Ile | Val | Ile | Ala | Lys | Met | Asp | Ser | Thr | Ala | Asn | Glu | Val | |
| | | | 420 | | | | | 425 | | | | | 430 | | | |
| gag | gcc | gtc | aaa | gtg | cac | agc | ttc | ccc | aca | ctc | aag | ttc | ttt | cct | gcc | 1344 |
| Glu | Ala | Val | Lys | Val | His | Ser | Phe | Pro | Thr | Leu | Lys | Phe | Phe | Pro | Ala | |
| | | 435 | | | | | 440 | | | | | 445 | | | | |
| agt | gcc | gac | agg | acg | gtc | att | gat | tac | aac | ggg | gaa | cgc | acg | ctg | gat | 1392 |
| Ser | Ala | Asp | Arg | Thr | Val | Ile | Asp | Tyr | Asn | Gly | Glu | Arg | Thr | Leu | Asp | |
| 450 | | | | | 455 | | | | | 460 | | | | | | |
| ggt | ttt | aag | aaa | ttc | ctg | gag | agc | ggt | ggc | cag | gat | ggg | gca | ggg | gat | 1440 |
| Gly | Phe | Lys | Lys | Phe | Leu | Glu | Ser | Gly | Gly | Gln | Asp | Gly | Ala | Gly | Asp | |
| 465 | | | | | 470 | | | | | 475 | | | | | 480 | |
| gat | gac | gat | ctc | gag | gac | ctg | gaa | gaa | gca | gag | gag | cca | gac | atg | gag | 1488 |
| Asp | Asp | Asp | Leu | Glu | Asp | Leu | Glu | Glu | Ala | Glu | Glu | Pro | Asp | Met | Glu | |
| | | | | 485 | | | | | 490 | | | | | 495 | | |
| gaa | gac | gat | gat | cag | aaa | gct | gtg | aaa | gat | gaa | ctg | taa | | | | 1527 |
| Glu | Asp | Asp | Asp | Gln | Lys | Ala | Val | Lys | Asp | Glu | Leu | | | | | |
| | | | 500 | | | | | 505 | | | | | | | | |

<210> SEQ ID NO 141
<211> LENGTH: 508
<212> TYPE: PRT
<213> ORGANISM: Homo sapiens

<400> SEQUENCE: 141

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
                20                  25                  30

Asn Phe Ala Glu Ala Leu Ala Ala His Lys Tyr Leu Leu Val Glu Phe

-continued

```
                35                  40                  45
Tyr Ala Pro Trp Cys Gly His Cys Lys Ala Leu Ala Pro Glu Tyr Ala
 50                  55                  60
Lys Ala Ala Gly Lys Leu Lys Ala Glu Gly Ser Glu Ile Arg Leu Ala
 65                  70                  75                  80
Lys Val Asp Ala Thr Glu Glu Ser Asp Leu Ala Gln Gln Tyr Gly Val
                 85                  90                  95
Arg Gly Tyr Pro Thr Ile Lys Phe Phe Arg Asn Gly Asp Thr Ala Ser
                100                 105                 110
Pro Lys Glu Tyr Thr Ala Gly Arg Glu Ala Asp Asp Ile Val Asn Trp
            115                 120                 125
Leu Lys Lys Arg Thr Gly Pro Ala Ala Thr Thr Leu Pro Asp Gly Ala
            130                 135                 140
Ala Ala Glu Ser Leu Val Glu Ser Ser Glu Val Ala Val Ile Gly Phe
145                 150                 155                 160
Phe Lys Asp Val Glu Ser Asp Ser Ala Lys Gln Phe Leu Gln Ala Ala
                165                 170                 175
Glu Ala Ile Asp Asp Ile Pro Phe Gly Ile Thr Ser Asn Ser Asp Val
                180                 185                 190
Phe Ser Lys Tyr Gln Leu Asp Lys Asp Gly Val Val Leu Phe Lys Lys
            195                 200                 205
Phe Asp Glu Gly Arg Asn Asn Phe Glu Gly Glu Val Thr Lys Glu Asn
            210                 215                 220
Leu Leu Asp Phe Ile Lys His Asn Gln Leu Pro Leu Val Ile Glu Phe
225                 230                 235                 240
Thr Glu Gln Thr Ala Pro Lys Ile Phe Gly Gly Glu Ile Lys Thr His
                245                 250                 255
Ile Leu Leu Phe Leu Pro Lys Ser Val Ser Asp Tyr Asp Gly Lys Leu
            260                 265                 270
Ser Asn Phe Lys Thr Ala Ala Glu Ser Phe Lys Gly Lys Ile Leu Phe
            275                 280                 285
Ile Phe Ile Asp Ser Asp His Thr Asp Asn Gln Arg Ile Leu Glu Phe
290                 295                 300
Phe Gly Leu Lys Lys Glu Glu Cys Pro Ala Val Arg Leu Ile Thr Leu
305                 310                 315                 320
Glu Glu Glu Met Thr Lys Tyr Lys Pro Glu Ser Glu Glu Leu Thr Ala
                325                 330                 335
Glu Arg Ile Thr Glu Phe Cys His Arg Phe Leu Glu Gly Lys Ile Lys
            340                 345                 350
Pro His Leu Met Ser Gln Glu Leu Pro Glu Asp Trp Asp Lys Gln Pro
            355                 360                 365
Val Lys Val Leu Val Gly Lys Asn Phe Glu Asp Val Ala Phe Asp Glu
            370                 375                 380
Lys Lys Asn Val Phe Val Glu Phe Tyr Ala Pro Trp Cys Gly His Cys
385                 390                 395                 400
Lys Gln Leu Ala Pro Ile Trp Asp Lys Leu Gly Glu Thr Tyr Lys Asp
                405                 410                 415
His Glu Asn Ile Val Ile Ala Lys Met Asp Ser Thr Ala Asn Glu Val
                420                 425                 430
Glu Ala Val Lys Val His Ser Phe Pro Thr Leu Lys Phe Phe Pro Ala
            435                 440                 445
Ser Ala Asp Arg Thr Val Ile Asp Tyr Asn Gly Glu Arg Thr Leu Asp
            450                 455                 460
```

```
Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Pro Asp Met Glu
            485                 490                 495

Glu Asp Asp Asp Gln Lys Ala Val Lys Asp Glu Leu
            500                 505
```

<210> SEQ ID NO 142
<211> LENGTH: 1527
<212> TYPE: DNA
<213> ORGANISM: Artificial Sequence
<220> FEATURE:
<223> OTHER INFORMATION: Synthetic DNA

<400> SEQUENCE: 142

```
atgttgagaa gagctttgtt gtgtttggcc gttgccgcct tggttagagc cgacgcccca      60
gaggaggagg accacgtctt ggttttgaga aagtccaact tcgctgaggc tttggctgcc     120
cacaagtact tgttggttga gttctacgcc ccatggtgtg gtcactgtaa ggctttggcc     180
ccagagtacg ccaaggccgc tggtaagttg aaggctgagg gttccgagat cagattggcc     240
aaggttgacg ccaccgagga gtccgacttg gcccaacaat acggtgttag aggttaccca     300
accatcaagt tcttcagaaa cggtgacacc gcttccccaa aggagtacac cgctggtaga     360
gaggctgacg acatcgttaa ctggttgaag aagagaaccg gtccagctgc caccaccttg     420
ccagacggtg ctgctgctga gtccttggtg gagtcctccg aggttgctgt catcggtttc     480
ttcaaggacg ttgagtccga ctccgccaag caattcttgc aagctgctga ggccatcgac     540
gacatcccat tcggtatcac ctccaactcc gacgttttct ccaagtacca attggacaag     600
gacggtgttg tcttgttcaa gaagttcgac gagggtagaa acaacttcga gggtgaggtc     660
accaaggaga acttgttgga cttcatcaag cacaaccaat tgccattggt tatcgagttc     720
accgagcaaa ccgccccaaa gatcttcggt ggtgagatca agacccacat cttgttgttc     780
ttgccaaagt ccgtttccga ctacgacggt aagttgtcca acttcaagac cgctgccgag     840
tccttcaagg gtaagatctt gttcatcttc atcgactccg accaccgga caaccaaaga     900
atcttggagt tcttcggttt gaagaaggag gagtgtccag ccgttagatt gatcaccttg     960
gaggaggaga tgaccaagta caagccagag tccgaggagt tgaccgctga gaatcacc    1020
gagttctgtc acagattctt ggagggtaag atcaagccac acttgatgtc caagagttg    1080
ccagaggact gggacaagca accagtcaag gttttggttg gtaagaactt cgaggacgtt    1140
gctttcgacg agaagaagaa cgtcttcgtt gagttctacg ccccatggtg tggtcactgt    1200
aagcaattgg ctccaatctg gacaagttg ggtgagacct acaaggacca cgagaacatc    1260
gtcatcgcca agatggactc caccgccaac gaggttgagg ccgttaaggt tcactccttc    1320
ccaaccttga agttcttccc agcctccgcc gacagaaccg tcatcgacta caacggtgag    1380
agaaccttgg acgttttcaa gaagttcttg gagtccggtg gtcaagacgg tgctggtgac    1440
gacgacgact ggaggactt ggaggaggct gaggagccag acatggagga ggacgacgac    1500
caaaaggctg ttaaggacga gttgtaa                                        1527
```

<210> SEQ ID NO 143
<211> LENGTH: 1407
<212> TYPE: DNA
<213> ORGANISM: Homo sapiens
<220> FEATURE:
<221> NAME/KEY: CDS
<222> LOCATION: (1)..(1407)

<400> SEQUENCE: 143

```
atg ggc cgc ggc tgg gga ttc ttg ttt ggc ctc ctg ggc gcc gtg tgg      48
Met Gly Arg Gly Trp Gly Phe Leu Phe Gly Leu Leu Gly Ala Val Trp
1               5                   10                  15 ctg ctc agc tcg ggc cac gga gag gag cag ccc ccg gag aca gcg gca      96
Leu Leu Ser Ser Gly His Gly Glu Glu Gln Pro Pro Glu Thr Ala Ala
            20                  25                  30 cag agg tgc ttc tgc cag gtt agt ggt tac ttg gat gat tgt acc tgt     144
Gln Arg Cys Phe Cys Gln Val Ser Gly Tyr Leu Asp Asp Cys Thr Cys
        35                  40                  45 gat gtt gaa acc att gat aga ttt aat aac tac agg ctt ttc cca aga     192
Asp Val Glu Thr Ile Asp Arg Phe Asn Asn Tyr Arg Leu Phe Pro Arg
50                  55                  60 cta caa aaa ctt ctt gaa agt gac tac ttt agg tat tac aag gta aac     240
Leu Gln Lys Leu Leu Glu Ser Asp Tyr Phe Arg Tyr Tyr Lys Val Asn
65                  70                  75                  80 ctg aag agg ccg tgt cct ttc tgg aat gac atc agc cag tgt gga aga     288
Leu Lys Arg Pro Cys Pro Phe Trp Asn Asp Ile Ser Gln Cys Gly Arg
                85                  90                  95 agg gac tgt gct gtc aaa cca tgt caa tct gat gaa gtt cct gat gga     336
Arg Asp Cys Ala Val Lys Pro Cys Gln Ser Asp Glu Val Pro Asp Gly
            100                 105                 110 att aaa tct gcg agc tac aag tat tct gaa gaa gcc aat aat ctc att     384
Ile Lys Ser Ala Ser Tyr Lys Tyr Ser Glu Glu Ala Asn Asn Leu Ile
        115                 120                 125 gaa gaa tgt gaa caa gct gaa cga ctt gga gca gtg gat gaa tct ctg     432
Glu Glu Cys Glu Gln Ala Glu Arg Leu Gly Ala Val Asp Glu Ser Leu
130                 135                 140 agt gag gaa aca cag aag gct gtt ctt cag tgg acc aag cat gat gat     480
Ser Glu Glu Thr Gln Lys Ala Val Leu Gln Trp Thr Lys His Asp Asp
145                 150                 155                 160 tct tca gat aac ttc tgt gaa gct gat gac att cag tcc cct gaa gct     528
Ser Ser Asp Asn Phe Cys Glu Ala Asp Asp Ile Gln Ser Pro Glu Ala
                165                 170                 175 gaa tat gta gat ttg ctt ctt aat cct gag cgc tac act ggt tac aag     576
Glu Tyr Val Asp Leu Leu Leu Asn Pro Glu Arg Tyr Thr Gly Tyr Lys
            180                 185                 190 gga cca gat gct tgg aaa ata tgg aat gtc atc tac gaa gaa aac tgt     624
Gly Pro Asp Ala Trp Lys Ile Trp Asn Val Ile Tyr Glu Glu Asn Cys
        195                 200                 205 ttt aag cca cag aca att aaa aga cct tta aat cct ttg gct tct ggt     672
Phe Lys Pro Gln Thr Ile Lys Arg Pro Leu Asn Pro Leu Ala Ser Gly
210                 215                 220 caa ggg aca agt gaa gag aac act ttt tac agt tgg cta gaa ggt ctc     720
Gln Gly Thr Ser Glu Glu Asn Thr Phe Tyr Ser Trp Leu Glu Gly Leu
225                 230                 235                 240 tgt gta gaa aaa aga gca ttc tac aga ctt ata tct ggc cta cat gca     768
Cys Val Glu Lys Arg Ala Phe Tyr Arg Leu Ile Ser Gly Leu His Ala
                245                 250                 255 agc att aat gtg cat ttg agt gca aga tat ctt tta caa gag acc tgg     816
Ser Ile Asn Val His Leu Ser Ala Arg Tyr Leu Leu Gln Glu Thr Trp
            260                 265                 270 tta gaa aag aaa tgg gga cac aac att aca gaa ttt caa cag cga ttt     864
Leu Glu Lys Lys Trp Gly His Asn Ile Thr Glu Phe Gln Gln Arg Phe
        275                 280                 285 gat gga att ttg act gaa gga gaa ggt cca aga agg ctt aag aac ttg     912
Asp Gly Ile Leu Thr Glu Gly Glu Gly Pro Arg Arg Leu Lys Asn Leu
290                 295                 300 tat ttt ctc tac tta ata gaa cta agg gct tta tcc aaa gtg tta cca     960
Tyr Phe Leu Tyr Leu Ile Glu Leu Arg Ala Leu Ser Lys Val Leu Pro
```

```
                305                 310                 315                 320
ttc ttc gag cgc cca gat ttt caa ctc ttt act gga aat aaa att cag          1008
Phe Phe Glu Arg Pro Asp Phe Gln Leu Phe Thr Gly Asn Lys Ile Gln
                    325                 330                 335 gat gag gaa aac aaa atg tta ctt ctg gaa ata ctt cat gaa atc aag          1056
Asp Glu Glu Asn Lys Met Leu Leu Leu Glu Ile Leu His Glu Ile Lys
            340                 345                 350 tca ttt cct ttg cat ttt gat gag aat tca ttt ttt gct ggg gat aaa          1104
Ser Phe Pro Leu His Phe Asp Glu Asn Ser Phe Phe Ala Gly Asp Lys
        355                 360                 365 aaa gaa gca cac aaa cta aag gag gac ttt cga ctg cat ttt aga aat          1152
Lys Glu Ala His Lys Leu Lys Glu Asp Phe Arg Leu His Phe Arg Asn
    370                 375                 380 att tca aga att atg gat tgt gtt ggt tgt ttt aaa tgt cgt ctg tgg          1200
Ile Ser Arg Ile Met Asp Cys Val Gly Cys Phe Lys Cys Arg Leu Trp
385                 390                 395                 400 gga aag ctt cag act cag ggt ttg ggc act gct ctg aag atc tta ttt          1248
Gly Lys Leu Gln Thr Gln Gly Leu Gly Thr Ala Leu Lys Ile Leu Phe
                405                 410                 415 tct gag aaa ttg ata gca aat atg cca gaa agt gga cct agt tat gaa          1296
Ser Glu Lys Leu Ile Ala Asn Met Pro Glu Ser Gly Pro Ser Tyr Glu
            420                 425                 430 ttc cat cta acc aga caa gaa ata gta tca tta ttc aac gca ttt gga          1344
Phe His Leu Thr Arg Gln Glu Ile Val Ser Leu Phe Asn Ala Phe Gly
        435                 440                 445 aga att tct aca agt gtg aaa gaa tta gaa aac ttc agg aac ttg tta          1392
Arg Ile Ser Thr Ser Val Lys Glu Leu Glu Asn Phe Arg Asn Leu Leu
    450                 455                 460 cag aat att cat taa                                                      1407
Gln Asn Ile His
465

<210> SEQ ID NO 144
<211> LENGTH: 468
<212> TYPE: PRT
<213> ORGANISM: Homo sapiens

<400> SEQUENCE: 144

Met Gly Arg Gly Trp Gly Phe Leu Phe Gly Leu Leu Gly Ala Val Trp
1               5                   10                  15

Leu Leu Ser Ser Gly His Gly Glu Glu Gln Pro Pro Glu Thr Ala Ala
                20                  25                  30

Gln Arg Cys Phe Cys Gln Val Ser Gly Tyr Leu Asp Asp Cys Thr Cys
            35                  40                  45

Asp Val Glu Thr Ile Asp Arg Phe Asn Asn Tyr Arg Leu Phe Pro Arg
        50                  55                  60

Leu Gln Lys Leu Leu Glu Ser Asp Tyr Phe Arg Tyr Tyr Lys Val Asn
65                  70                  75                  80

Leu Lys Arg Pro Cys Pro Phe Trp Asn Asp Ile Ser Gln Cys Gly Arg
                85                  90                  95

Arg Asp Cys Ala Val Lys Pro Cys Gln Ser Asp Glu Val Pro Asp Gly
            100                 105                 110

Ile Lys Ser Ala Ser Tyr Lys Tyr Ser Glu Glu Ala Asn Asn Leu Ile
        115                 120                 125

Glu Glu Cys Glu Gln Ala Glu Arg Leu Gly Ala Val Asp Glu Ser Leu
    130                 135                 140

Ser Glu Glu Thr Gln Lys Ala Val Leu Gln Trp Thr Lys His Asp Asp
145                 150                 155                 160
```

```
Ser Ser Asp Asn Phe Cys Glu Ala Asp Asp Ile Gln Ser Pro Glu Ala
            165                 170                 175
Glu Tyr Val Asp Leu Leu Asn Pro Glu Arg Tyr Thr Gly Tyr Lys
        180                 185                 190
Gly Pro Asp Ala Trp Lys Ile Trp Asn Val Ile Tyr Glu Glu Asn Cys
        195                 200                 205
Phe Lys Pro Gln Thr Ile Lys Arg Pro Leu Asn Pro Leu Ala Ser Gly
        210                 215                 220
Gln Gly Thr Ser Glu Glu Asn Thr Phe Tyr Ser Trp Leu Glu Gly Leu
225                 230                 235                 240
Cys Val Glu Lys Arg Ala Phe Tyr Arg Leu Ile Ser Gly Leu His Ala
                245                 250                 255
Ser Ile Asn Val His Leu Ser Ala Arg Tyr Leu Leu Gln Glu Thr Trp
                260                 265                 270
Leu Glu Lys Lys Trp Gly His Asn Ile Thr Glu Phe Gln Gln Arg Phe
            275                 280                 285
Asp Gly Ile Leu Thr Glu Gly Glu Gly Pro Arg Arg Leu Lys Asn Leu
        290                 295                 300
Tyr Phe Leu Tyr Leu Ile Glu Leu Arg Ala Leu Ser Lys Val Leu Pro
305                 310                 315                 320
Phe Phe Glu Arg Pro Asp Phe Gln Leu Phe Thr Gly Asn Lys Ile Gln
                325                 330                 335
Asp Glu Glu Asn Lys Met Leu Leu Leu Glu Ile Leu His Glu Ile Lys
                340                 345                 350
Ser Phe Pro Leu His Phe Asp Glu Asn Ser Phe Ala Gly Asp Lys
            355                 360                 365
Lys Glu Ala His Lys Leu Lys Glu Asp Phe Arg Leu His Phe Arg Asn
        370                 375                 380
Ile Ser Arg Ile Met Asp Cys Val Gly Cys Phe Lys Cys Arg Leu Trp
385                 390                 395                 400
Gly Lys Leu Gln Thr Gln Gly Leu Gly Thr Ala Leu Lys Ile Leu Phe
                405                 410                 415
Ser Glu Lys Leu Ile Ala Asn Met Pro Glu Ser Gly Pro Ser Tyr Glu
                420                 425                 430
Phe His Leu Thr Arg Gln Glu Ile Val Ser Leu Phe Asn Ala Phe Gly
            435                 440                 445
Arg Ile Ser Thr Ser Val Lys Glu Leu Glu Asn Phe Arg Asn Leu Leu
        450                 455                 460
Gln Asn Ile His
465

<210> SEQ ID NO 145
<211> LENGTH: 1407
<212> TYPE: DNA
<213> ORGANISM: Artificial Sequence
<220> FEATURE:
<223> OTHER INFORMATION: Synthetic DNA

<400> SEQUENCE: 145
atgggtagag gttggggttt cttgttcggt tgttgggtg ctgtttggtt gttgtcctcc      60
ggtcacggtg aggagcaacc accagagacc gctgctcaaa gatgtttctg tcaagtttcc     120
ggttacttgg acgactgtac ctgtgacgtt gagaccatcg acagattcaa caactacaga     180
ttgttcccaa gattgcaaaa gttgttggag tccgactact tcagatacta caaggttaac     240
ttgaagagac catgtccatt ctggaacgac atctcccaat gtggtagaag agactgtgct     300
```

-continued

```
gttaagccat gtcaatccga cgaggttcca gacggtatca agtccgcttc ctacaagtac    360
tccgaggagg ctaacaactt gatcgaggag tgtgagcaag ctgagagatt gggtgctgtt    420
gacgagtcct tgtccgagga gacccaaaag gctgttttgc aatggaccaa gcacgacgac    480
tcctccgaca acttctgtga ggctgacgac atccaatccc cagaggctga gtacgttgac    540
ttgttgttga acccagagag atacaccggt tacaagggtc cagacgcttg aagatctgg    600 aacgttatct acgaggagaa ctgtttcaag ccacaaacca tcaagagacc attgaaccca    660
ttggcttccg gtcaaggtac ctccgaggag aacaccttct actcctggtt ggagggtttg    720
tgtgttgaga agagagcttt ctacagattg atctccggtt tgcacgcttc catcaacgtt    780
cacttgtccg ctagatactt gttgcaagag acctggttgg agaagaagtg gggtcacaac    840
atcaccgagt tccaacaaag gttcgacggt atcttgaccg agggtgaggg tccaagaaga    900
ttgaagaact tgtacttctt gtacttgatc gagttgagag ctttgtccaa ggttttgcca    960
ttcttcgaga gaccagactt ccaattgttc accggtaaca agatccaaga cgaggagaac   1020
aagatgttgt tgttggagat cttgcacgag atcaagtcct tcccattgca cttcgacgag   1080
aactccttct tcgctggtga caagaaggag gctcacaagt tgaaggagga cttcagattg   1140
cacttcagaa acatctccag aatcatggac tgtgttggtt gtttcaagtg tagattgtgg   1200
ggtaagttgc aaacccaagg tttgggtacc gctttgaaga tcttgttctc cgagaagttg   1260
atcgctaaca tgccagagtc cggtccatcc tacgagttcc acttgaccag acaagagatc   1320
gtttccttgt tcaacgcttt cggtagaatc tccacctccg ttaaggagtt ggagaacttc   1380
agaaacttgt tgcaaaacat ccactaa                                      1407
```

<210> SEQ ID NO 146
<211> LENGTH: 1404
<212> TYPE: DNA
<213> ORGANISM: Homo sapiens
<220> FEATURE:
<221> NAME/KEY: CDS
<222> LOCATION: (1)..(1404)

<400> SEQUENCE: 146

```
atg agc caa ggg gtc cgc cgg gca ggc gct ggg cag ggg gta gcg gcc     48
Met Ser Gln Gly Val Arg Arg Ala Gly Ala Gly Gln Gly Val Ala Ala
1               5                   10                  15 gcg gtg cag ctg ctg gtc acc ctg agc ttc ctg cgg agc gtc gtc gag    96
Ala Val Gln Leu Leu Val Thr Leu Ser Phe Leu Arg Ser Val Val Glu
            20                  25                  30 gcg cag gtc act gga gtt ctg gat gat tgc ttg tgt gat att gac agc   144
Ala Gln Val Thr Gly Val Leu Asp Asp Cys Leu Cys Asp Ile Asp Ser
        35                  40                  45 atc gat aac ttc aat acc tac aaa atc ttc ccc aaa ata aaa aaa ttg   192
Ile Asp Asn Phe Asn Thr Tyr Lys Ile Phe Pro Lys Ile Lys Lys Leu
    50                  55                  60 caa gag aga gac tat ttt cgt tat tac aag gtt aat ctg aag cga cct   240
Gln Glu Arg Asp Tyr Phe Arg Tyr Tyr Lys Val Asn Leu Lys Arg Pro
65                  70                  75                  80 tgt cct ttc tgg gca gaa gat ggc cac tgt tca ata aaa gac tgt cat   288
Cys Pro Phe Trp Ala Glu Asp Gly His Cys Ser Ile Lys Asp Cys His
                85                  90                  95 gtg gag ccc tgt cca gag agt aaa att ccg gtt gga ata aaa gct ggg   336
Val Glu Pro Cys Pro Glu Ser Lys Ile Pro Val Gly Ile Lys Ala Gly
            100                 105                 110 cat tct aat aag tac ttg aaa atg gca aac aat acc aaa gaa tta gaa   384
His Ser Asn Lys Tyr Leu Lys Met Ala Asn Asn Thr Lys Glu Leu Glu
        115                 120                 125
```

```
gtt tgt gag caa gct aat aaa ctg gga gca att aac agc aca tta agt      432
Val Cys Glu Gln Ala Asn Lys Leu Gly Ala Ile Asn Ser Thr Leu Ser
    130                 135                 140 aat caa agc aaa gaa gct ttc att gac tgg gca aga tat gat gat tca      480
Asn Gln Ser Lys Glu Ala Phe Ile Asp Trp Ala Arg Tyr Asp Asp Ser
145                 150                 155                 160 cgg gat cac ttt tgt gaa ctt gat gat gag aga tct cca gct gct cag      528
Arg Asp His Phe Cys Glu Leu Asp Asp Glu Arg Ser Pro Ala Ala Gln
                165                 170                 175 tat gta gac cta ttg ctg aac cca gag cgt tac act ggc tat aaa ggg      576
Tyr Val Asp Leu Leu Leu Asn Pro Glu Arg Tyr Thr Gly Tyr Lys Gly
            180                 185                 190 acc tct gca tgg aga gtg tgg aac agc atc tat gaa gag aac tgt ttc      624
Thr Ser Ala Trp Arg Val Trp Asn Ser Ile Tyr Glu Glu Asn Cys Phe
        195                 200                 205 aag cct cga tct gtt tat cgt cct tta aat cct ctg gcg cct agc cga      672
Lys Pro Arg Ser Val Tyr Arg Pro Leu Asn Pro Leu Ala Pro Ser Arg
    210                 215                 220 ggc gaa gat gat gga gaa tca ttc tac aca tgg cta gaa ggt ttg tgt      720
Gly Glu Asp Asp Gly Glu Ser Phe Tyr Thr Trp Leu Glu Gly Leu Cys
225                 230                 235                 240 ctg gag aaa aga gtc ttc tat aag ctt ata tcg gga ctt cat gct agc      768
Leu Glu Lys Arg Val Phe Tyr Lys Leu Ile Ser Gly Leu His Ala Ser
                245                 250                 255 atc aat tta cat cta tgc gca aat tat ctt ttg gaa gaa acc tgg ggt      816
Ile Asn Leu His Leu Cys Ala Asn Tyr Leu Leu Glu Glu Thr Trp Gly
            260                 265                 270 aag ccc agt tgg gga cct aat att aaa gaa ttc aaa cac cgc ttt gac      864
Lys Pro Ser Trp Gly Pro Asn Ile Lys Glu Phe Lys His Arg Phe Asp
        275                 280                 285 cct gtg gaa acc aag gga gaa ggt cca aga agg ctc aag aat ctt tac      912
Pro Val Glu Thr Lys Gly Glu Gly Pro Arg Arg Leu Lys Asn Leu Tyr
    290                 295                 300 ttt tta tac ttg att gag ctt cga gct ttg tca aag gtg gct cca tat      960
Phe Leu Tyr Leu Ile Glu Leu Arg Ala Leu Ser Lys Val Ala Pro Tyr
305                 310                 315                 320 ttt gag cgc tca att gtc gat ctt tac act gga aat gca gaa gaa gat     1008
Phe Glu Arg Ser Ile Val Asp Leu Tyr Thr Gly Asn Ala Glu Glu Asp
                325                 330                 335 gct gac aca aaa act ctt cta ctg aat atc ttt caa gat aca aag tcc     1056
Ala Asp Thr Lys Thr Leu Leu Leu Asn Ile Phe Gln Asp Thr Lys Ser
            340                 345                 350 ttt ccc atg cac ttt gat gag aaa tcc atg ttt gca ggt gac aaa aaa     1104
Phe Pro Met His Phe Asp Glu Lys Ser Met Phe Ala Gly Asp Lys Lys
        355                 360                 365 ggg gcc aag tca cta aag gag gaa ttc cga tta cat ttc aag aat atc     1152
Gly Ala Lys Ser Leu Lys Glu Glu Phe Arg Leu His Phe Lys Asn Ile
    370                 375                 380 tcc cgt ata atg gac tgt gtt gga tgt gac aaa tgc aga tta tgg gga     1200
Ser Arg Ile Met Asp Cys Val Gly Cys Asp Lys Cys Arg Leu Trp Gly
385                 390                 395                 400 aaa tta cag act cag ggt tta gga act gcc ctg aag ata tta ttc tct     1248
Lys Leu Gln Thr Gln Gly Leu Gly Thr Ala Leu Lys Ile Leu Phe Ser
                405                 410                 415 gaa aaa gaa atc caa aag ctt cca gag aat agt cca tct aaa ggc ttc     1296
Glu Lys Glu Ile Gln Lys Leu Pro Glu Asn Ser Pro Ser Lys Gly Phe
            420                 425                 430 caa ctc acc cga cag gaa ata gtt gct ctt tta aat gct ttt gga agg     1344
Gln Leu Thr Arg Gln Glu Ile Val Ala Leu Leu Asn Ala Phe Gly Arg
        435                 440                 445
```

```
ctt tct aca agt ata aga gac tta cag aat ttt aaa gtc tta tta caa    1392
Leu Ser Thr Ser Ile Arg Asp Leu Gln Asn Phe Lys Val Leu Leu Gln
        450                 455                 460 cac agt agg taa                                                    1404
His Ser Arg
465

<210> SEQ ID NO 147
<211> LENGTH: 467
<212> TYPE: PRT
<213> ORGANISM: Homo sapiens

<400> SEQUENCE: 147

Met Ser Gln Gly Val Arg Arg Ala Gly Ala Gln Gly Val Ala Ala
1               5                   10                  15

Ala Val Gln Leu Leu Val Thr Leu Ser Phe Leu Arg Ser Val Val Glu
            20                  25                  30

Ala Gln Val Thr Gly Val Leu Asp Asp Cys Leu Cys Asp Ile Asp Ser
        35                  40                  45

Ile Asp Asn Phe Asn Thr Tyr Lys Ile Phe Pro Lys Ile Lys Lys Leu
50                  55                  60

Gln Glu Arg Asp Tyr Phe Arg Tyr Tyr Lys Val Asn Leu Lys Arg Pro
65                  70                  75                  80

Cys Pro Phe Trp Ala Glu Asp Gly His Cys Ser Ile Lys Asp Cys His
                85                  90                  95

Val Glu Pro Cys Pro Glu Ser Lys Ile Pro Val Gly Ile Lys Ala Gly
            100                 105                 110

His Ser Asn Lys Tyr Leu Lys Met Ala Asn Asn Thr Lys Glu Leu Glu
        115                 120                 125

Val Cys Glu Gln Ala Asn Lys Leu Gly Ala Ile Asn Ser Thr Leu Ser
    130                 135                 140

Asn Gln Ser Lys Glu Ala Phe Ile Asp Trp Ala Arg Tyr Asp Asp Ser
145                 150                 155                 160

Arg Asp His Phe Cys Glu Leu Asp Asp Glu Arg Ser Pro Ala Ala Gln
                165                 170                 175

Tyr Val Asp Leu Leu Leu Asn Pro Glu Arg Tyr Thr Gly Tyr Lys Gly
            180                 185                 190

Thr Ser Ala Trp Arg Val Trp Asn Ser Ile Tyr Glu Glu Asn Cys Phe
        195                 200                 205

Lys Pro Arg Ser Val Tyr Arg Pro Leu Asn Pro Leu Ala Pro Ser Arg
    210                 215                 220

Gly Glu Asp Asp Gly Glu Ser Phe Tyr Thr Trp Leu Glu Gly Leu Cys
225                 230                 235                 240

Leu Glu Lys Arg Val Phe Tyr Lys Leu Ile Ser Gly Leu His Ala Ser
                245                 250                 255

Ile Asn Leu His Leu Cys Ala Asn Tyr Leu Leu Glu Glu Thr Trp Gly
            260                 265                 270

Lys Pro Ser Trp Gly Pro Asn Ile Lys Glu Phe Lys His Arg Phe Asp
        275                 280                 285

Pro Val Glu Thr Lys Gly Glu Gly Pro Arg Arg Leu Lys Asn Leu Tyr
    290                 295                 300

Phe Leu Tyr Leu Ile Glu Leu Arg Ala Leu Ser Lys Val Ala Pro Tyr
305                 310                 315                 320

Phe Glu Arg Ser Ile Val Asp Leu Tyr Thr Gly Asn Ala Glu Glu Asp
                325                 330                 335
```

Ala Asp Thr Lys Thr Leu Leu Leu Asn Ile Phe Gln Asp Thr Lys Ser
             340                 345                 350

Phe Pro Met His Phe Asp Glu Lys Ser Met Phe Ala Gly Asp Lys Lys
         355                 360                 365

Gly Ala Lys Ser Leu Lys Glu Glu Phe Arg Leu His Phe Lys Asn Ile
     370                 375                 380

Ser Arg Ile Met Asp Cys Val Gly Cys Asp Lys Cys Arg Leu Trp Gly
385                 390                 395                 400

Lys Leu Gln Thr Gln Gly Leu Gly Thr Ala Leu Lys Ile Leu Phe Ser
                 405                 410                 415

Glu Lys Glu Ile Gln Lys Leu Pro Glu Asn Ser Pro Ser Lys Gly Phe
             420                 425                 430

Gln Leu Thr Arg Gln Glu Ile Val Ala Leu Leu Asn Ala Phe Gly Arg
         435                 440                 445

Leu Ser Thr Ser Ile Arg Asp Leu Gln Asn Phe Lys Val Leu Leu Gln
     450                 455                 460

His Ser Arg
465

<210> SEQ ID NO 148
<211> LENGTH: 1404
<212> TYPE: DNA
<213> ORGANISM: Artificial Sequence
<220> FEATURE:
<223> OTHER INFORMATION: Synthetic DNA

<400> SEQUENCE: 148
atgtcccaag gtgttagaag agctggtgct ggtcaaggtg ttgctgctgc tgttcaattg      60
ttggttacct tgtccttctt gagatccgtt gttgaggctc aagttaccgg tgttttggac     120
gactgtttgt gtgacatcga ctccatcgac aacttcaaca cctacaagat cttcccaaag     180
atcaagaagt tgcaagagag agactacttc agatactaca aggttaactt gaagagacca     240
tgtccattct gggctgagga cggtcactgt tccatcaagg actgtcacgt tgagccatgt     300
ccagagtcca gatcccagt tggtatcaag gctggtcact ccaacaagta cttgaagatg     360
gctaacaaca ccaaggagtt ggaggtttgt gagcaagcta acaagttggg tgctatcaac     420
tccaccttgt ccaaccaatc caaggaggct ttcatcgact gggctagata cgacgactcc     480
agagaccact tctgtgagtt ggacgacgag agatccccag ctgctcaata cgttgacttg     540
ttgttgaacc cagagagata caccggttac aagggtaccct ccgcttggag agtttggaac     600
tccatctacg aggagaactg tttcaagcca agatccgttt acagaccatt gaacccattg     660
gctccatcca gggtgagga cgacggtgag tccttctaca cctggttgga gggttttgtgt     720 ttggagaaga gagttttcta caagttgatc tccggtttgc acgcttccat caacttgcac     780
ttgtgtgcta actacttgtt ggaggagacc tgggtaagc catcctgggg tccaaacatc     840
aaggagttca gcacagatt cgacccagtt gagaccaagg gtgagggtcc aagaagattg     900
aagaacttgt acttcttgta cttgatcgag ttgagagctt tgtccaaggt tgctccatac     960
ttcgagagat ccatcgttga cttgtacacc ggtaacgctg aggaggacgc tgacaccaag    1020
accttgttgt tgaacatctt ccaagacacc aagtccttcc caatgcactt cgacgagaag    1080
tccatgttcg ctggtgacaa gaagggtgct aagtccttga aggaggagtt cagattgcac    1140
ttcaagaaca tctcccagaat catggactgt gttggttgtg acaagtgtag attgtggggt    1200
aagttgcaaa cccaaggttt gggtaccgct ttgaagatct tgttctccga aggagagatc    1260
caaaagttgc cagagaactc cccatccaag ggtttccaat tgaccagaca agagatcgtt    1320

```
gctttgttga acgctttcgg tagattgtcc acctccatca gagacttgca aaacttcaag    1380
gttttgttgc aacactccag ataa                                          1404

<210> SEQ ID NO 149
<211> LENGTH: 1965
<212> TYPE: DNA
<213> ORGANISM: Homo sapiens
<220> FEATURE:
<221> NAME/KEY: CDS
<222> LOCATION: (1)..(1965)

<400> SEQUENCE: 149 atg aag ctc tcc ctg gtg gcc gcg atg ctg ctg ctg ctc agc gcg gcg    48
Met Lys Leu Ser Leu Val Ala Ala Met Leu Leu Leu Leu Ser Ala Ala
1               5                  10                  15 cgg gcc gag gag gag gac aag aag gag gac gtg ggc acg gtg gtc ggc    96
Arg Ala Glu Glu Glu Asp Lys Lys Glu Asp Val Gly Thr Val Val Gly
                20                  25                  30 atc gac ctg ggg acc acc tac tcc tgc gtc ggc gtg ttc aag aac ggc   144
Ile Asp Leu Gly Thr Thr Tyr Ser Cys Val Gly Val Phe Lys Asn Gly
            35                  40                  45 cgc gtg gag atc atc gcc aac gat cag ggc aac cgc atc acg ccg tcc   192
Arg Val Glu Ile Ile Ala Asn Asp Gln Gly Asn Arg Ile Thr Pro Ser
        50                  55                  60 tat gtc gcc ttc act cct gaa ggg gaa cgt ctg att ggc gat gcc gcc   240
Tyr Val Ala Phe Thr Pro Glu Gly Glu Arg Leu Ile Gly Asp Ala Ala
65                  70                  75                  80 aag aac cag ctc acc tcc aac ccc gag aac acg gtc ttt gac gcc aag   288
Lys Asn Gln Leu Thr Ser Asn Pro Glu Asn Thr Val Phe Asp Ala Lys
                85                  90                  95 cgg ctc atc ggc cgc acg tgg aat gac ccg tct gtg cag cag gac atc   336
Arg Leu Ile Gly Arg Thr Trp Asn Asp Pro Ser Val Gln Gln Asp Ile
                100                 105                 110 aag ttc ttg ccg ttc aag gtg gtt gaa aag aaa act aaa cca tac att   384
Lys Phe Leu Pro Phe Lys Val Val Glu Lys Lys Thr Lys Pro Tyr Ile
            115                 120                 125 caa gtt gat att gga ggt ggg caa aca aag aca ttt gct cct gaa gaa   432
Gln Val Asp Ile Gly Gly Gly Gln Thr Lys Thr Phe Ala Pro Glu Glu
        130                 135                 140 att tct gcc atg gtt ctc act aaa atg aaa gaa acc gct gag gct tat   480
Ile Ser Ala Met Val Leu Thr Lys Met Lys Glu Thr Ala Glu Ala Tyr
145                 150                 155                 160 ttg gga aag aag gtt acc cat gca gtt gtt act gta cca gcc tat ttt   528
Leu Gly Lys Lys Val Thr His Ala Val Val Thr Val Pro Ala Tyr Phe
                165                 170                 175 aat gat gcc caa cgc caa gca acc aaa gac gct gga act att gct ggc   576
Asn Asp Ala Gln Arg Gln Ala Thr Lys Asp Ala Gly Thr Ile Ala Gly
                180                 185                 190 cta aat gtt atg agg atc atc aac gag cct acg gca gct gct att gct   624
Leu Asn Val Met Arg Ile Ile Asn Glu Pro Thr Ala Ala Ala Ile Ala
            195                 200                 205 tat ggc ctg gat aag agg gag ggg gag aag aac atc ctg gtg ttt gac   672
Tyr Gly Leu Asp Lys Arg Glu Gly Glu Lys Asn Ile Leu Val Phe Asp
        210                 215                 220 ctg ggt ggc gga acc ttc gat gtg tct ctt ctc acc att gac aat ggt   720
Leu Gly Gly Gly Thr Phe Asp Val Ser Leu Leu Thr Ile Asp Asn Gly
225                 230                 235                 240 gtc ttc gaa gtt gtg gcc act aat gga gat act cat ctg ggt gga gaa   768
Val Phe Glu Val Val Ala Thr Asn Gly Asp Thr His Leu Gly Gly Glu
                245                 250                 255
```

```
gac ttt gac cag cgt gtc atg gaa cac ttc atc aaa ctg tac aaa aag    816
Asp Phe Asp Gln Arg Val Met Glu His Phe Ile Lys Leu Tyr Lys Lys
            260                 265                 270 aag acg ggc aaa gat gtc agg aaa gac aat aga gct gtg cag aaa ctc    864
Lys Thr Gly Lys Asp Val Arg Lys Asp Asn Arg Ala Val Gln Lys Leu
        275                 280                 285 cgg cgc gag gta gaa aag gcc aaa cgg gcc ctg tct tct cag cat caa    912
Arg Arg Glu Val Glu Lys Ala Lys Arg Ala Leu Ser Ser Gln His Gln
    290                 295                 300 gca aga att gaa att gag tcc ttc tat gaa gga gaa gac ttt tct gag    960
Ala Arg Ile Glu Ile Glu Ser Phe Tyr Glu Gly Glu Asp Phe Ser Glu
305                 310                 315                 320 acc ctg act cgg gcc aaa ttt gag gag ctc aac atg gat ctg ttc cgg   1008
Thr Leu Thr Arg Ala Lys Phe Glu Glu Leu Asn Met Asp Leu Phe Arg
                325                 330                 335 tct act atg aag ccc gtc cag aaa gtg ttg gaa gat tct gat ttg aag   1056
Ser Thr Met Lys Pro Val Gln Lys Val Leu Glu Asp Ser Asp Leu Lys
            340                 345                 350 aag tct gat att gat gaa att gtt ctt gtt ggt ggc tcg act cga att   1104
Lys Ser Asp Ile Asp Glu Ile Val Leu Val Gly Gly Ser Thr Arg Ile
        355                 360                 365 cca aag att cag caa ctg gtt aaa gag ttc ttc aat ggc aag gaa cca   1152
Pro Lys Ile Gln Gln Leu Val Lys Glu Phe Phe Asn Gly Lys Glu Pro
    370                 375                 380 tcc cgt ggc ata aac cca gat gaa gct gta gcg tat ggt gct gct gtc   1200
Ser Arg Gly Ile Asn Pro Asp Glu Ala Val Ala Tyr Gly Ala Ala Val
385                 390                 395                 400 cag gct ggt gtg ctc tct ggt gat caa gat aca ggt gac ctg gta ctg   1248
Gln Ala Gly Val Leu Ser Gly Asp Gln Asp Thr Gly Asp Leu Val Leu
                405                 410                 415 ctt gat gta tgt ccc ctt aca ctt ggt att gaa act gtg gga ggt gtc   1296
Leu Asp Val Cys Pro Leu Thr Leu Gly Ile Glu Thr Val Gly Gly Val
            420                 425                 430 atg acc aaa ctg att cca agg aac aca gtg gtg cct acc aag aag tct   1344
Met Thr Lys Leu Ile Pro Arg Asn Thr Val Val Pro Thr Lys Lys Ser
        435                 440                 445 cag atc ttt tct aca gct tct gat aat caa cca act gtt aca atc aag   1392
Gln Ile Phe Ser Thr Ala Ser Asp Asn Gln Pro Thr Val Thr Ile Lys
    450                 455                 460 gtc tat gaa ggt gaa aga ccc ctg aca aaa gac aat cat ctt ctg ggt   1440
Val Tyr Glu Gly Glu Arg Pro Leu Thr Lys Asp Asn His Leu Leu Gly
465                 470                 475                 480 aca ttt gat ctg act gga att cct cct gct cct cgt ggg gtc cca cag   1488
Thr Phe Asp Leu Thr Gly Ile Pro Pro Ala Pro Arg Gly Val Pro Gln
                485                 490                 495 att gaa gtc acc ttt gag ata gat gtg aat ggt att ctt cga gtg aca   1536
Ile Glu Val Thr Phe Glu Ile Asp Val Asn Gly Ile Leu Arg Val Thr
            500                 505                 510 gct gaa gac aag ggt aca ggg aac aaa aat aag atc aca atc acc aat   1584
Ala Glu Asp Lys Gly Thr Gly Asn Lys Asn Lys Ile Thr Ile Thr Asn
        515                 520                 525 gac cag aat cgc ctg aca cct gaa gaa atc gaa agg atg gtt aat gat   1632
Asp Gln Asn Arg Leu Thr Pro Glu Glu Ile Glu Arg Met Val Asn Asp
    530                 535                 540 gct gag aag ttt gct gag gaa gac aaa aag ctc aag gag cgc att gat   1680
Ala Glu Lys Phe Ala Glu Glu Asp Lys Lys Leu Lys Glu Arg Ile Asp
545                 550                 555                 560 act aga aat gag ttg gaa agc tat gcc tat tct cta aag aat cag att   1728
Thr Arg Asn Glu Leu Glu Ser Tyr Ala Tyr Ser Leu Lys Asn Gln Ile
                565                 570                 575
```

```
gga gat aaa gaa aag ctg gga ggt aaa ctt tcc tct gaa gat aag gag    1776
Gly Asp Lys Glu Lys Leu Gly Gly Lys Leu Ser Ser Glu Asp Lys Glu
        580                 585                 590 acc atg gaa aaa gct gta gaa gaa aag att gaa tgg ctg gaa agc cac    1824
Thr Met Glu Lys Ala Val Glu Glu Lys Ile Glu Trp Leu Glu Ser His
    595                 600                 605 caa gat gct gac att gaa gac ttc aaa gct aag aag aag gaa ctg gaa    1872
Gln Asp Ala Asp Ile Glu Asp Phe Lys Ala Lys Lys Lys Glu Leu Glu
610                 615                 620 gaa att gtt caa cca att atc agc aaa ctc tat gga agt gca ggc cct    1920
Glu Ile Val Gln Pro Ile Ile Ser Lys Leu Tyr Gly Ser Ala Gly Pro
625                 630                 635                 640 ccc cca act ggt gaa gag gat aca gca gaa aaa gat gag ttg tag        1965
Pro Pro Thr Gly Glu Glu Asp Thr Ala Glu Lys Asp Glu Leu
                645                 650

<210> SEQ ID NO 150
<211> LENGTH: 654
<212> TYPE: PRT
<213> ORGANISM: Homo sapiens

<400> SEQUENCE: 150

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
    115                 120                 125

Gln Val Asp Ile Gly Gly Gly Gln Thr Lys Thr Phe Ala Pro Glu Glu
130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
    195                 200                 205

Tyr Gly Leu Asp Lys Arg Glu Gly Glu Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270
```

```
Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
        290                 295                 300

Ala Arg Ile Glu Ile Glu Ser Phe Tyr Glu Gly Asp Phe Ser Glu
305                 310                 315                 320

Thr Leu Thr Arg Ala Lys Phe Glu Leu Asn Met Asp Leu Phe Arg
                325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
        370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 151
<211> LENGTH: 1965
<212> TYPE: DNA
<213> ORGANISM: Artificial Sequence
<220> FEATURE:
<223> OTHER INFORMATION: Synthetic DNA
```

<400> SEQUENCE: 151

```
atgaagttgt ccttggttgc tgctatgttg ttgttgttgt ccgctgctag agctgaggag      60
gaggacaaga aggaggacgt tggtaccgtt gttggtatcg acttgggtac cacctactcc     120
tgtgttggtg ttttcaagaa cggtagagtt gagatcatcg ctaacgacca aggtaacaga     180
atcaccccat cctacgttgc tttcaccccca gagggtgaga gattgatcgg tgacgctgct     240
aagaaccaat tgacctccaa cccagagaac accgttttcg acgctaagag attgatcggt     300
agaacctgga acgacccatc cgttcaacaa gacatcaagt tcttgccatt caaggttgtt     360
gagaagaaga ccaagccata catccaagtt gacatcggtg gtggtcaaac caagaccttc     420
gctccagagg agatctccgc tatggttttg accaagatga aggagaccgc tgaggcttac     480
ttgggtaaga aggttaccca cgctgttgtt accgttccag cttacttcaa cgacgctcaa     540
agacaagcta ccaaggacgc tggtaccatc gctggtttga acgttatgag aatcatcaac     600
gagccaaccg ctgctgctat cgcttacggt ttggacaaga gagagggtga aagaacatc     660
ttggttttcg acttgggtgg tggtaccttc gacgtttcct tgttgaccat cgacaacggt     720
gttttcgagt tgttgctac caacggtgac acccacttgg gtggtgagga cttcgaccaa     780
agagttatgg agcacttcat caagttgtac aagaagaaga ccggtaagga cgttagaaag     840
gacaacagag ctgttcaaaa gttgagaaga gaggttgaga aggctaagag agctttgtcc     900
tcccaacacc aagctagaat cgagatcgag tccttctacg agggtgagga cttctccgag     960
accttgacca gagctaagtt cgaggagttg aacatggact tgttcagatc caccatgaag    1020
ccagttcaaa aggttttgga ggactccgac ttgaagaagt ccgacatcga cgagatcgtt    1080
ttggttggtg gttccaccag aatcccaaag atccaacaat tggttaagga gttcttcaac    1140
ggtaaggagc catccagagg tatcaaccca gacgaggctg ttgcttacgg tgctgctgtt    1200
caagctggtg ttttgtccgg tgaccaagac accggtgact tggttttgtt ggacgttttgt    1260
ccattgacct tgggtatcga gaccgttggt ggtgttatga ccaagttgat cccaagaaac    1320
accgttgttc aaccaagaa gtcccaaatc ttctccaccg cttccgacaa ccaaccaacc    1380
gttaccatca aggtttacga gggtgagaga ccattgacca aggacaacca cttgttgggt    1440
accttcgact tgaccggtat cccaccagct ccaagaggtg ttccacaaat cgaggttacc    1500
ttcgagatcg acgttaacgg tatcttgaga gttaccgctg aggacaaggg taccggtaac    1560
aagaacaaga tcaccatcac caacgaccaa aacagattga ccccagagga gatcgagaga    1620
atggttaacg acgctgagaa gttcgctgag gaggacaaga agttgaagga gagaatcgac    1680
accagaaacg agttggagtc ctacgcttac tccttgaaga accaaatcgg tgacaaggag    1740
aagttgggtg gtaagttgtc ctccgaggac aaggagacca tggagaaggc tgttgaggag    1800
aagatcgagt ggttggagtc ccaccaagac gctgacatcg aggacttcaa ggctaagaag    1860
aaggagttgg aggagatcgt tcaaccaatc atctccaagt tgtacggttc cgctggtcca    1920
ccaccaaccg gtgaggagga caccgctgag aaggacgagt tgtaa                      1965
```

<210> SEQ ID NO 152
<211> LENGTH: 1965
<212> TYPE: DNA
<213> ORGANISM: Cricetulus griseus

<400> SEQUENCE: 152

```
atgaagttcc ctatggtggc ggcggcgctg ctgctgctct cgcgcggtgcg ggccgaggag      60
gaggacaaga aggaggatgt gggcacggtg gtcggcatcg acctgggac cacctattcc    120
```

```
tgcgttggtg tgttcaagaa cggccgcgtg gagatcatag ccaacgatca gggcaaccgc    180
atcacgccgt cgtatgtggc cttcactcct gaaggcgagc gtctgattgg cgatgcggcc    240
aagaaccagc tcacctccaa tcccgagaac acggtcttcg acgccaagcg cctcatcgga    300
cgcacttgga atgacccttc agtgcagcag gacatcaagt tcttgccttt caaggtggtt    360
gaaaagaaaa ctaaaccata cattcaagtt gatattggag gtgggcaaac caaaacattt    420
gccccagaag aaatttctgc catggttctc actaaaatga agaaactgc tgaagcatat    480 ttgggaaaga aggttaccca tgcagttgtt actgtgccgg cttacttcaa tgatgcccag    540
cgccaagcaa ccaaagatgc tggcaccatt gctggactga atgtcatgcg gatcatcaat    600
gagcccacag cagctgctat tgcgtatggc ctggataaga gagagggcga agaacatc      660 ctcgttttg acctgggcgg tggaaccttc gatgtgtctc ttctgaccat tgacaatggt    720
gtctttgaag tggtggccac gaatggagac actcatctcg gtggggaaga ctttgatcag    780 cggggttatgg aacacttcat caagctgtac aaaaagaaaa ctgggaaaga cgttagaaaa    840
gacaacagag ctgtgcagaa acttcgtcgt gaggtggaaa aggctaagcg agccctgtct    900
tctcagcatc aagcaagaat tgagatagag tccttctttg aaggagaaga cttctctgag    960
accctgactc gggccaaatt tgaagagttg aacatggacc tgttccgatc taccatgaag   1020
ccagtccaga aagtgttgga agactctgat ctgaagaaat cagacattga tgaaattgtt   1080
cttgtcggtg ggtctactcg gattcccaag attcagcagc tggtgaaaga gttcttcaat   1140
ggcaaggagc catcccgtgg cataaaccca gatgaggctg tagcatacgg tgctgctgtc   1200
caggctggtg tcctctctgg tgatcaagat acaggtgatc tggtactgct tgatgtatgt   1260
cctcttacac ttggtattga aacagtggga ggtgtcatga ccaaactgat tccaaggaac   1320
actgtggtac ccaccaagaa gtctcagatc ttttccacag cttctgataa tcagccaact   1380
gtaacaatca aggtctatga aggtgaacga ccctaacaa agacaacca tcttctgggt   1440 acatttgatc tgactggaat tcctcctgct cctcgtgggg tacccagat tgaagtcacc   1500 tttgagatag atgttaatgg tattcttcga gtgacagctg aagacaaagg tacagggaac   1560
aaaaacaaaa tcacaattac caatgaccaa atcgcctga cacctgaaga aattgaaagg   1620
atggttaatg atgcagagaa gtttgctgag gaagacaaaa agctcaaaga gcgcattgat   1680
accaggaacg agttggaaag ctatgcttac tctctcaaga accagattgg agataaagaa   1740
aagctgggcg gtaaacttc ctctgaagat aaagaaacca tggagaaagc tgtagaggaa   1800
aagattgaat ggctgaaaag ccaccaggat gcagacattg aagactttaa agctaaaaag   1860
aaggaactag aggaaattgt tcagcctatt attagcaaac tctatggaag tgcaggccct   1920
cccccaactg gtgaagagga tacatcagaa aaagatgagt tgtag                    1965

<210> SEQ ID NO 153
<211> LENGTH: 1530
<212> TYPE: DNA
<213> ORGANISM: Cricetulus griseus

<400> SEQUENCE: 153
atgctgagcc gttctctgct gtgcctggcc ctggctggg tggccagggt gggcgccgac      60
gccccggagg aggaggacaa cgtcctggtg ctgaagaaga gcaacttcgc agaggcgctg    120
gcggcacaca actacctgct ggtggagttc tatgccccgt ggtgtggcca ctgcaaagct    180
ctggcccctg agtatgccaa agccgctgca aagctgaagg cagaaggctc cgagattcga    240
ctcgccaagg tggacgccac cgaagagtct gacctggctc agcagtatgg cgtccgcggc    300
```

```
taccctacaa tcaagttctt caagaatgga gacacagcgt cccctaagga gtacacagct    360
ggcagggaag ctgacgacat tgtgaactgg ctgaagaagc gaacaggtcc tgctgccaca    420
accctgtctg acaccgcagc ggccgagacc ttgatagact caagcgaggt ggctgtcatc    480
ggtttcttca aggatgtaga gtcagactct gccaagcagt tcttgctggc ggctgaggct    540
gtcgatgaca tacctttggg gatcacgtcc aacagtggtg tgttctccaa gtaccagctg    600
gacaaggatg gggtggtcct cttttaagaag tttgatgaag gccgaaacaa ctttgaaggt    660
gaggtcacca aggagaagct gctagacttc attaagcaca accaactgcc tttggtcatc    720
gagttcactg aacagacagc cccgaagatt tttggaggtg aaatcaagac acacattctg    780
ctattcctgc ccaagagtgt atctgactac gatggcaagt gggcaacttc aagaaagca    840 gccgaaggct tcaagggcaa gatcctgttt atcttcatcg acagcgacca cactgacaac    900
cagcgtatcc tggagttctt tggcctgaag aaggaggagt gtccagctgt gcggcttatt    960
accctagagc aagaaatgac caagtacaaa ccagagtcag atgagctaac agctgagaag   1020
atcacagaat tttgccaccg cttcctggag ggcaagatca agccccactt gatgagccag   1080
gaactgcctg aagactggga taaacagcca gtgaaagtgc tagttgggaa aaactttgaa   1140
gaagttgctt ttgatgagaa aaagaacgtc tttgtggaat tctatgcccc ctggtgtggc   1200
cactgcaagc agctagcccc catttgggac aaactgggag agacatacaa ggatcatgaa   1260
aatatcatca ttgctaagat ggactcaaca gctaatgagg tggaagccgt caaagtgcac   1320 agtttccccca ccctgaagtt cttcccagca actgcagaca gaacggtcat tgattataat   1380
ggtgagcgga cgctagacgg ttttaagaaa ttcctggaga gtggtggcca ggatggtgca   1440
ggagacgatg atgatgtgga cctagaggaa gctttagagc cagacatgga ggaggatgat   1500
gaccagaaag ctgtaaagga cgaattgtag                                    1530

<210> SEQ ID NO 154
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 154
atgcatttac aactcgtcc                                                 19

<210> SEQ ID NO 155
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 155
atgcatttag tggatgtttt g                                              21

<210> SEQ ID NO 156
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 156
atgcatttat ctggagtgtt g                                              21
```

```
<210> SEQ ID NO 157
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 157
cgggcccccc ctcgagtcta tgctccaaga cct                                    33

<210> SEQ ID NO 158
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 158
taccgtcgac ctcgatcaac aaccactgat tcc                                    33

<210> SEQ ID NO 159
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 159
agttctagag cggccatcct atacctgtcg tgcct                                  35

<210> SEQ ID NO 160
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 160
accgcggtgg cggccgctcg tgttgttcca ggtaatcc                               38

<210> SEQ ID NO 161
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 161
ggtagaggac cgtatgtagc                                                   20

<210> SEQ ID NO 162
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 162
caatgaaacg tttccgtagg t                                                 21

<210> SEQ ID NO 163
<211> LENGTH: 18
<212> TYPE: DNA
<213> ORGANISM: Artificial Sequence
<220> FEATURE:
<223> OTHER INFORMATION: Synthetic oligonucleotide primer
```

```
<400> SEQUENCE: 163
tgcgaaatcg ggccctct                                                18

<210> SEQ ID NO 164
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 164
ccggagtttg cacggctac                                               19

<210> SEQ ID NO 165
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 165
cggtgacgac ttcgactagt cgag                                         24

<210> SEQ ID NO 166
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 166
cggtgctgtt ggcgtcgtca tgggtg                                       26

<210> SEQ ID NO 167
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 167
ggcgcgttcc aattccactc tgctg                                        25

<210> SEQ ID NO 168
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 168
cgacgagtcc tctcaccagg aggttg                                       26

<210> SEQ ID NO 169
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 169
gtacctgctg gtggagttct                                              20
```

```
<210> SEQ ID NO 170
<211> LENGTH: 9
<212> TYPE: PRT
<213> ORGANISM: Artificial Sequence
<220> FEATURE:
<223> OTHER INFORMATION: Synthetic peptide

<400> SEQUENCE: 170

Arg Val Asp Phe Asn Val Pro Leu Asp
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic peptide

<400> SEQUENCE: 171

Glu Gly Lys Glu Leu Pro Gly Val Ala
1               5
```

METHOD FOR HIGH-LEVEL SECRETORY PRODUCTION OF PROTEIN

CROSS REFERENCE TO RELATED APPLICATIONS

This application is a National Stage of International Application No. PCT/JP2008/070155 filed Oct. 29, 2008, claiming priority based on Japanese Patent Application Nos. 2007-283731 filed Oct. 31, 2007 and 2007-288845 filed Nov. 6, 2007, the contents of all of which are incorporated herein by reference in their entirety.

TECHNICAL FIELD

The present invention relates to a method for high-level secretory production of a protein, mainly in yeast.

BACKGROUND ART

When secretory proteins are expressed, signal sequences thereof are recognized by signal recognition particles (SRPs), and the secretory proteins then pass through the translocon and enter into the endoplasmic reticulum. When secretory proteins pass through the translocon, the higher-order structures thereof are loosened, and the proteins are folded in the endoplasmic reticulum (ER). Protein folding can spontaneously occur, and various molecular chaperones assist such folding. A native conformation formed in the endoplasmic reticulum is critical for secretion, and misfolded proteins cannot enter the secretory pathway located downstream. When proteins are not correctly folded in the endoplasmic reticulum, proteins of having abnormal higher-order structures are disadvantageously aggregated therein. Such disturbance in modification that takes place in the endoplasmic reticulum (i.e., addition of a sugar chain or a disulfide bond) and deteriorated transportation from the endoplasmic reticulum cause "endoplasmic reticulum stress." As a means for dealing with such endoplasmic reticulum stress, a stress response referred to as "unfolded protein response (UPR)" is induced in eukaryotic cells. Transcription induction and translation regulation of UPR are responses that restore accumulated abnormal proteins. There is also a mechanism referred to as "ER-associated degradation (ERAD)" that degrades and eliminates abnormal proteins, so as to maintain homeostasis in the endoplasmic reticulum. Further, molecular chaperones that loosen the aggregated proteins for the purpose of folding are known, as well as molecular chaperones that assist protein folding in the endoplasmic reticulum. For example, HSP104 can perform a reaction that cannot be performed with the aid of other chaperones that cooperate with HSP70 and solubilizes proteins from the aggregates (Glover J R, Lindquist S, Hsp104, Hsp70, and Hsp40: A novel chaperone system that rescues previously aggregated proteins, Cell, 1998, 94:73-82).

Meanwhile, antibody molecules form aggregates of a proper conformation (H2L2) through the formation of a disulfide bond between the antibody heavy chain and the antibody light chain or between antibody heavy chains and forming an intramolecular disulfide bond of the antibody heavy chain and the antibody light chain. In the case of eukaryotic cells such as yeast cells, introduction of a disulfide bond via protein oxidative folding is carried out by the oxidative protein disulfide isomerase (PDI) in the endoplasmic reticulum (Benjamin P. Tu and Jonathan S. Weissman, Oxidative protein folding in eukaryotes: Mechanisms and consequences, J. Cell Biol., 2004, 164: 341-346). PDI that is reduced via oxidization of substrate proteins is reoxidized by oxidative ERO1 localized in the vicinity of the membrane (Mezghrani, A., Fassio, A., Benham, A., Simmen, T., Braakman, I., and Sitia, R., Manipulation of oxidative protein folding and PDI redox state in mammalian cells, EMBO. J., 2001, 20: 6288-6296 and Frand, A. R. and C. A. Kaiser, Ero1p oxidizes protein disulfide isomerase in a pathway for disulfide bond formation in the endoplasmic reticulum, Mol. Cell, 1999, 4: 469-477). In the yeast endoplasmic reticulum, there are 5 types of PDI families (i.e., PDI1, EUG1, MPD1, MPD2, and EPS1) (Per Norgaard, Vibeke Westphal, Christine Tachibana, Lene Alsoe, Bjorn Holst, Jakob R. Winther, Functional Differences in Yeast Protein Disulfide Isomerases, J. Cell Biology, 2001, 152 (3): 553-562). Among such PDI families, those that are confirmed to form an intramolecular disulfide bond with ERO1 are limited to PDI1 and MPD2. It is also reported that efficiency for protein oxidative folding is improved by BiP/Kar2, which functions in cooperation with PDI (Marcus Mayer, Ursula Kies, Robert Kammermeier, and Johannes Buchner, BiP and PDI Cooperate in the Oxidative Folding of Antibodies in Vitro, J. Biol. Chem., 2000, 275 (38): 29421-29425). BiP/Kar2 is also associated with induction by active HAC1 of various genes associated with the aforementioned UPR. Active HAC1 is activated by splicing of HAC1 by the IRE1 transmembrane kinase/nuclease. IRE1 to which BiP/Kar2 has bound is dissociated when BiP/Kar2 acts on a protein having an abnormal structure in the endoplasmic reticulum, it exhibits nuclease activity through the formation of a dimmer, and it produces active HAC1 by splicing HAC1 (Cox J S., Shamu C E., Walter P., Transcriptional induction of genes encoding endoplasmic reticulum resident proteins requires a transmembrane protein kinase, Cell, 1993, 73: 1197-1206 and Sidrauski C. and Walter P., The transmembrane kinase Ire1p is a site-specific endonuclease that initiates mRNA splicing in the unfolded protein response, Cell, 1997, 90 (6): 1031-1039). Also, Bip/Kar2 is associated with protein folding in the endoplasmic reticulum in cooperation with SCJ1 located in the endoplasmic reticulum (Susana Silberstein, Gabriel Schlenstedt, Pam A. Silver, and Reid Gilmore, A Role for the DnaJ Homologue Scj1p in Protein Folding in the Yeast Endoplasmic Reticulum, J. Cell Biol., 1998, 143 (4): 921-933).

Thus, it has been demonstrated that various molecular chaperones are associated with correct folding of secretory proteins. Also, attempts to increase the amount of secretory proteins produced with the aid of molecular chaperones have been made. When an S—S bond produces abundant human serum albumin in the yeast *K. lactis*, for example, the amount of production is increased by 15 times upon introduction of ERO1 or PDI1 (Tiziana Lodi, Barbara Neglia, and Claudia Donnini, Secretion of human serum albumin by *Kluyveromyces lactis* overexpressing K1PDI1 and K1ERO1, Applied. Environ. Microbiol., 2005, 71 (8): 4359-4363). However, simultaneous introduction of ERO1 and PDI1 does not lead to any further improvement, and it merely advances the timing of production. Also, IL-1β having no S—S bond has no effects. It has been also reported that the amount of secretory production was increased by 8 times via coexpression of RatPDI and Bip, when producing single-chain antibody fragments (scFvs) in *S. cerevisiae* (Shusta, E. V., Raines, R. T., Pluckthun, A., and Wittrup, K. D., Increasing the secretory capacity of *Saccharomyces cerevisiae* for production of single-chain antibody fragments, Nat. Biotechnol., 1998, 16: 773-777). In this report, it was concluded that Bip prevents aggregation and the amount of secretory production of PDI was increased by isomerase activity instead of chaperone activity. When producing single-chain antibody fragments (scFvs) in *Pichia pastries*, also, the amount of secretory production was increased by 3 times via coexpression with Bip; however, use of PDI or PDI in combination with Bip could not yield any effects (Damasceno, Leonardo, et al., Coooverexpression of chaperones for enhanced secretion of a single-chain antibody fragment in *Pichia pastris*. Applied. Microbio. Biotech. (2007) 74 (2): 381-389). Further, the effects of an increased PDI level on secretion of IL-15 and the tumor necrosis factor receptor (i.e., Fc fusion protein (TNFR:Fc)) were inspected in CHO cells. As a result, PDI overexpression allowed retention of TNFR:Fc (i.e., proteins rich in disulfide bonds) in the cells, but IL-15 was not retained in the cells (Davis R., Schooley K., Rasmussen B., Thomas J., Reddy P., Effect of PDI overexpression on recombinant protein secretion in CHO cells. Biotechnol. Prog., 2000, 16: 736-743). This suggests that PDI overexpression disadvantageously results in a decrease in the amount of secretory production in CHO cells.

As described above, attempts to improve secretory production of proteins such as antibodies via coexpression of molecular chaperones that assist protein folding have been made. However, effects cannot be always attained because of types or combinations of host cells or molecular chaperones. In an example of antibody production, single-stranded antibodies are merely produced, and a method for effectively producing high-molecular-weight proteins or aggregate proteins, including complete antibodies, has not yet been discovered.

DISCLOSURE OF THE INVENTION

Accordingly, the present invention is intended to provide a means for high-level secretory production of proteins and, more particularly, proteins having complicated structures, such as antibodies, in yeast or other host cells.

The present inventors have conducted concentrated studies in order to attain the above object. As a result, they discovered that coexpression of one or more types of molecular chaperone genes with the targets of expression (i.e., foreign protein genes) in yeast or other host cells would result in an increase in the amount of secretory production of foreign proteins. Further, they discovered that activity of protein O-mannosyltransferase (PMT) associated with O-sugar chain addition to a yeast-specific protein, which inhibits aggregation of heteromultimers such as antibodies, may be inhibited to further improve productivity by approximately 2 to 45 times. The present invention has been completed based on such findings.

Specifically, the present invention includes the following inventions.

(1) A transformed host cell into which one or a combination of two or more of the chaperone genes (a) to (c) below have been introduced:

(a) a gene comprising DNA which consists of the nucleotide sequence as shown in SEQ ID NO: 1, 3, 5, 7, 9, 11, or 13;

(b) a gene which hybridizes under stringent conditions to a DNA consisting of a nucleotide sequence complementary to DNA consisting of the nucleotide sequence as shown in SEQ ID NO: 1, 3, 5, 7, 9, 11, or 13 and encodes a protein having activity of accelerating foreign protein secretion; and (c) a gene which consists of a nucleotide sequence having at least 80% homology with the nucleotide sequence as shown in SEQ ID NO: 1, 3, 5, 7, 9, 11, or 13 and encodes a protein having activity of accelerating foreign protein secretion.

(2) A transformed host cell into which one or a combination of two or more of the genes encoding the chaperone proteins (d) to (f) below have been introduced:

(d) a protein which consist of the amino acid sequence as shown in SEQ ID NO: 2, 4, 6, 8, 10, 12, or 14;

(e) a protein which consist of an amino acid sequence having at least 80% homology with the amino acid sequence as shown in SEQ ID NO: 2, 4, 6, 8, 10, 12, or 14 and has activity of accelerating foreign protein secretion; and (f) a protein which consist of an amino acid sequence derived from the amino acid sequence as shown in SEQ ID NO: 2, 4, 6, 8, 10, 12, or 14 by deletion, substitution, and/or addition of one or several amino acids and has activity of accelerating foreign protein secretion.

(3) A transformed host cell into which one or a combination of two or more of the chaperone genes (g) or (h) below have been introduced;

(g) a gene encoding PDI1, MPD1, SCJ1, ERO1, FKB2, JEM1, LHS1, MPD2, ERJ5, or EUG1 derived from *S. cerevisiae* or a homologous gene thereof; or (h) a gene encoding PDI, ERO1-Lα, ERO1-Lβ, or GRP78 derived from a human, a homologous gene thereof, or a codon-modified gene thereof.

(4) A transformed host cell into which a gene selected from the group consisting of one or a combination of two or more of the chaperone genes (i) to (xii) below, a homologous gene thereof, or a codon-modified gene thereof has been introduced:

(i) a gene encoding PDI1 derived from *O. minuta;*

(ii) a gene encoding PDI1 derived from *S. cerevisiae;*

(iii) a gene encoding PDI derived from a human;

(iv) a gene encoding ERO1 derived from *O. minuta;*

(v) a gene encoding ERO1 derived from a human;

(vi) a gene encoding Kar2 derived from *O. minuta;*

(vii) a gene encoding PDI1 and a gene encoding ERO1 derived from *O. minuta;*

(viii) a gene encoding PDI1 and a gene encoding Kar2 derived from *O. minuta;*

(ix) a gene encoding PDI derived from a human and a gene encoding ERO1 derived from *O. minuta;*

(x) a gene encoding PDI1, a gene encoding ERO1, and a gene encoding Kar2 derived from *O. minuta;*

(xi) a gene encoding PDI, a gene encoding ERO1-Lβ, and a gene encoding GRP78 derived from a human; and (xii) a gene encoding PDI derived from a human, a gene encoding ERO1 derived from *O. minuta*, and a gene encoding GRP78 derived from a human.

(5) The transformed host cell according to any of (1) to (4), wherein the host cell is a eukaryotic cell.

(6) The transformed host cell according to (5), wherein the eukaryotic cell is a yeast cell.

(7) The transformed host cell according to (6), wherein the yeast is methanol-assimilating yeast.

(8) The transformed host cell according to (7), wherein the methanol-assimilating yeast is *Ogataea minuta*.

(9) The transformed host cell according to (6), wherein the yeast is *Saccharomyces cerevisiae*.

(10) The transformed host cell according to any of (1) or (9), into which a gene encoding a foreign protein has been introduced.

(11) The transformed host cell according to (10), wherein the foreign protein is a multimeric protein.

(12) The transformed host cell according to (11), wherein the multimeric protein is a heteromultimer.

(13) The transformed host cell according to (12), wherein the heteromultimer is an antibody or a functional fragment thereof.

(14) The transformed host cell according to (10), wherein the foreign protein is glycosyltransferase.

(15) A method for producing a protein comprising culturing the transformed host cell according to any of (10) to (14) in a medium and sampling a target protein from the culture product.

(16) The method for producing a protein according to (15), wherein culture is carried out under conditions in which protein O-mannosyltransferase (PMT) activity is inhibited.

(17) The method for producing a protein according to (16), wherein protein O-mannosyltransferase (PMT) activity is inhibited with the addition of an inhibitor of PMT activity to the medium.

(18) The method for producing a protein according to (17), wherein the inhibitor of PMT activity is 5-[[3,4-(1-phenylmethoxy)phenyl]methylene]-4-oxo-2-thioxo-3-thiazolidineacetic acid.

(19) The method for producing a protein according to (16), wherein protein O-mannosyltransferase (PMT) activity is inhibited via destruction of the PMT gene.

(20) The method for producing a protein according to (16), wherein protein O-mannosyltransferase (PMT) activity is inhibited via destruction of the PMT gene and with the addition of an inhibitor of PMT activity to the medium.

(21) The method for producing a protein according to (20), wherein the inhibitor of PMT activity is 5-[[3,4-(1-phenylmethoxy)phenyl]methylene]-4-oxo-2-thioxo-3-thiazolidineacetic acid.

(22) The method for producing a protein according to any of (19) to (21), wherein destruction of the PMT gene is single destruction of the PMT5 gene or the PMT6 gene or double destruction of the PMT5 gene and the PMT6 gene.

(23) Any of the chaperone genes (a) to (c) below derived from *Ogataea minuta*:

(a) a gene comprising DNA which consists of the nucleotide sequence as shown in SEQ ID NO: 1, 3, 5, 7, 9, 11, or 13;

(b) a gene which hybridizes under stringent conditions to a DNA consisting of a nucleotide sequence complementary to DNA consisting of the nucleotide sequence as shown in SEQ ID NO: 1, 3, 5, 7, 9, 11, or 13 and encodes a protein having activity of accelerating foreign protein secretion; and (c) a gene which consists of a nucleotide sequence having at least 80% homology with the nucleotide sequence as shown in SEQ ID NO: 1, 3, 5, 7, 9, 11, or 13 and encodes a protein having activity of accelerating foreign protein secretion.

(24) A gene encoding any of the chaperone proteins (d) to (f) below:

(d) a protein which consist of the amino acid sequence as shown in SEQ ID NO: 2, 4, 6, 8, 10, 12, or 14;

(e) a protein which consist of an amino acid sequence having at least 80% homology with the amino acid sequence as shown in SEQ ID NO: 2, 4, 6, 8, 10, 12, or 14 and has activity of accelerating foreign protein secretion; and (f) a protein which consist of an amino acid sequence derived from the amino acid sequence as shown in SEQ ID NO: 2, 4, 6, 8, 10, 12, or 14 by deletion, substitution, and/or addition of one or several amino acids and has activity of accelerating foreign protein secretion.

(25) An expression vector comprising the gene according to (23) or (24).

(26) An expression vector comprising the gene (g) or (h) below:

(g) a gene encoding PDI1, MPD1, SCJ1, ERO1, FKB2, JEM1, LHS1, MPD2, ERJ5, or EUG1 derived from *S. cerevisiae* or a homologous gene thereof; or (h) a gene encoding PDI, ERO1-Lα, ERO1-Lβ, or GRP78 derived from a human, a homologous gene thereof, or a codon-modified gene thereof.

Figure 1:
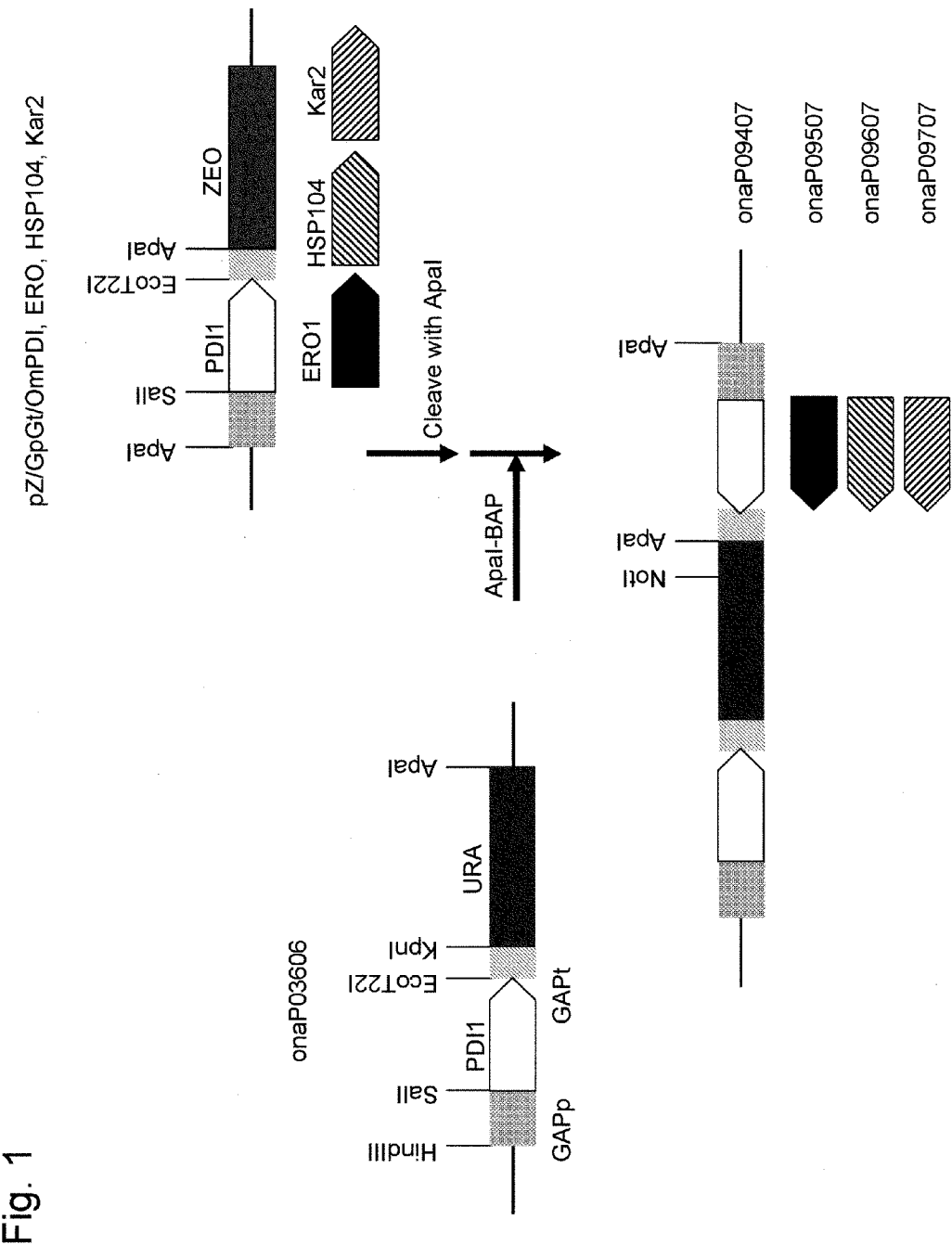
FIG. 1 shows the construction of expression vectors for various chaperone proteins derived from *O. minuta* (onaP03606, onaP09407, onaP09507, onaP09607, and onaP09707).

This patent application claims priority from Japanese Patent Application Nos. 2007-283731 filed on Oct. 31, 2007 and 2007-288845 filed on Nov. 6, 2007, and includes part or all of the contents as disclosed in the descriptions thereof.

Hereafter, the present invention is described in detail.

1. Gene Used for High-Level Secretory Production of a Protein

High-level secretory production of a protein in the present invention involves the use of a gene encoding a set of molecular chaperones (hereafter such gene is referred to as a "chaperone gene") that functions in protein folding and inhibition of degradation or aggregation of a denatured protein in the endoplasmic reticulum.

Examples of chaperone genes that are used in the present invention include PDI1, MPD1, SCJ1, EUG1, ERO1, HSP104, and Kar2 genes derived from the *Ogataea minuta* (*O. minuta*) strain, which was newly obtained in the present invention. The PDI1, MPD1, SCJ1, EUG1, ERO1, HSP104, and Kar2 genes derived from *Ogataea minuta* (*O. minuta*) each consists of a nucleotide sequence as shown in SEQ ID NOs: 1, 3, 5, 7, 9, 11, or 13, and amino acid sequences deduced based on such nucleotide sequences are as shown in SEQ ID NOs: 2, 4, 6, 8, 10, 12, or 14.

The chaperone gene used in the present invention may be a gene encoding a protein consisting of an amino acid sequence derived from the amino acid sequence as shown in SEQ ID NO: 2, 4, 6, 8, 10, 12, or 14 by deletion, substitution, and/or addition of one or several amino acids, provided that such gene has activity of accelerating foreign protein secretion.

The number of amino acids that may be deleted, substituted, and/or added is preferably 1 to several. The number represented by the term "several" is not particular limited. For example, such number is 20 or smaller, preferably 10 or smaller, more preferably 7 or smaller, and further preferably 5 or smaller, approximately. The term "mutation" used herein primarily refers to a mutation that is artificially introduced via a known method for preparing a mutant protein, and the term may refers to a mutation that is similar to one existing in nature.

Also, the chaperone gene used in the present invention may be a gene encoding a protein which consists of an amino acid sequence having at least 80% homology with the amino acid sequence as shown in SEQ ID NO: 2, 4, 6, 8, 10, 12, or 14 and has activity of accelerating foreign protein secretion. The term "at least 80% homology" preferably refers to at least 85% homology, more preferably at least 90% homology, and most preferably at least 95% homology. Protein homology search can be carried out with the use of, for example, the DNA Databank of Japan (DDBJ) via FASTA, BLAST, or other programs.

The term "activity of accelerating foreign protein secretion" used herein refers to activity of high-level secretion of a correctly folded foreign protein in a host cell based on activity of molecular chaperones for protein folding (e.g., formation of a disulfide bond), activity of refolding a denatured protein into a normal protein, and activity of inhibiting denatured protein aggregation in the endoplasmic reticulum.

Also, the term " . . . has activity of accelerating foreign protein secretion" refers that such activity is substantially equivalent to activity of a protein having the amino acid sequence as shown in SEQ ID NO: 2, 4, 6, 8, 10, 12, or 14.

The chaperone gene used in the present invention may be a gene which hybridizes under stringent conditions to a DNA consisting of a nucleotide sequence complementary to DNA comprising the nucleotide sequence as shown in SEQ ID NO: 1, 3, 5, 7, 9, 11, or 13 and encodes a protein having activity of accelerating foreign protein secretion.

Under the aforementioned "stringent conditions," a so-called specific hybrid is formed, but a non-specific hybrid is not formed. Under such conditions, for example, complementary strands of a highly homologous nucleic acid, i.e., a nucleic acid consisting of a nucleotide sequence having at least 80%, preferably at least 85%, more preferably at least 90%, and most preferably at least 95% homology to the nucleotide sequence as shown in SEQ ID NO: 1, 3, 5, 7, 9, 11, or 13 undergo hybridization, but complementary strands of a nucleic acid having lower homology levels would not undergo hybridization. More specifically, the sodium concentration is 15 to 750 mM, preferably 50 to 750 mM, and more preferably 300 to 750 mM, the temperature is 25° C. to 70° C., preferably 50° C. to 70° C., and more preferably 55° C. to 65° C., and formamide concentration is 0% to 50%, preferably 20% to 50%, and more preferably 35% to 45%. Under stringent conditions, further, a filter is generally washed at sodium salt concentration of 15 to 600 mM, preferably 50 to 600 mM, and more preferably 300 to 600 mM, and temperature is 50° C. to 70° C., preferably 55° C. to 70° C., and more preferably 60° C. to 65° C., after hybridization.

A person skilled in the art can easily obtain such homologous genes by referring to, for example, Molecular Cloning (Sambrook, J. et al., Molecular Cloning: A Laboratory Manual 2nd ed., Cold Spring Harbor Laboratory Press, 10 Skyline Drive Plainview, N.Y., 1989). Also, nucleotide sequence homology search can be carried out via FASTA, BLAST, or other programs.

The amino acid mutation mentioned above, such as deletion, substitution, and/or addition, can be introduced via a technique known in the art, such as the Kunkel method or the Gapped duplex method, or a technique in accordance therewith. For example, mutagenesis kits utilizing site-directed mutagenesis, such as a Mutant-K (Takara Bio), Mutant-G (Takara Bio), or LA PCR in vitro Mutagenesis series kit (Takara Bio), can be used.

The chaperone gene used in the present invention may be a chaperone gene derived from another organism species, such as other types of yeast, mold, or a human. As chaperone gene derived from another organism species, a chaperone gene derived from a human that corresponds to the aforementioned chaperone gene (the PDI1, MPD1, SCJ1, EUG1, ERO1, HSP104, or Kar2 gene) derived from *Ogataea minuta* is preferable. A chaperone gene other than the aforementioned chaperone genes may also be used.

Examples of chaperone genes derived from a human include PDI (GenBank Accession No. BC010859; SEQ ID NO: 140), ERO1-Lα (GenBank Accession No. AF081886; SEQ ID NO: 143), ERO1-Lβ (GenBank Accession No. BC044573; SEQ ID NO: 146), and GRP78 (GenBank Accession No. AL354710; SEQ ID NO: 149).

Also, examples of chaperone genes derived from *Saccharomyces cerevisiae* include PDI1 (Primary SGDID: S000000548; SEQ ID NO: 120), MPD1 (Primary SGDID: S000005814; SEQ ID NO: 122), SCJ1 (Primary SGDID: S000004827; SEQ ID NO: 124), ERO1 (Primary SGDID: S000004599; SEQ ID NO: 126), FKB2 (Primary SGDID: S000002927; SEQ ID NO: 128), JEM1 (Primary SGDID: S000003609; SEQ ID NO: 130), LHS1 (Primary SGDID: S000001556; SEQ ID NO: 132), MPD2 (Primary SGDID: S000005448; SEQ ID NO: 134), ERJ5 (Primary SGDID: S000001937; SEQ ID NO: 136), and EUG1 (Primary SGDID: S000002926; SEQ ID NO: 138). Sequence information regarding the genes derived from *Saccharomyces cerevisiae* is available from SGD (*Saccharomyces* genome database: http://www.yeastgenome.org/).

Such chaperone genes derived from other organism species may also be genes homologous thereto, provided that such genes have activity of accelerating foreign protein secretion. Extent of such sequence homology, the number of deletion, substitution, or addition of amino acids, stringent conditions, and methods for mutagenesis are as described above.

Also, chaperone genes derived from other organism species may be codon-modified genes that are modified so as to improve translation efficiency via substitution of a nucleotide sequence with a codon that is frequently used in a host cell (the term "codon-modified" may be occasionally referred to as "synthesized" herein). DNA having a modified nucleotide sequence can be artificially synthesized. In the case of a long DNA sequence, a sequence is first divided into several fragments, fragments are synthesized in advance, and the resultants are then bound to each other at the end. Thus, DNA of interest can be synthesized.

In the present invention, one or more types of the aforementioned chaperone genes are used in combination. When two or more genes are used in combination, such genes may be derived from the same or different organism species.

Preferable examples of the chaperone genes that are used in the present invention include the PDI1 gene derived from *O. minuta*, the PDI1 gene derived from *S. cerevisiae*, the PDI gene derived from a human, the PDI gene derived from a human (a codon-modified gene), the ERO1 gene derived from *O. minuta*, the ERO1 gene derived from a human, and the Kar2 gene derived from *O. minuta*.

Further preferable examples of the chaperone genes that are used in the present invention include a combination of the PDI1 gene and the ERO1 gene derived from *O. minuta*, a combination of the PDI1 gene and the Kar2 gene derived from *O. minuta*, a combination of the PDI gene derived from a human (a codon-modified gene) and the ERO1 gene derived from *O. minuta*, a combination of the PDI1 gene, the ERO1 gene, and the Kar2 gene derived from *O. minuta*, a combination of the PDI gene, the ERO1-Lβ gene, and the GRP78 gene derived from a human (codon-modified genes), and a combination of the PDI gene derived from a human (a codon-modified gene), the ERO gene derived from *O. minuta*, and the GRP78 gene derived from a human (a codon-modified gene).

The term "codon-modified gene" used with regard to the chaperone gene derived from a human refers to a gene in which frequency of a codon to be used is optimized in accordance with that of *O. minuta*.

In the present invention, the aforementioned genes used for high-level secretory production of proteins and genes encoding foreign proteins that are the targets of high-level secretory production described below (hereafter these genes are referred to as "target genes") can be obtained by a general technique of preparing mRNA and synthesizing cDNA using reverse transcriptase. As an example of the aforementioned general technique, a cDNA library derived from a cell or tissue in which the target gene is expressed is subjected to screening with the use of a DNA probe synthesized from a fragment of the target gene, so as to isolate the gene of interest. mRNA can be prepared by a technique generally used in the art. For example, the aforementioned cell or tissue may be treated with a guanidine reagent or a phenol reagent to obtain total RNA, following which poly (A)+ RNA (mRNA) is then obtained via the affinity column method using oligo (dT) cellulose columns or poly U-sepharose using sepharose 2B as a carrier or a batch technique. Further, poly (A)+ RNA may be fractionated via sucrose density gradient centrifugation or via other means. Subsequently, the obtained mRNA is used as a template to synthesize single-stranded cDNA using oligo dT primers and reverse transcriptase, and double-stranded cDNA is synthesized from the single-stranded cDNA using DNA synthetase I, DNA ligase, RNaseH, and the like. The synthesized double-stranded cDNA is blunt-ended using T4 DNA synthetase, subjected to ligation of an adaptor (e.g., an EcoRI adaptor), phosphorylation, or the like, incorporated into a λ phage, such as λgt11, and then packaged in vitro to prepare a cDNA library. In addition to a λ phage, plasmid vectors may be used to prepare cDNA library. Thereafter, a strain having DNA of interest (i.e., a positive clone) may be selected from the cDNA library.

When the target gene is isolated from genomic DNA or when a fragment containing a promoter region and a terminator region is isolated, genomic DNA is extracted from a cell strain of a source organism, and the target gene is selected in accordance with a common technique (Molecular Cloning, 1989; Methods in enzymology 194, 1991). Genomic DNA can be extracted by the method of Cryer et al. (Methods in Cell Biology, 12, 39-44, 1975) or the method of P. Philippsen et al. (Methods Enzymol., 194, 169-182, 1991), for example. When the source is a yeast strain, for example, a yeast protoplast is prepared, and the yeast protoplast is then subjected to a conventional technique, such as known DNA extraction techniques, alcohol precipitation techniques after removal of cell residues at a high salt concentration, or alcohol precipitation techniques after phenol or chloroform extraction.

The target gene can be obtained by, for example, PCR (PCR Technology, Henry A. Erlich, Stockton Press, 1989). When amplifying the target gene via PCR, a synthesized 20 mer to 30 mer single-stranded DNA is used as a primer, and genomic DNA is used as a template. The nucleotide sequence of the amplified gene is confirmed and then used.

A fragment containing a target gene whose sequence is unknown can be obtained by (a) preparing a gene library by a conventional technique and (b) selecting a clone of interest from the resulting gene library to be amplified. A gene library can be prepared by obtaining chromosome DNA from a cell line of a source organism via a conventional technique, partially digesting the chromosome DNA with adequate restriction enzymes for fragmentation, ligating the resulting fragment to an adequate vector, and then introducing the vector into an adequate host cell. Alternatively, mRNA may be extracted from a cell, cDNA may be synthesized therefrom, the synthesized cDNA may be ligated to an adequate vector, and the vector may be introduced into an adequate host cell, so that a gene library can be prepared. In such a case, a plasmid that is known as a conventional vector for gene library preparation can be used, and phages, cosmids, or other vectors can be extensively used. A host cell that is subjected to transformation or transduction may be selected in accordance with vector type.

Clones that carry target gene fragments are selected from the above gene library via colony hybridization, plaque hybridization, or other means involving the use of label probes containing sequences specific to the target genes.

Also, the target genes can be subjected to chemical total synthesis. For example, two pairs of complementary oligonucleotides are prepared and then annealed, several annealed DNA strands are ligated with the aid of DNA ligase, or several partially complementary oligonucleotides are prepared and gaps are filled by PCR. Thus, genes can be synthesized.

DNA sequences of genes can be determined by a conventional technique, such as the dideoxy method (Sanger et al., Proc. Natl. Acad. Sci., U.S.A., 74, 5463-5467, 1977). Further, the above DNA nucleotide sequences can be easily determined with the use of a commercially available sequencing kit or the like.

2. Expression Vector

The present invention provides a vector comprising a single type of the chaperone gene, a vector comprising two or more copies of a single type of the chaperone genes, or a vector comprising a combination of two or more of the chaperone genes. In order to express the chaperone gene in a host cell, a vector comprising either gene may be used to carry out transformation. Alternatively, a vector comprising a plurality of genes may be used to carry out transformation. Also, such expression vector may comprise a gene encoding a foreign protein. Alternatively, an expression vector comprising a gene encoding a foreign protein may be prepared separately. In such a case, vectors are cotransfected into a host cell.

A gene encoding a foreign protein is not particularly limited. Examples include: various enzyme genes, such as the lysozyme gene, the α-amylase gene, and the α-galactosidase gene, and in particular, glycosyltransferase genes that are necessary for production of pharmaceutically useful glycoproteins, such as the erythropoietin (EPO) gene and the granulocyte colony-stimulating factor (G-CSF) genes; various interferon genes that are and physiologically active proteins, such as interferon α and interferon γ genes; various interleukin genes, such as IL1 and IL2 genes; various cytokine genes, such as the erythropoietin (EPO) gene and the granulocyte colony-stimulating factor (G-CSF) gene; and growth factor genes. These genes may be obtained via any means.

The present invention is particularly effective on a protein that is highly hydrophobic and a protein whose secretory production is insufficient due to composite formation. Thus, the aforementioned foreign protein includes a multimeric protein, such as an antibody or its functional fragment, i.e., a heteromultimer.

An expression regulation region may be adequately added to the chaperone gene or a gene encoding a foreign protein to constitute an expression vector as a protein expression unit. A protein expression unit comprises, in the direction of a reading frame of transcription, at least a promoter region, the above gene, and a transcription terminator region. A promoter that can be used herein may be an inducible expression promoter or constitutive expression promoter. Examples of inducible expression promoters include promoters involved in methanol metabolism of methanol-assimilating yeast, such as alcohol oxidase (AOX) gene promoter, dihydroxyacetone synthase (DAS) gene promoter, and formate dehydrogenase (FDH) gene promoter. An example of another inducible promoter that can be used is a copper-inducible (CUP) promoter. Examples of constitutive expression promoters include promoters of the glyceraldehyde-3-phosphate dehydrogenase (TDH, GAP) gene, the phosphoglycerokinase (PGK) gene, the phosphotriose isomerase (TPI) gene, the enolase (ENO) gene, the actin (ACT) gene, the cytochrome c (CYC) gene, the trehalose synthase (TPS) gene, and the alcohol dehydrogenase (ADH) gene. Also, a transcription terminator may be a sequence having activity of terminating transcription from a promoter. It may be a sequence of the same or a different gene of the promoter.

In order to realize high-level secretory production of foreign proteins, use of a potent promoter is necessary. When production of a protein that is less likely to fold or less likely to be secreted is attempted with the use of a highly active promoter, hyposecretion may disadvantageously occur. Such hyposecretion occurs due to the following reasons. That is, protein production exceeds the capacity of the ribosome where translation is performed and the endoplasmic reticulum wherein folding and secretion are performed. This causes excessively produced proteins to be denatured, aggregated, ubiquitinated in cells, and degraded by the proteosome. Accordingly, promoters that can attain an expression level to the extent that resulting proteins would be denatured and would not undergo aggregation or the resulting proteins would not exceed the secretion capacity may be adequately selected. Alternatively, activity of the promoters may be attenuated and the promoters of interest may then be used. Molecules that form heteromultimers are likely to be affected as described above among multimeric proteins. In particular, molecules such as antibodies are heterotetramers comprising two molecules each of the heavy chain and of the light chain being aggregated. Thus, the expression level is an important factor for realizing adequate aggregation.

The expression vector of the present invention can comprise a selection marker for selecting a transformant. For examples, expression vectors for yeast can comprise auxotrophic marker genes selected from among His1, His2, His3, His4, His5, His6, Leu2, Arg1, Arg2, Arg3, Trp1, Lys2, Ade1, Ade2, Ura3, and Ura5 genes.

As selection markers, drug-resistant markers that impart resistance to drugs such as cerulenin, aureobasidin, Zeocin, canavanine, cycloheximide, hygromycin, blasticidin, tetracycline, kanamycin, ampicillin, and neomycin can be used, in addition to the aforementioned auxotrophic markers. Thus, transformants can be selected. Also, genes that impart solvent resistance to ethanol, osmotic resistance to glycerol or salt, metal ion resistance to copper, and the like may be used as markers, so that transformants can be selected.

3. Transformed Host Cell

The transformed host cell of the present invention comprises the gene described in 1. above or the expression vector described in 2. above introduced therein.

An example of a host cell to be transformed is an eucaryotic cell, and preferably a yeast strain. Examples of yeast strains include methanol-assimilating yeast strains, such as *Ogataea minuta, Pichia pastoris, Hansenulla polymorpha* (*Pichia angusta*), and *Candida boidinii* and yeast strains, such as *Saccharomyces cerevisiae, Kluyveromyces lactis, Yarowia lipolytica*, and *Shizosaccharomyces pombe*. More specifically, the *Ogataea minuta* YK3 strain (Δoch1Δpep4Δprb1Δyps1Δura3Δade1) can be used as the *Ogataea minuta* strain, and the *Saccharomyces cerevisiae* BY4741 strain (MATa Δhis3Δleu2Δmet15Δ ura3) can be used as the *Saccharomyces cerevisiae* strains, although the yeast strains are not limited thereto.

Further, the present invention is intended to obtain a host cell in which the endoplasmic reticulum (ER), which is essential for secretion, is enhanced. Accordingly, the present invention is applicable to animal cells or other cells.

In the present invention, an expression vector can be introduced into a host cell by any method, provided that an introduced gene is stably present and adequately expressed in a host. Examples of such methods that are generally employed include the calcium phosphate method (Ito et al., Agric. Biol. Chem., 48, 341, 1984), electroporation (Becker, D. M. et al., 1990; Methods. Enzymol., 194, 182-187), use of spheroplasts (Creggh et al., Mol. Cell. Biol., 5, 3376, 1985), the lithium acetate method (Itoh, H., 1983; J. Bacteriol. 153, 163-168), and lipofection.

4. Method for Producing Protein

In the present invention, proteins can be produced by culturing the transformed host cells via a conventional technique and sampling the proteins from the culture product, followed by purification. The term "culture product" used herein refers to culture cells, cultured fungus bodies, or destroyed cells or fungus bodies, in addition to a culture supernatant.

The transformed host cell can be cultured in a medium in accordance with a conventional method used for culture of the host cell.

When the transformed host cell is a microorganism, such as yeast, either a natural or synthetic medium may be used as a medium for culture, provided that it contains carbon sources, nitrogen sources, and inorganic salts assimilable by the microorganism and is capable of efficient culture of the transformant. Any carbon sources assimilable by the microorganism may be used, and examples thereof include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extracts; and corn steep liquor. Examples of inorganic salts include: monopotassium phosphate, dipotassium phosphate, magnesium phosphate, magnesium sulfate, sodium chloride, iron(I) sulfate, manganese sulfate, copper sulfate, and calcium carbonate. In accordance with the type of selection marker, an antibiotic agent, such as aureobasidin, ampicillin, or tetracycline, may be adequately added to a medium. Alternatively, an amino acid that can be supplied by a gene complementing auxotrophy (e.g., Leu, Ura, or Trp) may be removed.

When culturing the transformed host cell, in the case of yeast, for example, the pH level of the medium is preferably adjusted to 4 to 7. The culture temperature is between 15° C.

and 32° C., and preferably around 28° C. When a protein having a complicated steric structure as an antibody is expressed, culture may be preferably carried out at a low temperature, in order to more effectively fold such a protein in the cell. The culture duration is generally about 24 to 1,000 hours, and culture can be carried out via batch culture, such as static, shake, agitation, or aeration culture, or via continuous culture.

An expression product of a gene of a foreign protein from the culture product (i.e., a culture solution or cultured cells) can be confirmed via SDS-PAGE, Western blotting, ELISA, or the like.

The produced proteins may be isolated and purified via conventional techniques for protein isolation and purification. When target proteins are produced in the fungus bodies or cells after culture, the fungus bodies or cells may be pulverized using, for example, an ultrasonic pulverizer, a French press, a Manton-Gaulin homogenizer, Dinomil, or the like, to obtain target proteins. When the target proteins are produced outside the fungus body or cells, the culture solution is used as it is, or the fungus body or cells are removed via centrifugation or the like. Thereafter, the target proteins are collected via extraction using an organic solvent, subjected to various chromatography techniques (e.g., hydrophobic, reversed-phase, affinity, or ion-exchange chromatography), gel filtration using molecular sieves, electrophoresis using polyacrylamide gel, or the like, according to need. These techniques may be employed solely or in combinations of two or more. Thus, the target proteins may be isolated and purified.

The above culture and purification techniques are examples, and methods are not limited thereto. The amino acid sequence of the purified gene product can be confirmed by a conventional method of amino acid analysis, such as automated amino acid sequencing via the Edman degradation technique.

In the present invention, when yeast is used as a host cell, the aforementioned culture is more preferably carried out under conditions in which protein O-mannosyltransferase (PMT) activity is inhibited.

An O-sugar chain is formed in a mammalian cell upon the addition of GalNAc by peptide O-GalNAc transferase, which is present mainly in the Golgi apparatus. Such sugar chain addition takes place after protein folding. In contrast, O-sugar chain formation in yeast and mold cells is initiated upon the addition of mannose to a serine or threonine residue of the protein by a protein-O-mannosyltransferase (PMT) encoded by the PMT gene. Such addition is referred to as PMT activity. The addition of mannose takes place in parallel with protein folding in the endoplasmic reticulum (ER) in the cell. Thus, an unnecessary sugar chain may be disadvantageously added to a site at which such addition would not take place in the case of expression of mammalian proteins. Consequently, such unnecessary modification would cause insufficient formation of aggregates and lower the activity.

By performing culture under conditions in which protein O-mannosyltransferase (PMT) activity is inhibited, accordingly, formation of an unnecessary O sugar chain can be inhibited. This also accelerates protein assembly and enables maintenance of indigenous physical properties and activity of proteins. In the present invention, effects of high-level secretory production of proteins via introduction of the chaperone gene can further produce synergistic effects by regulating the O-sugar chain formation enhanced by URP via inhibition of PMT activity.

Addition of an O-sugar chain peculiar to yeast or a mold can be inhibited by, for example, the two methods described below. These methods can be performed in combination.

(1) Culture and production are carried out under conditions in which PMT activity that undergoes addition of an O-sugar chain peculiar to yeast or a mold is inhibited.

(2) Cells in which PMT activity that undergoes addition of an O-sugar chain peculiar to yeast or a mold is inhibited are used.

The protein O-mannosyltransferase (PMT) activity of (1) above can be inhibited with the addition of an inhibitor of PMT activity (i.e., a PMT inhibitor) to the medium, for example. An example of an inhibitor of PMT activity that can be used is the rhodanine-3-acetic acid derivative (Bioorganic & Medicinal Chemistry Letters 14, pp. 3975-3978, 2004). Specific examples of the rhodanine-3-acetic acid derivative include 5-[[3,4-(1-phenylmethoxy)phenyl]methylene]-4-oxo-2-thioxo-3-thiazolidineacetic acid (compound (1c) described in Bioorganic & Medicinal Chemistry Letters, Vol. 14, p. 3975, 2004) and {(5Z)-4-oxo-5-[3-(1-phenylethoxy)-4-(2-phenylethoxy)benzylidene]-2-thioxo-1,3-thiazolidin-3-yl}acetic acid (compound (5a) described in Bioorganic & Medicinal Chemistry Letters, Vol. 14, p. 3975, 2004). PMT is important for generation of mannoproteins that constitute the yeast cell wall. Excessively lowered PMT activity would adversely affect the growth of yeast. When inducible expression systems are used, accordingly, the addition of an inhibitor of PMT activity at the time of expression of genes of foreign proteins, following cell growth, would be more effective. Thus, high-quality target proteins in which O-sugar chain modification is inhibited can be produced at the maximum level.

The protein O-mannosyltransferase (PMT) activity described in (2) above can be inhibited by disrupting the PMT gene or inhibiting expression of such gene. In S. cerevisiae, PMT is encoded by at least 6 genes; i.e., the PMT1 gene (GenBank: L19169), the PMT2 gene (GenBank: L05146), the PMT3 gene (GenBank: X83797), the PMT4 gene (GenBank: X83798), the PMT5 gene (GenBank: X95644), and the PMT6 gene (GenBank: Z72984), and these genes independently form a homodimer (PMT4p) or a heterodimer (PMT1p/PMT2p) and exhibit activity. Deficiency of the PMT gene may be single or double deficiency. As described above, PMT is an important gene for the growth of yeast. When activity, such as PMT gene deficiency, is eliminated or extremely lowered, the cell wall becomes fragile. Thus, the use of a PMT gene-deficient strain requires attention. A strain in which the PMT gene has been destroyed is preferably a strain in which either the PMT5 or PMT6 gene has been destroyed or a strain in which both the PMT5 gene and the PMT6 gene have been destroyed.

Examples of methods for suppressing the PMT gene include a method involving the use of antisense RNA or RNAi and a method involving attenuating a promoter.

BEST MODES FOR CARRYING OUT THE INVENTION

Hereafter, the present invention is described in detail with reference to the examples, although the technical scope of the present invention is not limited to the examples. Plasmids, restriction enzymes, DNA modifying enzymes, and the like that are used in the examples of the present invention are commercially available products, and these products can be used in accordance with conventional techniques. Also, procedures of DNA cloning, nucleotide sequencing, host cell transformation, culture of transformed host cells, sampling and purification of enzymes from culture products, and the like are well-known in the art or can be learned through existing publications.

Example 1

Construction of Vector for Antibody Gene Introduction (1) Construction of Vector for Antibody Gene Introduction Carrying a Zeocin-Resistant Gene as a Selection Marker and Comprising the Gap Gene Promoter and the Terminator Cassette In order to prepare a Zeocin-resistant gene marker, a synthesized DNA fragment as shown in SEQ ID NO: 15 was subjected to double digestion with HindIII and KpnI restriction enzymes to obtain a DNA fragment containing a Zeocin-resistant gene.

pOMexGP1U disclosed in WO 2003/091431 was cleaved with SpeI, blunt-ended, and then ligated. The SalI site and the EcoT22I site of the resulting plasmid were subjected to linker change with the SpeI site and the BamHI site, respectively. Thus, the pOMexGP1UΔSp plasmid was obtained. The resulting pOMexGP1UΔSp was subjected to double digestion with HindIII and KpnI restriction enzymes to isolate a fragment containing the GAP gene promoter and the terminator, and a DNA fragment containing the Zeocin-resistant gene marker was introduced therein to obtain the pOMexGP1Z plasmid.

After the nucleotide sequences of the restriction enzyme sites (the XbaI site on the 5' side and the BamHI site on the 3' site) were added to the both ends of the heavy chain gene of the anti-TRAIL receptor antibody gene (WO 2001/083560, synthesized by Takara Bio while taking the frequency of the use of codons of O. minuta into consideration), the resultant was digested with XbaI and BamHI to obtain a fragment of the antibody heavy chain gene.

The resulting artificially synthesized antibody heavy chain gene was used as a template to carry out PCR using the SynCH-F primer and the SynCH-R primer shown below at 94° C. for 30 seconds, 55° C. for 30 seconds, and 72° C. for 2 minutes, and this cycle was repeated 20 times. Thus, a constant region of the antibody heavy chain gene was obtained.

```
                                    (SEQ ID NO: 16)
SynCH-F:
5'-GGAGCTCAAAAAGCTAGCACCAAGGGTCCATCCGTTTTCC-3'

(SEQ ID NO: 17)
SynCH-R:
5'-CAGATCTTTACTTACCTGGGGACAAGGACAAG-3'
```

The resulting DNA fragment was subjected to double digestion with the SacI and BglII restriction enzymes, and the resultant was introduced into pOMexGP1Z, which had been subjected to double digestion with the SacI and BamHI restriction enzymes. The resulting vector was designated as pOMexGPZ/SynCH. A variable region of the antibody heavy chain gene can be introduced into a site between the SacI and the NheI restriction enzyme sites of this vector.

(2) Construction of a Vector for Antibody Gene Introduction Carrying the ADE1 Gene as a Selection Marker and Comprising the Gap Gene Promoter and the Terminator Cassette pOMexGP1U disclosed in WO 2003/091431 was treated with EcoT22I and blunt-ended. The BamHI linker was introduced therein to obtain pOMexGP2U. pOMexGP2U was treated with SalI and blunt-ended. The SpeI linker was introduced therein to obtain pOMexGP3U. pOMexGP3U was digested with HindIII and KpnI to isolate a fragment of approximately 2.0 kb comprising the GAP expression cassette. The resulting fragment was ligated to a fragment of approximately 5.0 kb comprising the ADE1 marker isolated by treating pOMex4A (disclosed in WO 2003/091431) with HindIII and KpnI to obtain pOMexGP1A. The fragment obtained by cleaving pOMexGP1A with the BsiWI restriction enzyme was blunt-ended, and the NdeI linker (Takara Bio) was introduced. The resulting plasmid was designated as pOMexGP2A.

After the nucleotide sequences of the restriction enzyme sites (the XbaI site on the 5' side and the BamHI site on the 3' site) were added to the both ends of the light chain gene of the anti-TRAIL receptor antibody gene (WO 2001/083560, synthesized by Takara Bio while taking the frequency of the use of codons of *O. minuta* into consideration), the resultant was digested with XbaI and BamHI to obtain a fragment of the antibody light chain gene.

The resulting artificially synthesized antibody light chain gene was used as a template to carry out PCR using the SynCL-F primer and the SynCL-R primer shown below at 94° C. for 30 seconds, 55° C. for 30 seconds, and 72° C. for 2 minutes, and this cycle was repeated 20 times. Thus, a constant region of the antibody light chain gene was obtained.

```
                                    (SEQ ID NO: 18)
SynCL-F primer:
5'-GACTAGTAAAAACGTACGGTTGCTGCTCCATCCGTTTTCAT
C-3'

(SEQ ID NO: 19)
SynCL-R primer:
5'-CAGATCTTTAGCACTCACCTCTGTTGAAGGAC-3'
```

The resulting DNA fragment was subjected to double digestion with the SpeI and BglII restriction enzymes, and the resultant was introduced into pOMexGP2A, which had been subjected to double digestion with the SpeI and BamHI restriction enzymes. The resulting vector was designated as pOMexGPA/SynCL. A variable region of the antibody light chain gene can be introduced into a site between the SpeI and the BsiWI restriction enzymes of this vector.

Example 2

Construction of Expression Vector for Antibody Gene

In order to express the Kar2 signal derived from *O. minuta* (hereafter refers to as the "OmKar2 signal") and the light chain and the heavy chain of the anti-TRAIL receptor antibody as a fusion protein, the OmKar2 signal sequence was ligated to the anti-TRAIL receptor antibody gene (WO 2001/083560, synthesized by Takara Bio while taking the frequency of the use of codons of *O. minuta* into consideration) via overlap extension PCR using the oligonucleotide primers below.

```
For OmKar2 signal and heavy chain of anti-TRAIL
receptor antibody
                                    (SEQ ID NO: 20)
Om-Kar2-Sac:
5'-GGAGCTCATGTTTAAGTTCAACCGCTC-3'

(SEQ ID NO: 21)
OmKar-SanH-R3:
5'-CAACGAGTTGAACCTCCGCCTCTGCTTCCACG-3'

(SEQ ID NO: 22)
OmKar-SanH-F3:
5'-CGTGGAAGCAGAGGCGGAGGTTCAACTCGTTG-3'
```

-continued

```
                                        (SEQ ID NO: 23)
SanH-Nhe:
5'-GGCTAGCGGAGGAAACGGTAAC-3'

For OmKar2 signal and light chain of anti-TRAIL
receptor antibody
                                        (SEQ ID NO: 24)
Om-Kar2-Spe:
5'-GACTAGTATGTTTAAGTTCAACCGCTC-3'

(SEQ ID NO: 25)
OmKar-SanL-R3:
5'-GGGTCATCTGGATGTCCGCCTCTGCTTCCACG-3'

(SEQ ID NO: 26)
OmKar-SanL-F3:
5'-CGTGGAAGCAGAGGCGGACATCCAGATGACCC-3'

(SEQ ID NO: 27)
SanL-Bsi:
5'-GCGTACGCTTGATCTCAACC-3'
```

The region of the OmKar2 signal sequence was amplified using genomic DNA of *O. minuta* prepared using the Y-DER Yeast DNA Extraction Reagent (PIERCE, 78870) as a template. With the use of AccuPrime Pfx DNA Polymerase (Invitrogen, 12344-024), PCR was carried out using the Om-Kar2-Sac and OmKar-SanH-R3 primers for the heavy chain and the Om-Kar2-Spe and OmKar-SanL-R3 primers for the light chain at 95° C. for 10 seconds, 55° C. for 30 seconds, and 68° C. for 30 seconds, and this cycle was repeated 30 times. Thus, the amplified target DNA fragments of about 0.1 kb were recovered.

The antibody gene region was amplified using DNA obtained by synthesizing the codon of the anti-TRAIL receptor antibody cDNA (WO 2001/083560) in accordance with the frequency of the codon of *O. minuta* used as a template. With the use of AccuPrime Pfx DNA Polymerase (Invitrogen, 12344-024), PCR was carried out using the OmKar-SanH-F3 and SanH-Nhe primers for the heavy chain and the OmKar-SanL-F3 and SanL-Bsi primers for the light chain at 95° C. for 10 seconds, 55° C. for 30 seconds, 68° C. for 30 seconds, and this cycle was repeated 30 times. The amplified target DNA fragment of the heavy chain variable region of approximately 0.36 kb and that of the light chain variable region of approximately 0.33 kb were recovered.

Subsequently, the amplified OmKar2 signal region for the heavy chain and the heavy chain variable region were used as templates, PCR was carried out using the Om-Kar2-Sac and SanH-Nhe primers and AccuPrime Pfx DNA Polymerase (Invitrogen, 12344-024) at 95° C. for 10 seconds, 55° C. for 30 seconds, and 68° C. for 30 seconds, and this cycle was repeated 30 times. Thus, an amplified target DNA fragment of approximately 0.47 kb was recovered. Also, the amplified OmKar2 signal region for the light chain and the light chain variable region were used as templates, and PCR was carried out using the Om-Kar2-Spe and SanL-Bsi primers and AccuPrime Pfx DNA Polymerase (Invitrogen, 12344-024) at 95° C. for 10 seconds, 55° C. for 30 seconds, and 68° C. for 30 seconds, and this cycle was repeated 30 times. Thus, an amplified target DNA fragment of approximately 0.43 kb was recovered. The recovered DNA fragments were cloned into pCR2.1-TOPO. Based on the nucleotide sequences of the inserted DNA fragments, the OmKar2 signal-antibody heavy chain variable region and the OmKar2 signal-antibody light chain variable region were confirmed to have genes that are fused in frame to each other. From a plasmid having a DNA fragment, the nucleotide sequence thereof had been confirmed, a DNA fragment containing the OmKar signal-antibody heavy chain variable region was recovered via digestion with SacI and NheI with the use of the SacI restriction enzyme site introduced into the Om-Kar2-Sac primer and the NheI restriction enzyme site introduced into the SanH-Nhe primer. Separately, the SpeI restriction enzyme site introduced into the Om-Kar2-Spe primer and the BsiWI restriction enzyme site introduced into the SanL-Bsi primer were used to recover a DNA fragment containing the OmKar signal-antibody light chain variable regions via digestion with SpeI and BsiWI.

In order to express the antibody heavy chain and the antibody light chain in *O. minuta*, a DNA fragment encoding the OmKar signal-antibody heavy chain variable region recovered via double digestion with SacI and NheI restriction enzymes and a DNA fragment encoding the OmKar signal-antibody light chain variable region recovered via double digestion with SpeI and BsiWI restriction enzymes were ligated to the expression vector pOMexGPZ/SynCH for the human IgG1γ-chain constant region obtained via double digestion with SacI and NheI restriction enzymes (prepared in Example 1) and the expression vector pOMexGPA/SynCL for the human IgG1κ-chain constant region obtained via double digestion with SpeI and BsiWI restriction enzymes (prepared in Example 1), respectively. The resulting plasmids were designated as onaP02706 and onaP03106.

Example 3

Construction of Expression Vector for Chaperone Gene Alone (1) Construction of Constitutive Expression Vector for OmPDI1 Gene The gene consisiting of the nucleotide sequence as shown in SEQ ID NO: 1 (1551 bp) is deduced to encode a protein consisiting of the amino acid sequence as shown in SEQ ID NO: 2 (516 amino acid residues).

The above protein has nucleotide sequence homology of about 60.5% to PDI1 (YCL043C) of *S. cerevisiae* and putative amino acid sequence homology of about 46.9%. The protein was deduced to be a functional homolog that also comprises two thioredoxin-like domains, CGHC (Cys-Gly-His-Cys), in PDI1 of *S. cerevisiae*, and it was designated as OmPDI1 as PDI1 of *O. minuta*. Since the nucleotide sequence of OmPDI1 comprises the cleavage sites for EcoT22I and SalI restriction enzymes, the EcoT22I and SalI restriction enzyme sites were modified via overlap extension PCR using the oligonucleotide primers below.

```
                                        (SEQ ID NO: 28)
OMPDI1SAL:   5'-GGTCGACATGAAGTTATTTGGATTGAC-3'

(SEQ ID NO: 29)
OMPDI1T22I:  5'-GATGCATTTACAACTCGTCGTGAGCCAC-3'

(SEQ ID NO: 30)
OMPDI912F:   5'-GAGATACGGTATGCACGCCAAGAAC-3'

(SEQ ID NO: 31)
OMPDI936R:   5'-GTTCTTGGCGTGCATACCGTATCTC-3'

(SEQ ID NO: 32)
OMPDI1321F:  5'-GTTGCCGGTGTTGACATCGCCGG-3'

(SEQ ID NO: 33)
OMPDI1343R:  5'-CCGGCGATGTCAACACCGGCAAC-3'
```

PCR was carried out using the genomic DNA of *O. minuta* prepared using the Y-DER yeast DNA extraction reagent (78870, PIERCE) as a template, the OMPDI1SAL and the OMPDI936R primers, the OMPDI912F and the OMPDI1343R primers, and the OMPDI1321F and the OMPDI1T22I primers, and AccuPrime Pfx DNA Polymerase (Invitrogen, 12344-024) at 95° C. for 10 seconds, 55° C. for 30 seconds, and 68° C. for 60 seconds, and this cycle was repeated 30 times. Thus, target DNA fragments of approximately 0.94 kb, approximately 0.43 kb, and approximately 0.23 kb were amplified. Subsequently, PCR was carried out using the amplified fragments above and the OMPDI1SAL and the OMPDI1T22I primers at 95° C. for 10 seconds, 55° C. for 30 seconds, and 68° C. for 90 seconds, and this cycle was repeated 30 times. The amplified target DNA fragment of approximately 1.6 kb was further amplified, and the resultant was cloned into pCR2.1-TOPO. Based on the nucleotide sequence of the inserted DNA fragment, it was confirmed that the target fragment had the OmPDI1 gene. From a plasmid carrying the DNA fragment with a confirmed nucleotide sequence, a DNA fragment containing OmPDI1 was recovered via digestion with SalI and EcoT22I, with the use of the SalI restriction enzyme site introduced into the OMPDI1SAL primer and the EcoT22I restriction enzyme site introduced into the OMPDI1T22I primer. In order to constitutively express OmPDI1 in O. minuta, OmPDI1 was ligated to pOMexGP1U disclosed in WO 2003/091431 recovered via digestion with SalI and EcoT22I. The resulting plasmid was designated as onaP03606.

(2) Construction of Constitutive Expression Vector for OmMPD1 Gene

The gene consisting of the nucleotide sequence as shown in SEQ ID NO: 3 (936 bp) is deduced to encode a protein consisiting of the amino acid sequence as shown in SEQ ID NO: 4 (311 amino acid residues).

The above protein has nucleotide sequence homology of about 47.3% to MPD1 (YOR288C) of S. cerevisiae and putative amino acid sequence homology of about 31.2%. The protein was deduced to be a functional homolog that also comprises one thioredoxin-like domain, CGHC (Cys-Gly-His-Cys), contained in MPD1 derived from S. cerevisiae, and it was designated as OmMPD1 as MPD1 derived from O. minuta. The resultant was amplified via PCR using the oligonucleotide primers below.

```
                                    (SEQ ID NO: 34)
OMIC1379SAL:    5'-GGTCGACATGAAAGTGGCAAGTTTG-3'

(SEQ ID NO: 35)
OMIC1379T22I:   5'-GATGCATTCATAGCTCATCTTTTTC-3'
```

PCR was carried out using the genomic DNA of O. minuta prepared using the Y-DER yeast DNA extraction reagent (78870, PIERCE) as a template and AccuPrime Pfx DNA Polymerase (Invitrogen, 12344-024) at 95° C. for 10 seconds, 55° C. for 30 seconds, and 68° C. for 60 seconds, and this cycle was repeated 30 times. Thus, a target DNA fragment of approximately 0.94 kb was amplified, and the resultant was into pCR2.1-TOPO. Based on the nucleotide sequence of the inserted DNA fragment, it was confirmed that the target fragment had the OmMPD1 gene. From a plasmid carrying the DNA fragment with a confirmed nucleotide sequence, a DNA fragment containing OmMPD1 was recovered via digestion with SalI and EcoT22I, with the use of the SalI restriction enzyme site introduced into the OMIC1379SAL primer and the EcoT22I restriction enzyme site introduced into the OMIC1379T22I primer. In order to constitutively express OmMPD1 in O. minuta, OmMPD1 was ligated to pOMexGP1U disclosed in WO 2003/091431 recovered via digestion with SalI and EcoT22I. The resulting plasmid was designated as onaP04006.

(3) Construction of Constitutive Expression Vector for OmSCJ1 Gene

The gene consisting of the nucleotide sequence as shown in SEQ ID NO: 5 (930 bp) is deduced to encode a protein consisiting of the amino acid sequence as shown in SEQ ID NO: 6 (309 amino acid residues).

The above protein has nucleotide sequence homology of about 54.8% to SCJ1 (YMR214W) of S. cerevisiae and putative amino acid sequence homology of about 36.6%. The protein was deduced to be a functional homolog that comprises the central cysteine-rich (CR) domain of the DnaJ protein of CXXCXGXG and a region partially homologous to the DnaJ-C terminal region, and it was designated as OmSCJ1 as SCJ1 of O. minuta. The resultant was amplified via PCR using the oligonucleotide primers below.

```
                                    (SEQ ID NO: 36)
OMSCJ1SAL:      5'-GGTCGACATGTTTATGGAGATCGGAG-3'

(SEQ ID NO: 37)
OMSCJ1T22I:     5'-GATGCATTCACAGCTCGTCGTGCAAC-3'
```

PCR was carried out using the genomic DNA of O. minuta prepared using the Y-DER yeast DNA extraction reagent (78870, PIERCE) as a template and AccuPrime Pfx DNA Polymerase (Invitrogen, 12344-024) at 95° C. for 10 seconds, 55° C. for 30 seconds, and 68° C. for 60 seconds, and this cycle was repeated 30 times. Thus, a target DNA fragment of approximately 0.93 kb was amplified, and the resultant was cloned into pCR2.1-TOPO. Based on the nucleotide sequence of the inserted DNA fragment, it was confirmed that the target fragment had the OmSCJ1 gene. From a plasmid carrying the DNA fragment with a confirmed nucleotide sequence, a DNA fragment containing OmSCJ1 was recovered via digestion with SalI and EcoT22I, with the use of the SalI restriction enzyme site introduced into the OMSCJ1SAL primer and the EcoT22I restriction enzyme site introduced into the OMSCJ1T22I primer. In order to constitutively express OmSCJ1 in O. minuta, OmSCJ1 was ligated to pOMexGP1U disclosed in WO 2003/091431 recovered via digestion with SalI and EcoT22I. The resulting plasmid was designated as onaP03806.

(4) Construction of Constitutive Expression Vector for OmEUG1 Gene

The gene consisting of the nucleotide sequence as shown in SEQ ID NO: 7 (1137 bp) is deduced to encode a protein consisiting of the amino acid sequence as shown in SEQ ID NO: 8 (378 amino acid residues).

Although the above protein did not show obvious homology to the protein disulfide isomerase family of S. cerevisiae, the protein comprised thioredoxin-like domains of CHSC in a region comprising residues 52 to 55 and of CGYC in a region comprising residues 174 to 177 from the N terminus. Five types of protein disulfide isomerases having thioredoxin-like domains are known in S. cerevisiae; however, those having two thioredoxin-like domains in the molecules are limited to PDI1 and EUG1. Since P5 that belongs to the human PDI family is the only isomerase having two thioredoxin-like domains from the N-terminus to the central region of the molecule (Gene, 1995, 164, pp. 377-378), the above protein is deduced to function as a protein disulfide isomerase. Also, the protein was deduced to have the ER retention domain of KDEL at the C terminus and to function as protein disulfide isomerase in the yeast endoplasmic reticulum.

Accordingly, the above protein was deduced to be a functional homolog of EUG1 derived from *S. cerevisiae*, and it was designated as OmEUG1 as EUG1 of *O. minuta*. Since the nucleotide sequence of OmEUG1 comprises cleavage sites for EcoT22I and SalI restriction enzymes, the EcoT22I and the SalI restriction enzyme sites were modified via overlap extension PCR using the oligonucleotide primers below.

```
                                        (SEQ ID NO: 38)
OMEUG1SAL:    5'-GGTCGACATGAAAGTCACGTCTATCTGG-3'

(SEQ ID NO: 39)
OMEUG1T22I:   5'-GATGCATTCACAGCTCATCCTTGGCTGG-3'

(SEQ ID NO: 40)
OMEUG819F:    5'-GATACACGCAGTTGACGAGCTG-3'

(SEQ ID NO: 41)
OMEUG840R:    5'-CAGCTCGTCAACTGCGTGTATC-3'

(SEQ ID NO: 42)
OMEUG925F:    5'-GACAACGCATTGTCGAAAGAAG-3'

(SEQ ID NO: 43)
OMEUG946R:    5'-CTTCTTTCGACAATGCGTTGTC-3'
```

PCR was carried out using the genomic DNA of *O. minuta* prepared using the Y-DER yeast DNA extraction reagent (78870, PIERCE) as a template, the OMEUG1SAL and the OMEUG840R primers, the OMEUG819F and the OMEUG946R primers, and the OMEUG925F and the OMEUG1T22I primers, and AccuPrime Pfx DNA Polymerase (Invitrogen, 12344-024) at 95° C. for 10 seconds, 55° C. for 30 seconds, and 68° C. for 60 seconds, and this cycle was repeated 30 times. Thus, target DNA fragments of approximately 0.84 kb, approximately 0.13 kb, and approximately 0.21 kb were amplified. Subsequently, PCR was carried out using the above amplified fragments, the OMEUG1SAL and the OMEUG1T22I primers, and AccuPrime PfxDNA Polymerase (Invitrogen, 12344-024) at 95° C. for 10 seconds, 55° C. for 30 seconds, and 68° C. for 90 seconds, and this cycle was repeated 30 times. Thus, a target DNA fragment of approximately 1.1 kb was amplified and the resultant was cloned into pCR2.1-TOPO. Based on the nucleotide sequence of the inserted DNA fragment, it was confirmed that the target fragment had the OmEUG1 gene. From a plasmid carrying the DNA fragment with a confirmed nucleotide sequence, a DNA fragment containing OmEUG1 was recovered via digestion with SalI and EcoT22I with the utilization of the SalI restriction enzyme site introduced into the OMEUG1SAL primer and the EcoT22I restriction enzyme site introduced into the OMEUG1T22I primer. In order to constitutively express OmEUG1 in *O. minuta*, OmEUG1 was ligated to pOMexGP1U digested with SalI and EcoT22I disclosed in WO 2003/091431. The resulting plasmid was designated as onaP03706.

(5) Construction of Constitutive Expression Vector for OmERO1 Gene

The gene consisiting of the nucleotide sequence as shown in SEQ ID NO: 9 (1728 bp) is deduced to encode a protein consisiting of the amino acid sequence as shown in SEQ ID NO: 10 (575 amino acid residues).

The above protein has nucleotide sequence homology of about 37.4% to ERO1 (YML130C) of *S. cerevisiae* and putative amino acid sequence homology of about 35.1%. It is known that ERO1 of *S. cerevisiae* comprises 14 Cys residues and at least 10 Cys residues are associated with disulfide bond (Cell, 2007, 129, pp. 333-344). In particular, it is demonstrated that 4 Cys residues are important for ERO1 activity, Cys100-Cys105 is referred to as "shuttle disulfide" and associated with oxidation of PDI1, and Cys352-Cys355 is associated with reoxidation of reduced shuttle disulfide (Moll. Cell, 1999, 4, pp. 469-477). Homology search between *S. cerevisiae* ERO1 and SEQ ID NO: 10 demonstrates that Cys125-Cys130, which is equivalent to shuttle Cys of *S. cerevisiae* Cys100-Cys105, and Cys384-Cys387, which is equivalent to active Cys of *S. cerevisiae* Cys352-Cys355, are conserved. Thus, the above protein is deduced to have endoplasmic oxidoreductase-like activity. Thus, the above protein is deduced to be a functional homolog of *S. cerevisiae* ERO1, and it was designated as OmERO1 as ERO1 of *O. minuta*. Since the OmERO1 nucleotide sequence comprises a cleavage site for the SalI restriction enzyme, the SalI restriction enzyme site was modified via overlap extension PCR using the oligonucleotide primers below.

```
                                        (SEQ ID NO: 44)
OMEROSAL:     5'-GGTCGACATGAAGCACGTGATAAGTGGC-3'

(SEQ ID NO: 45)
OMEROT22I:    5'-GATGCATTTATAGCTCCAAACGATACAG-3'

(SEQ ID NO: 46)
OMERO166F:    5'-GAGTTTGAGTCCACGCCTTTCCGCG-3'

(SEQ ID NO: 47)
OMERO190R:    5'-CGCGGAAAGGCGTGGACTCAAACTC-3'
```

PCR was carried out using the genomic DNA of *O. minuta* prepared using the Y-DER yeast DNA extraction reagent (78870, PIERCE) as a template, the OMEROSAL and OMERO190R primers and the OMERO166F and OMEROT22I primers, and AccuPrime Pfx DNA Polymerase (Invitrogen, 12344-024) at 95° C. for 10 seconds, 55° C. for 30 seconds, and 68° C. for 60 seconds, and this cycle was repeated 30 times. Thus, target DNA fragments of approximately 0.19 kb and approximately 1.56 kb were amplified. Subsequently, PCR was carried out using the above amplified fragments, the OMEROSAL and OMEROT22I primers, and AccuPrime PfxDNA Polymerase (Invitrogen, 12344-024) at 95° C. for 10 seconds, 55° C. for 30 seconds, and 68° C. for 120 seconds, and this cycle was repeated 30 times. Thus, a target DNA fragment of approximately 1.73 kb was amplified and the resultant was cloned into pCR2.1-TOPO. Based on the nucleotide sequence of the inserted DNA fragment, it was confirmed that the target fragment had the OmERO1 gene. From a plasmid carrying the DNA fragment with a confirmed nucleotide sequence, a DNA fragment containing OmERO1 was recovered via digestion with SalI and EcoT22I with the utilization of the SalI restriction enzyme site introduced into the OMEROSAL primer and the EcoT22I restriction enzyme site introduced into the OMEROT22I primer. In order to constitutively express OmERO1 in *O. minuta*, OmERO1 was ligated to pOMexGP1U recovered via digestion with SalI and EcoT22I disclosed in WO 2003/091431. The resulting plasmid was designated as onaP03906.

(6) Construction of Constitutive Expression Vector for OmHSP104 Gene

The gene consisiting of the nucleotide sequence as shown in SEQ ID NO: 11 (2700 bp) is deduced to encode a protein consisiting of the amino acid sequence as shown in SEQ ID NO: 12 (899 amino acid residues).

The above protein has nucleotide sequence homology of about 60.4% to HSP104 (YLL026W) of *S. cerevisiae* and putative amino acid sequence homology of about 63.4%. HSP104 of *S. cerevisiae* is a molecular chaperone that belongs to the HSP100/Clp family, and it cooperates with a molecular chaperone that belongs to the HSP70/HSP40 family and an auxiliary chaperone thereof to regenerate an aggregated protein. The above protein has two domains in its molecule; i.e., the Clp amino terminal domain and the AAA+ domain, and it is deduced to have HSP104-like activity. Thus, the above protein was deduced to be a functional homolog of *S. cerevisiae* HSP104 and designated as OmHSP104 as HSP104 of *O. minuta*.

PCR was carried out using the genomic DNA of *O. minuta* prepared using the Y-DER yeast DNA extraction reagent (78870, PIERCE) as a template, the OmHSP104salF primer (5'-GGTCGACATGGATTCTACGCAATTTAC-3': SEQ ID NO: 48), the OmHSP104EcoTR primer (5'-GATGCATT-TAATCGAGATCAGGACTGC-3': SEQ ID NO: 49), and AccuPrime Pfx DNA Polymerase (Invitrogen, 12344-024) at 95° C. for 10 seconds, 55° C. for 30 seconds, and 68° C. for 180 seconds, and this cycle was repeated 30 times. Thus, a target DNA fragment of approximately 2.7 kb was amplified and the resultant was cloned into pCR2.1-TOPO. Based on the nucleotide sequence of the inserted DNA fragment, it was confirmed that the target fragment had the OmHSP104 gene. From a plasmid carrying the DNA fragment with a confirmed nucleotide sequence, a DNA fragment containing OmHSP104 was recovered via digestion with SalI and EcoT22I with the utilization of the SalI restriction enzyme site introduced into the OmHSP104salF primer and the EcoT22I restriction enzyme site introduced into the OmHSP104EcoTR primer. In order to constitutively express OmHSP104 in *O. minuta*, OmHSP104 was ligated to pOMexGP1U recovered via digestion with SalI and EcoT22I disclosed in WO 2003/091431. The resulting plasmid was designated as onaP07107.

(7) Construction of Constitutive Expression Vector for OmKar2 Gene

The gene consisiting of the nucleotide sequence as shown in SEQ ID NO: 13 (1998 bp) is deduced to encode a protein consisiting of the amino acid sequence as shown in SEQ ID NO: 14 (665 amino acid residues).

The above protein has nucleotide sequence homology of about 60.4% to Kar2 (YJL034W) of *S. cerevisiae* and putative amino acid sequence homology of about 74.6%. Thus, the protein of interest was deduced to be a functional homolog and designated as OmKar2 as Kar2 of *O. minuta*. The OmKar2 nucleotide sequence comprises cleavage sites for HindIII and KpnI restriction enzymes. In order to recover an expression cassette comprising a region from a promoter to a terminator after cloning into pOMEGPU-1, the HindIII and KpnI restriction enzyme sites were modified via overlap extension PCR using the oligonucleotide primers below.

```
                                            (SEQ ID NO: 50)
OMKAR-F:  5'-GGTCGACATGTTTAAGTTCAACCGCTCTG-3'

(SEQ ID NO: 51)
OMKAR-R:  5'-GATGCATTCACAGCTCATCATGATCCCAG-3'

(SEQ ID NO: 52)
Kar1-F:   5'-CACTAAGGATGCTGGAACCATTGCCGGTCTGGAAG-3'

(SEQ ID NO: 53)
Kar1-R:   5'-CTTCCAGACCGGCAATGGTTCCAGCATCCTTAGTG-3'

(SEQ ID NO: 54)
Kar2-F:   5'-CCAGCCCCAAGAGGAACCCCACAAATTGAGGTGAC-3'

(SEQ ID NO: 55)
Kar2-R:   5'-GTCACCTCAATTTGTGGGGTTCCTCTTGGGGCTGG-3'

(SEQ ID NO: 56)
Kar3-F:   5'-CGGATTCGGCTCCAAACTTGATGAGGATGACAAGG-3'

(SEQ ID NO: 57)
Kar3-R:   5'-CCTTGTCATCCTCATCAAGTTTGGAGCCGAATCCG-3'
```

PCR was carried out using the genomic DNA of *O. minuta* prepared using the Y-DER yeast DNA extraction reagent (78870, PIERCE) as a template, the OMKAR-F and the Kar1-R primers, the Kar1-F and the Kar2-R primers, the Kar2-F and the Kar3-R primers, and the Kar3-F and the OMKAR-R primers, and AccuPrime Pfx DNA Polymerase (Invitrogen, 12344-024) at 95° C. for 10 seconds, 55° C. for 30 seconds, and 68° C. for 60 seconds, and this cycle was repeated 30 times. Thus, target DNA fragments of approximately 0.6 kb, approximately 0.95 kb, approximately 0.3 kb, and approximately 0.2 kb were amplified. Subsequently, PCR was carried out using the above amplified fragments, the OMKAR-F and the OMKAR-R primers, and AccuPrime PfxDNA Polymerase (Invitrogen, 12344-024) at 95° C. for 10 seconds, 55° C. for 30 seconds, and 68° C. for 90 seconds, and this cycle was repeated 30 times. Thus, a target DNA fragment of approximately 2.0 kb was amplified and the resultant was cloned into pCR2.1-TOPO. Based on the nucleotide sequence of the inserted DNA fragment, it was confirmed that the target fragment had the OmKar2 gene. From a plasmid carrying the DNA fragment with a confirmed nucleotide sequence, a DNA fragment containing OmKar2 was recovered via digestion with SalI and EcoT22I with the utilization of the SalI restriction enzyme site introduced into the OMKAR-F primer and the EcoT22I restriction enzyme site introduced into the OMKAR-R primer. In order to constitutively express OmKar2 in *O. minuta*, OmKar2 was ligated to pOMexGP1U recovered via digestion with SalI and EcoT22I disclosed in WO 2003/091431. The resulting plasmid was designated as onaP09007.

(8) Construction of Constitutive Expression Vector for ScPDI1 Gene

PDI1 (YCL043C) of *S. cerevisiae* consists of amino acid sequence (SEQ ID NO: 121) composed of 522 amino acid residues encoded by a 1569-bp nucleotide sequence (SEQ ID NO: 120). PCR was carried out using genomic DNA of *S. cerevisiae* prepared using the Y-DER Yeast DNA Extraction Reagent (PIERCE, 78870) as a template, the ScPDI-sal-F primer (5'-GGTCGACATGAAGTTTTCTGCTGGTG-3': SEQ ID NO: 58), the ScPDI-EcoT-R primer (5'-GATGCATT-TACAATTCATCGTGAATG-3' SEQ ID NO: 59), and AccuPrime Pfx DNA Polymerase (Invitrogen, 12344-024) at 95° C. for 10 seconds, 55° C. for 30 seconds, and 68° C. for 90 seconds, and this cycle was repeated 30 times. Thus, a target DNA fragment of approximately 1.6 kb was amplified and the resultant was cloned into pCR2.1-TOPO. Based on the nucleotide sequence of the inserted DNA fragment, it was confirmed that the target fragment had the *S. cerevisiae* PDI1 (ScPDI1) gene. From a plasmid carrying the DNA fragment with a confirmed nucleotide sequence, a DNA fragment containing ScPDI1 was recovered via digestion with SalI and EcoT22I with the utilization of the SalI restriction enzyme site introduced into the ScPDI-sal-F primer and the EcoT22I restriction enzyme site introduced into the ScPDI-EcoT-R primer. In order to constitutively express ScPDI1 in *O. minuta*, ScPDI1 was ligated to pOMexGP1U recovered via digestion with SalI and EcoT22I disclosed in WO 2003/091431. The resulting plasmid was designated as onaP09307.

(9) Construction of Constitutive Expression Vector for Human PDI Gene

Human PDI (hPDI, Accession No. P07237) consists of amino acid sequence (SEQ ID NO: 141) composed of 508 amino acid residues encoded by a 1527-bp nucleotide sequence (SEQ ID NO: 140). Human full-length cDNA clone, AK095938, lacks a 20-bp DNA sequence (5'-GTAC-CTGCTGGTGGAGTTCT-3') (SEQ ID NO: 169) from residues 126 to 145 from an initiation codon. A lacking 20-bp region was restored via overlap extension PCR using AK095938 as a template. Subsequently, PCR was carried out using the SalmodifiedPDI-F primer (5'-GGTCGACATGCT-GCGCCGCGCTCTGC-3': SEQ ID NO: 60), the EcoTmodifiedPDI-R primer (5'-GATGCATTTACAGT-TCATCTTTCACAG-3': SEQ ID NO: 61), and AccuPrime Pfx DNA Polymerase (Invitrogen, 12344-024) at 95° C. for 10 seconds, 55° C. for 30 seconds, and 68° C. for 90 seconds, and this cycle was repeated 30 times. Thus, a target DNA fragment of approximately 1.5 kb was amplified and the resultant was cloned into pCR2.1-TOPO. Based on the nucleotide sequence of the inserted DNA fragment, it was confirmed that the target fragment had the hPDI gene. From a plasmid carrying the DNA fragment with a confirmed nucleotide sequence, a DNA fragment containing hPDI was recovered via digestion with SalI and EcoT22I with the utilization of the SalI restriction enzyme site introduced into the SalmodifiedPDI-F primer and the EcoT22I restriction enzyme site introduced into the EcoTmodifiedPDI-R primer. In order to constitutively express hPDI in *O. minuta*, hPDI was ligated to pOMexGP1U recovered via digestion with SalI and EcoT22I disclosed in WO 2003/091431. The resulting plasmid was designated as onaP09207.

(10) Construction of Constitutive Expression Vector for Codon-Modified Human PDI Gene Human PDI (hPDI, Accession No. P07237) consists of amino acid sequence composed of 508 amino acid residues encoded by a 1527-bp nucleotide sequence. The hPDI gene was synthesized by taking codon preference of *O. minuta* into consideration (Operon Biotechnologies). From a plasmid carrying the DNA fragment with a confirmed nucleotide sequence, a DNA fragment (SEQ ID NO: 142) containing synthesized hPDI was recovered via digestion with SalI and EcoT22I with the utilization of the SalI restriction enzyme site and the EcoT22I restriction enzyme site, which had been introduced at the time of synthesis. In order to constitutively express synthesized hPDI in *O. minuta*, synthesized hPDI was ligated to pOMexGP1U recovered via digestion with SalI and EcoT22I disclosed in WO 2003/091431. The resulting plasmid was designated as onaP09107.

Example 4

Construction of Expression Vector for Chaperone Gene Combination (1) Construction of pZ/GpGt Vector for Second Chaperone Introduction In order to coexpress two chaperone genes, a vector comprising the GAP promoter and the GAP terminator and carrying, as a selection marker, a Zeocin-resistant gene was constructed in the following manner. In order to substitute the cleavage site for the HindIII restriction enzyme located upstream of the GAP promoter and the cleavage site for the KpnI restriction enzyme located downstream of the GAP terminator of pOMexGP1U with the ApaI restriction enzyme recognition sequence, GGGCCC, PCR was carried out using the GAPp-02Apa primer (5'-GCAGGGCCCTACTGGT-TCAAGG-3': SEQ ID NO: 62), the GAPt-02Apa primer (5'-GCAGGGCCCGCTCGAATCGAC-3': SEQ ID NO: 63), and AccuPrime Pfx DNA Polymerase (Invitrogen, 12344-024) at 95° C. for 10 seconds, 55° C. for 30 seconds, and 68° C. for 120 seconds, and this cycle was repeated 30 times. The resulting target DNA fragment of approximately 2.1 kb was cloned into pCR2.1-TOPO. Based on the nucleotide sequence of the inserted DNA fragment, it was confirmed that the target fragment comprised the GAP promoter region and the GAP terminator region. The DNA fragment with a confirmed nucleotide sequence was introduced into the ApaI site of the pOMexGPZ/SynCH-AA vector, substituted with the ApaI restriction enzyme recognition sequence via insertion of the pApa I linker (Takara Bio, 4605P) into the HindIII restriction enzyme recognition sequence located upstream of the GAP promoter and the KpnI restriction enzyme recognition sequence located downstream of the GAP terminator of pOMexGPZ/SynCH. Thus, the pZ/GpGt vector comprising the GAP promoter and the GAP terminator that can be selected with the use of a Zeocin-resistant gene was constructed.

(2) Construction of Coexpression and Constitutive Expression Vector for OmPDI1 Gene and OmERO1 Gene The OmERO1 region was recovered from the OmERO1 constitutive expression vector, onaP03906, with the aid of the SalI and EcoT22I restriction enzymes. After pZ/GpGt was digested with the SalI and EcoT22I restriction enzymes, an OmERO1-containing SalI-EcoT22I fragment was introduced to construct pZ/GpGt/OmERO1. Subsequently, pZ/GpGt/OmERO1 was digested with the ApaI restriction enzyme, and a fragment comprising the GAP promoter-OmERO1-GAP terminator (i.e., the OmERO1 expression cassette) was recovered. The recovered OmERO1 expression cassette was introduced into the ApaI restriction enzyme site of the OmPDI1 expression vector, onaP03606, the insertion direction was confirmed via PCR, and a vector into which the OmPDI1 and OmERO1 expression cassette was introduced in inverse orientation with respect to each other around the URA3 marker of the OmPDI1 expression vector, onaP03606, was selected. The resulting coexpression vector for OmPDI1 and OmERO1 was designated as onaP09507 (FIG. 1).

(3) Construction of Coexpression and Constitutive Expression Vector for OmPDI1 Gene and OmKar2 Gene The OmKar2 region was recovered from the OmKar2 constitutive expression vector, onaP09007, with the aid of the SalI and EcoT22I restriction enzymes. After pZ/GpGt was digested with the SalI and EcoT22I restriction enzymes, an OmKar2-containing SalI-EcoT22I fragment was introduced to construct pZ/GpGt/OmKar2. Subsequently, pZ/GpGt/OmKar2 was digested with the ApaI restriction enzyme, and a fragment comprising the GAP promoter-OmKar2-GAP terminator (i.e., the OmKar2 expression cassette) was recovered. The recovered OmKar2 expression cassette was introduced into the ApaI restriction enzyme site of the OmPDI1 expression vector, onaP03606, the insertion direction was confirmed via PCR, and a vector into which the OmPDI1 and OmKar2 expression cassette was introduced in inverse orientation with respect to each other around the URA3 marker of the OmPDI1 expression vector, onaP03606, was selected. The resulting coexpression vector for OmPDI1 and OmKar2 was designated as onaP09707 (FIG. 1).

(4) Construction of Coexpression and Constitutive Expression Vector for OmPDI1 Gene and OmHSP104 Gene The OmHSP104 region was recovered from the OmHSP104 constitutive expression vector, onaP07107, with the aid of the SalI and EcoT22I restriction enzymes. After pZ/GpGt was digested with the SalI and EcoT22I restriction enzymes, an OmHSP104-containing SalI-EcoT22I fragment was introduced to construct pZ/GpGt/OmHSP104. Subsequently, pZ/GpGt/OmHSP104 was digested with the ApaI restriction enzyme, and a fragment comprising the GAP promoter-OmHSP104-GAP terminator (i.e., the OmHSP104 expression cassette) was recovered. The recovered OmHSP104 expression cassette was introduced into the ApaI restriction enzyme site of the OmPDI1 expression vector, onaP03606, the insertion direction was confirmed via PCR, and a vector into which the OmPDI1 and OmHSP104 expression cassette was introduced in inverse orientation with respect to each other around the URA3 marker of the OmPDI1 expression vector, onaP03606, was selected. The resulting coexpression vector for OmPDI1 and OmHSP104 was designated as onaP09607 (FIG. 1).

(5) Construction of Constitutive Expression Vector Comprising Two Copies of OmPDI1 Gene Expression Cassettes The OmPDI1 region was recovered from the OmPDI1 constitutive expression vector, onaP03606, with the aid of the SalI and EcoT22I restriction enzymes. After pZ/GpGt was digested with the SalI and EcoT22I restriction enzymes, an OmPDI1-containing SalI-EcoT22I fragment was introduced to construct pZ/GpGt/OmPDI1. Subsequently, pZ/GpGt/OmPDI1 was digested with the ApaI restriction enzyme, and a fragment comprising the GAP promoter-OmPDI1-GAP terminator (i.e., the OmPDI1 expression cassette) was recovered. The recovered OmPDI1 expression cassette was introduced into the ApaI restriction enzyme site of the OmPDI1 expression vector, onaP03606, the insertion direction was confirmed via PCR, and a vector into which an expression cassette of the first copy, OmPDI1, and an expression cassette of the second copy, OmPDI1, were introduced in inverse orientation with respect to each other around the URA3 marker of the OmPDI1 expression vector, onaP03606, was selected. The resulting coexpression vector comprising two copies of the OmPDI1 expression cassettes was designated as onaP09407 (FIG. 1).

Figure 2:
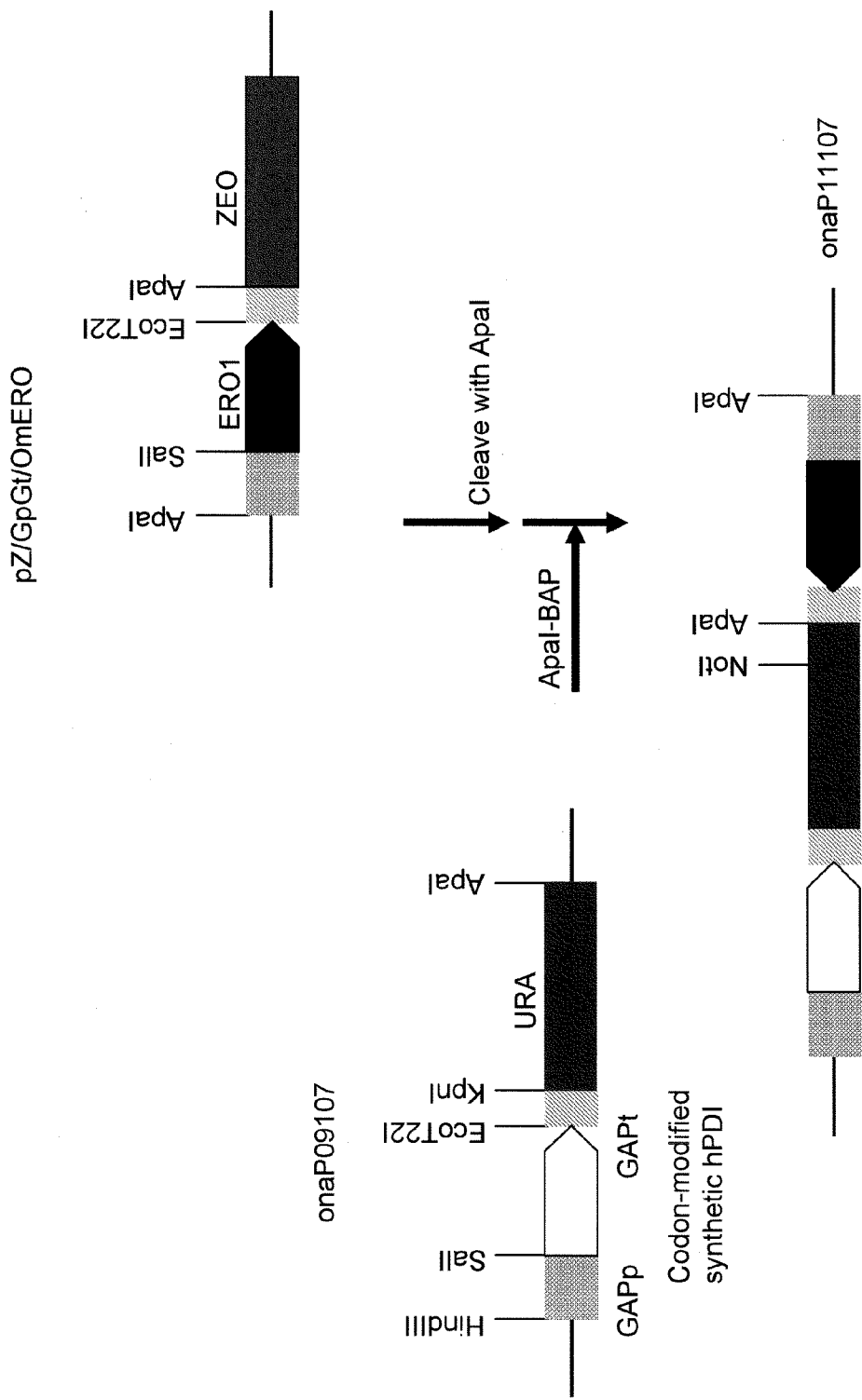
FIG. 2 shows the construction of the coexpression vector (onaP11107) for a human-derived chaperone protein (codon-modified Human PDI) and for an *O. minuta*-derived chaperone protein (OmERO1).

(6) Construction of Coexpression and Constitutive Expression Vector for hPDI Gene and OmERO1 Gene The OmERO1 region was recovered from the OmERO1 constitutive expression vector, onaP03906, with the aid of the SalI and EcoT22I restriction enzymes. After pZ/GpGt was digested with the SalI and EcoT22I restriction enzymes, an OmERO1-containing SalI-EcoT22I fragment was introduced to construct pZ/GpGt/OmERO1. Subsequently, pZ/GpGt/OmERO1 was digested with the ApaI restriction enzyme, and a fragment comprising the GAP promoter-OmERO1-GAP terminator (i.e., the OmERO1 expression cassette) was recovered. The recovered OmERO1 expression cassette was introduced into the ApaI restriction enzyme site of the constitutive expression vector for the codon-modified Human PDI gene, onaP09107, the insertion direction was confirmed via PCR, and a vector into which the codon-modified Human PDI and OmERO1 expression cassette was introduced in inverse orientation with respect to each other around the URA3 marker of the codon-modified Human PDI constitutive vector, onaP09107, was selected. The resulting coexpression vector for codon-modified Human PDI and OmERO1 was designated as onaP11107 (FIG. 2).

(7) Construction of Coexpression and Constitutive Expression Vector for OmPDI1, OmERO1, and OmKar2 Genes A coexpression vector for three chaperone genes was constructed in the following manner.

(7-1) Construction of a Foreign Gene-Expressing Vector (pOMexPGHy) with a Phosphoglycerine Kinase (PGK1) Promoter and a Terminator Using a Hygromycin B-Resistant Gene as a Selection Marker The PGK1 gene encoding phosphoglycerine kinase was obtained from the *Ogataea minuta* IFO10746 strain, and the nucleotide sequence thereof was determined.

(i) Preparation of Probes

DNA degenerate primers comprising nucleotide sequences corresponding to the conserved amino acid sequences, i.e., RVDFNVPLD (SEQ ID NO: 170) and EGKELPGVA (SEQ ID NO: 171), derived from *Saccharomyces cerevisiae* (GenBank accession number: P00560) and *Candida maltosa* (GenBank accession number: P41757) were synthesized in the following manner.

```
                                    (SEQ ID NO: 64)
PPG5:  5'-GN GTN GAY TTY AAY GTN CCN TTR GA-3'

(SEQ ID NO: 65)
PPG3:  5'-GY NAC DCC NGG YAA YTC YTT DCC YTC-3'
```

The PPG5 primer (SEQ ID NO: 64) corresponds to the amino acid sequence, RVDFNVPLD, and the PPG3 primer (SEQ ID NO: 65) is a sequence of a complementary strand of a nucleotide sequence corresponding to the amino acid sequence, EGKELPGVA. Chromosome DNA of the *O. minuta* IFO10746 strain was used as a template, PCR was carried out using PPG5 and PPG3 primers at 94° C. for 30 seconds, 50° C. for 1 minute, and 72° C. for 1 minute, and this cycle was repeated 25 times. The amplified DNA fragment (approximately 1.2 kb) was recovered and cloned using the TOPO TA Cloning Kit. Plasmid DNA was isolated from the resulting clone, and the nucleotide sequence was determined. Thus, a clone having a nucleotide sequence encoding an amino acid sequence having high homology to the amino acid sequence of the PGK1 gene derived from *S. cerevisiae* and *C. maltosa* in the plasmid-inserted DNA fragment was selected. The 1.2-kb DNA-inserted fragment was recovered after the plasmid was cleaved with EcoRI, followed by agarose gel electrophoresis.

(ii) Preparation and Screening of Library

Chromosome DNA of the *O. minuta* IFO10746 strain was cleaved with various restriction enzymes and 0.8% agarose gel electrophoresis was performed. The separated DNA was transferred on the Hybond N+ nylon membrane (GE Healthcare Bio-Sciences). The DNA fragment obtained above was labeled with the use of the AlkPhos DIRECT (RPN3690, GE Healthcare Bio-Sciences), followed by Southern hybridization. Hybridization was carried out in accordance with a conventional technique (Molecular cloning 2nd edn., ed. Sambrook, J., et al., Cold Spring Harbor Laboratory U.S.A., 1989). As a result, the PGK1 gene was considered to be present in a BamHI fragment of approximately 9.0 kb. In order to clone the DNA fragment, genome library was prepared. Chromosome DNA of *O. minuta* was cleaved with BamHI and subjected to agarose electrophoresis, and a DNA fragment of approximately 9.0 kb was recovered from the gel. The recovered DNA fragment was ligated to the BamHI-cleaved pUC118 and transformed into the *E. coli* DH5α strain in accordance with the method of Hanahan (Gene, 10, 63, 1980) to prepare library. Approximately 4,000 clones were screened via colony hybridization using the aforementioned DNA fragments as probes. From among the obtained positive clones, the pOMPGK1 plasmids carrying PGK1 genes were selected.

(iii) Nucleotide Sequencing

The nucleotide sequence in the BamHI region in the pOMPGK1 plasmid was determined by the primer walking method, and the determined sequence was found to have the nucleotide sequence as shown in SEQ ID NO: 66. The nucleotide sequence as shown in SEQ ID NO: 66 comprises an open reading frame comprising 1,254 base pairs from nucleotides 4,766 to 6,016. Homology between the amino acid sequence as shown in SEQ ID NO: 67 that is deduced based on the open reading frame and phosphoglycerine kinases derived from *Saccharomyces cerevisiae* and *Candida maltosa* was inspected. As a result, the former homology was found to be 74%, and the latter homology was found to be 81%.

(iv) Construction of Foreign Gene-Expressing Cassette Using PGK1 Gene Promoter and Terminator An expression cassette that introduces a foreign gene between a fragment containing the PGK1 gene promoter and a fragment containing a terminator of the *O. minuta* was prepared. In order to introduce the SpeI, BglII, and BamHI sites between the PGK1 gene promoter and the terminator, the following primers were synthesized.

(SEQ ID NO: 68)
OPGK-P-F:
5'-AAGCTTGACAATGTAGGAGATCATAAACACATCGTGCGCGTC-3'

(SEQ ID NO: 69)
OPGK-P-R:
5'-GGATCCAGATCTCATATGACTAGTTGCTAGTTCTATGCGGCGTTAGT
GTTTACACTACGACAGCT-3'

(SEQ ID NO: 70)
OPGK-T-F:
5'-GGATCCGTGGGATTTGCGTGATCTACGTAGTGGTTATTTT-3'

(SEQ ID NO: 71)
OPGK-T-R:
5'-GGTACCGCAGTGAAAGGCGATGCCACCATGTGCAAGGAGTTC-3'

Using pOMPGK1 above as a template, PCR was carried out using the OPGK-P-F primer (SEQ ID NO: 68) and the OPGK-P-R primer (SEQ ID NO: 69) at 94° C. for 30 seconds, 55° C. for 1 minute, and 72° C. for 1 minute, and this cycle was repeated 20 times. Also, PCR was carried out using the OPGK-T-F primer (SEQ ID NO: 70) and the OPGK-T-R primer (SEQ ID NO: 71) at 94° C. for 30 seconds, 55° C. for 1 minute, and 72° C. for 1 minute, and this cycle was repeated 20 times. The amplified 1.5-kb and 1.0-kb DNA fragments were recovered and cloned using the TOPO TA Cloning Kit. The nucleotide sequences of the insertion DNA fragments were determined to select clones having the correct nucleotide sequences. The 1.5-kb and 1.0-kb insertion DNA fragments were isolated as the HindIII-BamHI fragment and the BamHI-KpnI fragment, respectively.

The aforementioned 1.0-kb BamHI-KpnI fragment was introduced between BamHI and KpnI of pOMex5H described in WO 2003/091431. Thereafter, the aforementioned 1.5-kb HindIII-BamHI fragment was introduced between HindIII and BamHI of the obtained plasmid. The resulting plasmid was designated as pOMexPGHy. pOMexPGHy is a foreign gene-expressing vector comprising SpeI, BglII, and BamHI sites in the PGK1 gene expression cassette.
(7-2) Construction of Coexpression Vector for OmPDI1 and OmERO1 Via Expression Regulation by GAP Promoter and for OmKar2 Via Expression Regulation by PGK Promoter The PGK promoter and PGK terminator regions were cloned via PCR from the pOMexPGHy vector prepared in the above-described manner. The PGK promoter region was subjected to PCR using the OmPGKp-01Hd primer (5'-GGAAGCTTGACAATGTAGGAGATCATAAACA-3': SEQ ID NO: 72) and the OmPGKp-02Sal primer (5'-GGTCGACTGCTAGTTCTATGCGGC-3': SEQ ID NO: 73) and the PGK terminator region was subjected to PCR using the OmPGKt-01EcoT primer (5'-GGATGCATGTGGGATTTGCGTGATCTAC-3': SEQ ID NO: 74) and the OmPGKt-02Kpn primer (5'-GGGTACCAGGGTCGATTTTCTTGGTCG-3': SEQ ID NO: 75) at 95° C. for 10 seconds, 55° C. for 30 seconds, and 68° C. for 90 seconds with the use of AccuPrime Pfx DNA Polymerase (Invitrogen, 12344-024), and this cycle was repeated 30 times. The resulting target DNA fragments of approximately 1.5 kb and approximately 0.5 kb were cloned into pCR2.1-TOPO. Based on the nucleotide sequence of the inserted DNA fragment, it was confirmed that the target fragments comprised the PGK promoter and PGK terminator regions.

Figure 3:
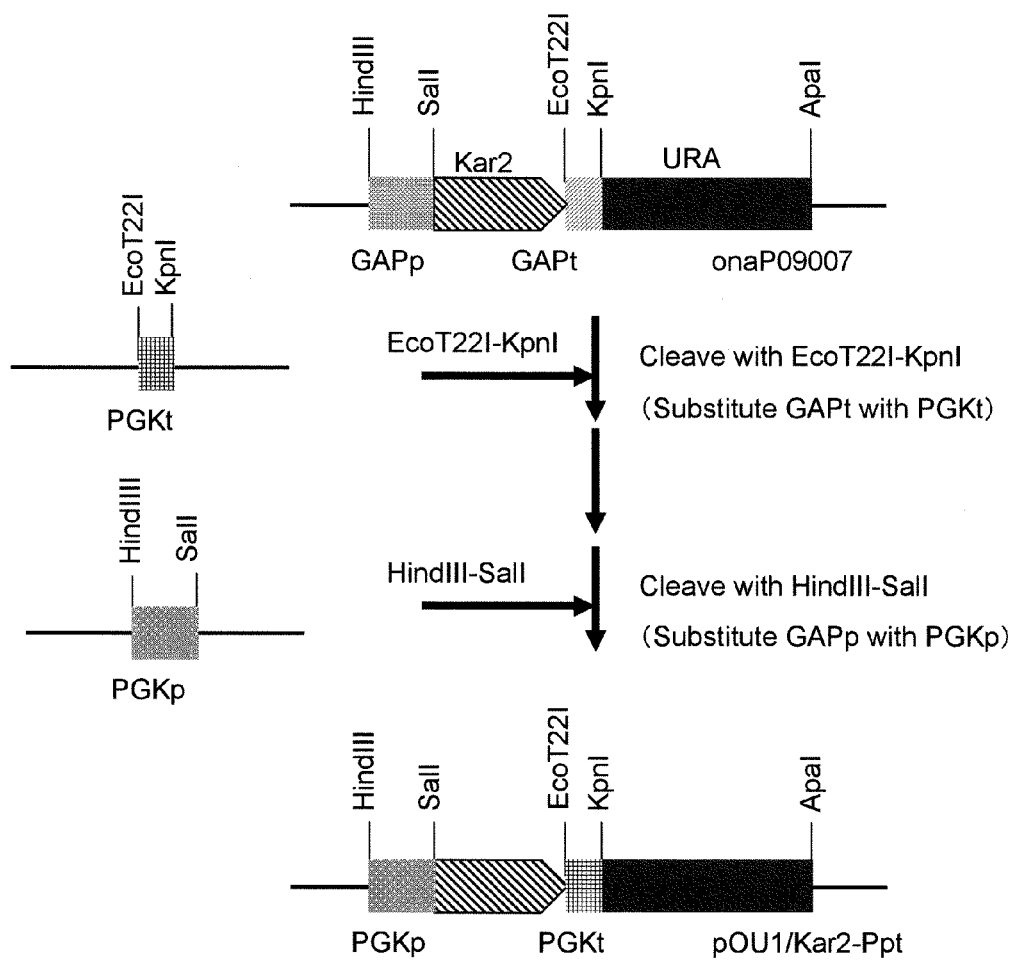
FIG. 3 shows the construction of the OmKar2 expression vector (pOU1/Kar2-Ppt) via regulation of the PGK promoter.

Subsequently, the constitutive expression vector for the OmKar2 gene, onaP09007, was digested with the EcoT22I and KpnI restriction enzymes and the resultant was ligated to the PGK terminator region recovered via digestion with the EcoT22I and KpnI restriction enzymes. Further, the resulting plasmid was digested with the HindIII and SalI restriction enzymes, and the resultant was ligated to the PGK terminator region recovered via digestion with the HindIII and SalI restriction enzymes. In the resulting plasmid, the GAP promoter and the GAP terminator were substituted with the PGK promoter and the PGK terminator, and OmKar2 expression was regulated by the PGK promoter. Thus, it was designated as the pOU1/Kar2Ppt vector (FIG. 3). The HindIII restriction enzyme site of pOU1/Kar2Ppt was blunt-ended, the cleavage site for the KpnI restriction enzyme was introduced with the use of the pKpnI linker (Takara Bio, 4668P), and the resulting vector was designated as pOU1/Kar2-PptK.

Figure 4:
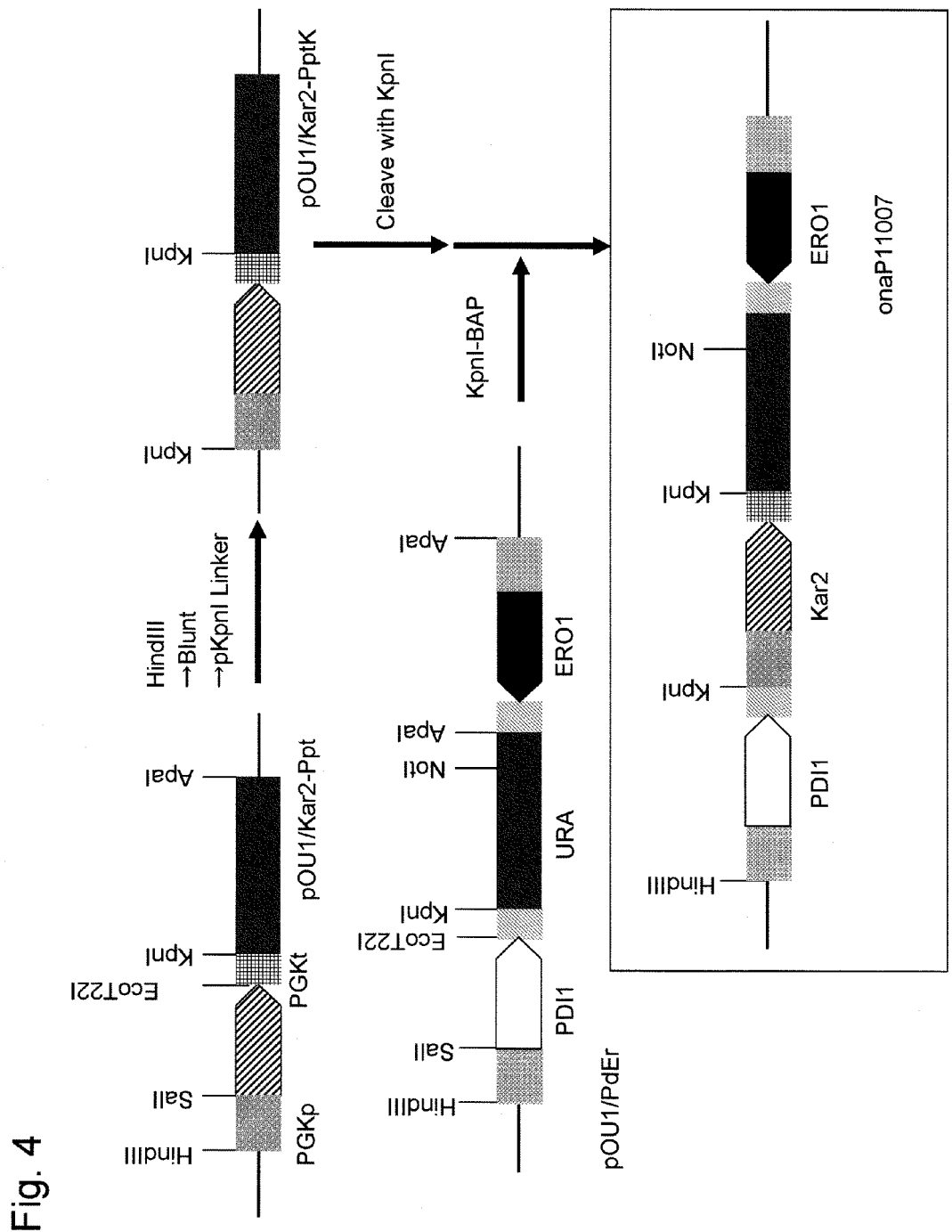
FIG. 4 shows the construction of the coexpression vector (onaP11007) for three types of chaperone proteins (OmPDI1, OmERO1, and OmKar2) derived from *O. minuta*.

Subsequently, pOU1/Kar2-PptK was digested with the KpnI restriction enzyme, a fragment containing the PGK promoter-OmKar2-PGK terminator (i.e., the OmKar2 expression cassette) was recovered, and the resultant was introduced into the KpnI restriction enzyme site of the coexpression vector for OmPDI1 and OmERO1, onaP09507, to construct the coexpression vector for OmPDI1, OmERO1, and OmKar2, onaP11007 (FIG. 4).

Example 5

Preparation of Chaperone-Introduced Yeast Strain
(*O. minuta*)

All the constitutive expression vectors for the chaperone gene constructed in Example 4 were digested with the NotI restriction enzyme and then introduced into the *O. minuta* YK5 strain (Δoch1 Δyps1 Δura3 Δade1: a strain in which the *Ogataea minuta* protease YPS1 gene has been destroyed) via electroporation. Electroporation was carried out under the conditions described in WO 2003/091431. After electroporation, the resultant was applied on Casamino-U agar medium that had been sterilized via steaming under pressure (6.7 g/l of Yeast Nitrogen Base without amino acids, 0.5 g/l of casamino acid, 20 g/l of glucose, 20 mg/l of L-tryptophan, 20 mg/l of adenine, and 20 g/l of Bacto agar), followed by multiplication at 30° C. for approximately 2 to 3 days. The grown transformant was allowed to grow again on Casamino-U agar medium, a transformant into which the chaperone gene, expression of which is regulated by the GAP promoter, was selected via colony-PCR. Part of yeast that had been multiplied on Casamino-U agar medium was suspended in 10 μl of a 0.25% SDS solution, 90 μl of sterilized water was added, and yeast cells were then removed via centrifugation at 2,700×g and 4° C. for 5 minutes. The obtained supernatant was designated as a DNA solution. A strain that was confirmed to have been amplified with the use of the GAPpforS-F primer (5'-GATCTCAGGCCGAGTCAAGAC-3': SEQ ID NO: 76) designed in the GAP promoter sequence and the primer shown below was designated as a strain into which a constitutive expression vector for the chaperone gene had been introduced. When constructing a coexpression vector for three chaperone genes, OmKar2 was expressed with the use of the PGK promoter. Thus, introduction of the PGK promoter-OmKar2-PGK terminator expression cassette was confirmed with the use of the PGKpforS-F primer (5'-TAACGCCGCATAGAACTAGC-3': SEQ ID NO: 77)

designed in the PGK promoter sequence and the OMKAR-R primer (5'-GATGCATTCACAGCTCATCATGATCCCAG-3': SEQ ID NO: 51).

(p1) A primer used for confirming introduction of OmPDI1 and 2 copies of OmPDI1 OMPDI1T22I: 5'-GATGCATTTA-CAACTCGTCGTGAGCCAC-3' (SEQ ID NO: 29)

(p2) A primer used for confirming introduction of OmMPD1 OMIC1379T22I: 5'-GATGCATTCATAGCT-CATCTTTTTC-3' (SEQ ID NO: 35)

(p3) A primer used for confirming introduction of OmSCJ1 OMSCJ1T22I: 5'-GATGCATTCACAGCTCGTCGTG-CAAC-3' (SEQ ID NO: 37)

(p4) A primer used for confirming introduction of OmEUG1 OMEUG1T22I: 5'-GATGCATTCACAGCTCATCCTTG-GCTGG-3' (SEQ ID NO: 39)

(p5) A primer used for confirming introduction of OmERO1 OMEROT22I: 5'-GATGCATTTATAGCTCCAAACGATA-CAG-3' (SEQ ID NO: 45)

(p6) A primer used for confirming introduction of OmHSP104 OmHSP104EcoTR: 5'-GATGCATTTAATC-GAGATCAGGACTGC-3' (SEQ ID NO: 49)

(p7) A primer used for confirming introduction of OmKar2 OMKAR-R: 5'-GATGCATTCACAGCTCATCATGATC-CCAG-3' (SEQ ID NO: 51)

(p8) A primer used for confirming introduction of ScPDI1 ScPDI-EcoT-R: 5'-GATGCATTTACAATTCATCGT-GAATG-3' (SEQ ID NO: 59)

(p9) A primer used for confirming introduction of hPDI EcoT-modifiedPDI-R: 5'-GATGCATTTACAGTTCATCTTTCA-CAG-3' (SEQ ID NO: 61)

(p10) A primer used for confirming introduction of synthesized hPDI ShPDI-ttaR: 5'-GATGCATTTACAACTCGTC-CTTAAC-3' (SEQ ID NO: 78)

(p11) A primer used for confirming introduction of OmPDI1+ OmERO1 OMPDI1T22I: 5'-GATGCATTTA-CAACTCGTCGTGAGCCAC-3' (SEQ ID NO: 29) and OMEROT22I: 5'-GATGCATTTATAGCTCCAAACGATA-CAG-3' (SEQ ID NO: 45)

(p12) A primer used for confirming introduction of OmPDI1+ OmKar2 OMPDI1T22I: 5'-GATGCATTTA-CAACTCGTCGTGAGCCAC-3' (SEQ ID NO: 29) and OMKAR-R: 5'-GATGCATTCACAGCTCATCATGATC-CCAG-3' (SEQ ID NO: 51)

(p13) A primer used for confirming introduction of OmPDI1+ OmHSP104 OMPDI1T22I: 5'-GATGCATTTA-CAACTCGTCGTGAGCCAC-3' (SEQ ID NO: 29) and OmHSP104EcoTR: 5'-GATGCATTTAATCGAGATCAG-GACTGC-3' (SEQ ID NO: 49)

(p14) A primer used for confirming introduction of synthesized hPDI+OmERO1 ShPDI-ttaR: 5'-GATGCATTTA-CAACTCGTCCTTAAC-3' (SEQ ID NO: 78) and OMEROT22I: 5'-GATGCATTTATAGCTCCAAACGATA-CAG-3' (SEQ ID NO: 45):

(p15) A primer used for confirming introduction of OmPDI1+ OmERO1+OmKar2 OMPDI1T22I: 5'-GATGCATTTA-CAACTCGTCGTGAGCCAC-3' (SEQ ID NO: 29), OMEROT22I: 5'-GATGCATTTATAGCTCCAAACGATA-CAG-3' (SEQ ID NO: 45), and OMKAR-R: 5'-GATGCAT-TCACAGCTCATCATGATCCCAG-3' (SEQ ID NO: 51)

A target fragment was amplified via PCR using TaKaRa LA Taq™ with GC Buffer (Takara Bio, RR02AG) at 94° C. for 30 seconds, 55° C. for 30 seconds, and 72° C. for 60 to 180 seconds, and this cycle was repeated 30 times. The transformants below, which were confirmed to have been amplified, were designated as strains constitutively expressing chaperone.

(E1) The strain constitutively expressing OmPDI1, the ona03306 strain (E2) The strain constitutively expressing OmMPD1, the ona03406 strain (E3) The strain constitutively expressing OmSCJ1, the ona03506 strain (E4) The strain constitutively expressing OmEUG1, the ona03706 strain (E5) The strain constitutively expressing OmERO1, the ona03606 strain (E6) The strain constitutively expressing OmHSP104, the ona13407 strain (E7) The strain constitutively expressing OmKar2, the ona23007 strain (E8) The strain constitutively expressing ScPDI1, the ona26907 strain (E9) The strain constitutively expressing hPDI, the ona31107 strain (E10) The strain constitutively expressing synthetic hPDI, the ona30807 strain (E11) The strain constitutively expressing OmPDI1+ OmERO1, the ona27607 strain (E12) The strain constitutively expressing OmPDI1+ OmKar2, the ona30507 strain (E13) The strain constitutively expressing OmPDI1+Om-HSP104, the ona27707 strain (E14) The strain constitutively expressing 2 copies of OmPDI1, the ona27207 strain (E15) The strain constitutively expressing synthetic hPDI+ OmERO1, the ona45007 strain (E16) The strain constitutively expressing OmPDI1+ OmERO1+OmKar2, the ona44607 strain Example 6

Construction of Antibody-Producing Yeast Strain (*O. minuta*)

The expression vector for the anti-TRAIL receptor antibody gene (WO 2001/083560) constructed in Example 2 was introduced into the yeast strain (*O. minuta*) to prepare an antibody-producing yeast strain. As the yeast strain (*O. minuta*), the ona01206 strain prepared from *O. minuta* YK5 strain in the following manner was used.

When the *O. minuta* YK5 strain did not complement a ura3 deletion mutation, the growth capacity was lowered, and the initiation codon of the ura3 gene was deleted. In order to complement a ura3 deletion mutation, accordingly, homologous recombination was carried out using the OmURA3 fragment to complement a ura3 deletion mutation. After the *O. minuta* YK5 strain was transformed with the use of the OmURA3 fragment via electroporation, the transformant was applied on Casamino-U agar medium, which had been sterilized via steaming under pressure, and the transformant was allowed to grow at 30° C. for approximately 2 to 3 days. The grown transformant was allowed to grow again on Casamino-U agar medium, part of yeast that had grown on Casamino-U agar medium was suspended in 10 μl of a 0.25% SDS solution, 90 μl of sterilized water was added, and yeast cells were removed via centrifugation at 2,700×g and 4° C. for 5 minutes. The obtained supernatant was designated as a DNA solution. With the use of the OmURA3F primer (5'-ATGTCCTCGACTAAGACATACGC-3': SEQ ID NO: 79) and the OmURA3R primer (5'-TCATGCGACACGACT-CAAATAAG-3': SEQ ID NO: 80), which had been designed at the initiation codon side and the termination codon side of the ura3 gene, respectively, a target fragment of approximately 0.8 kb was amplified using TaKaRa LA Taq™ with GC Buffer (Takara Bio, RR02AG) (94° C. for 30 seconds, 55° C. for 30 seconds, and 72° C. for 60 seconds, and this cycle was repeated 30 times). The transformant, which was confirmed to have been amplified, was designated as the ona01206 strain as a ura3 candidate strain.

Subsequently, the expression vector for the anti-TRAIL receptor antibody gene (WO 2001/083560) constructed in Example 2 was introduced into the ona01206 strain via electroporation. As an antibody heavy chain, 1 μg of onaP02706 digested with the Sse8387I restriction enzyme was used. As an antibody light chain, 1 μg of onaP03106 digested with the NotI restriction enzyme was used. After electroporation, the transformant was applied on Casamino-U-A agar medium to which Zeocin™ (Invitrogen, R250-01) had been added at a concentration of 100 μg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 μg/ml, and the resultant was designated as an antibody secretory-producing strain. The antibody-producing strain was cultured in the following manner. With the use of 2×YP-P6-GG medium (the medium was prepared by dissolving 20 g of Difco yeast extract and 40 g of Bacto peptone in 900 ml of pure water, sterilizing the solution via steaming under pressure, and adding 100 ml of separately sterilized 10× phosphate buffer (pH 6.0) (1M $KH_2PO_4$, 0.15M $(NH_4)_2SO_4$, 0.375N KOH), 10 ml of a separately sterilized 50% glucose solution, and 25 ml of separately sterilized 80% glycerine), 800 μl to 1000 μl of 2×YP-P6-GG medium was introduced into a 96-deep well plate (Greiner, 780271), the strains were sowed with the use of a toothpick, and the top of the plate was sealed with $CO_2$-permeable plate sealers (Greiner, 676051). Culture was carried out at an agitation speed of 310 rpm, an amplitude of 50 mm, at 30° C. for 3 or 4 days. The yeast cells were removed from the culture solution via centrifugation at 2,700×g and 4° C. for 5 minutes to prepare a culture supernatant, and the resultant was designated as a secretory antibody sample.

Figure 5:
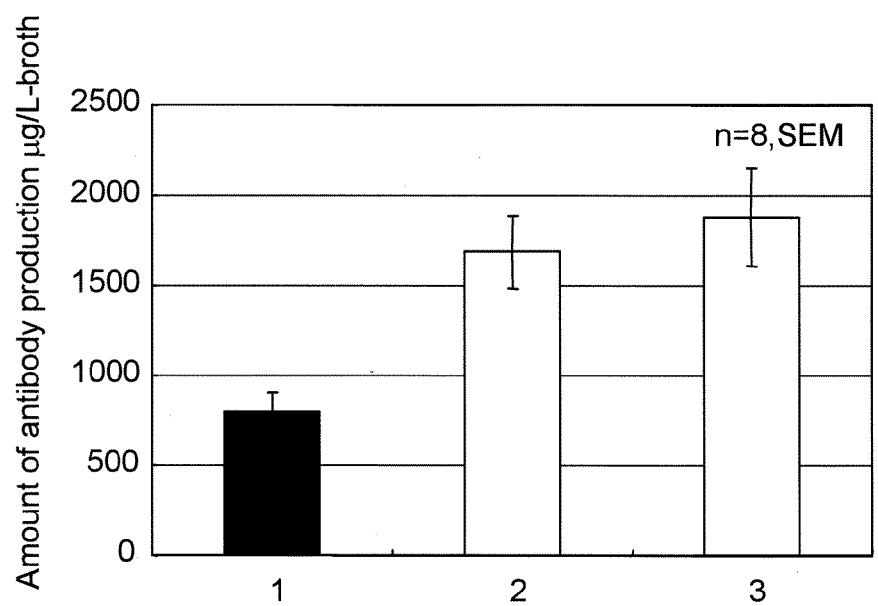
FIG. 5 is a chart showing the results of measuring the amount of secreted antibodies of an antibody-producing yeast strain (i.e., the ona02306 strain) cultured with or without the addition of an inhibitor of O-mannosylation (rhodanine-3-acetic acid derivative 1c) (1: 1c was not added; 2: 100 μl of medium containing 20 μM 1c was added on day 3; 3: 100 μl of medium containing 20 μM 1c was added on day 2 and day 3).

The secreted and produced antibodies were subjected to quantitative assay via sandwich ELISA. TRAIL receptor proteins that were antigens of the anti-TRAIL receptor antibodies were adsorbed on a 96-well plate, a secretory antibody sample was added, and detection was carried out using a peroxidase-labeled human IgG specific Fc antibody (Peroxidase-labeled affinity purified antibody to human IgG (Fc) (KPL, 04-10-20)) and the ABTS peroxidase substrate (KPL, 50-66-01). The selected antibody-producing yeast strain, ona02306, exhibited the capacity for secreting and producing an antibody at approximately 0.8 mg/l (FIG. 5).

Example 7

Effects of Inhibition of O-Sugar Chain Addition of Yeast-Producing Antibody Caused by the Addition of an Inhibitor of Protein Mannosyl Transferase (PMT) on Antibody Production The antibody-producing yeast obtained in Example 6 was cultured under conditions in which formation of O-sugar chain via the addition of PMT inhibitors is inhibited (PMT inhibitors, rhodanine-3-acetic acid derivative: 5-[[3,4-(1-phenylmethoxy)phenyl]methylene]-4-oxo-2-thioxo-3-thiazolidineacetic acid (compound 1c described in Bioorganic & Medicinal Chemistry Letters, Vol. 14, p. 3975, 2004, was added to the medium). With the use of 2×YP-P6-GG medium [(the medium was prepared by dissolving 20 g of Difco yeast extract and 40 g of Bacto peptone in 900 ml of pure water, sterilizing the solution via steaming under pressure, and adding 100 ml of separately sterilized 10× phosphate buffer (pH 6.0) (1M $KH_2PO_4$, 0.15M $(NH_4)_2SO_4$, 0.375N KOH), 10 ml of a separately sterilized 50% glucose solution, and 25 ml of separately sterilized 80% glycerine), 800 μl of 2×YP-P6-GG medium was introduced into a 96-deep well plate (Greiner, 780271), the strains were sowed with the use of a toothpick, and the top of the plate was sealed with $CO_2$-permeable plate sealers (Greiner, 676051). Control culture was carried out at an agitation speed of 310 rpm, an amplitude of 50 mm, at 30° C. for 2 days, 100 μl of 2×YP-P6-GG medium was added, and 100 μl of 2×YP-P6-GG medium was further added on day 3. In the case of culture involving single addition of a rhodanine-3-acetic acid derivative 1c, culture was carried out at an agitation speed of 310 rpm, an amplitude of 50 mm, at 30° C. for 2 days, 100 μl of 2×YP-P6-GG medium was added, and 100 μl of 2×YP-P6-GG medium containing 20 μM of 1c was further added on day 3. In the case of culture involving addition of a rhodanine-3-acetic acid derivative 1c twice, culture was carried out at an agitation speed of 310 rpm, an amplitude of 50 mm, at 30° C. for 2 days, 100 μl of 2×YP-P6-GG medium containing 20 μM of 1c was added, and 100 μl of 2×YP-P6-GG medium containing 20 μM of 1c was further added on day 3.

Secretion and production of an antibody were confirmed via sandwich ELISA or Western blotting. Yeast cells were removed from the culture product via centrifugation at 2,700×g and 4° C. for 5 minutes, and the resulting culture supernatant was designated as a sample of secreted antibody. The secreted and produced antibodies were subjected to quantitative assay via sandwich ELISA. TRAIL receptor proteins that were antigens of the anti-TRAIL receptor antibodies were adsorbed on a 96-well plate, the sample of secreted antibody was added, and detection was carried out using a peroxidase-labeled human IgG specific Fc antibody (Peroxidase-labeled affinity purified antibody to human IgG (Fc) (KPL, 04-10-20)) and the ABTS peroxidase substrate (KPL, 50-66-01).

Western blotting was carried out as follows. After the protein was subjected to SDS-PAGE under reducing and non-reducing conditions, the separated protein was blotted to a PVDF membrane, and the antibody heavy chain and the light chain were detected using Anti-human IgG (γ-chain specific) (Sigma, I-3382) and Goat anti human kappa b&f affinity purified (Bethyl, A-80-115A) as the primary antibodies. Peroxidase conjugated affinity purified anti-goat IgG (H&L) (Rabbit) (Rockland, #605-4313) was used as the secondary antibody. Detection was carried out using ECL Advance Western blotting detection kit (GE, RPN2135).

Figure 6:
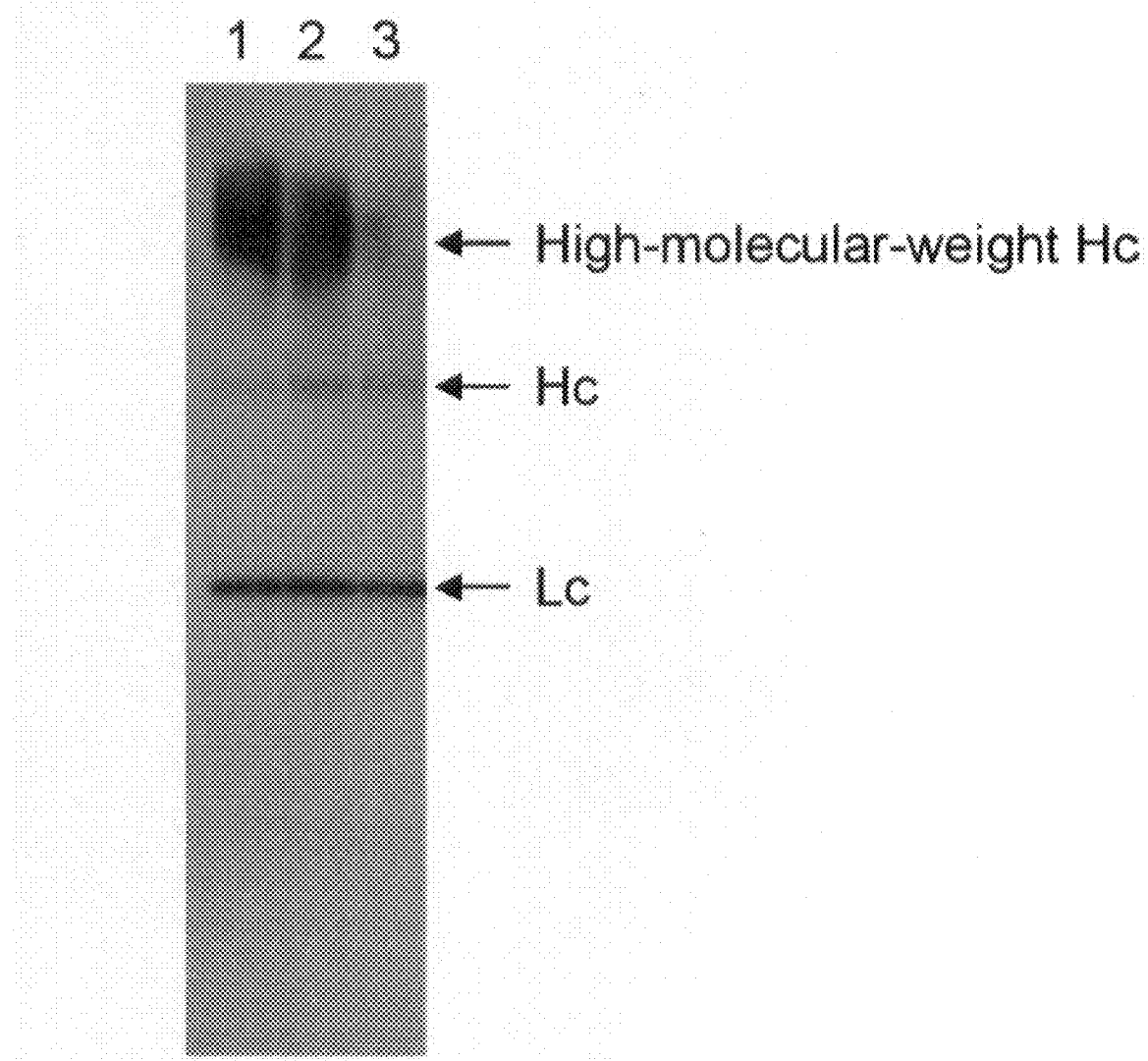
FIG. 6 shows the results of Western blot analysis of antibodies secreted in the culture supernatant of an antibody-producing yeast strain (i.e., the ona02306 strain) cultured with or without the addition of an inhibitor of O-mannosylation (rhodanine-3-acetic acid derivative 1c) (1: 1c was not added; 2: 100 μl of medium containing 20 μM 1c was added on day 3; 3: 100 μl of medium containing 20 μM 1c was added on day 2 and day 3).

As shown in FIG. 5, a control sample (the ona02306 strain) exhibited the amount of secretion and production of an antibody at 0.8 mg/l. With a single addition of PMT inhibitors, the amount of antibody production was increased to approximately 1.7 mg/l, and it was increased to approximately 1.9 mg/l; i.e., about 2.1 to about 2.4 times greater, via the addition of PMT inhibitors twice. That is, the amount of antibody production was increased by approximately 2.1 to approximately 2.4 times via the addition of PMT inhibitors (FIG. 5). Also, Western blot analysis demonstrated that, in control culture, a high-molecular-weight antibody heavy chain with a smaller mobility than the antibody heavy chain was detected via reducing electrophoresis by an antibody heavy chain-specific antibody, although the high-molecular-weight antibody heavy chain was decreased via the addition of PMT inhibitors to culture (FIG. 6: reducing SDS-PAGE/WB, antibody Hc and antibody Lc were simultaneously detected). When transformed yeast was to be cultured with the use of a 96-deep well plate (Greiner, 780271) with the addition of PMT inhibitors, accordingly, culture was carried out at 30° C. for 2 days, and culture was further carried out by adding 100 μl of 2×YP-P6-GG medium containing 20 μm of 1c and then 100 μl of 2×YP-P6-GG medium containing 20 μm of 1c 3 days later.

Example 8

Construction of Antibody-Producing Yeast Strain (*O. minuta*) that Constitutively Expresses Chaperone The expression vector for the anti-TRAIL receptor antibody gene (WO 2001/083560) constructed in Example 2 was introduced into each of the strains constitutively expressing chaperone alone bred in Example 5 via electroporation. As an antibody heavy chain, 1 μg of onaP02706 digested with the Sse8387I restriction enzyme was used. As an antibody light chain, 1 μg of onaP03106 digested with the NotI restriction enzyme was used. After electroporation, the transformant was applied on Casamino-U-A agar medium to which Zeocin™ (Invitrogen, R250-01) had been added at a concentration of 100 μg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 μg/ml and a strain that secretes and produces an antibody was screened for. The ona08906 strain was selected as the strain constitutively expressing OmSCJ1 and having the antibody gene introduced therein, the ona09206 strain was selected as the strain constitutively expressing OmEUG1 and having the antibody gene introduced therein, the ona09406 strain was selected as the strain constitutively expressing OmERO1 and having the antibody gene introduced therein, the ona26407 strain was selected as the strain constitutively expressing OmKar2 and having the antibody gene introduced therein, the ona09506 strain was selected as the strain constitutively expressing OmPDI1 and having the antibody gene introduced therein, and the ona15807 strain was selected as the strain constitutively expressing OmHSP104 and having the antibody gene introduced therein.

Example 9

Effects of Chaperone on Secretory Production of Antibody

Figure 7:
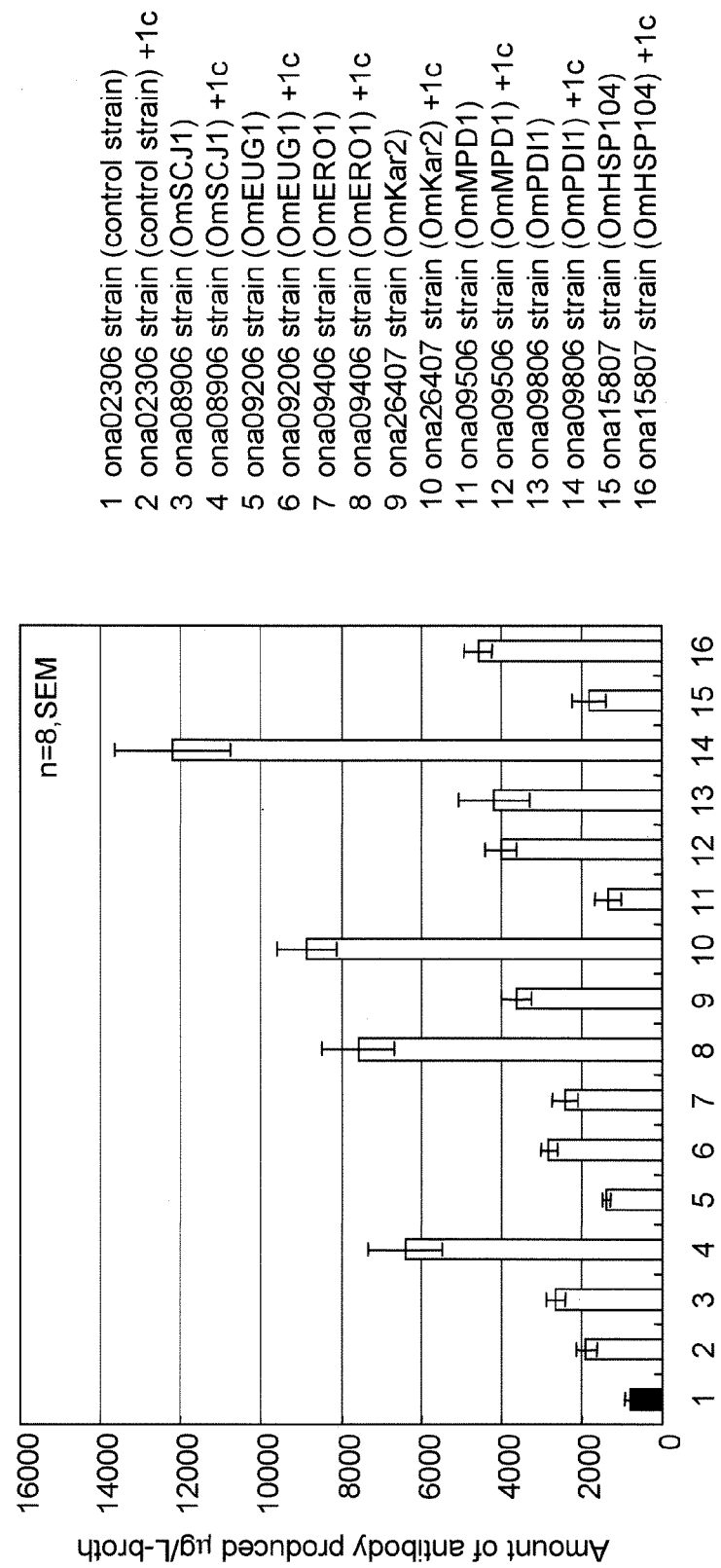
FIG. 7 is a chart showing the results of measuring the amount of secreted antibodies of an antibody-producing yeast strains (cultured with or without the addition of an inhibitor of O-mannosylation (rhodanine-3-acetic acid derivative 1c)) into which gene of a single chaperone protein (SCJ1, EUG1, ERO1, Kar2, MPD1, PDI1, and HSP104) derived from *O. minuta* strain had been introduced.
Figure 8:
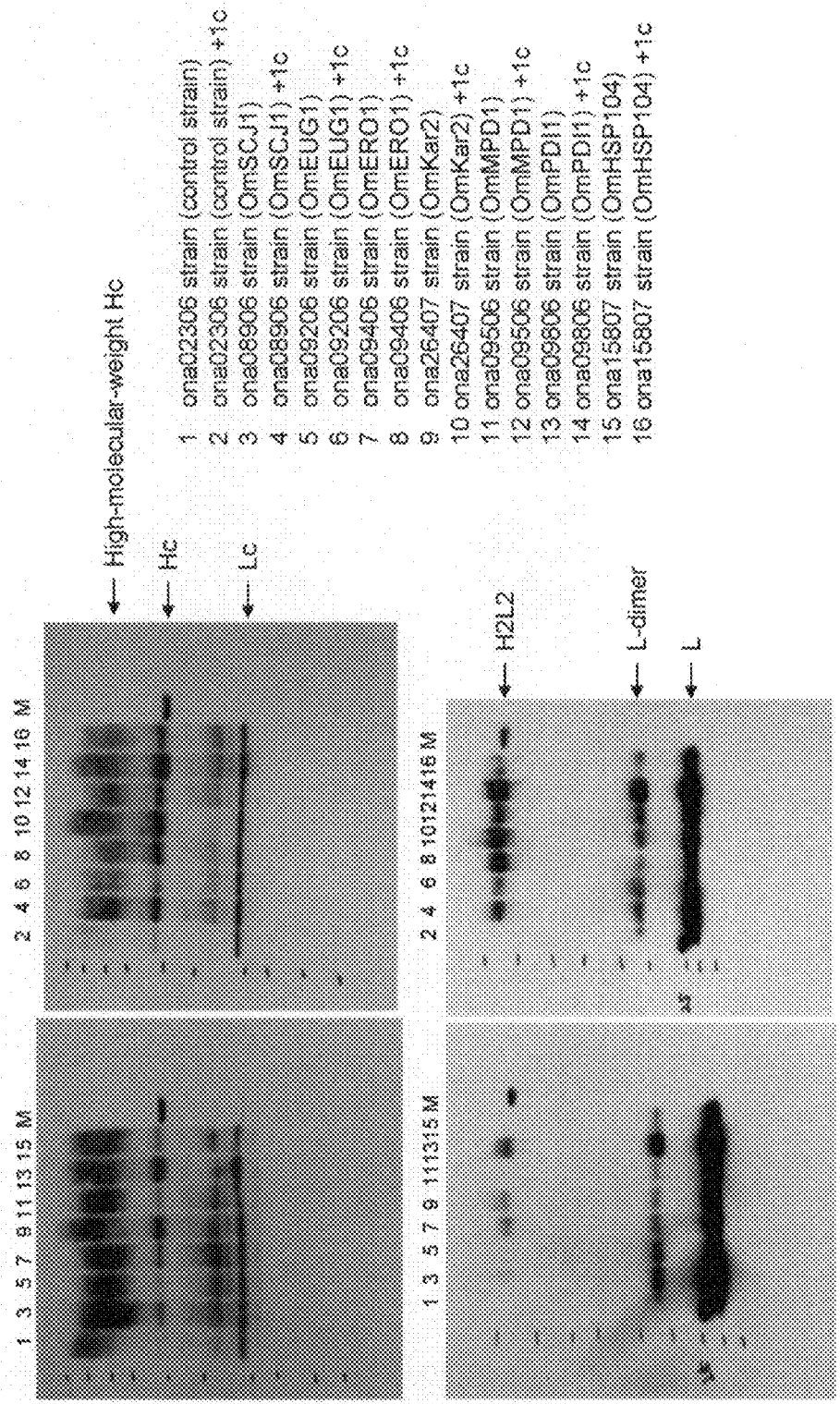
FIG. 8 shows the results of Western blot analysis of antibodies secreted in the culture supernatant of an antibody-producing yeast strains (cultured with or without the addition of an inhibitor of O-mannosylation (rhodanine-3-acetic acid derivative 1c)) into which gene of a single chaperone protein (SCJ1, EUG1, ERO1, Kar2, MPD1, PDI1, and HSP104) derived from *O. minuta* strain had been introduced (top: reducing SDS-PAGE/WB; antibody Hc and antibody Lc are simultaneously detected; bottom: non-reducing SDS-PAGE/WB; antibody Lc is detected).

With the use of the strain constitutively expressing chaperone and having the antibody gene introduced therein obtained in Example 8, the effects of chaperone introduction on secretory production of antibody were examined. Also, the effects of enhancing secretory production of antibody caused by the addition of PMT inhibitors that were found in Example 7 were examined. As shown in FIG. 7, a control strain (i.e., the ona02306 strain) exhibited the amount of antibody secretory production of approximately 0.8 mg/l, the strain constitutively expressing OmSCJ1 and having the antibody gene introduced therein (i.e., the ona08906 strain) exhibited that of approximately 2.6 mg/l, the strain constitutively expressing OmEUG1 and having the antibody gene introduced therein (i.e., the ona09206 strain) exhibited that of 1.4 mg/l, the strain constitutively expressing OmERO1 and having the antibody gene introduced therein (i.e., the ona09406 strain) exhibited that of 2.4 mg/l, the strain constitutively expressing OmKar2 and having the antibody gene introduced therein (i.e., the ona26407 strain) exhibited that of 3.6 mg/l, the strain constitutively expressing OmMPD1 and having the antibody gene introduced therein (i.e., the ona09506 strain) exhibited that of 1.3 mg/l, the strain constitutively expressing OmPDI1 and having the antibody gene introduced therein (i.e., the ona09806 strain) exhibited that of 4.2 mg/l, and the strain constitutively expressing OmHSP104 and having the antibody gene introduced therein (i.e., the ona15807 strain) exhibited that of 1.8 mg/l. By enhancing chaperone expression, the capacity for antibody secretory production was improved by approximately 2 to 5 times. Further, addition of PMT inhibitors to culture was found to improve the amount of antibody secretory production of all the produced strains, as shown in FIG. 7. In the case of the strain constitutively expressing OmPDI1 and having the antibody gene introduced therein (i.e., the ona09806 strain), in particular, the amount of antibody secretory production was found to be improved by approximately 15 times higher than that obtained via control culture of the strain into which the antibody gene had been introduced (i.e., the ona02306 strain) constructed in Example 6. As shown in FIG. 8, it was clearly confirmed via Western blot analysis following non-reducing electrophoresis that a full-length antibody (H2L2) would be secreted and produced.

Example 10

Effects of Chaperone Combination

The expression vector for the anti-TRAIL receptor antibody gene (WO 2001/083560) constructed in Example 2 was introduced into the strain constitutively expressing two types of chaperones bred in Example 5 via electroporation. As an antibody heavy chain, 1 μg of onaP02706 digested with the Sse8387I restriction enzyme was used. As an antibody light chain, 1 μg of onaP03106 digested with the NotI restriction enzyme was used. After electroporation, the transformant was applied on Casamino-U-A agar medium to which Zeocin™ (Invitrogen, R250-01) had been added at a concentration of 100 μg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 μg/ml, and a strain that secretes and produces an antibody was screened for. The ona32507 strain was selected as the strain carrying two OmPDI1 expression units and constitutively expressing OmPDI1 and having the antibody gene introduced therein (i.e., the 2×OmPDI1 strain), the ona33407 strain was selected as the strain constitutively expressing OmPDI1/OmHSP104 and having the antibody gene introduced therein, the ona40007 strain was selected as the strain constitutively expressing OmPDI1/OmKar2 and having the antibody gene introduced therein, and the ona33107 strain was selected as the strain constitutively expressing OmPDI1/OmERO1 and having the antibody gene introduced therein.

Figure 9:
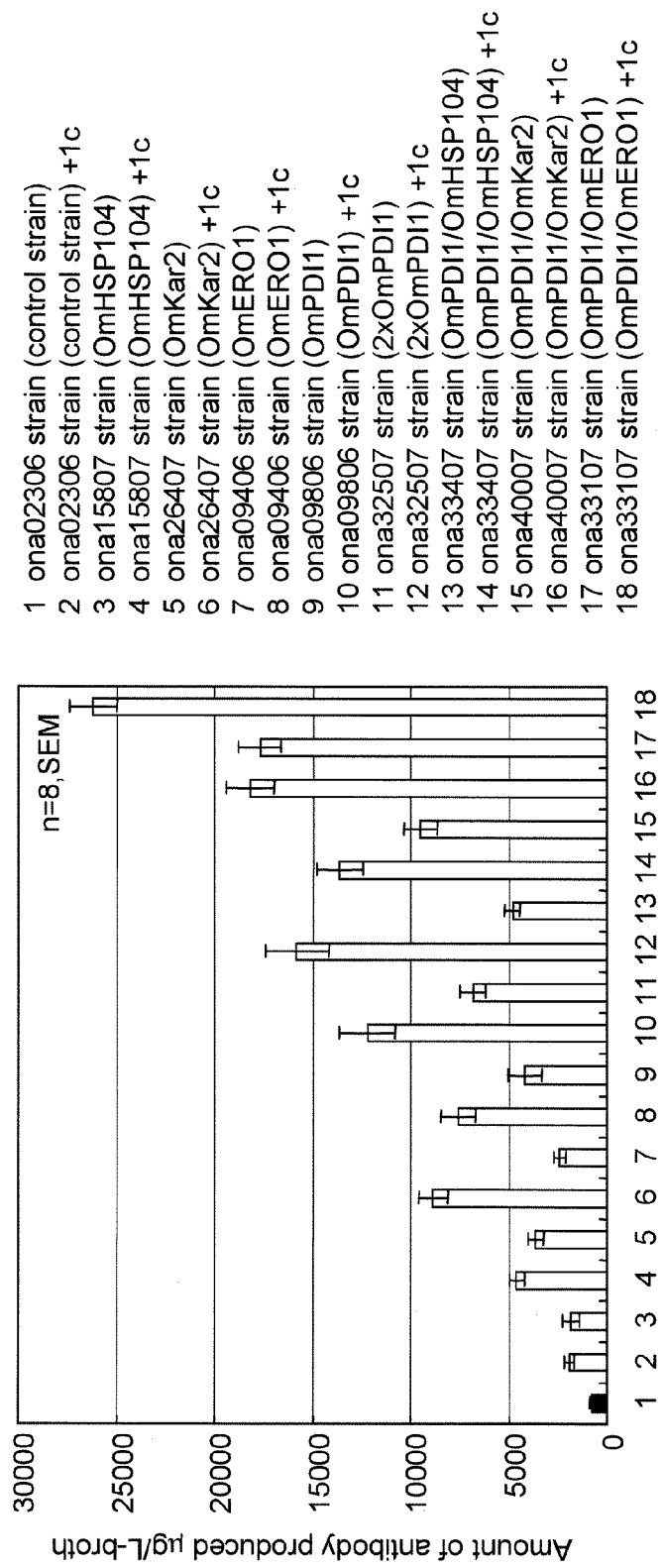
FIG. 9 is a chart showing the results of measuring the amount of secreted antibodies of an antibody-producing yeast strains (cultured with or without the addition of an inhibitor of O-mannosylation (rhodanine-3-acetic acid derivative 1c)) into which genes of a plurality of chaperone proteins (2×PDI1, PDI1/HSP104, PDI1/Kar2, and PDI1/ERO1) derived from *O. minuta* strain had been introduced.

As shown in FIG. 9, a control strain into which the antibody gene had been introduced (i.e., the ona02306 strain) exhibited the amount of antibody secretory production of approximately 0.8 mg/l and approximately 1.9 mg/l when PMT inhibitors were added, the strain constitutively expressing OmHSP104 and having the antibody gene introduced therein (i.e., the ona15807 strain) exhibited that of approximately 1.8 mg/l and approximately 4.6 mg/l when PMT inhibitors were added, the strain constitutively expressing OmKar2 and having the antibody gene introduced therein (i.e., the ona26407 strain) exhibited that of approximately 3.6 mg/l and approximately 8.9 mg/l when PMT inhibitors were added, the strain constitutively expressing OmERO1 and having the antibody gene introduced therein (i.e., the ona09406 strain) exhibited that of approximately 2.4 mg/l and approximately 7.6 mg/l when PMT inhibitors were added, and the strain constitutively expressing OmPDI1 and having the antibody gene introduced therein (i.e., the ona09806 strain) exhibited that of approximately 4.2 mg/l and approximately 12.2 mg/l when PMT inhibitors were added. In contrast, the strain constitutively expressing 2×OmPDI1 and having the antibody gene introduced therein (i.e., the ona32507 strain) exhibited the amount of antibody secretory production of approximately 6.8 mg/l and approximately 15.8 mg/l when PMT inhibitors were added, the strain constitutively expressing OmPDI1/OmHSP104 and having the antibody gene introduced therein (i.e., the ona33407 strain) exhibited that of approximately 4.8 mg/l and approximately 13.6 mg/l when PMT inhibitors were added, the strain constitutively expressing OmPDI1/OmKar2 and having the antibody gene introduced therein (i.e., the ona40007 strain) exhibited that of approximately 9.5 mg/l and approximately 18.2 mg/l when PMT inhibitors were added, and the strain constitutively expressing OmPDI1/OmERO1 and having the antibody gene introduced therein (i.e., the ona33107 strain) exhibited that of approximately 17.7 mg/l and approximately 26.2 mg/l when PMT inhibitors were added. The capacity for antibody secretory production that had been improved by approximately 2 to 5 times by enhancing chaperone expression alone was further improved, when chaperone expression was enhanced in combination. When expression of OmPDI1 and that of OmERO1 were enhanced, in particular, the capacity for antibody secretory production was improved by approximately 22 times, and it was improved by approximately 33 times with the addition of PMT inhibitors to culture.

Figure 10:
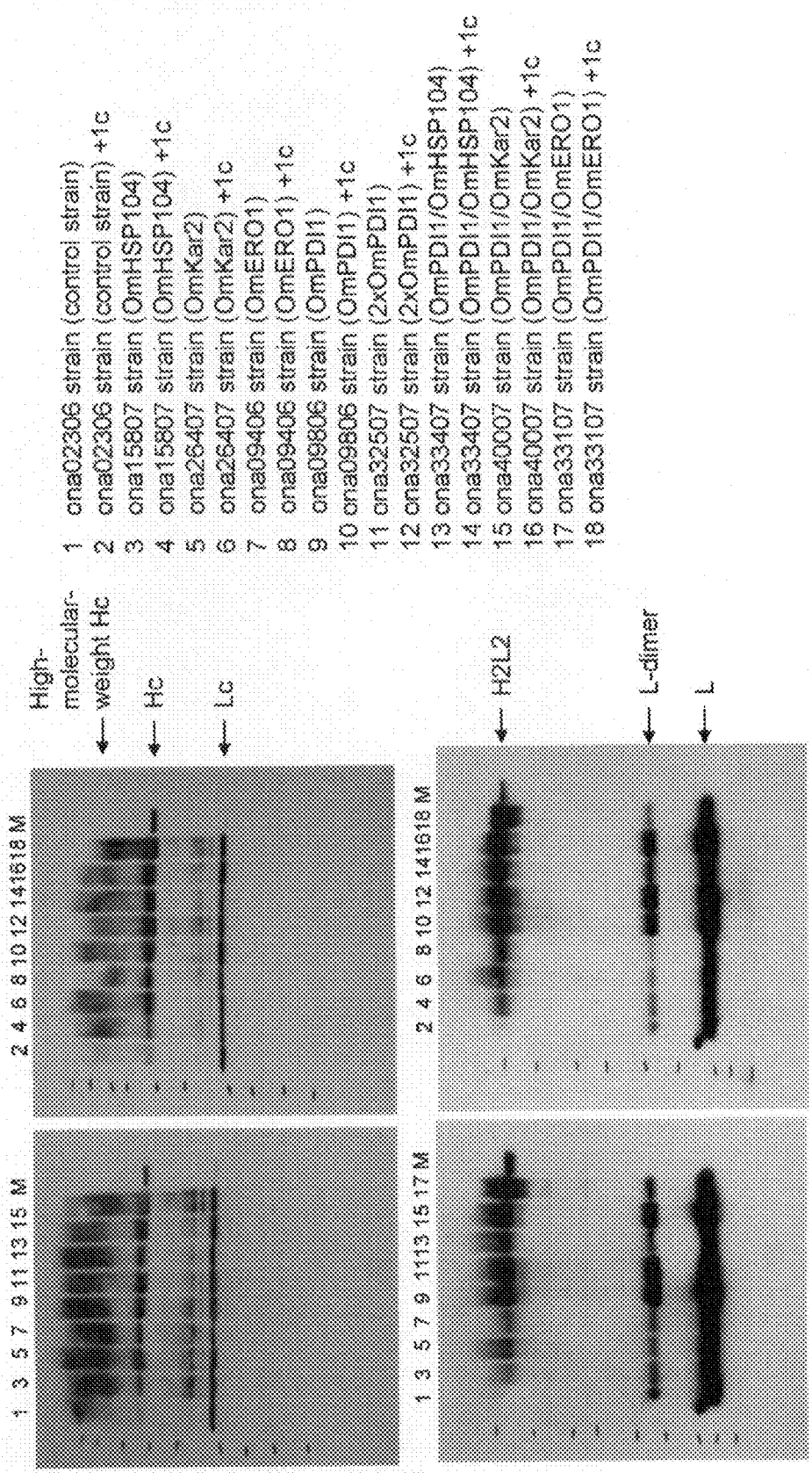
FIG. 10 shows the results of Western blot analysis of antibodies secreted in the culture supernatant of an antibody-producing yeast strains (cultured with or without the addition of an inhibitor of O-mannosylation (rhodanine-3-acetic acid derivative 1c)) into which genes of a plurality of chaperone proteins (2×PDI1, PDI1/HSP104, PDI1/Kar2, and PDI1/ERO1) derived from *O. minuta* strain had been introduced (top: reducing SDS-PAGE/WB; antibody Hc and antibody Lc are simultaneously detected; bottom: non-reducing SDS-PAGE/WB; antibody Lc is detected).

As shown in FIG. 10, it was confirmed via Western blot analysis following non-reducing electrophoresis that the amount of a full-length antibody (H2L2) secreted, which was deduced to be correctly folded, was apparently increased.

Example 11

Effects of Constitutive Expression of Heterologous Protein Disulfide Isomerase (PDI) on Secretory Production of Antibody The expression vector for the anti-TRAIL receptor antibody gene (WO 2001/083560) constructed in Example 2 was introduced into the strain constitutively expressing heterologous PDI alone bred in Example 5 via electroporation. As an antibody heavy chain, 1 µg of onaP02706 digested with the Sse8387I restriction enzyme was used. As an antibody light chain, 1 µg of onaP03106 digested with the NotI restriction enzyme was used. After electroporation, the transformant was applied on Casamino-U-A agar medium to which Zeocin™ (Invitrogen, R250-01) had been added at a concentration of 100 µg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 µg/ml, and a strain that secretes and produces an antibody was screened for. The ona32207 strain was selected as the strain constitutively expressing Saccharomyces cerevisiae ScPDI1 and having the antibody gene introduced therein, the ona38907 strain was selected as the strain constitutively expressing human PDI and having the antibody gene introduced therein, and the ona39307 strain was selected as the strain constitutively expressing synthetic human PDI (i.e., human PDI with the codon usage being optimized in accordance with that of O. minuta) and having the antibody gene introduced therein.

Figure 11:
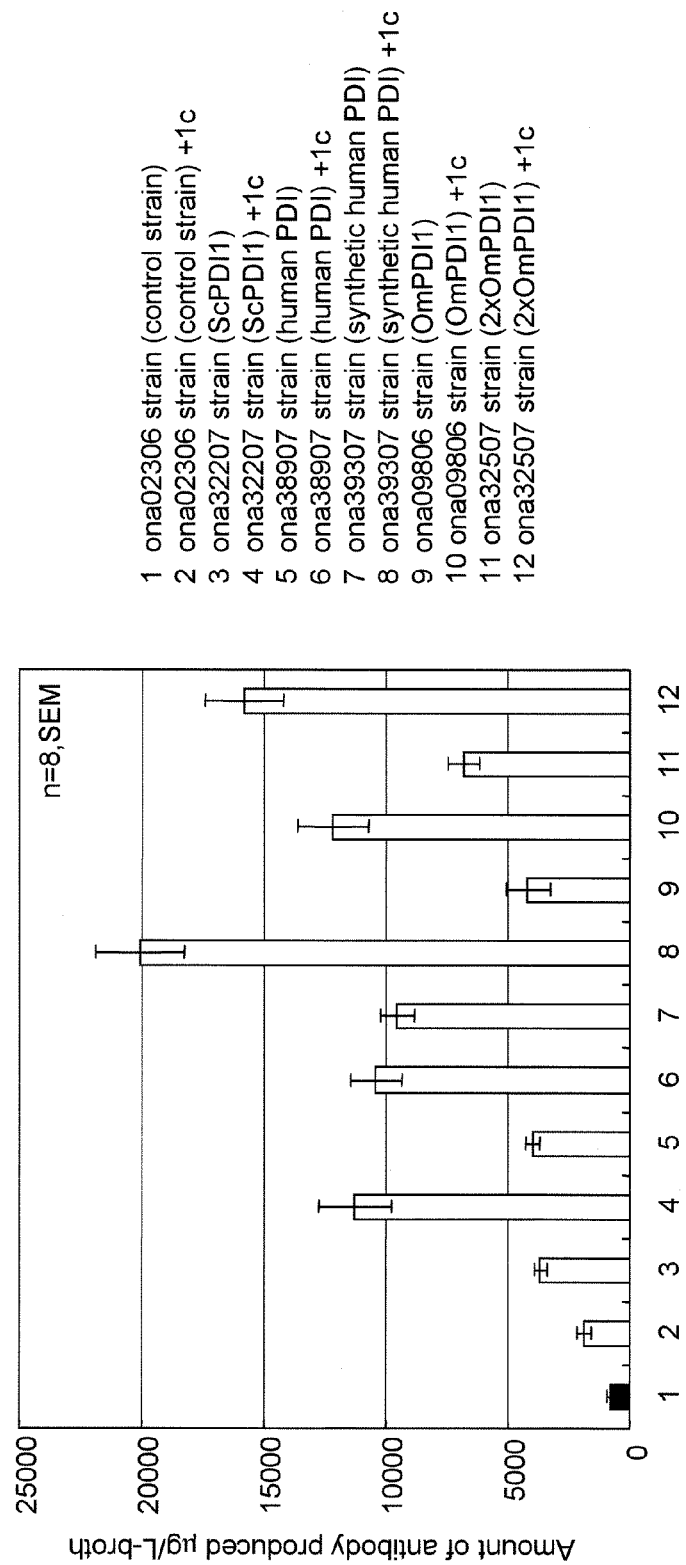
FIG. 11 is a chart showing the results of measuring the amount of secreted antibodies of an antibody-producing yeast strains (cultured with or without the addition of an inhibitor of O-mannosylation (rhodanine-3-acetic acid derivative 1c)) into which genes of chaperone proteins (PDI1) derived from *S. cerevisiae*, a human, and a synthesized human had been introduced.

As shown in FIG. 11, a control strain into which the antibody gene had been introduced (i.e., the ona02306 strain) exhibited the amount of antibody secretory production of approximately 0.8 mg/l and approximately 1.9 mg/l when PMT inhibitors were added, the strain constitutively expressing OmPDI1 and having the antibody gene introduced therein (i.e., the ona09806 strain) exhibited that of approximately 4.2 mg/l and 12.2 mg/l when PMT inhibitors were added, the strain constitutively expressing 2×OmPDI1 and having the antibody gene introduced therein (i.e., the ona32507 strain) exhibited that of approximately 6.8 mg/l and approximately 15.8 mg/l when PMT inhibitors were added, the strain constitutively expressing ScPDI1 and having the antibody gene introduced therein (i.e., the ona32207 strain) exhibited that of approximately 3.7 mg/l and approximately 11.3 mg/l when PMT inhibitors were added, the strain constitutively expressing hPDI and having the antibody gene introduced therein (i.e., the ona38907 strain) exhibited that of approximately 4.0 mg/l and approximately 10.4 mg/l when PMT inhibitors were added, and the strain constitutively expressing synthetic hPDI and having the antibody gene introduced therein (i.e., the ona39307 strain) exhibited that of approximately 9.5 mg/l and approximately 20.1 mg/l when PMT inhibitors were added. When expression of a functional homolog; i.e., heterologous PDI, was enhanced in addition to constitutive expression of O. minuta PDI1, the capacity of antibody secretory production was also found to be improved. In the case of hPDI synthesized by taking the frequency of codon use of O. minuta into consideration, in particular, addition of PMT inhibitors to culture resulted in an improvement in the capacity for antibody secretory production to approximately 25 times higher than that of the control and approximately 1.6 times higher than that obtained upon introduction of OmPDI1 and addition of PMT inhibitors to culture.

Example 12

Effects of Chaperone Combination

The expression vector for the anti-TRAIL receptor antibody gene (WO 2001/083560) constructed in Example 2 was introduced into each of the strain constitutively expressing synthetic human PDI and OmERO1 and the strain constitutively expressing OmPDI1, OmERO1, and OmKar2 bred in Example 5 via electroporation. As an antibody heavy chain, 1 µg of onaP02706 digested with the Sse8387I restriction enzyme was used. As an antibody light chain, 1 µg of onaP03106 digested with the NotI restriction enzyme was used. After electroporation, the transformant was applied on Casamino-U-A agar medium to which Zeocin™ (Invitrogen, R250-01) had been added at a concentration of 100 µg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 μg/ml, and a strain that secretes and produces an antibody was screened for. The ona49707 strain was selected as a strain into which the gene of an antibody constitutively expressing synthetic human PDI/OmERO1 had been introduced, and the ona48707 strain was selected as the strain into which the gene of an antibody constitutively expressing OmPDI1, OmERO1, and OmKar2 had been introduced.

Figure 12:
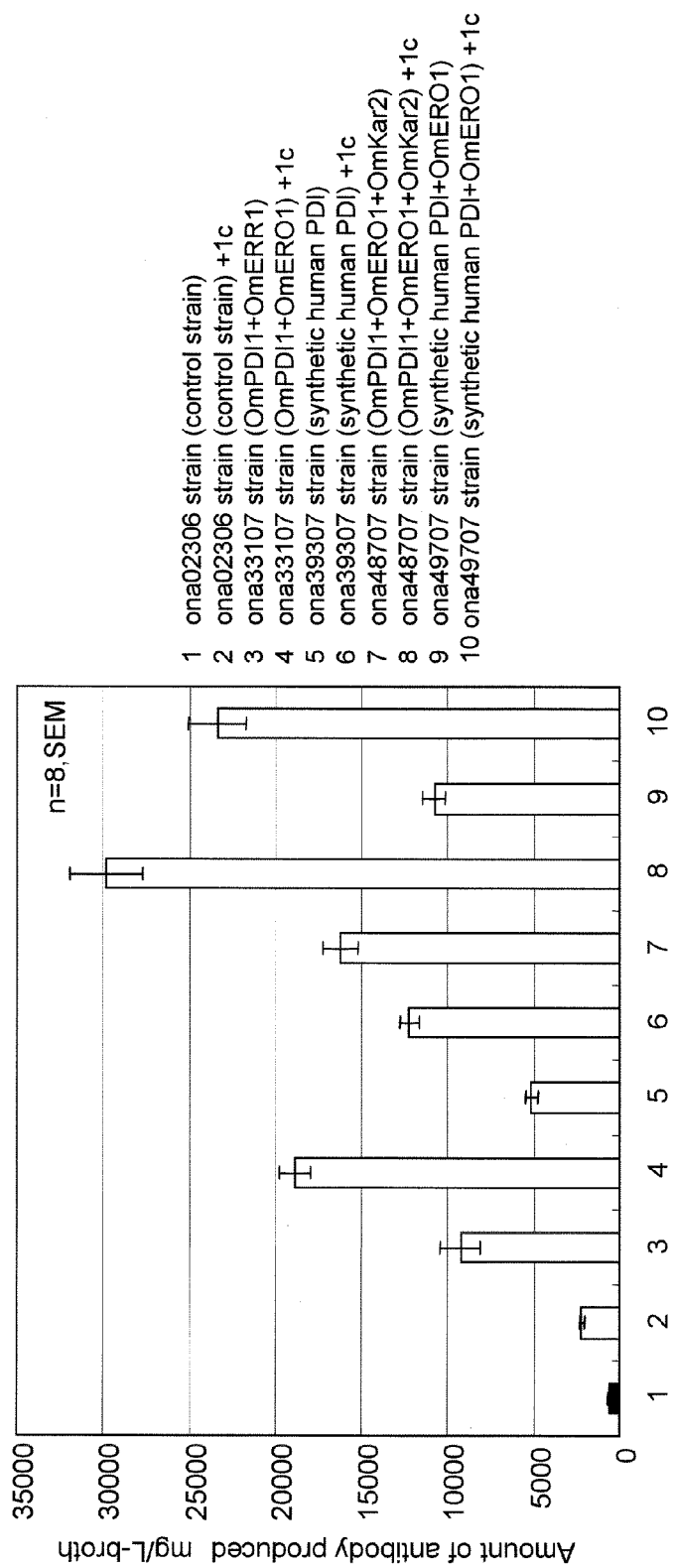
FIG. 12 is a chart showing the results of measuring the amount of secreted antibodies of an antibody-producing yeast strains (cultured with or without the addition of an inhibitor of O-mannosylation (rhodanine-3-acetic acid derivative 1c)) into which combinations of genes of three types of chaperone proteins derived from *O. minuta* strain (PDI1/EPO1/Kar2) and genes of chaperone proteins derived from different species (human PDI/OmERO1) had been introduced.

As shown in FIG. 12, a control strain into which the antibody gene had been introduced (i.e., the ona02306 strain) exhibited the amount of antibody secretory production of approximately 0.65 mg/l and approximately 2.2 mg/l when PMT inhibitors were added, the strain constitutively expressing synthetic human PDI and having the antibody gene introduced therein (i.e., the ona39307 strain) exhibited that of approximately 5.1 mg/l and approximately 12.3 mg/l when PMT inhibitors were added, and the strain constitutively expressing OmPDI1/OmERO1 and having the antibody gene introduced therein (i.e., the ona33107 strain) exhibited that of approximately 9.2 mg/l and approximately 18.9 mg/l when f PMT inhibitors were added. In contrast, the strain constitutively expressing synthetic human PDI/OmERO1 and having the antibody gene introduced therein (i.e., the ona49707 strain) exhibited the amount of antibody secretory production of approximately 10.8 mg/l and approximately 23.4 mg/l when PMT inhibitors were added, and the strain constitutively expressing OmPDI1/OmERO1/OmKar2 and having the antibody gene introduced therein (i.e., the ona48707 strain) exhibited that of approximately 16.2 mg/l and approximately 29.8 mg/l when PMT inhibitors were added. When expression of heterologous PDI; i.e., synthetic human PDI and OmERO1, was enhanced, the capacity of antibody secretory production was increased by at least 20%, compared with the case when expression of OmPDI1 and OmERO1 was enhanced. That is, the capacity of antibody secretory production was approximately 36 times higher than that of the control. When expression of OmPDI1, OmERO1, and OmKar2 was enhanced in combination, the capacity of antibody secretory production was further improved, which was approximately 45.8 times higher than that of the control.

Example 13

Construction of Expression Vector for Antibody Gene

In order to express a secretory signal of Kar2 (YJL034W) derived from *S. cerevisiae* (hereafter referred to as "ScKar2 signal") and the light and heavy chains of the anti-TRAIL receptor antibody as a fusion protein, the ScKar2 signal gene was ligated to the anti-TRAIL receptor antibody gene (WO 2001/083560) via overlap extension PCR using the oligonucleotide primers below.

```
For heavy chain of ScKar2 signal-anti-TRAIL
receptor antibody
                                    (SEQ ID NO: 81)
BipXba-F:
5'-GTCTAGATGTTTTTCAACAGACTAAG-3'

(SEQ ID NO: 82)
BipTraH-R:
5'-GACTCCACCAGCTGTACTTCAGTTCCGTAGTTTTCTACATC-3'

(SEQ ID NO: 83)
BipTraH-F:
5'-GATGTAGAAAACTACGGAACTGAAGTACAGCTGGTGGAGTC-3'
```

```
                                    (SEQ ID NO: 84)
H04:
5'-GGTCGACTCATTTACCCGGGGACAG-3'

For light chain of ScKar2 signal-anti-TRAIL
receptor antibody
                                    (SEQ ID NO: 85)
BipXba-F:
5'-GTCTAGATGTTTTTCAACAGACTAAG-3'

(SEQ ID NO: 86)
BipTraL-R:
5'-GATTGGGTCATCTGAATGTCAGTTCCGTAGTTTTCTACATC-3'

(SEQ ID NO: 87)
BipTraL-F:
5'-GATGTAGAAAACTACGGAACTGACATTCAGATGACCCAATC-3'

(SEQ ID NO: 88)
L04:
5'-GGTCGACCTAACACTCTCCCCTGT-3'
```

The ScKar2 signal gene region was amplified using genomic DNA of *S. cerevisiae* prepared using the Y-DER Yeast DNA Extraction Reagent (PIERCE) as a template. PCR was carried out at 95° C. for 10 seconds, 55° C. for 30 seconds, and 68° C. for 60 seconds using the BipXba-F primer and the BipTraH-R primer for the heavy chain, and this cycle was repeated 30 times. Also, PCR was carried out at 95° C. for 10 seconds, 55° C. for 30 seconds, and 68° C. for 60 seconds using the BipXba-F primer and the BipTraL-R primer and AccuPrime Pfx DNA Polymerase (Invitrogen, 12344-024) for the light chain, and this cycle was repeated 30 times. The amplified target DNA fragments of approximately 0.15 kb were recovered.

The antibody gene region was amplified using the anti-TRAIL receptor antibody cDNA (WO 2001/083560) as a template. PCR was carried out at 95° C. for 10 seconds, 55° C. for 30 seconds, and 68° C. for 90 seconds using the BipTraH-F primer and the H04 primer for the heavy chain. Also, PCR was carried out at 95° C. for 10 seconds, 55° C. for 30 seconds, and 68° C. for 90 seconds using the BipTraL-F primer and the L04 primer for the light chain and AccuPrime Pfx DNA Polymerase (Invitrogen, 12344-024), and this cycle was repeated 30 times. The amplified target DNA fragment of a heavy chain region of approximately 1.35 kb and that of a light chain region of approximately 0.65 kb were recovered.

Subsequently, PCR was carried out at 95° C. for 10 seconds, 55° C. for 30 seconds, and 68° C. for 90 seconds using the ScKar2 signal region for the heavy chain and the heavy chain region of approximately 1.35 kb as templates, the BipXba-F primer and the H04 primer, and AccuPrime Pfx DNA Polymerase (Invitrogen, 12344-024), and this cycle was repeated 30 times. The amplified target DNA fragment of approximately 1.5 kb was recovered. Also, PCR was carried out at 95° C. for 10 seconds, 55° C. for 30 seconds, and 68° C. for 60 seconds using the ScKar2 signal region for the light chain and the light chain region of approximately 0.65 kb as templates and the BipXba-F primer and the L04 primer, and this cycle was repeated 30 times. The amplified target DNA fragment of approximately 0.8 kb was recovered. The recovered DNA fragments were cloned into pCR2.1-TOPO. Based on the nucleotide sequence of the inserted DNA fragment, it was confirmed that the target fragments each comprised the gene in which the ScKar signal-antibody heavy chain was fused in frame to the ScKar2 signal-antibody light chain. The XbaI restriction enzyme site introduced into the BipXba-F primer and the SalI restriction enzyme site introduced into the H04 and L04 primers were used to recover a DNA fragment encoding the ScKar2 signal-antibody heavy chain and the ScKar2 signal-antibody light chain via digestion with XbaI and SalI.

In order to express the antibody heavy chain and the antibody light chain in *S. cerevisiae*, a DNA fragment encoding the ScKar2 signal-antibody heavy chain and the ScKar2 signal-antibody light chain recovered via digestion with XbaI and SalI was ligated to the XbaI-SalI site in the glyceraldehyde-3-phosphoric dehydrogenase gene (TDH3, GAP) promoter-terminator cassette introduced into *E. coli*/yeast shuttle vector YEp352 (Yeast 2, pp. 163-167, 1986). The resultants were designated as the YEp352GAP-II-ScKarHc and YEp352GAP-II-ScKarLc plasmids.

Figure 13:
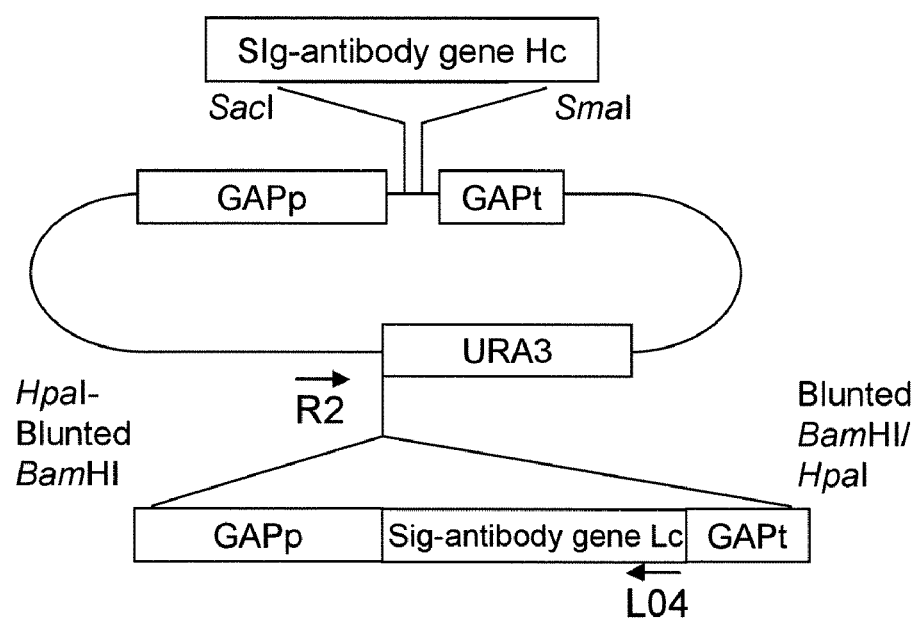
FIG. 13 shows construction of an antibody expression vector, YEp352 GAP-II-ScKarHc/ScKarLc.

Subsequently, a gene fragment encoding BamHI-GAP promoter-ScKar2 signal-antibody light chain-GAP terminator-BamHI was recovered from YEp352GAP-II-ScKarLc using the BamHI restriction enzyme sites located at both ends of the GAP promoter-terminator cassette. Subsequently, YEp352GAP-II-ScKarHc was digested with the HpaI restriction enzyme. These fragments were blunt-ended, ligated to each other, and transformed into *E. coli* JM109. The obtained clones were arbitrarily selected, subjected to colony PCR (94° C. for 30 seconds, 55° C. for 30 seconds, and 72° C. for 60 seconds) using the 352-HpaI-R2 primer (5'-CAAAAT-GAAGCACAGATGC-3': SEQ ID NO: 89), the L04 primer (5'-GGTCGACCTAACACTCTCCCCTGT-3': SEQ ID NO: 88), and TaKaRa LA Taq™ with GC Buffer (Takara Bio, RR02AG), and this cycle was repeated 30 times. Clones into which the GAP promoter-ScKar2 signal-antibody heavy chain-GAP terminator and the GAP promoter-ScKar2 signal-antibody light chain-GAP terminator were inserted in inverse orientation with respect to each other were selected. From the transformants that were confirmed to have been amplified, a vector into which BamHI-GAP promoter-ScKar2 signal-antibody light chain-GAP terminator-BamHI had been introduced at the blunt-ended HpaI restriction enzyme site of YEp352GAP-II-ScKarHc was selected, and it was designated as YEp352 GAP-II-ScKarHc/ScKarLc (FIG. 13).

Example 14

Construction of Expression Vector for Chaperone Gene Alone (1) Construction of Constitutive Expression Vector for *S. cerevisiae* PDI1 (Sc PDI1) Gene PDI1 of Sc (YCL043C: SEQ ID NO: 120 (nucleotide sequence), SEQ ID NO: 121 (amino acid sequence)) was amplified using genomic DNA of *S. cerevisiae* prepared using the Y-DER Yeast DNA Extraction Reagent (PIERCE) as a template. PCR was carried out using the PDI1-sac primer (5'-CGAGCTCATGAAGTTTTCTGCTGGTG-3': SEQ ID NO: 90), the PDI1-sma primer (5'-GCCCGGGTTACAAT-TCATCGTGAATG-3': SEQ ID NO: 91), and AccuPrime Pfx DNA Polymerase (Invitrogen, 12344-024) at 95° C. for 10 seconds, 55° C. for 30 seconds, and 68° C. for 90 seconds, and this cycle was repeated 30 times. A target DNA fragment of approximately 1.6 kb was recovered and cloned into pCR2.1-TOPO. Thereafter, the nucleotide sequence of the inserted DNA fragment was confirmed. In order to express ScPDI1 in *S. cerevisiae*, the gene encoding ScPDI1 recovered via digestion with SacI and SmaI with the use of the SacI and SmaI restriction enzyme sites introduced into the PDI1-sac primer and the PDI1-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScPDI1.

(2) Construction of Constitutive Expression Vector for ScMPD1 Gene

ScMPD1 (YOR288C: SEQ ID NO: 122 (nucleotide sequence), SEQ ID NO: 123 (amino acid sequence)) was amplified using genomic DNA of *S. cerevisiae* prepared using the Y-DER Yeast DNA Extraction Reagent (PIERCE) as a template. PCR was carried out using the MPD1-sac primer (5'-CGAGCTCATGTTATTTCTTAATATTATTAAG-3': SEQ ID NO: 92), the MPD1-sma primer (5'-GCCCGGGC-TACAATTCGTCGTGCTTGTTTCC-3': SEQ ID NO: 93), and AccuPrime Pfx DNA Polymerase (Invitrogen, 12344-024) at 95° C. for 10 seconds, 55° C. for 30 seconds, and 68° C. for 60 seconds, and this cycle was repeated 30 times. A target DNA fragment of approximately 0.96 kb was recovered and cloned into pCR2.1-TOPO. Thereafter, the nucleotide sequence of the inserted DNA fragment was confirmed. In order to express ScMPD1 in *S. cerevisiae*, the gene encoding ScMPD1 recovered via digestion with SacI and SmaI with the use of the SacI and SmaI restriction enzyme sites introduced into the MPD1-sac primer and the MPD1-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScMPD1.

(3) Construction of Constitutive Expression Vector for ScSCJ1 Gene

ScSCJ1 (YMR214W: SEQ ID NO: 124 (nucleotide sequence), SEQ ID NO: 125 (amino acid sequence)) was amplified using genomic DNA of *S. cerevisiae* prepared using the Y-DER Yeast DNA Extraction Reagent (PIERCE) as a template. PCR was carried out using the SCJ1-sac primer (5'-CGAGCTCATGATTCCAAAATTATATATAC-3': SEQ ID NO: 94), the SCJ1-sma primer (5'-GCCCGGGCTA-CAACTCATCTTTGAGC-3': SEQ ID NO: 95), and AccuPrime Pfx DNA Polymerase (Invitrogen, 12344-024) at 95° C. for 10 seconds, 55° C. for 30 seconds, and 68° C. for 60 seconds, and this cycle was repeated 30 times. A target DNA fragment of approximately 1.1 kb was recovered and cloned into pCR2.1-TOPO. Thereafter, the nucleotide sequence of the inserted DNA fragment was confirmed. In order to express ScSCJ1 in *S. cerevisiae*, the gene encoding ScMPD1 recovered via digestion with SacI and SmaI with the use of the SacI and SmaI restriction enzyme sites introduced into the SCJ1-sac primer and the SCJ1-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScSCJ1.

(4) Construction of Constitutive Expression Vector for ScERO1 Gene

ScERO1 (YML130C: SEQ ID NO: 126 (nucleotide sequence), SEQ ID NO: 127 (amino acid sequence)) was amplified using genomic DNA of *S. cerevisiae* prepared using the Y-DER Yeast DNA Extraction Reagent (PIERCE) as a template. PCR was carried out using the ERO1-sac2 primer (5'-CGAGCTCATGAGATTAAGAACCGCCATTG-3': SEQ ID NO: 96), the ERO1-sma2 primer (5'-GCCCGGGTTAT-TGTATATCTAGCTTATAG-3': SEQ ID NO: 97), and AccuPrime Pfx DNA Polymerase (Invitrogen, 12344-024) at 95° C. for 10 seconds, 55° C. for 30 seconds, and 68° C. for 120 seconds, and this cycle was repeated 30 times. A target DNA fragment of approximately 1.7 kb was recovered and cloned into pCR2.1-TOPO. Thereafter, the nucleotide sequence of the inserted DNA fragment was confirmed. In order to express ScERO1 in *S. cerevisiae*, the gene encoding ScERO1 recovered via digestion with SacI and SmaI with the use of the SacI and SmaI restriction enzyme sites introduced into the ERO1-sac2 primer and the ERO1-sma2 primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScERO1.

(5) Construction of Constitutive Expression Vector for ScFKB2 Gene

ScFKB2 (FPR2/YDR519W: SEQ ID NO: 128 (nucleotide sequence), SEQ ID NO: 129 (amino acid sequence)) was amplified using genomic DNA of *S. cerevisiae* prepared using the Y-DER Yeast DNA Extraction Reagent (PIERCE) as a template. PCR was carried out using the FKB2-sac primer (5'-CGAGCTCATGATGTTTAATATTTACC-3': SEQ ID NO: 98), the FKB2-sma primer (5'-GCCCGGGCTAGGCG-GCTGATTTCACG-3': SEQ ID NO: 99), and AccuPrime Pfx DNA Polymerase (Invitrogen, 12344-024) at 95° C. for 10 seconds, 55° C. for 30 seconds, and 68° C. for 30 seconds, and this cycle was repeated 30 times. A target DNA fragment of approximately 0.5 kb was recovered and cloned into pCR2.1-TOPO. Thereafter, the nucleotide sequence of the inserted DNA fragment was confirmed. In order to express ScFKB2 in *S. cerevisiae*, the gene encoding ScFKB2 recovered via digestion with SacI and SmaI with the use of the SacI and SmaI restriction enzyme sites introduced into the FKB2-sac primer and the FKB2-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScFKB2.

(6) Construction of Constitutive Expression Vector for ScJEM1 Gene

ScJEM1 (YJL073W: SEQ ID NO: 130 (nucleotide sequence), SEQ ID NO: 131 (amino acid sequence)) was amplified using genomic DNA of *S. cerevisiae* prepared using the Y-DER Yeast DNA Extraction Reagent (PIERCE) as a template. PCR was carried out using the JEM1-sac primer (5'-CGAGCTCATGATACTGATCTCGGGATACTGTC-3': SEQ ID NO: 100), the JEM1-sma primer (5'-GCCCGGGT-CAAAGCCCAAAATTCATTTTAAAG-3': SEQ ID NO: 101), and AccuPrime Pfx DNA Polymerase (Invitrogen, 12344-024) at 95° C. for 10 seconds, 55° C. for 30 seconds, and 68° C. for 120 seconds, and this cycle was repeated 30 times. A target DNA fragment of approximately 1.9 kb was recovered and cloned into pCR2.1-TOPO. Thereafter, the nucleotide sequence of the inserted DNA fragment was confirmed. In order to express ScJEM1 in *S. cerevisiae*, the gene encoding ScJEM1 recovered via digestion with SacI and SmaI with the use of the SacI and SmaI restriction enzyme sites introduced into the JEM1-sac primer and the JEM1-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScJEM1.

(7) Construction of Constitutive Expression Vector for ScLHS1 Gene

ScLHS1 (YKL073W: SEQ ID NO: 132 (nucleotide sequence), SEQ ID NO: 133 (amino acid sequence)) was amplified using genomic DNA of *S. cerevisiae* prepared using the Y-DER Yeast DNA Extraction Reagent (PIERCE) as a template. PCR was carried out using the LHS1.1-sac primer (5'-CGAGCTCATGCGAAACGTTTTAAGGCTTT-3': SEQ ID NO: 102), the LHS1-sma primer (5'-GCCCGGGC-TATAATTCATCATGCAAAATG-3': SEQ ID NO: 103), and AccuPrime Pfx DNA Polymerase (Invitrogen, 12344-024) at 95° C. for 10 seconds, 55° C. for 30 seconds, and 68° C. for 180 seconds, and this cycle was repeated 30 times. A target DNA fragment of approximately 2.65 kb was recovered and cloned into pCR2.1-TOPO. Thereafter, the nucleotide sequence of the inserted DNA fragment was confirmed. In order to express ScLHS1 in *S. cerevisiae*, the gene encoding ScLHS1 recovered via digestion with SacI and SmaI with the use of the SacI and SmaI restriction enzyme sites introduced into the LHS1.1-sac primer and the LHS1-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351GAP-II-ScLHS1.

(8) Construction of Constitutive Expression Vector for ScMPD2 Gene

ScMPD2 (YOL088C: SEQ ID NO: 134 (nucleotide sequence), SEQ ID NO: 135 (amino acid sequence)) was amplified using genomic DNA of *S. cerevisiae* prepared using the Y-DER Yeast DNA Extraction Reagent (PIERCE) as a template. PCR was carried out using the MPD2-sac primer (5'-CGAGCTCATGAAATTGCACGGCTTTTTATTTTC-3': SEQ ID NO: 104), the MPD2-sma primer (5'-GC-CCGGGTCAAAGCTCGTCATGACTACTGG-3': SEQ ID NO: 105), and AccuPrime Pfx DNA Polymerase (Invitrogen, 12344-024) at 95° C. for 10 seconds, 55° C. for 30 seconds, and 68° C. for 60 seconds, and this cycle was repeated 30 times. A target DNA fragment of approximately 0.8 kb was recovered and cloned into pCR2.1-TOPO. Thereafter, the nucleotide sequence of the inserted DNA fragment was confirmed. In order to express Sc MPD2 in *S. cerevisiae*, the gene encoding ScMPD2 recovered via digestion with SacI and SmaI with the use of the SacI and SmaI restriction enzyme sites introduced into the MPD2-sac primer and the MPD2-sma primer was ligated to the SacI-SmaI site in the glyceraldehyde-3-phosphoric dehydrogenase gene (TDH3, GAP) promoter-terminator cassette introduced into the *E. coli*/yeast shuttle vector YEp351 (Yeast 2, pp. 163-167, 1986). The resulting plasmid was designated as YEp351 GAP-II-Sc-MPD2.

(9) Construction of Constitutive Expression Vector for ScERJ5 Gene

ScERJ5 (YFR041C: SEQ ID NO: 136 (nucleotide sequence), SEQ ID NO: 137 (amino acid sequence)) was amplified using genomic DNA of *S. cerevisiae* prepared using the Y-DER Yeast DNA Extraction Reagent (PIERCE) as a template. PCR was carried out using the YFR041C-sac primer (5'-CGAGCTCATGAACGGTTACTGGAAAC-3': SEQ ID NO: 106), the YFR041C-sma primer (5'-GC-CCGGGTCATTTACGTGAATAGATC-3': SEQ ID NO: 107), and AccuPrime Pfx DNA Polymerase (Invitrogen, 12344-024) at 95° C. for 10 seconds, 55° C. for 30 seconds, and 68° C. for 60 seconds, and this cycle was repeated 30 times. A target DNA fragment of approximately 0.9 kb was recovered and cloned into pCR2.1-TOPO. Thereafter, the nucleotide sequence of the inserted DNA fragment was confirmed. In order to express ScERJ5 in *S. cerevisiae*, the gene encoding ScERJ5 recovered via digestion with SacI and SmaI with the use of the SacI and SmaI restriction enzyme sites introduced into the YFR041C-sac primer and the YFR041C-sma primer was ligated to the SacI-SmaI site in the glyceraldehyde-3-phosphoric dehydrogenase gene (TDH3, GAP) promoter-terminator cassette introduced into the E. coli/yeast shuttle vector YEp351 (Yeast 2, pp. 163-167, 1986). The resulting plasmid was designated as YEp351GAP-II-ScERJ5.

(10) Construction of Constitutive Expression Vector for ScEUG1 Gene

ScEUG1 (YDR518W: SEQ ID NO: 138 (nucleotide sequence), SEQ ID NO: 139 (amino acid sequence)) was amplified using genomic DNA of S. cerevisiae prepared using the Y-DER Yeast DNA Extraction Reagent (PIERCE) as a template. PCR was carried out using the EUG1-sac primer (5'-CGAGCTCATGCAAGTGACCACAAGATT-3': SEQ ID NO: 108), the EUG1-sma primer (5'-GCCCGGGTTATAAT-TCATCATGTACGG-3': SEQ ID NO: 109), and AccuPrime Pfx DNA Polymerase (Invitrogen, 12344-024) at 95° C. for 10 seconds, 55° C. for 30 seconds, and 68° C. for 90 seconds, and this cycle was repeated 30 times. A target DNA fragment of approximately 1.5 kb was recovered and cloned into pCR2.1-TOPO. Thereafter, the nucleotide sequence of the inserted DNA fragment was confirmed. In order to express ScEUG1 in S. cerevisiae, the gene encoding ScEUG1 recovered via digestion with SacI and SmaI with the use of the SacI and SmaI restriction enzyme sites introduced into the EUG1-sac primer and the EUG1-sma primer was ligated to the SacI-SmaI site in the glyceraldehyde-3-phosphoric dehydrogenase gene (TDH3, GAP) promoter-terminator cassette introduced into the E. coli/yeast shuttle vector YEp351 (Yeast 2, pp. 163-167, 1986). The resulting plasmid was designated as YEp351GAP-II-ScEUG1.

Example 15

Effects of Chaperone on Antibody Secretory Production

Competent cells of the ZUO1/YGR285C strain (MATa Δhis3 Δleu2 Δmet15 Δura3Δ zuo1) derived from the S. cerevisiae BY4741 strain were prepared using the Frozen-EZ Yeast Transformation II Kit (ZYMO RESARCH). The S. cerevisiae ZUO1/YGR285C strain was sowed in 5 ml of YPAD medium (YPD medium containing 0.04% adenine (Sigma)), and yeast cells resulting from overnight culture at 30° C. and 310 rpm were used. The expression vectors constructed in Example 13 and in Example 14 were introduced into the S. cerevisiae ZUO1/YGR285C strain using the Frozen-EZ Yeast Transformation II Kit (ZYMO RESARCH), and transformants grown on ST agar medium containing 2% agar (the Yeast Nitrogen Base and Ammonium sulfate medium (Sigma) containing 2% glucose, 0.04% adenine, and 0.3M KCl and lacking uracil and leucine) were each selected as a yeast strain expressing an antibody constitutively expressing chaperone.

YEp352 GAP-II-ScKarHc/ScKarLc carrying the antibody heavy chain and light chain expression unit comprises an URA3 marker gene that complements uracil-requiring mutation of a host. In contrast, YEp351 GAP-II (a control vector into which the gene is not introduced), YEp351GAP-II-ScPDI1 (the ScPDI1 expression vector), YEp351GAP-II-Sc-MPD1 (the ScMPD1 expression vector), YEp351GAP-II-ScSCJ1 (the ScSCJ1 expression vector), YEp351GAP-II-ScERO1 (the ScERO1 expression vector), YEp351GAP-II-ScFKB2 (the ScFKB2 expression vector), YEp351GAP-II-ScJEM1 (the ScJEM1 expression vector), YEp351GAP-II-ScLHS1 (the ScLHS1 expression vector), YEp351GAP-II-ScMPD2 (ScMPD2 expression vector), YEp351GAP-II-ScERJ5 (the ScERJ5 expression vector), and YEp351GAP-II-ScEUG1 (the ScEUG1 expression vector) each has a LEU2 marker gene that complements leucine-requiring mutation of a host. Host cells were transformed so that they can grow only when the expression vector for the gene of an antibody and the constitutive expression vector for chaperone are introduced, and 10 types of yeast strains expressing an antibody constitutively expressing chaperone were constructed from the S. cerevisiae ZUO1/YGR285C strain.

ST medium (500 μl) (Yeast Nitrogen Base and Ammonium sulfate medium containing 2% glucose, 0.04% adenine, and 0.3M KCl and lacking uracil and leucine (Sigma)) was applied onto a 96-deep well plate (Greiner, 780271), the transformant was sowed with the use of a toothpick, the top of the plate was sealed with $CO_2$-permeable plate sealers (Greiner, 676051), and culture was carried out at an agitation speed of 310 rpm, an amplitude of 50 mm, at 30° C. for 3 days. Control culture was carried out by applying 1 ml of YPAD medium to a 96-deep well plate (Greiner, 780271). In the case of culture involving the addition of PMT inhibitors, 1 ml of YPAD medium to which the rhodanine-3-acetic acid derivative 1c had been initially added to a final concentration of 10 μM was applied to the plate. The culture solution that had been cultured in ST medium was sowed to a final concentration of 5%, and the top of the plate was sealed with $CO_2$-permeable plate sealers (Greiner, 676051). Thereafter, culture was carried out at an agitation speed of 310 rpm, an amplitude of 50 mm, at 30° C. for 3 days. The culture supernatant was prepared from the culture solution and it was designated as a sample containing an antibody secreted and produced by yeast. Antibody secretory production was confirmed via sandwich ELISA. Yeast cells were removed from the culture product via centrifugation at 2,700×g and 4° C. for 5 minutes, and the resulting culture supernatant was designated as a sample of secreted antibody. Sandwich ELISA was carried out by adsorbing the TRAIL receptor proteins that were antigens of the anti-TRAIL receptor antibodies on a 96-well plate, adding the sample of secreted antibody, and performing detection using a peroxidase-labeled human IgG specific Fc antibody (Peroxidase-labeled affinity purified antibody to human IgG (Fc) (KPL, 04-10-20)) and the ABTS peroxidase substrate (KPL, 50-66-01).

Figure 14:
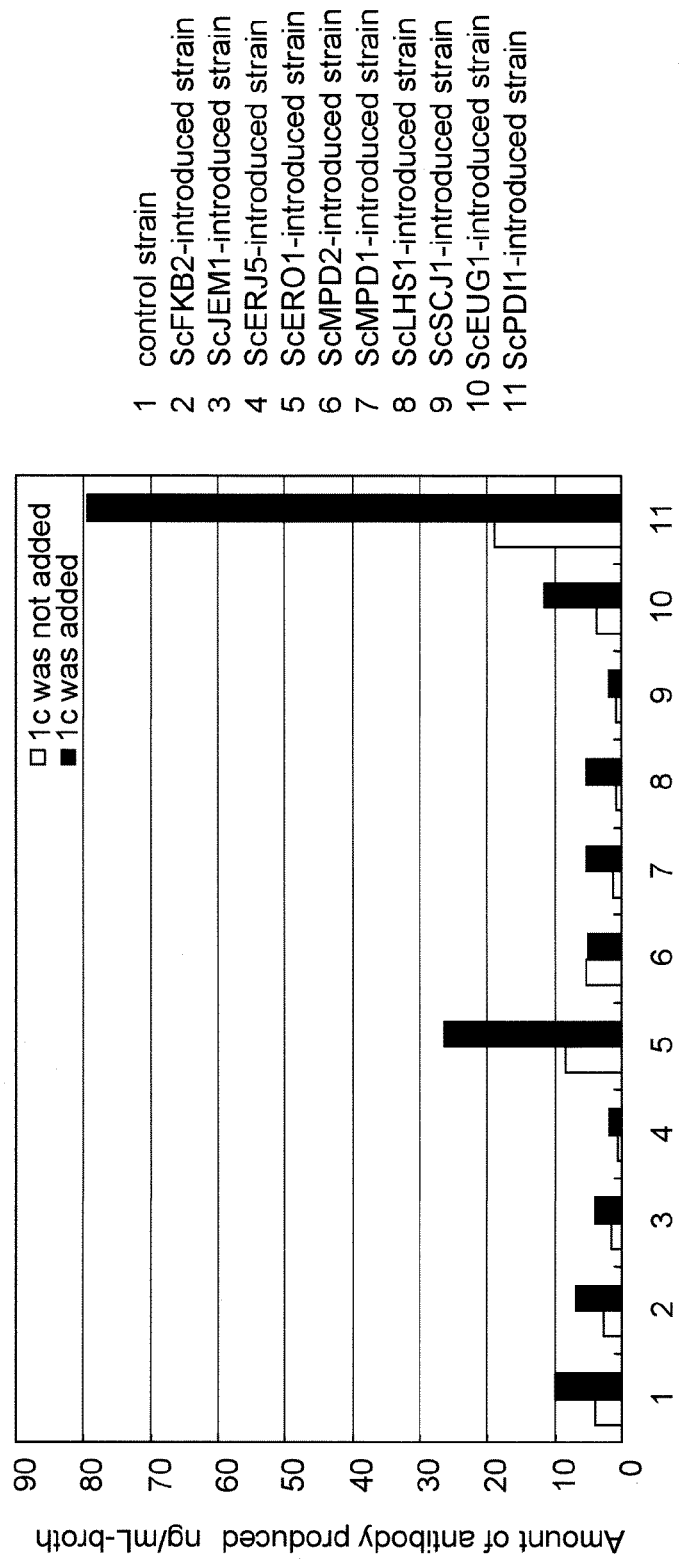
FIG. 14 is a chart showing the results of measuring the amount of secreted antibodies of an antibody-producing yeast strains (cultured with or without the addition of an inhibitor of O-mannosylation (rhodanine-3-acetic acid derivative 1c)) into which the gene of the chaperone protein (PDI1) derived from *S. cerevisiae* had been introduced.

As shown in FIG. 14, a control strain exhibited the amount of antibody secretory production of 3.9 ng/ml. When addition of an O-sugar chain was suppressed, however, the control strain exhibited an approximately 2.5 times greater amount of antibody secretory production; i.e., 10 ng/ml, and effects of suppression of O-sugar chain addition were observed. When addition of an O-sugar chain was suppressed, the strains into which each of ScERO1 and ScPDI1 had been introduced each exhibited approximately 7 times and approximately 20 times greater amounts of antibody secretory production; i.e., 26.4 ng/ml and 79.2 ng/ml.

Example 16

Construction of Coexpression Strain for OmPDI1 and Human Alpha-2,3-Sialic Acid Transferase (ST3GalI)

(1) Construction of ST3GalI Expression Vector

A gene encoding a sequence comprising 3 repeats of the FLAG sequence (3× FLAG) was amplified. The gene was amplified via PCR using the P3× FLAG-CMV-13 expression vector (Sigma, E4776) as a template and the 5'-3×FLAG primer (5'-atcatcatcatgcccgggccgactacaaagaccat-3': SEQ ID NO: 110), the 3'-3× FLAG primer (5'-gcaccgtctcggatcccttgt-catcgtcatcctt-3': SEQ ID NO: 111) to which the SrfI site and the BamHI site had been added, respectively. The resulting fragment was inserted into the *O. minuta* expression vector, pOMEA1-His6, (Akeboshi et al., 2007, Appl. Environ. Microbiol., 73:4805-4812) cleaved with SrfI and BamHI using the In-Fusion Dry-Down PCR Cloning Kit (Takara Bio, Z9602N). The resulting vector was designated as pOMEA1-6H3F.

Subsequently, a gene encoding a catalyst site of ST3GalI was amplified. The ST3GalI gene is present in human chromosome 8 and its cDNA nucleotide sequence is registered with a public database, GenBank, under the Accession No. L29555. The catalyst domain of the ST3GalI gene was first amplified via PCR using the 3FLAG-ST3Gal1-F primer (5'-GATGACGATGACAAGGGATCCaactactcccacaccatgg-3': SEQ ID NO: 112) and the 3FLAG-ST3Gal1-R primer (5'-GCACCGTCTCGGATCCtcatctccccttgaagatccggat-3': SEQ ID NO: 113). An entry clone of human glycosyltransferase library prepared in the NEDO SG project was used as a template (Shimma et al., 2006, Appl. Environ. Microbiol., 72, 7003-7012). The obtained fragment was inserted into the BamHI site of pOMEA1-6H3F using the In-Fusion Dry-Down PCR Cloning Kit (Takara Bio, Z9602N). After the nucleotide sequence was confirmed, the fragment was designated as the expression vector, pOMEA1-6H3F-ST3Gal1.

(2) Construction of ST3GalI Expression Strain

The pOMEA1-6H3F-ST3Gal1 plasmid was cleaved with the NotI restriction enzyme, and the *O. minuta* TK10-1-2 strain was then transformed. Transformation was carried out by the lithium acetate method. After transformation, the resultant was applied on SD-Ade medium (2% glucose, 0.17% Yeast Nitrogen Base without amino acids (Difco), nucleic acid bases except for adenine, and amino acids mixture (20 to 400 mg/l)), and culture was carried out at 30° C. for 2 days. Whether or not the expression vector was incorporated into a chromosome was confirmed via colony PCR described in Example 5 and the transformant was designated as the YT-1 strain.

Subsequently, the *O. minuta*-derived PDI1 expression vector (onaP03606) constructed in Example 3 was introduced. Also, transformation was carried out using pOMexGP1U containing no OmPDI1 as a control. After the YT-1 strain was transformed in the manner described above, the transformant was applied on SD-Ura medium (2% glucose, 0.17% Yeast Nitrogen Base without amino acids (Difco), nucleic acid bases except for uracil, and amino acid mixture (20 to 400 mg/l)), and culture was carried out at 30° C. for 2 days. Whether or not the expression vector was incorporated into a chromosome was confirmed via colony PCR described in Example 5, the strain into which pOMexGP1U (control plasmid) had been introduced was designated as the YT-2 strain, and the strain into which onaP03606 had been introduced was designated as the YT-3 strain.

Example 17

Expression of Human Alpha-2,3-Sialic Acid Transferase (ST3GalI)

The YT-2 strain and the YT-3 strain were inoculated in 5 ml of YPAD+KCl medium (2% polypeptone, 1% yeast extract, 2% glucose, adenine (40 mg/l), 0.3 M potassium chloride), and preculture was carried out at 30° C. overnight. Subsequently, 1 ml of a preculture solution was inoculated in 150 ml of YPAD+KCl medium, and culture was carried out at 30° C. for 48 hours. The strains were recovered, resuspended in 100 ml of BMMY+2% casamino acid medium (1% yeast extract, 2% polypeptone, 1.34% Yeast Nitrogen Base without amino acids (Difco), 0.1 M KPi (pH 6.0), 2% casamino acid, 1% methanol), and cultured at 20° C. for 96 hours. Methanol was added to a concentration of 0.5% every 12 hours. After the completion of culture, the culture product was subjected to centrifugation to remove yeast cells, and the resulting solution was designated as a crude enzyme solution.

Figure 15:
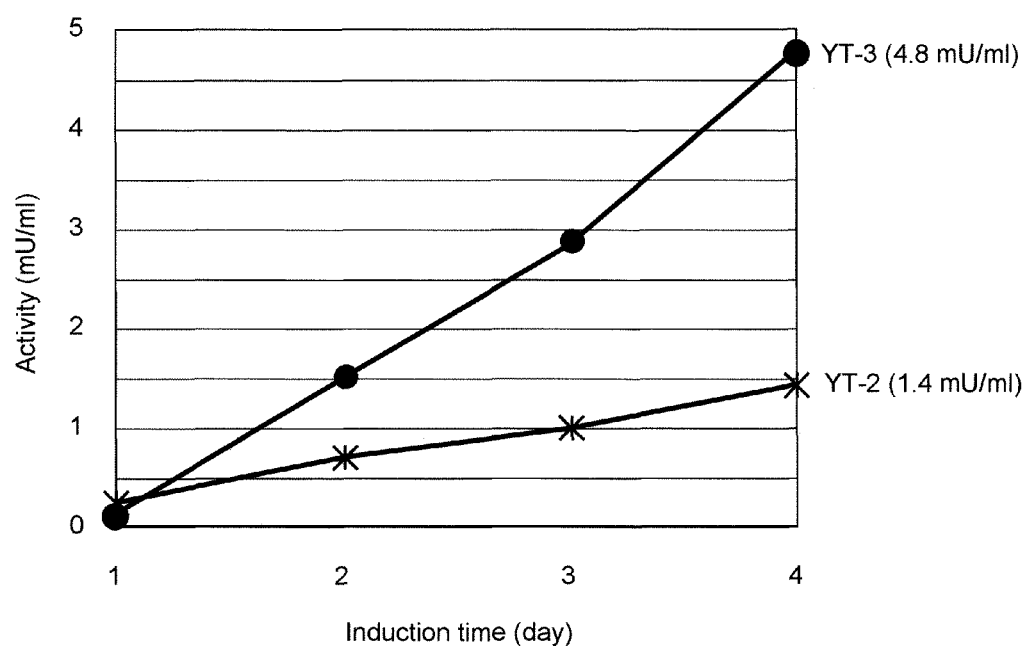
FIG. 15 shows changes in activity values for sialic acid transferase (ST3Gal1) expressed in a strain (YT-2) into which the *O. minuta*-derived chaperone protein (PDI1) gene was not introduced and in a strain (YT-3) into which the PDI1 gene had been introduced with the elapse of time.

Enzyme activity was assayed in the following manner. A crude enzyme solution (2 μl) was added to 18 μl of a reaction solution (0.1 M Tris-HCl (pH 7.5), 1 mM $MnCl_2$, 5 mM CMP-NeuAc, 50 μM core 1-pNP), and the reaction was initiated. After the reaction was carried out at 37° C. for 30 minutes, the reaction was terminated via boiling, and HPLC analysis was carried out. A Cosmosil 5C18-ARII column (4.6×250 mm, Nacalai Tesque, Inc.) was used, and a mixture of 0.2 M triethylamine-acetic acid (pH 7.0, solution A) and acetonitrile (solution B) (solution A:solution B=9:1) was used as a mobile phase. The column was equilibrated, the sample was injected therein, and elution was carried out 20 minutes thereafter. Detection was carried out using a UV detector (detection wavelength: 300 nm). A core1-pNP substrate was eluted 14.5 minutes later, and a reaction product, sialylcore1-pNP, was eluted 17 minutes later. The reaction product was quantified based on the peak area, and the result was designated as activity (U). The unit "1 U" was defined as the amount of an enzyme that is necessary to produce 1 μmol of the reaction product per minute. FIG. 15 shows changes in expression levels of the enzyme with the elapse of time during culture. As a result, increased enzyme activity was observed in the ST3GalI-expressing strain (YT-3) into which OmPDI1 had been introduced, compared with the strain into which no OmPDI1 had been introduced (YT-2), and difference in the expression levels became as great as approximately 3.4 times 96 hours later.

Western blot analysis was then carried out. The culture supernatants in amounts equivalent to "10 μU" of the YT-2 strain and the YT-3 strain were subjected to treatment with EndoHf (NEB, P0703S) in accordance with the protocol, applied, and then subjected to SDS-PAGE. After electrophoresis, the product was transferred to a PVDF membrane, and Western blotting was carried out in accordance with a conventional technique. A mouse anti-FLAG M2 antibody (Sigma, F1804) was used as a primary antibody and an anti-mouse IgG antibody-alkaline phosphatase composite was used as a secondary antibody. Detection was carried out using CDP-Star and an image analyzer, LAS1000 (Fujifilm Corporation). Further, signals were quantified using Image Gauge (Fujifilm Corporation).

Figure 16:
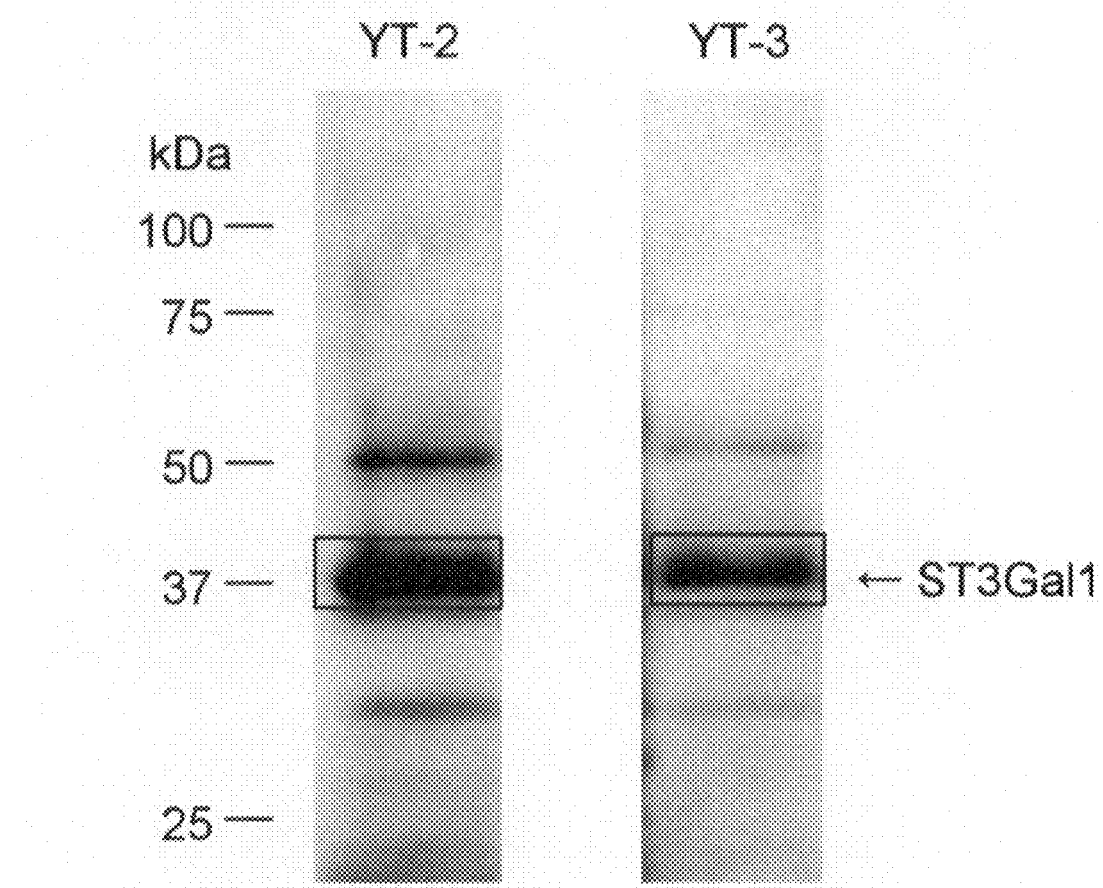
FIG. 16 shows the results of Western blot analysis of sialic acid transferase (ST3Gal1) expressed in a strain (YT-2) into which the *O. minuta*-derived chaperone protein (PDI1) gene was not introduced and in a strain (YT-3) into which the PDI1 gene had been introduced.

The results are shown in FIG. 16 and in Table 1. Even though Western blot analysis was carried out in addition to enzyme activity assay, the intensity of the ST3GalI signal derived from the strain into which OmPDI1 had been introduced (YT-3) was found to be attenuated to as low as 0.6 times. It was thus considered that introduction of OmPDI1 resulted in promotion of normal disulfide bond formation in ST3GalI molecules, and the number of correctly folded proteins was increased, which in turn elevated the specific activity by approximately 1.6 times.

TABLE 1

| Chaperone-expressing strain | Signal intensity (AU) | Specific activity (pU/AU) |
|---|---|---|
| YT-2 | 4694842 | 2.13 |
| YT-3 | 2976349 | 3.36 |

Example 18

Construction of Coexpression Strain for an Expression Vector for Chaperone Gene Combination and an Expression Vector for Human Alpha-2,3-Sialic Acid Transferase (ST3GalI)

Figure 17:
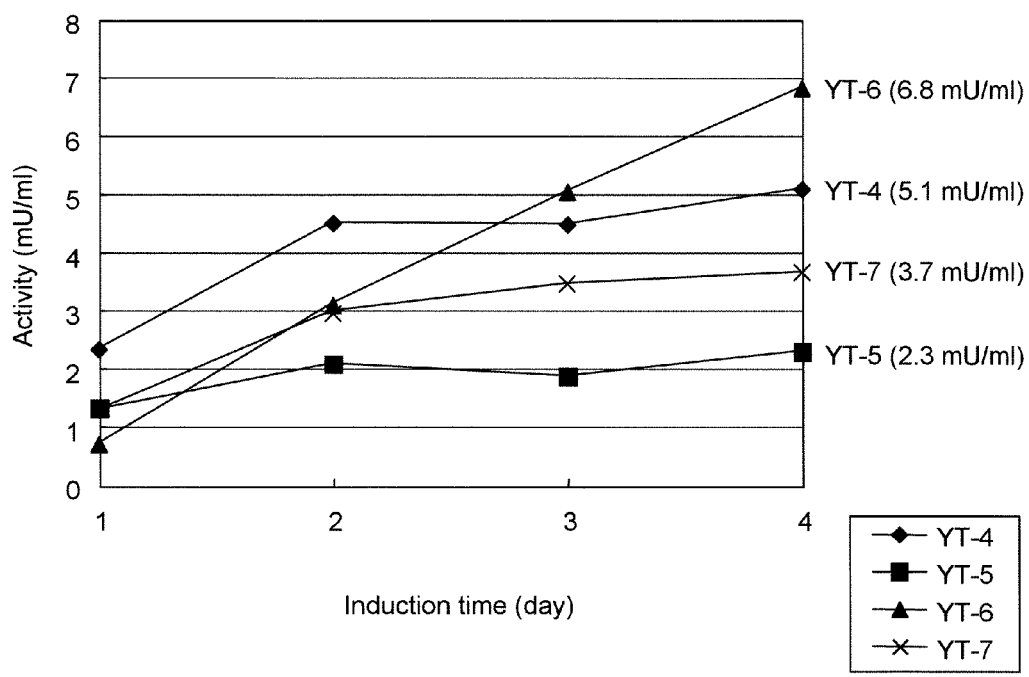
FIG. 17 shows changes in activity values for sialic acid transferase (ST3Gal1) expressed in strains (YT-4, YT-5, YT-6, and YT-7) into which genes of the *O. minuta*-derived chaperone proteins (PDI1x2, PDI1/OmKar2, PDI1/ERO1, and PDI1/HSP104) had been introduced with the elapse of time.
Figure 18:
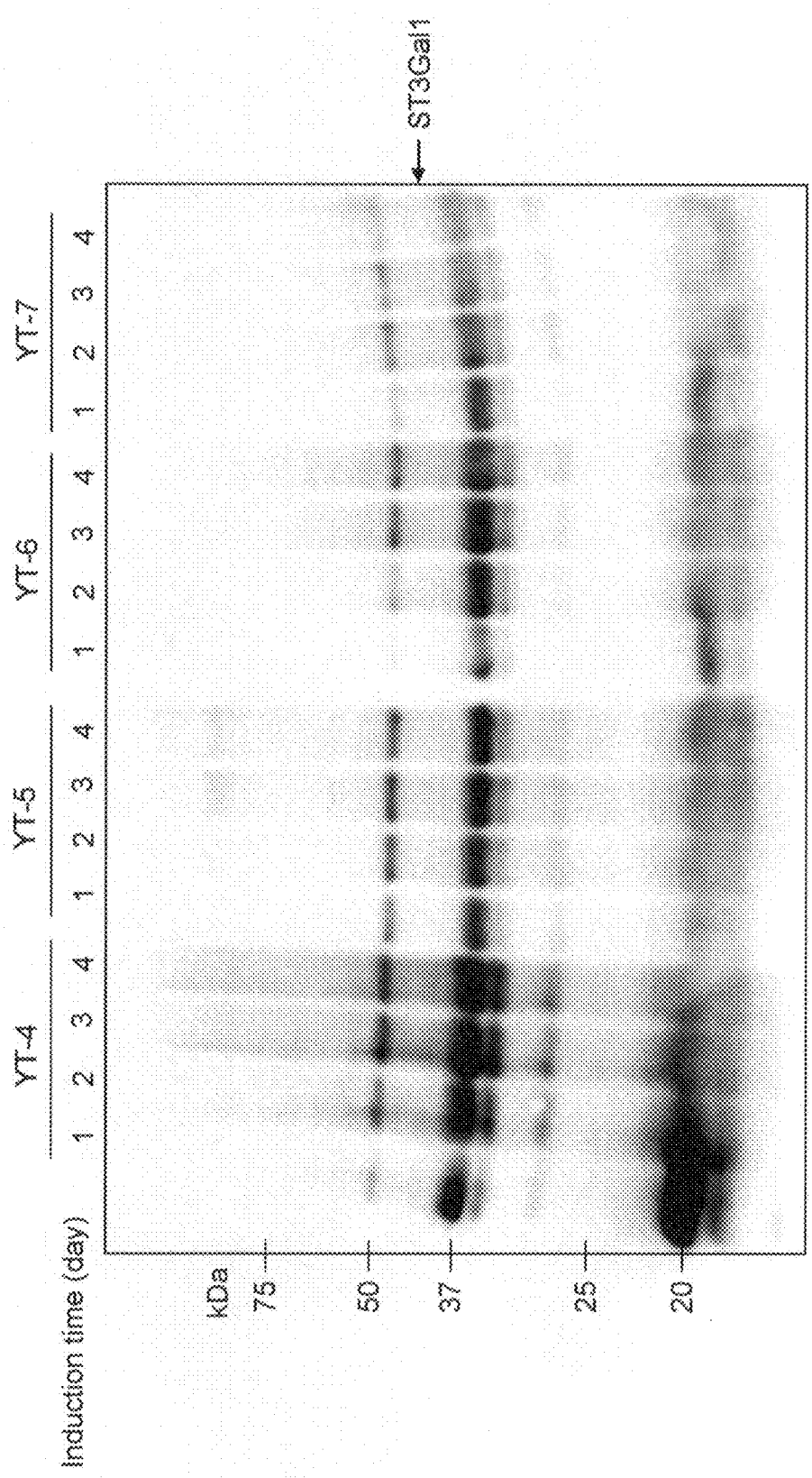
FIG. 18 shows the results of Western blot analysis of sialic acid transferase (ST3Gal1) expressed in strains (YT-4, YT-5, YT-6, and YT-7) into which genes of the *O. minuta*-derived chaperone proteins (PDI1x2, PDI1/OmKar2, PDI1/ERO1, and PDI1/HSP104) had been introduced.

The expression vector for various chaperone gene combinations derived from *O. minuta* prepared in Example 4 was introduced into the YT-1 strain of Example 17. In the same manner as in Example 16, plasmids were cleaved with NotI to transform the YT-1 strain. After transformation, the resultant was applied on SD-Ura medium (2% glucose, 0.17% Yeast Nitrogen Base without amino acids (Difco), nucleic acid bases except for uracil, and amino acid mixture (20 to 400 mg/l)) and culture was carried out at 30° C. for 2 days. Whether or not the expression vector was incorporated into a chromosome was confirmed via colony PCR described in Example 5, an expressed strain having a coexpression vector (onaP09407) carrying two copies of the OmPDI1 expression cassette was designated as the YT-4 strain, an expressed strain having a coexpression vector (onaP09707) for OmPDI1 and OmKar2 was designated as the YT-5 strain, an expressed strain having a coexpression vector (onaP09507) for OmPDI1 and OmERO1 was designated as the YT-6 strain, and an expressed strain having a coexpression vector (onaP09607) for OmPDI1 and OmHSP104 was designated as the YT-7 strain. Culture was carried out in the same manner as in Example 17, enzyme expression from each strain was assayed with the elapse of time, and the results are shown in FIG. 17. Also, 30 μl of the culture supernatant was subjected to treatment with EndoHf (NEB, P0703S) in accordance with the protocol and then Western blot analysis. The results are shown in FIG. 18, and quantified signal intensities and specific activities determined based thereon are shown in Table 2.

TABLE 2

| Chaperone-expressing strain | Signal intensity (AU) | Activity (mU/ml) | Specific activity (pU/AU) |
|---|---|---|---|
| YT-4-1 | 5003576.86 | 2.32 | 13.9 |
| YT-4-2 | 5967631.86 | 4.50 | 23.7 |
| YT-4-3 | 6004529.86 | 4.47 | 22.3 |
| YT-4-4 | 5686573.24 | 5.08 | 26.8 |
| YT-5-1 | 3619105.78 | 1.29 | 10.7 |
| YT-5-2 | 3926906.78 | 2.07 | 15.8 |
| YT-5-3 | 4530942.78 | 1.86 | 12.3 |
| YT-5-4 | 4603909.78 | 2.29 | 14.9 |
| YT-6-1 | 2225292.78 | 0.70 | 9.4 |
| YT-6-2 | 4312501.78 | 3.10 | 21.6 |
| YT-6-3 | 4786891.78 | 5.03 | 31.5 |
| YT-6-4 | 4057802.78 | 6.81 | 50.3 |
| YT-7-1 | 3381700.78 | 1.28 | 11.4 |
| YT-7-2 | 3208548.78 | 2.98 | 27.9 |
| YT-7-3 | 2435370.00 | 3.45 | 42.5 |
| YT-7-4 | 1912043.00 | 3.65 | 57.3 |

Enzyme expression levels substantially stopped increasing 2 days after induction in the YT-4, -5, and -7 strains; however, activity kept increasing at significant levels up to 4 days after induction in the YT-6 strain, and activity per ml of the culture supernatant of the YT-6 strain was the highest at the end. Although no clear increase in specific activity was observed in the YT-4 and YT-5 expression strains, an increase was observed in specific activity with the elapse of time in the YT-6 and YT-7 strains. Thus, it was considered that coexpression of ERO1 or HSP104 would result in an increase in the number of enzyme molecules that were correctly folded.

Example 19

Construction of Expression Vector for Chaperone Gene Alone (1) Construction of Constitutive Expression Vector for Chinese Hamster GRP78/BiP Gene The Chinese hamster GRP78 gene (Accession No. M17169: SEQ ID NO: 152) was cloned in the following manner to construct an expression vector.

At the outset, total RNA was extracted from the CHO/dhFr-strain (ATCC CRL-9096) cell obtained via culture in Ex325 medium with the use of the QuickPrep total RNA Extraction Kit (GE Healthcare Life Sciences, 27-9271-01). Purified total RNA (600 ng) was used to synthesize cDNA via reverse transcription using ReverTra Ace-α-(TOYOBO, FSK-101). PCR was carried out using the resulting cDNA as a template, the CHOGRP78-F primer (5'-ACCCTCGAGAT-GAAGTTCCCTATGGTGG-3': SEQ ID NO: 114), the CHOGRP78-R primer (5'-ACCGCGGCCGCCTACAACT-CATC-3': SEQ ID NO: 115), and AccuPrime Pfx DNA Polymerase (Invitrogen, 12344-024) at 95° C. for 10 seconds, 55° C. for 30 seconds, and 68° C. for 120 seconds, and this cycle was repeated 30 times. A target DNA fragment of approximately 2 kb was recovered and cloned into pCR2.1-TOPO. Thereafter, the nucleotide sequence of the inserted DNA fragment was confirmed. The CHO GRP78 gene recovered via digestion with XhoI and NotI was ligated to the XhoI-NotI site in pME18s (Accession No. AB009864) with the use of the XhoI and NotI restriction enzyme sites introduced into the CHOGRP78-F primer and the CHOGRP78-R primer. The resulting plasmid was designated as pME18s/choGRP78.

(2) Construction of Constitutive Expression Vector for Chinese Hamster PDI Gene

The Chinese hamster PDI gene (Accession No. AF364317: SEQ ID NO: 153) was cloned in the following manner to construct an expression vector.

PCR was carried out using the resulting cDNA as a template as in the case of (1) above, the CHOPDI-F primer (5'-ACCCTCGAGATGCTGAGCCGTTCTC-3': SEQ ID NO: 116), the CHOPDI-R primer (5'-ACCGCGGCCGC-CTACAATTCGTCCTTTAC-3': SEQ ID NO: 117), and AccuPrime Pfx DNA Polymerase (Invitrogen, 12344-024) at 95° C. for 10 seconds, 55° C. for 30 seconds, and 68° C. for 90 seconds, and this cycle was repeated 30 times. A target DNA fragment of approximately 1.5 kb was recovered and cloned into pCR2.1-TOPO. Thereafter, the nucleotide sequence of the inserted DNA fragment was confirmed. The CHO PDI gene recovered via digestion with XhoI and NotI was ligated to the XhoI-NotI site in pME18s (Accession No. AB009864) with the use of the XhoI and NotI restriction enzyme sites introduced into the CHOPDI-F primer and the CHOPDI-R primer. The resulting plasmid was designated as pME18s/choPDI.

(3) Construction of Constitutive Expression Vector for Human ERO1-Lβ Gene

The human ERO1-Lβ gene (Accession No. NM_019891: SEQ ID NO: 146) was cloned in the following manner to construct an expression vector.

At the outset, total RNA was extracted from the FreeStyle 293-F cell (Invitrogen, R790-07) obtained via culture in Freestyle 293 Medium (Invitrogen, 12338-018) with the use of the QuickPrep total RNA Extraction Kit (GE Healthcare Life Sciences, 27-9271-01). Purified total RNA (600 ng) was used to synthesize cDNA via reverse transcription using ReverTra Ace-α-(TOYOBO, FSK-101). PCR was carried out using the resulting cDNA as a template, the hERO-F primer (5'-AC-CCTCGAGATGAGCCAAGGG-3': SEQ ID NO: 118), the hERO-R primer (5'-ACCCTCGAGTTACCTACTGTGTTG-TAATAAGAC-3': SEQ ID NO: 119), and AccuPrime Pfx DNA Polymerase (Invitrogen, 12344-024) at 95° C. for 10 seconds, 55° C. for 30 seconds, and 68° C. for 90 seconds, and this cycle was repeated 30 times. A target DNA fragment of approximately 1.4 kb was recovered and cloned into pCR2.1-TOPO. Thereafter, the nucleotide sequence of the inserted DNA fragment was confirmed. The human ERO1-Lβ gene recovered via digestion with XhoI was ligated to the XhoI site of pME18s (Accession No. AB009864) with the use of the XhoI restriction enzyme site introduced into the hERO-F primer and the hERO-R primer. The resulting plasmid was designated as pME18s/hERO1-Lβ.

(4) Construction of Antibody Expression Vector

The light chain and the heavy chain of the anti-TRAIL receptor antibody gene (WO 2001/083560) was introduced into the pcDNA3.1 (+) expression vector (Invitrogen, V790-20), and the resultant was designated as pcDNA3.1 (+)/expAB.

Example 20

Effects of Chaperone on Antibody Secretory Production

The constitutive expression vectors for various chaperone genes constructed in Example 19 (1) to (3) were introduced into the COS-1 cells to examine the effects of chaperone introduction on secretory production of antibody.

The COS-1 cells were sowed on a 24-well microplate (IWAKI SI-Tech, 3820-024N) at $1.5 \times 10^5$ cells/well, and the anti-TRAIL receptor antibody-expressing vector, pcDNA3.1 (+)/expAB, and the constitutive expression vectors for various chaperone genes were cotransfected with the use of Lipofectamine 2000 (Invitrogen, 11668-027) 24 hours after the initiation of culture. After the gene was introduced, culture was carried out for 48 hours, the culture supernatant was clarified via centrifugation at 21,600×g at 4° C. for 3 minutes, and the resultant was designated as a secretory antibody sample.

Figure 19:
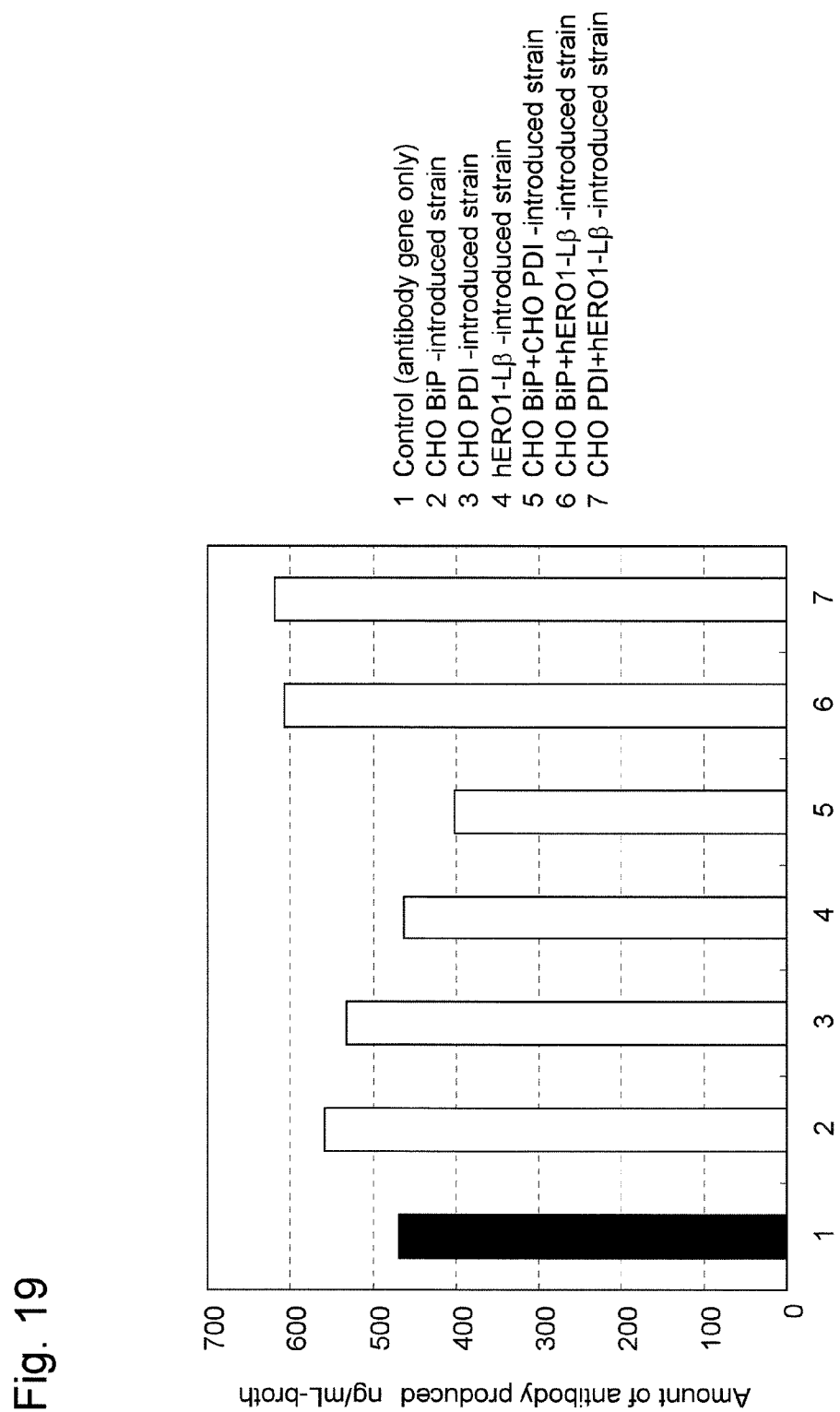
FIG. 19 is a chart showing the results of measuring the amount of secreted antibodies of an antibody-producing animal cell lines (i.e., the COS-1 cell) into which genes of the CHO-cell-derived chaperone proteins (CHOBiP and CHOPDI) and the human-derived chaperone protein (hERO1-Lβ) had been introduced.

The secreted and produced antibodies were subjected to quantitative assay via sandwich ELISA. The TRAIL receptor protein (i.e., the antigen of the anti-TRAIL receptor antibody) was adsorbed on a 96-well plate, the sample of secreted antibody was added, and detection was carried out using a peroxidase-labeled human IgG specific Fc antibody (Peroxidase-labeled affinity purified antibody to human IgG (Fc) (KPL, 04-10-20)) and the ABTS peroxidase substrate (KPL, 50-66-01). As shown in FIG. 19, improvement in the amount of production by approximately 19% and approximately 13% was observed in the CHO BiP-introduced strain and the CHO PDI-introduced strain, compared with the control strain (i.e., a strain into which only the antibody gene was introduced). When chaperone genes were introduced in combination, also, the amount of secretory production was found to increase by approximately 30% in the strain into which CHO BiP+human ERO1-Lβ and CHO PDI+human ERO1-Lβ had been introduced, compared with the control strain (i.e., a strain into which only the antibody gene was introduced).

Example 21

Construction of Expression Vector for Chaperone Gene Alone (1) Construction of Constitutive Expression Vector for Human ERO1-Lα gene Human ERO1-Lα (hERO1-Lα, Accession No. Q96HE7) is a functional homolog of OmERO1 and it comprises an amino acid sequence composed of 468 amino acid residues (SEQ ID NO: 144) encoded by a 1,407-bp nucleotide sequence (SEQ ID NO: 143). The hERO1-Lα gene was synthesized by taking codon preference of *O. minuta* into consideration (Operon Biotechnologies). From a plasmid carrying the DNA fragment with a confirmed nucleotide sequence, a DNA fragment (SEQ ID NO: 145) containing synthetic hERO1-Lα was recovered via digestion with SalI and EcoT22I with the use of the SalI restriction enzyme site and the EcoT22I restriction enzyme site that had been introduced at the time of synthesis. In order to constitutively express synthetic hERO1-Lα in *O. minuta*, hERO1-Lα was ligated to pOMexGP1U recovered via digestion with SalI and EcoT22I disclosed in WO 2003/091431. The resulting plasmid was designated as onaP17608.

(2) Construction of Constitutive Expression Vector for Human ERO1-Lβ Gene

Human ERO1-Lβ (hERO1-Lβ, Accession No. NP_063944) is a functional homolog of OmERO1 and it comprises an amino acid sequence composed of 467 amino acid residues (SEQ ID NO: 147) encoded by a 1,404-bp nucleotide sequence (SEQ ID NO: 146). The hERO1-Lβ gene was synthesized by taking codon preference of *O. minuta* into consideration (Operon Biotechnologies). From a plasmid carrying the DNA fragment with a confirmed nucleotide sequence, a DNA fragment (SEQ ID NO: 148) containing synthetic hERO1-Lα was recovered via digestion with SalI and EcoT22I with the use of the SalI restriction enzyme site and the EcoT22I restriction enzyme site that had been introduced at the time of synthesis. In order to constitutively express synthetic hERO1-Lβ in *O. minuta*, synthetic hERO1-Lβ was ligated to pOMexGP1U recovered via digestion with SalI and EcoT22I disclosed in WO 2003/091431. The resulting plasmid was designated as onaP17808.

(3) Construction of Constitutive Expression Vector for Human GRP78 Gene

Human GRP78 (hGRP78, Accession No. NP_005338) is a functional homolog of OmKar2 and it comprises an amino acid sequence composed of 654 amino acid residues (SEQ ID NO: 150) encoded by a 1,965-bp nucleotide sequence (SEQ ID NO: 149). The hGRP78 gene was synthesized by taking codon preference of *O. minuta* into consideration (Operon Biotechnologies). From a plasmid carrying the DNA fragment with a confirmed nucleotide sequence, a DNA fragment (SEQ ID NO: 151) containing synthetic hGRP78 was recovered via digestion with SalI and EcoT22I with the use of the SalI restriction enzyme site and the EcoT22I restriction enzyme site that had been introduced at the time of synthesis. In order to constitutively express synthetic hGRP78 in *O. minuta*, synthetic hGRP78 was ligated to pOMexGP1U recovered via digestion with SalI and EcoT22I disclosed in WO 2003/091431. The resulting plasmid was designated as onaP17408.

Example 22

Construction of Expression Vector for Chaperone Gene Combination (1) Construction of Coexpression and Constitutive Expression Vector for Synthetic hPDI Gene and Synthetic hERO1-Lα Gene The synthetic hERO1-Lα region was recovered from the constitutive expression vector for synthetic hERO1-Lα, onaP17608, with the use of SalI and EcoT22I restriction enzymes. After the pZ/GpGt vector constructed in Example 4 was digested with the SalI and EcoT22I restriction enzymes, the SalI-EcoT22I fragment containing synthetic hERO1-Lα was introduced to construct pZ/GpGt/synthetic hERO1-Lα. Subsequently, pZ/GpGt/synthetic hERO1-Lα was digested with the ApaI restriction enzyme, and a fragment containing GAP promoter-synthetic hERO1-Lα-GAP terminator (the synthetic hERO1-Lα expression cassette) was recovered. The recovered synthetic hERO1-Lα expression cassette was introduced into the ApaI restriction enzyme of the synthetic hPDI expression vector (onaP09107), the insertion direction was confirmed via PCR, and a vector into which the synthetic hPDI expression cassette and synthetic hERO1-Lα expression cassette was introduced in inverse orientation with respect to each other around the URA3 marker of the synthetic hPDI expression vector (onaP09107) was selected. The resulting coexpression vector for synthetic hPDI and synthetic hERO1-Lα was designated as onaP18208.

(2) Construction of Coexpression and Constitutive Expression Vector for Synthetic hPDI Gene and Synthetic hERO1-Lβ Gene The synthetic hERO1-Lβ region was recovered from the constitutive expression vector for synthetic hERO1-Lβ, onaP17608, with the use of SalI and EcoT22I restriction enzymes. After the pZ/GpGt vector constructed in Example 4 was digested with the SalI and EcoT22I restriction enzymes, the SalI-EcoT22I fragment containing synthetic hERO1-Lβ was introduced to construct pZ/GpGt/synthetic hERO1-Lβ. Subsequently, pZ/GpGt/synthetic hERO1-Lβ was digested with the ApaI restriction enzyme, and a fragment containing the GAP promoter-synthetic hERO1-Lβ-GAP terminator (the synthetic hERO1-Lβ expression cassette) was recovered. The recovered synthetic hERO1-Lβ expression cassette was introduced into the ApaI restriction enzyme of the synthetic hPDI expression vector (onaP09107), the insertion direction was confirmed via PCR, and a vector into which the synthetic hPDI expression cassette and the synthetic hERO1-Lβ expression cassette were inserted in inverse orientation with respect to each other around the URA3 marker of the synthetic hPDI expression vector (onaP09107) was selected. The resulting coexpression vector for synthetic hPDI1 and synthetic hERO1-Lβ was designated as onaP18308.

(3) Construction of Coexpression and Constitutive Expression Vector for Synthetic hPDI Gene and Synthetic hGRP78 Gene The synthetic hGRP78 region was recovered from the constitutive expression vector for synthetic hGRP78, onaP17408, with the use of SalI and EcoT22I restriction enzymes. After the pZ/GpGt vector constructed in Example 4 was digested with the SalI and EcoT22I restriction enzymes, the SalI-EcoT22I fragment containing synthetic hGRP78 was introduced to construct pZ/GpGt/synthetic hGRP78. Subsequently, pZ/GpGt/synthetic hGRP78 was digested with the ApaI restriction enzyme, and a fragment containing the GAP promoter-synthetic hGRP78-GAP terminator (the synthetic hGRP78 expression cassette) was recovered. The recovered synthetic hGRP78 expression cassette was introduced into the ApaI restriction enzyme of the synthetic hPDI expression vector (onaP09107), the insertion direction was confirmed via PCR, and a vector into which the synthetic hPDI expression cassette and synthetic hGRP78 expression cassette were inserted in inverse orientation with respect to each other around the URA3 marker of the synthetic hPDI expression vector (onaP09107) was selected. The resulting coexpression vector for synthetic hPDI1 and synthetic hGRP78 was designated as onaP18108.

(4) Construction of Coexpression and Constitutive Expression Vector for Synthetic hPDI Gene, Synthetic hERO1-Lα gene, and Synthetic hGRP78 Gene A coexpression vector for synthetic hPDI and synthetic hERO1-Lα via expression regulation by GAP promoter and for synthetic hGRP78 via expression regulation by PGK promoter was constructed in the following manner.

The PGK terminator region was recovered from the pOU1/Kar2-PptK plasmid constructed in Example 4 with the use of the EcoT22I and KpnI restriction enzymes. Also, the synthetic hGRP78 region was recovered from the onaP17408 plasmid with the use of the SalI and EcoT22I restriction enzymes. Three fragments; i.e., the pUC119 plasmid (Takara Bio, TKR-3319) prepared with the aid of the SalI and KpnI restriction enzymes, the PGK terminator region recovered via digestion with the EcoT22I and KpnI restriction enzymes, and the synthetic hGRP78 region recovered via digestion with the SalI and EcoT22I restriction enzymes, were ligated to each other to construct pUC119/synthetic hGRP78+PGKt. Subsequently, the PGK promoter region recovered from pOU1/Kar2-PptK with the aid of the KpnI and SalI restriction enzymes, the synthetic hGRP78 recovered from pUC119/synthetic hGRP78+PGKt with the aid of the SalI and KpnI restriction enzymes, and the pUC119 plasmid (Takara Bio, TKR-3319) prepared via digestion of the PGK terminator region with the KpnI restriction enzyme were subjected to 3-fragment ligation. Thus, pUC119/PGKp+synthetic hGRP78+PGKt was obtained. Subsequently, pUC119/PGKp+synthetic hGRP78+PGKt was digested with the KpnI restriction enzyme, a fragment containing the PGK promoter-synthetic hGRP78-PGK terminator (the synthetic hGRP78 expression cassette) was recovered, and the resultant was introduced into the KpnI restriction enzyme site of the coexpression vector (onaP18208) for synthetic hPDI and synthetic hERO1-Lα to construct a coexpression vector (onaP18508) for synthetic hPDI, synthetic hERO1-Lα, and synthetic hGRP78.

(5) Construction of Coexpression and Constitutive Expression Vector For Synthetic hPDI Gene, Synthetic hERO1-Lβ Gene, and Synthetic hGRP78 gene A coexpression vector for synthetic hPDI and synthetic hERO1-Lβ via expression regulation by GAP promoter and for synthetic hGRP78 via expression regulation by PGK promoter was constructed in the following manner.

The pUC119/PGKp+synthetic hGRP78+PGKt constructed in (4) above was digested with the KpnI restriction enzyme, a fragment containing the PGK promoter-synthetic hGRP78-PGK terminator (the synthetic hGRP78 expression cassette) was recovered, and the fragment was introduced into the KpnI restriction enzyme site of the coexpression vector (onaP18308) for synthetic hPDI and synthetic hERO1-Lβ to construct the coexpression vector (onaP18608) for synthetic hPDI, synthetic hERO1-Lβ, and synthetic hGRP78.

(6) Construction of Coexpression and Constitutive Expression Vector for Synthetic hPDI Gene, OmERO1 Gene, and Synthetic hGRP78 Gene A coexpression vector for synthetic hPDI and OmERO1 via expression regulation by GAP promoter and for synthetic hGRP78 via expression regulation by PGK promoter was constructed in the following manner.

The pUC119/PGKp+synthetic hGRP78+PGKt constructed in (4) above was digested with the KpnI restriction enzyme, a fragment containing the PGK promoter-synthetic hGRP78-PGK terminator (the synthetic hGRP78 expression cassette) was recovered, and the fragment was introduced into the KpnI restriction enzyme site of the coexpression vector (onaP11107) for synthetic hPDI and OmERO1 to construct the coexpression vector (onaP18708) for synthetic hPDI, OmERO1, and synthetic hGRP78.

Example 23

Preparation of Chaperone-Introduced Yeast Strain
(*O. minuta*)

All the constitutive expression vectors for chaperone genes constructed in Example 21 and in Example 22 were digested with the NotI restriction enzyme and then introduced into the *O. minuta* YK5 strain (Δoch1Δyps1Δura3Δade1: *Ogataea minuta* protease YPS1 gene-deficient strain) via electroporation. Electroporation was carried out under the conditions described in WO 2003/091431. After electroporation, the transformant was applied on Casamino-U agar medium that had been sterilized via steaming under pressure (6.7 g/l of Yeast Nitrogen Base without amino acids, 0.5 g/l of casamino acid, 20 g/l of glucose, 20 mg/l of L-tryptophan, 20 mg/l of adenine, and 20 g/l of Bacto agar), and the transformant was allowed to grow at 30° C. for approximately 2 to 3 days. The grown transformant was allowed to grow again on Casamino-U agar medium and a transformant into which chaperone, with its expression being regulated by the GAP promoter, had been introduced was selected via colony PCR. Part of yeast that had grown on Casamino-U agar medium was suspended in 10 μl of 0.25% SDS solution, 90 μl of sterilized water was added, and yeast cells were then removed via centrifugation at 2,700×g and 4° C. for 5 minutes. The obtained supernatant was designated as a DNA solution. A strain in which amplification was observed with the use of the GAPpforS-F primer designed within the GAP promoter sequence (5'-GATCTCAGGCCGAGTCAAGAC-3': SEQ ID NO: 76) and the primer shown below was designated as a strain into which a constitutive expression vector for chaperone had been introduced. Since synthetic hGRP78 was expressed with the use of the PGK promoter when constructing a coexpression vector for three chaperone genes, introduction of the PGK promoter-synthetic hGRP78-PGK terminator expression cassette was confirmed with the use of the PGKpforS-F primer that was designed within the PGK promoter sequence (5'-TAACGCCGCATAGAACTAGC-3': SEQ ID NO: 77) and the G78-EcoT-R primer (5'-ATGCATT-TACAACTCGTCC-3': SEQ ID NO: 154).

(p10) Primer used for confirming introduction of synthetic hPDI ShPDI-ttaR: 5'-GATGCATTTACAACTCGTCCT-TAAC-3' (SEQ ID NO: 78)

(p16) Primer used for confirming introduction of synthetic hERO1-Lα E1La-EcoT-R: 5'-ATGCATTTAGTGGAT-GTTTTG-3' (SEQ ID NO: 155)

(p17) Primer used for confirming introduction of synthetic hERO1-Lβ E1Lb-EcoT-R: 5'-ATGCATTTATCTGGAGT-GTTG-3' (SEQ ID NO: 156)

(p18) Primers used for confirming introduction of synthetic hPDI+ synthetic hERO1-Lα
ShPDI-ttaR: 5'-GATGCATTTACAACTCGTCCTTAAC-3' (SEQ ID NO: 78) and E1La-EcoT-R: 5'-ATGCATTTAGTG-GATGTTTTG-3' (SEQ ID NO: 155)

(p19) Primers used for confirming introduction of synthetic hPDI and synthetic hERO1-Lβ
ShPDI-ttaR: 5'-GATGCATTTACAACTCGTCCTTAAC-3' (SEQ ID NO: 78) and E1Lb-EcoT-R: 5'-ATGCATT-TATCTGGAGTGTTG-3' (SEQ ID NO: 156)

(p20) Primers used for confirming introduction of synthetic hPDI+ synthetic hGRP78 ShPDI-ttaR: 5'-GATGCATTTA-CAACTCGTCCTTAAC-3' (SEQ ID NO: 78) and G78-EcoT-R: 5'-ATGCATTTACAACTCGTCC-3' (SEQ ID NO: 154)

(p21) Primers used for confirming introduction of synthetic hPDI, synthetic hERO1-Lα, and synthetic hGRP78
ShPDI-ttaR: 5'-GATGCATTTACAACTCGTCCTTAAC-3' (SEQ ID NO: 78), E1La-EcoT-R: 5'-ATGCATTTAGTG-GATGTTTTG-3' (SEQ ID NO: 155), and G78-EcoT-R: 5'-ATGCATTTACAACTCGTCC-3' (SEQ ID NO: 154)

(p22) Primers used for confirming introduction of synthetic hPDI, synthetic hERO1-Lβ, and synthetic hGRP78
ShPDI-ttaR: 5'-GATGCATTTACAACTCGTCCTTAAC-3' (SEQ ID NO: 78), E1Lb-EcoT-R: 5'-ATGCATTTATCTG-GAGTGTTG-3' (SEQ ID NO: 156), and G78-EcoT-R: 5'-AT-GCATTTACAACTCGTCC-3' (SEQ ID NO: 154)

(p23) Primers used for confirming introduction of synthetic hPDI, OmERO1, and synthetic hGRP78
ShPDI-ttaR: 5'-GATGCATTTACAACTCGTCCTTAAC-3' (SEQ ID NO: 78), OMEROT22I: 5'-GATGCATTTAT-AGCTCCAAACGATACAG-3' (SEQ ID NO: 45), and G78-EcoT-R: 5'-ATGCATTTACAACTCGTCC-3' (SEQ ID NO: 154)

PCR was carried out using TaKaRa LA Taq™ with GC Buffer (Takara Bio, RR02AG) at 94° C. for 30 seconds, 55° C. for 30 seconds, and 72° C. for 60 to 180 seconds to amplify the target fragment, and this cycle was repeated 30 times. The transformants below in which amplification was observed were each designated as a constitutive expression strain for chaperone.

(E17) Constitutive expression strain for synthetic hERO1-Lα; the ona56407 strain (E18) Constitutive expression strain for synthetic hERO1-Lβ; the ona56907 strain (E19) Constitutive expression strain for synthetic hGRP78; the ona57007 strain (E20) Constitutive expression strain for synthetic hPDI and synthetic hERO1-Lα; the ona65708 strain (E21) Constitutive expression strain for synthetic hPDI and synthetic hERO1-Lβ; the ona66008 strain (E22) Constitutive expression strain for synthetic hPDI and synthetic hGRP78; the ona66108 strain (E23) Constitutive expression strain for synthetic hPDI, synthetic hERO1-Lα, and synthetic hGRP78; the ona68708 strain (E24) Constitutive expression strain for synthetic hPDI, synthetic hERO1-Lβ, and synthetic hGRP78; the ona68908 strain (E25) Constitutive expression strain for synthetic hPDI, OmERO1, and synthetic hGRP78; the ona69108 strain Example 24

Construction of Yeast Strain (*O. minuta*) Producing Antibody that Constitutively Expresses Chaperone The expression vector for the anti-TRAIL receptor antibody gene (WO 2001/083560) constructed in Example 2 was introduced into a strain that constitutively expresses a single chaperone gene, a strain that constitutively expresses two types of chaperone genes, and a strain that constitutively expresses three types of chaperone genes bred in Example 23, respectively, via electroporation. As an antibody heavy chain, 1 μg of onaP02706 digested with the Sse8387I restriction enzyme was used. As an antibody light chain, 1 μg of onaP03106 digested with the NotI restriction enzyme was used. After electroporation, the transformant was applied on Casamino-U-A agar medium to which Zeocin™ (Invitrogen, R250-01) had been added at a concentration of 100 μg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 μg/ml of agar medium, a strain that secretes and produces an antibody was screened for. The ona77108 strain was selected as the strain constitutively expressing synthetic hERO1-Lα and having the antibody gene introduced therein, the ona62508 strain was selected as the strain as the strain constitutively expressing synthetic hERO1-Lβ and having the antibody gene introduced therein, the ona61808 strain was selected as the strain constitutively expressing synthetic hGRP78 and having the antibody gene introduced therein, the ona77408 strain was selected as the strain constitutively expressing synthetic hPDI/synthetic hERO1-Lα and having the antibody gene introduced therein, the ona77808 strain was selected as the strain constitutively expressing synthetic hPDI/synthetic hERO1-Lβ and having the antibody gene introduced therein, the ona78208 strain was selected as the strain constitutively expressing synthetic hPDI/synthetic hGRP78 and having the antibody gene introduced therein, the ona78808 strain was selected as the strain constitutively expressing synthetic hPDI/synthetic hERO1-Lα/synthetic hGRP78 and having the antibody gene introduced therein, the ona79608 strain was selected as the strain constitutively expressing synthetic hPDI/synthetic hERO1-Lβ/synthetic hGRP78 and having the antibody gene introduced therein, and the ona80308 strain was selected as the strain constitutively expressing synthetic hPDI/OmERO1/synthetic hGRP78 and having the antibody gene introduced therein.

Example 25

Effects of Chaperone on Antibody Secretory Production

Figure 20:
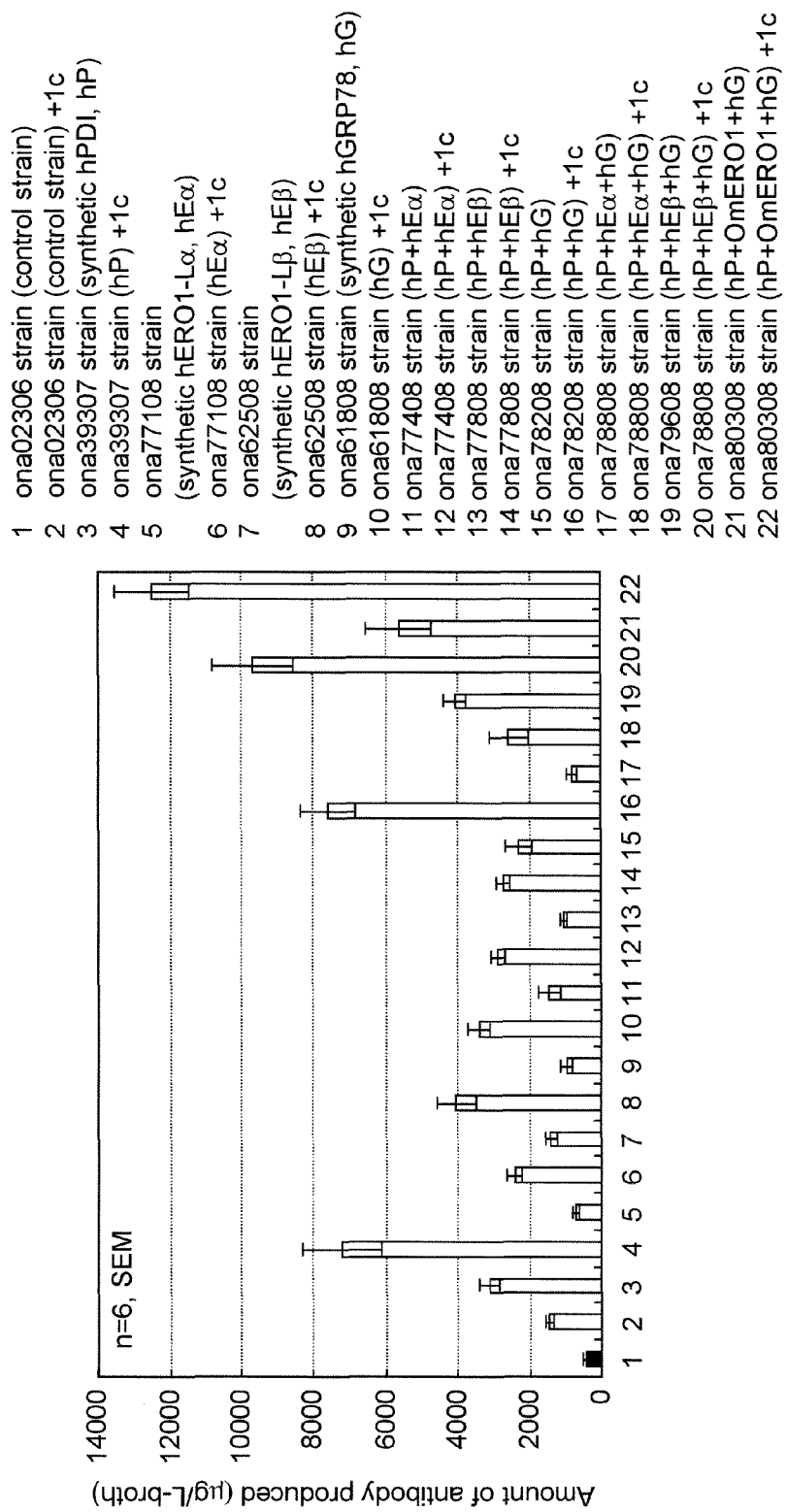
FIG. 20 is a chart showing the results of measuring the amount of secreted antibodies of an antibody-producing yeast strains (cultured with or without the addition of an inhibitor of O-mannosylation (rhodanine-3-acetic acid derivative 1c)) into which genes of the human-derived chaperone proteins (PDI, ERO1-Lα, ERO1-Lβ, and GRP78) had been introduced.
Figure 21:
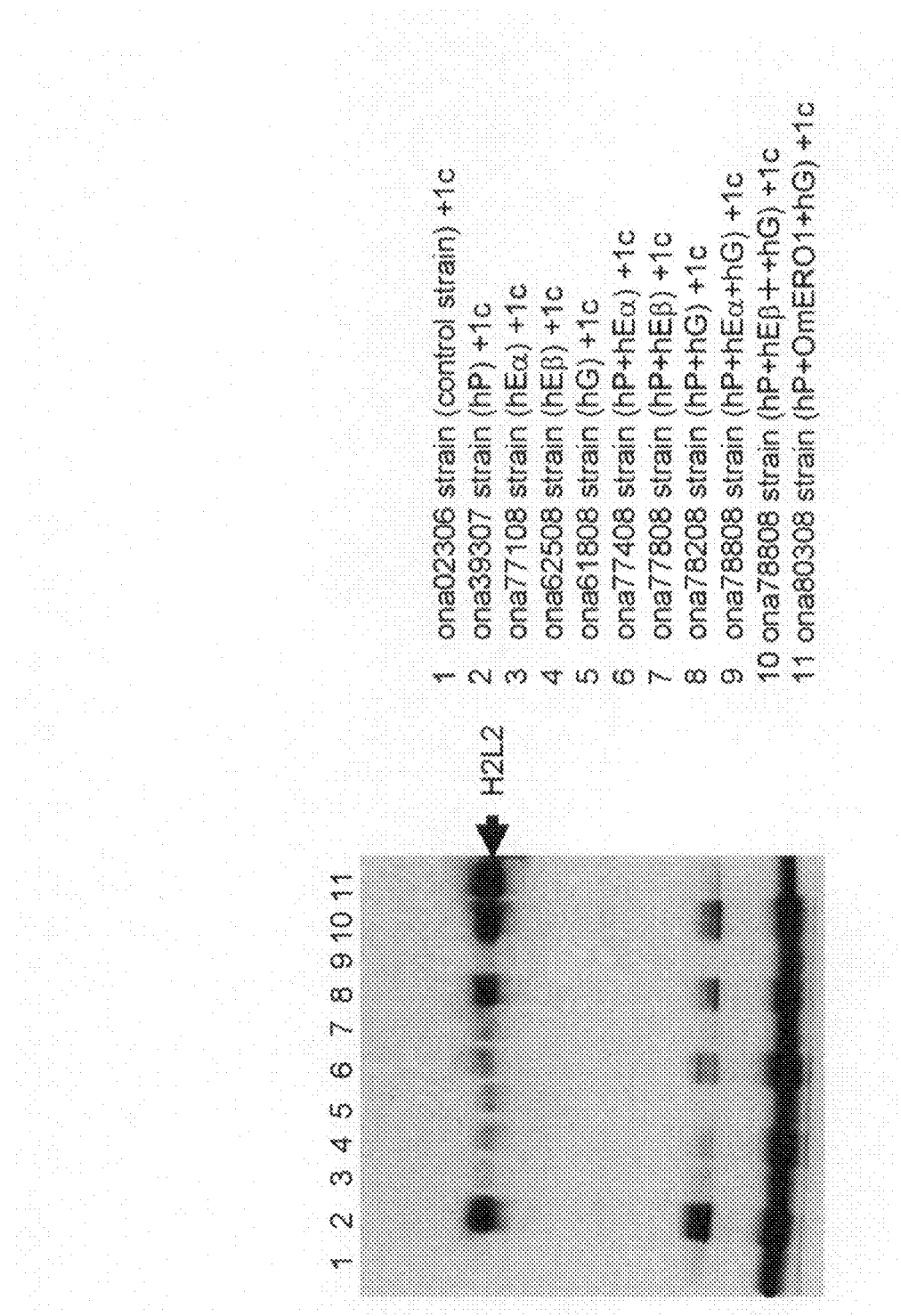
FIG. 21 shows the results of Western blot analysis of antibodies secreted in the culture supernatant of antibody-producing yeast strains (cultured with or without the addition of an inhibitor of O-mannosylation (rhodanine-3-acetic acid derivative 1c)) into which the genes of the human-derived chaperone proteins (PDI, ERO1-Lα, ERO1-Lβ, and GRP78) had been introduced.

With the use of the strain constitutively expressing human-derived chaperone and having the antibody gene introduced therein obtained in Example 24, effects of introduction of human-derived chaperone on antibody secretory production were examined. Also, effects of antibody secretory production enhancement with the addition of PMT inhibitors that were found in Example 7 were examined. As shown in FIG. 20, a control strain (i.e., the ona02306 strain) exhibited the amount of antibody secretory production of approximately 0.4 mg/l, the strain constitutively expressing synthetic hPDI and having the antibody gene introduced therein (i.e., the ona39307 strain) exhibited that of approximately 3.1 mg/l, the strain constitutively expressing hERO1-L and having the antibody gene introduced therein (i.e., the ona77108 strain) exhibited that of approximately 0.7 mg/l, the strain constitutively expressing hERO1-Lβ and having the antibody gene introduced therein (i.e., the ona62508 strain) exhibited that of approximately 1.4 mg/l, the strain constitutively expressing hGRP78 and having the antibody gene introduced therein (i.e., the ona61808 strain) exhibited that of approximately 1.0 mg/l, the strain constitutively expressing synthetic hPDI/synthetic hERO1-Lα and having the antibody gene introduced therein (i.e., the ona77408 strain) exhibited that of approximately 1.4 mg/l, the strain constitutively expressing synthetic hPDI/synthetic hERO1-Lβ and having the antibody gene introduced therein (i.e., the ona77808 strain) exhibited that of approximately 1.0 mg/l, the strain constitutively expressing synthetic hPDI/synthetic hGRP78 and having the antibody gene introduced therein (i.e., the ona78208 strain) exhibited that of approximately 2.3 mg/l, the strain constitutively expressing synthetic hPDI/synthetic hERO1-Lα/synthetic hGRP78 and having the antibody gene introduced therein (i.e., the ona78808 strain) exhibited that of approximately 0.8 mg/l, the strain constitutively expressing synthetic hPDI/synthetic hERO1-Lβ/synthetic hGRP78 and having the antibody gene introduced therein (i.e., the ona79608 strain) exhibited that of 4.1 mg/l, and the strain constitutively expressing synthetic hPDI/OmERO1/synthetic hGRP78 and having the antibody gene introduced therein (i.e., the ona80308 strain) exhibited that of approximately 5.6 mg/l. By enhancing expression of human-derived chaperone, the capacity of antibody secretory production was improved by approximately 2 to 13 times. By adding PMT inhibitors to the culture, further, all the antibody-producing strains exhibited the increased amounts of antibody secretory production, as shown in FIG. 20. In particular, the strain constitutively expressing synthetic hPDI/synthetic hERO1-Lβ/synthetic hGRP78 and having the antibody gene introduced therein (i.e., the ona79608 strain) exhibited the amount of antibody secretory production of 9.7 mg/l and the strain constitutively expressing synthetic hPDI/OmERO1/synthetic hGRP78 and having the antibody gene introduced therein (i.e., the ona80308 strain) exhibited that of approximately 12.5 mg/l. It was demonstrated that such strains exhibited the amount of antibody secretory production improved by approximately 23 times and approximately 30 times higher than that of a control culture. As shown in FIG. 21, it was confirmed via Western blot analysis following non-reducing electrophoresis that a full-length antibody (H2L2) was apparently secreted and produced. As in the case where expression of the $O.\ minuta$-derived chaperone gene(s) alone or in combination, the capacity for antibody secretory production was also improved when expression of the human-derived chaperone gene(s) was enhanced alone or in combination. By adding PMT inhibitors to the culture, further, the capacity for antibody secretory production was improved by approximately 23 to 30 times.

Example 26

Effects of Chaperone on Human Lysozyme Expression (1) Construction of Expression Vector for Human Lysozyme Human lysozyme (hLyz, Accession No. NM_000239) is encoded by the gene comprising 447 base pairs and comprises 148 amino acid residues. In order to efficiently express in $O.\ minuta$ and in order to express in the form of a fusion protein with the secretion signal (hereafter referred to as "aMF-secreting signal") of $S.\ cerevisiae$-derived MF alpha1 (GENBANK Accession Number; P01149) so as to efficiently secrete in $O.\ minuta$, the aMF-secretion signal-fused hLyz gene was synthesized by taking codon preference of $O.\ minuta$ into consideration. An expression vector was constructed by ligating a fragment containing the ADE1 marker that is obtained by digesting pOMex4A disclosed in WO 2003/091431 with the KpnI and ApaI restriction enzymes to a fragment containing the GAP promoter and the GAP terminator obtained by digesting pOMexGP1U disclosed in WO 2003/091431 with the KpnI and ApaI restriction enzymes, and the resultant was designated as the pOMEGPA-1 vector (SalI-EcoT22I). The aMF secretory signal-fused hLyz gene recovered via digestion with the SalI and EcoT22I restriction enzymes was introduced into pOMEGPA-1 (SalI-EcoT22I) prepared with the aid of the SalI and EcoT22I restriction enzymes to construct an expression vector for the aMF secretory signal-fused hLyz gene (onaP21808).

(2) Construction of Yeast Strain ($O.\ minuta$) Producing aMF Secretory Signal-Fused hLyz The expression vector for the aMF secretory signal-fused hLyz gene, onaP21808, constructed in (1) was introduced into the ona01206 strain complementing a ura3 deletion mutation of the $O.\ minuta$ YK5 strain constructed in Example 6, a strain constitutively expressing chaperone combination; i.e., OmPDI1, OmERO1, and OmKar2, of the $O.\ minuta$ YK5 strain bred in Example 5 (i.e., the ona44607 strain), and a strain constitutively expressing human-derived chaperone combination; i.e., synthetic hPDI, synthetic hERO1-Lβ, and synthetic hGRP78, bred in Example 23 (i.e., the ona68908 strain), respectively, via electroporation. With the use of 1 μg of onaP21808 digested with the NotI restriction enzyme, the transformants were applied on Casamino-U-A agar medium (6.7 g/l of Yeast Nitrogen Base without amino acids, 0.5 g/l of casamino acid, 20 g/l of glucose, 20 mg/l of L-tryptophan, and 20 g/l of Bacto agar) after electroporation, and the transformants were allowed to grow at 30° C. for approximately 2 to 3 days. The grown transformants were allowed to grow again on Casamino-U-A agar medium and then cultured.

(3) Effects of Chaperone on Secretory Production of Human Lysozyme

The expression vector for the aMF secretory signal-fused hLyz gene, onaP21808, was introduced into the ona01206 strain into which no chaperone combination was introduced, a strain that constitutively expresses a combination of *O. minuta*-derived chaperone genes; i.e., OmPDI1, OmERO1, and OmKar2, (i.e., the ona44607 strain), and a strain that constitutively expresses a combination of human-derived chaperone genes; i.e., synthetic hPDI, synthetic hERO1-Lβ, and synthetic hGRP78, (i.e., the ona68908 strain). Three clones were arbitrarily selected from the resulting colonies and cultured. With the use of 2× YP-P6-GG medium (the medium was prepared by dissolving 20 g of Difco yeast extract and 40 g of Bacto peptone in 900 ml of pure water, sterilizing the solution via steaming under pressure, and adding 100 ml of separately sterilized 10× phosphate buffer (pH 6.0) (1M $KH_2PO_4$, 0.15M $(NH_4)_2SO_4$, 0.375N KOH), 10 ml of a separately sterilized 50% glucose solution, and 25 ml of separately sterilized 80% glycerine), 800 μl of 2×YP-P6-GG medium was introduced into a 96-deep well plate (Greiner, 780271), the strains were sowed with the use of a toothpick, and the top of the plate was sealed with $CO_2$-permeable plate sealers (Greiner, 676051). After culture was carried out at an agitation speed of 310 rpm, an amplitude of 50 mm, at 30° C. for 2 days, 100 μl of 2×YP-P6-GG medium containing 20 μM rhodanine-3-acetic acid derivative 1c was added, and 100 μl of 2×YP-P6-GG medium containing 20 μM of 1c was added three days later. Yeast cells were removed from the cultured solution via centrifugation at 2,700×g and 4° C. for 5 minutes, a culture supernatant was prepared, and the resultant was designated as a sample of secreted human lysozyme.

The secreted and produced human lysozyme was evaluated via Western blot analysis and in terms of bacteriolytic activity. Western blot analysis was carried out by subjecting the secreted and produced human lysozyme to SDS-PAGE under reducing conditions, blotting the separated protein on the PVDF membrane, and performing detection using the ECL Advance Western blot detection kit (GE, RPN2135) with the use of the horseradish peroxidase-conjugated IgG fraction of polyclonal rabbit antiserum to human lysozyme (Nordic Immunological Laboratories, RAHu/Lys/PO).

Also, bacteriolytic activity was assayed in the following manner. Bacteria of *M. lysodeikticus* was used as a substrate, and it was suspended in 50 mM phosphate buffer to prepare a substrate solution with a concentration of 0.16 mg/ml. To 240 μl of this substrate solution, 10 μl of a culture supernatant (the secreted human lysozyme) was added, and the mixture was incubated at room temperature for 10 minutes. Thereafter, the absorbance at 450 nm was assayed. Since human lysozyme degrades a bacterial cell wall, human lysozyme exhibiting higher activity exhibits a lower absorbance. Thus, a unit of lysozyme activity was defined as the amount of an enzyme that is necessary for the absorbance at 450 nm to be lowered by 0.001 per minute. Also, the total amount of proteins in the culture supernatant was assayed using the DC protein assay kit II (Bio-Rad, 500-0112JA) using bovine serum albumin as the standard.

Figure 22:
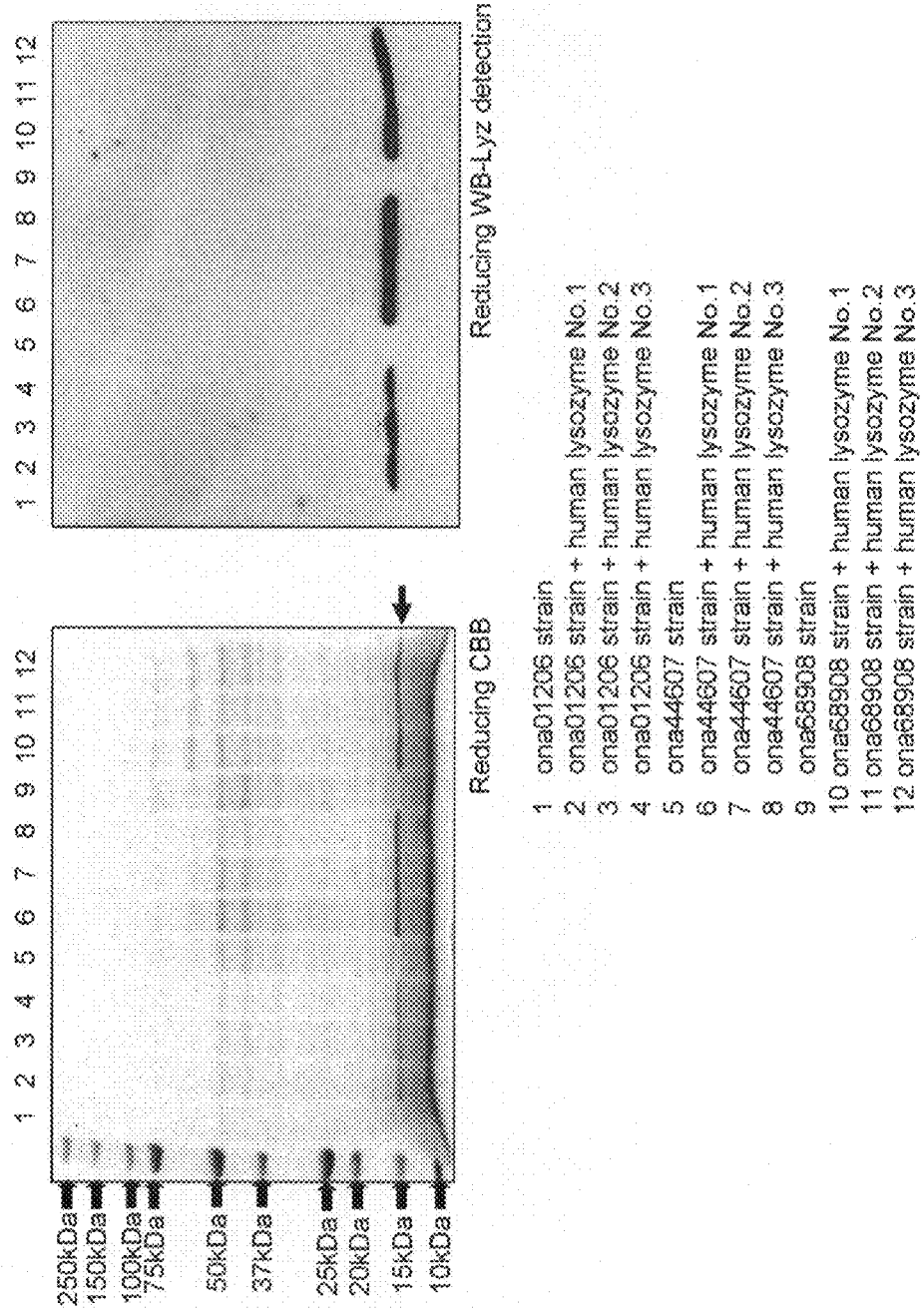
FIG. 22 shows the results of Western blot analysis attained when yeast aMF signal-fused human lysozyme is expressed in strains into which the coexpression vector for three types of the *O. minuta*-derived chaperone proteins (OmPDI1, OmERO1, and OmKar2) or the coexpression vector for three types of the human-derived chaperone proteins (synthesized hPDI, synthesized hERO1-Lβ, and synthesized hGRP78) had been introduced.

The results of Western blot analysis demonstrate that human lysozyme is expressed in all the tested strains (FIG. 22). Also, the strain into which *O. minuta*-derived chaperone genes; OmPDI1, OmERO1, and OmKar2, had been introduced or the strain into which human-derived chaperone genes; synthetic hPDI, synthetic hERO1-Lβ, and synthetic hGRP78 had been introduced were found to exhibit the capacity for secretion and production of human lysozyme improved by approximately 1.5 times or higher than that in the strain into which no chaperone had been introduced, based on the assayed bacteriolytic activity (Table 3).

TABLE 3

| Host | Chaperone introduced | Clone | Bacteriolytic activity (unit/ml) | Total amount of protein (mg/ml) | Specific activity (unit/mg) |
|---|---|---|---|---|---|
| Ona01206 | None | 1 | 23.0 | 51 | 0.45 |
| Ona01206 | None | 2 | 22.3 | 53 | 0.42 |
| Ona01206 | None | 3 | 22.0 | 52 | 0.43 |
| Ona44607 | PEK | 1 | 33.3 | 50 | 0.67 |
| Ona44607 | PEK | 2 | 34.0 | 51 | 0.67 |
| Ona44607 | PEK | 3 | 34.0 | 53 | 0.65 |
| Ona68908 | hPEβG | 1 | 36.0 | 53 | 0.68 |
| Ona68908 | hPEβG | 2 | 29.3 | 48 | 0.61 |
| Ona68908 | hPEβG | 3 | 33.3 | 51 | 0.65 |

PEK = OmPDI1 + OmERO1 + OmKar2
hPEβG = synthetic hPDI + synthetic hERO1-Lβ + synthetic hGRP78

Example 27

Construction of Constitutive Expression Strain for Chaperone Combination in Protein Mannosyl Transferase (PMT)-Deficient Strain of *O. minuta*

(1) Preparation of PMT4 Gene-Deficient Strain into which Genes of the *O. minuta*-Derived Chaperone Proteins (PDI1/EPO1/Kar2) Had been Introduced
(1-1) Preparation of PMT4 Gene-Deficient Vector PCR was carried out using chromosome DNA of the *O. minuta* IFO10746 strain as a template, the PMT4inf5'armF primer (5'-CGGGCCCCCCCTCGAGTCTATGCTCCAA-GACCT-3': SEQ ID NO: 157), and the PMT4 inf5'armR primer (5'-TACCGTCGACCTCGATCAACAACCACT-GATTCC-3': SEQ ID NO: 158) at 94° C. for 30 seconds, 55° C. for 1 minute, and 72° C. for 2 minutes, and this cycle was repeated 25 times. The amplified DNA fragment of approximately 2.2 kb was recovered, the recovered fragment was introduced into rURApBKS prepared with the aid of the XhoI restriction enzyme using the In-fusion kit (Clontech, 631774), and the nucleotide sequence of the inserted DNA fragment was confirmed. The resulting plasmid was designated as PMT4K/O5armrURA3. Further, PCR was carried out using chromosome DNA of the *O. minuta* IFO10746 strain as a template, the PMT4 inf3'armF primer (5'-AGT-TCTAGAGCGGCCATCCTATACCTGTCGTGCCT-3': SEQ ID NO: 159), and the PMT4 inf3'armR primer (5'-ACCGCGGTGGCGGCCGCTCGTGTTGTTC-CAGGTAATCC-3': SEQ ID NO: 160) at 94° C. for 30 seconds, 55° C. for 1 minute, and 72° C. for 2 minutes, and this cycle was repeated 25 times. The amplified DNA fragment of approximately 2.5 kb was recovered, the recovered fragment was introduced into PMT4K/O5armrURA3 prepared with the aid of the NotI restriction enzyme using the In-Fusion PCR Cloning kit (Clontech, 631774), and the nucleotide sequence of the inserted DNA fragment was confirmed. The resulting vector was designated as PMT4K/O/rURA3.

(1-2) Preparation of *O. minuta* PMT4-Deficient Strain (Δoch1Δyps1Δura3Δade1Δpmt4)

The PMT4 gene-deficient vector, PMT4K/O/rURA3, constructed in (1-1) above was digested with the XhoI and NotI restriction enzymes, and the resultant was introduced into the *O. minuta* YK5 (Δoch1Δyps1Δura3Δade1) strain via electroporation. In order to confirm that the PMT4 gene in this strain was destroyed, the primers shown below were synthesized.

```
                            (SEQ ID NO: 161)
PMT4PCR5'armF:  5'-GGTAGAGGACCGTATGTAGC-3'

(SEQ ID NO: 162)
PMT4PCR5'armR:  5'-CAATGAAACGTTTCCGTAGGT-3'

(SEQ ID NO: 163)
PMT4PCR3'armF3: 5'-TGCGAAATCGGGCCCTCT-3'

(SEQ ID NO: 164)
PMT4PCR3'armR3: 5'-CCGGAGTTTGCACGGCTAC-3'
```

Part of the transformed yeast that had been multiplied on Casamino-U agar medium was suspended in 10 μl of a 0.25% SDS solution, 90 μl of sterilized water was added, and yeast cells were then removed via centrifugation at 2,700×g and 4° C. for 5 minutes. The obtained supernatant was designated as a DNA solution. PCR was carried out using the PMT4PCR5'armF primer (SEQ ID NO: 161) and the PMT4PCR5'armR primer (SEQ ID NO: 162) at 94° C. for 30 seconds, 55° C. for 1 minute, and 72° C. for 2 minutes, and this cycle was repeated 25 times. In the strain into which the introduced fragment was incorporated into the PMT4 locus, an amplified fragment as deduced of 5.8 kb was detected. Similarly, PCR was carried out using the PMT4PCR3'armF primer (SEQ ID NO: 163) and the PMT4PCR3'armR primer (SEQ ID NO: 164) at 94° C. for 30 seconds, 55° C. for 1 minute, and 72° C. for 3 minutes, and this cycle was repeated 25 times. In the strain into which the introduced fragment was incorporated into the PMT4 locus, an amplified fragment as deduced of 7.4 kb was detected. The selected strain was designated as the *O. minuta* YK41 strain (Δoch1Δyps1Δura3Δade1Δpmt4::rURA3).

(1-3) Preparation of *O. minuta* PMT4-Deficient Strain (Δoch1Δyps1Δura3Δade1Δpmt4) Strain into which the Genes of Chaperones Had been Introduced The *O. minuta* YK41 strain (Δoch1Δyps1Δura3Δade1Δpmt4::rURA3) prepared in (1-2) above was cultured in YPDA medium and applied on 5-fluoroorotic acid (5-FOA) medium (Zymo Research, F9002) to obtain the grown uracil-requiring strain. The obtained strain was designated as the ona93608 strain (Δoch1Δyps1Δura3Δade1Δpmt4). Subsequently, the constitutive expression vector, onaP11007, for OmPDI1, OmERO1, and OmKar2 constructed in Example 4 was digested with the NotI restriction enzyme and introduced into the ona93608 strain via electroporation. The transformant was applied on Casamino-U agar medium, and the transformant was allowed to grow at 30° C. for approximately 2 to 3 days. The grown transformant was allowed to grow on Casamino-U agar medium again, and a transformant into which chaperone had been introduced was selected via colony PCR. Introduction of OmPDI1 was confirmed with the use of the GAPpforS-F primer (5'-GATCTCAGGC-CGAGTCAAGAC-3': SEQ ID NO: 76) and the OMPDI1T22I primer (5'-GATGCATTTACAACTCGTCGT-GAGCCAC-3': SEQ ID NO: 29) designed within the GAP promoter sequence, that of OmERO1 was confirmed with the use of GAPpforS-F (5'-GATCTCAGGCCGAGTCAAGAC-3': SEQ ID NO: 76) and OMEROT22I (5'-GATGCATTTAT-AGCTCCAAACGATACAG-3': SEQ ID NO: 45), and that of OmKar2 was confirmed with the use of the PGKpforS-F primer (5'-TAACGCCGCATAGAACTAGC-3': SEQ ID NO: 77) and the OMKAR-R primer (5'-GATGCATTCACAGCT-CATCATGATCCCAG-3': SEQ ID NO: 51) designed within the PGK promoter sequence. The obtained *O. minuta* PMT4-deficient strain (Δoch1Δyps1Δura3Δade1Δpmt4) into which the genes of chaperones (OmPDI1/OmERO1/OmKar2) had been introduced was designated as the ona96708 strain.

(2) Preparation of the PMT5 Gene-Deficient Strain into which the Genes of *O. minuta*-Derived Chaperone Proteins (PDI1/EPO1/Kar2) had been Introduced The *O. minuta* YK6 strain (Δoch1Δyps1Δura3Δade1Δpmt5::rURA3) disclosed in WO 2007/132949 was cultured in YPDA medium and applied on 5-fluoroorotic acid (5-FOA) medium (Zymo Research, F9002) to obtain a grown uracil-requiring strain. The obtained strain was designated as the ona64908 strain (Δoch1Δyps1Δura3Δade1Δpmt5). Subsequently, the constitutive expression vector, onaP11007, for OmPDI1, OmERO1, and OmKar2 constructed in Example 4 was digested with the NotI restriction enzyme and introduced into the ona64908 strain via electroporation. The transformant was applied on Casamino-U agar medium, and the transformant was allowed to grow at 30° C. for approximately 2 to 3 days. The grown transformant was allowed to grow on Casamino-U agar medium again, and a transformant into which chaperone had been introduced was selected via colony PCR. Introduction of OmPDI1 was confirmed with the use of the GAPpforS-F primer (5'-GATCTCAGGC-CGAGTCAAGAC-3': SEQ ID NO: 76) and the OMPDI1T22I primer (5'-GATGCATTTACAACTCGTCGT-GAGCCAC-3': SEQ ID NO: 29) designed within the GAP promoter sequence, that of OmERO1 was confirmed with the use of GAPpforS-F (5'-GATCTCAGGCCGAGTCAAGAC-3': SEQ ID NO: 76) and OMEROT22I (5'-GATGCATTTAT-AGCTCCAAACGATACAG-3': SEQ ID NO: 45), and that of OmKar2 was confirmed with the use of the PGKpforS-F primer (5'-TAACGCCGCATAGAACTAGC-3': SEQ ID NO: 77) and the OMKAR-R primer (5'-GATGCATTCACAGCT-CATCATGATCCCAG-3': SEQ ID NO: 51) designed within the PGK promoter sequence. The obtained PMT5-deficient strain of *O. minuta* (Δoch1Δyps1Δura3Δade1Δpmt5) into which the genes of chaperone (OmPDI1/OmERO1/OmKar2) had been introduced was designated as the ona69308 strain.

(3) Preparation of the PMT6 Gene-Deficient Strain into which the Genes of *O. minuta*-Derived Chaperone Proteins (PDI1/EPO1/Kar2) had been Introduced The *O. minuta* YK7 strain (Δoch1Δyps1Δura3Δade1Δpmt6::rURA3) disclosed in WO 2007/132949 was cultured in YPDA medium and applied on 5-fluoroorotic acid (5-FOA) medium (Zymo Research, F9002) to obtain a grown uracil-requiring strain. The obtained strain was designated as the ona65008 strain (Δoch1Δyps1Δura3Δade1Δpmt6). Subsequently, the constitutive expression vector, onaP11007, for OmPDI1, OmERO1, and OmKar2 constructed in Example 4 was digested with the NotI restriction enzyme and introduced into the ona65008 strain via electroporation. The transformant was applied on Casamino-U agar medium, and the transformant was allowed to grow at 30° C. for approximately 2 to 3 days. The grown transformant was allowed to grow on Casamino-U agar medium again, and a transformant into which chaperone had been introduced was selected via colony PCR. Introduction of OmPDI1 was confirmed with the use of the GAPpforS-F primer (5'-GATCTCAGGC-CGAGTCAAGAC-3': SEQ ID NO: 76) and the OMPDI1T22I primer (5'-GATGCATTTACAACTCGTCGT-GAGCCAC-3': SEQ ID NO: 29) designed within the GAP promoter sequence, that of OmERO1 was confirmed with the use of GAPpforS-F (5'-GATCTCAGGCCGAGTCAAGAC-3': SEQ ID NO: 76) and OMEROT22I (5'-GATGCATTTAT-AGCTCCAAACGATACAG-3': SEQ ID NO: 45), and that of OmKar2 was confirmed with the use of the PGKpforS-F primer (5'-TAACGCCGCATAGAACTAGC-3': SEQ ID NO: 77) and the OMKAR-R primer (5'-GATGCATTCACAGCT-CATCATGATCCCAG-3': SEQ ID NO: 51) designed within the PGK promoter sequence. The obtained *O. minuta* PMT6-deficient strain (Δoch1Δyps1Δura3Δade1Δpmt6) into which the genes of chaperones (OmPDI1/OmERO1/OmKar2) had been introduced was designated as the ona69508 strain.

(4) Preparation of the PMT5/PMT6 Double-Deficient Strain into which the Genes of *O. minuta*-Derived Chaperone Proteins (PDI1/EPO1/Kar2) Had been Introduced (4-1) Destruction of PMT5 Gene in PMT6 Gene-Deficient Strain The PMT5 gene-deficient vector, PMT5K/O/rURA3, disclosed in WO 2007/132949 was digested with the HindIII restriction enzyme and it was then introduced into the ona65008 strain (Δoch1Δyps1Δura3Δade1Δpmt6) prepared in (3) above via electroporation. Whether or not the PMT5 gene was destroyed in the strain was confirmed with the use of the primer disclosed in WO 2007/132949. Part of the transformant yeast that had been multiplied on Casamino-U agar medium was suspended in 10 µl of a 0.25% SDS solution, 90 µl of sterilized water was added, and yeast cells were then removed via centrifugation at 2,700×g and 4° C. for 5 minutes. The obtained supernatant was designated as a DNA solution. PCR was carried out using the gPMT5-5 primer (5'-CGGTGACGACTTCGACTAGTCGAG-3': SEQ ID NO: 165) and the gPMT5-2 primer (5'-CGGTGCTGTTG-GCGTCGTCATGGGTG-3': SEQ ID NO: 166) at 94° C. for 30 seconds, 55° C. for 1 minute, and 72° C. for 2 minutes, and this cycle was repeated 25 times. In the strain into which the introduced fragment was incorporated into the PMT5 locus, an amplified fragment as deduced of 4.9 kb was detected. Similarly, PCR was carried out using the gPMT5-3 primer (5'-GGCGCGTTCCAATTCCACTCTGCTG-3': SEQ ID NO: 167) and the gPMT5-4 primer (5'-CGACGAGTCCTCT-CACCAGGAGGTTG-3': SEQ ID NO: 168) at 94° C. for 30 seconds, 55° C. for 1 minute, and 72° C. for 2 minutes, and this cycle was repeated 25 times. In the strain into which the introduced fragment was incorporated into the PMT5 locus, an amplified fragment as deduced of 4.9 kb was detected. The selected strain was designated as the *O. minuta* YK51 strain (Δoch1Δyps1Δura3Δade1Δpmt6Δpmt5::rURA3).

(4-2) Preparation of *O. minuta* PMT5/PMT6 Double-Deficient Strain (Δoch1Δyps1Δura3Δade1Δpmt5Δpmt6) into which Chaperone Had been Introduced The *O. minuta* YK51 strain (Δoch1Δyps1Δura3Δade1Δpmt6Δpmt5::rURA3) prepared in (4-1) above was cultured in YPDA medium and applied on 5-fluoroorotic acid (5-FOA) medium (Zymo Research, F9002) to obtain a grown uracil-requiring strain. The obtained strain was designated as the ona15707 strain (Δoch1Δyps1Δura3Δade1Δpmt5Δpmt6). Subsequently, the constitutive expression vector, onaP11007, for OmPDI1, OmERO1, and OmKar2 constructed in Example 4 was digested with the NotI restriction enzyme and introduced into the ona15707 strain via electroporation. The transformant was applied on Casamino-U agar medium, and the transformant was allowed to grow at 30° C. for approximately 2 to 3 days. The grown transformant was allowed to grow on Casamino-U agar medium again, and a transformant into which chaperone had been introduced was selected via colony PCR. Introduction of OmPDI1 was confirmed with the use of the GAPpforS-F primer (5'-GATCTCAGGC-CGAGTCAAGAC-3': SEQ ID NO: 76) and the OMPDI1T22I primer (5'-GATGCATTTACAACTCGTCGT-GAGCCAC-3': SEQ ID NO: 29) designed within the GAP promoter sequence, that of OmERO1 was confirmed with the use of GAPpforS-F (5'-GATCTCAGGCCGAGTCAAGAC-3': SEQ ID NO: 76) and OMEROT22I (5'-GATGCATTTAT-AGCTCCAAACGATACAG-3': SEQ ID NO: 45), and that of OmKar2 was confirmed with the use of the PGKpforS-F primer (5'-TAACGCCGCATAGAACTAGC-3': SEQ ID NO: 77) and the OMKAR-R primer (5'-GATGCATTCACAGCT-CATCATGATCCCAG-3': SEQ ID NO: 51) designed within the PGK promoter sequence. The obtained *O. minuta* PMT5/PMT6 double-deficient strain (Δoch1Δyps1Δura3Δade1Δpmt5Δpmt6) into which the genes of chaperones (OmPDI1/OmERO1/OmKar2) had been introduced was designated as the ona56207 strain.

(5) Construction of Antibody-Producing Yeast Strain (*O. minuta*) Utilizing the PMT Gene-Deficient Strain into which Genes of the *O. minuta*-Derived Chaperone Proteins (PDI1/EPO1/Kar2) were Introduced The expression vectors for the anti-TRAIL receptor antibody gene (WO 2001/083560) constructed in Example 2 were introduced into the strains shown below prepared by introducing the chaperone genes (OmPDI1/OmERO1/OmKar2) into the PMT-deficient strains constructed in (1) to (4) above via electroporation.

*O. minuta* PMT4-deficient strain (Δoch1Δyps1Δura3Δade1Δpmt4) into which the genes of chaperones (OmPDI1/OmERO1/OmKar2) had been introduced (i.e., the ona96708 strain)

*O. minuta* PMT5-deficient strain (Δoch1Δyps1Δura3Δade1Δpmt5) into which the genes of chaperones (OmPDI1/OmERO1/OmKar2) had been introduced (i.e., the ona69308 strain)

*O. minuta* PMT6-deficient strain (Δoch1Δyps1Δura3Δade1Δpmt6) into which the genes of chaperones (OmPDI1/OmERO1/OmKar2) had been introduced (i.e., the ona69508 strain)

*O. minuta* PMT5/PMT6 double-deficient strain (Δoch1Δyps1Δura3Δade1Δpmt5Δpmt6) into which the genes of chaperones (OmPDI1/OmERO1/OmKar2) had been introduced (i.e., the ona56207 strain)

As an antibody heavy chain, 1 µg of onaP02706 digested with the Sse8387I restriction enzyme was used. As an antibody light chain, 1 µg of onaP03106 digested with the NotI restriction enzyme was used. After electroporation, the transformant was applied on Casamino-U-A agar medium to which Zeocin™ (Invitrogen, R250-01) had been added at a concentration of 100 µg/ml (6.7 g/l of Yeast Nitrogen Base without amino acids, 0.5 g/l of casamino acid, 20 g/l of glucose, 20 mg/l of L-tryptophan, and 20 g/l of Bacto agar), and the transformant was allowed to grow at 30° C. for approximately 2 to 3 days. The grown transformant was allowed to grow again on Casamino-U-A agar medium to which Zeocin™ (Invitrogen, R250-01) had been added at a concentration of 100 µg/ml, and a strain that secretes and produces an antibody was screened for. The ona98808 strain was selected as the *O. minuta* PMT4-deficient strain constitutively expressing the chaperones (OmPDI1/OmERO1/

OmKar2) and having the antibody gene introduced therein; the ona74108 strain was selected as the *O. minuta* PMT5-deficient strain constitutively expressing the chaperones (OmPDI1/OmERO1/OmKar2) and having the antibody gene introduced therein; the ona74608 strain was selected as the *O. minuta* PMT6-deficient strain constitutively expressing the chaperones (OmPDI1/OmERO1/OmKar2) and having the antibody gene introduced therein; and the ona67408 strain was selected as the *O. minuta* PMT5/PMT6 double-deficient strain constitutively expressing the chaperones (OmPDI1/OmERO1/OmKar2) and having the antibody gene introduced therein.

Example 28

Confirmation of capacity for antibody production of antibody-producing yeast strain (*O. minuta*) prepared by introducing genes of *O. minuta*-derived chaperone proteins (PDI1/EPO1/Kar2) into the Protein Mannosyl Transferase (PMT) gene-deficient strain of *O. minuta*

The capacity for antibody secretory production of the PMT-deficient strain constitutively expressing the chaperones (OmPDI1/OmERO1/OmKar2) and having the antibody gene introduced therein constructed in Example 27 (5), was confirmed. Also, effects of antibody secretory production enhancement with the addition of PMT inhibitors that were found in Example 7 were examined.

The antibody-producing strain was cultured in the following manner. With the use of 2× YP-P6-GG medium (the medium was prepared by dissolving 20 g of Difco yeast extract and 40 g of Bacto peptone in 900 ml of pure water, sterilizing the solution via steaming under pressure, and adding 100 ml of separately sterilized 10× phosphate buffer (pH 6.0) (1M $KH_2PO_4$, 0.15M $(NH_4)_2SO_4$, 0.375N KOH), 10 ml of a separately sterilized 50% glucose solution, and 25 ml of separately sterilized 80% glycerine), 800 µl of 2×YP-P6-GG medium was introduced into a 96-deep well plate (Greiner, 780271), the strains were sowed with the use of a toothpick, and the top of the plate was sealed with $CO_2$-permeable plate sealers (Greiner, 676051). Culture was carried out at an agitation speed of 310 rpm, an amplitude of 50 mm, at 30° C., and 100 µl each of 2×YP-P6-GG medium was added 2 and 3 days after the initiation of culture. Culture involving the addition of PMT inhibitors was carried out with the use of 2× YP-P6-GG medium (the medium was prepared by dissolving 20 g of Difco yeast extract and 40 g of Bacto peptone in 900 ml of pure water, sterilizing the solution via steaming under pressure, and adding 100 ml of separately sterilized 10× phosphate buffer (pH 6.0) (1M $KH_2PO_4$, 0.15M $(NH_4)_2SO_4$, 0.375N KOH), 10 ml of a separately sterilized 50% glucose solution, and 25 ml of separately sterilized 80% glycerine), 800 µl of 2× YP-P6-GG medium was introduced into a 96-deep well plate (Greiner, 780271), the strains were sowed with the use of a toothpick, and the top of the plate was sealed with $CO_2$-permeable plate sealers (Greiner, 676051). Culture involving the addition of the rhodanine-3-acetic acid derivative 1c was first carried out at an agitation speed of 310 rpm, an amplitude of 50 mm, at 30° C. for 2 days, 100 µl of 2× YP-P6-GG medium containing 20 µM 1c was added, and 100 µl of 2×YP-P6-GG medium containing 20 µM 1c was further added on day 3.

Secretion and production of an antibody were confirmed via Sandwich ELISA or Western blotting. Yeast cells were removed from the culture product via centrifugation at 2,700×g and 4° C. for 5 minutes, and the resulting culture supernatant was designated as a sample of secreted antibody. The secreted and produced antibodies were subjected to quantitative assay via sandwich ELISA. TRAIL receptor proteins that were antigens of the anti-TRAIL receptor antibodies were adsorbed on a 96-well plate, the sample of secreted antibody was added, and detection was carried out using a peroxidase-labeled human IgG specific Fc antibody (Peroxidase-labeled affinity purified antibody to human IgG (Fc), KPL, 04-10-20) and the ABTS peroxidase substrate (KPL, 50-66-01). Western blotting was carried out as follows. After the protein was subjected to SDS-PAGE under reducing and non-reducing conditions, the separated protein was blotted to a PVDF membrane, and the antibody heavy chain and light chain were detected using Anti-human IgG (γ-chain specific) (Sigma, I-3382) and Goat anti human kappa b&f affinity purified (Bethyl, A-80-115A) as the primary antibodies. Peroxidase conjugated affinity purified anti-goat IgG (H&L), rabbit, Rockland, #605-4313) was used as the secondary antibody. Detection was carried out using the ECL Advance Western blotting detection kit (GE, RPN2135).

Figure 23:
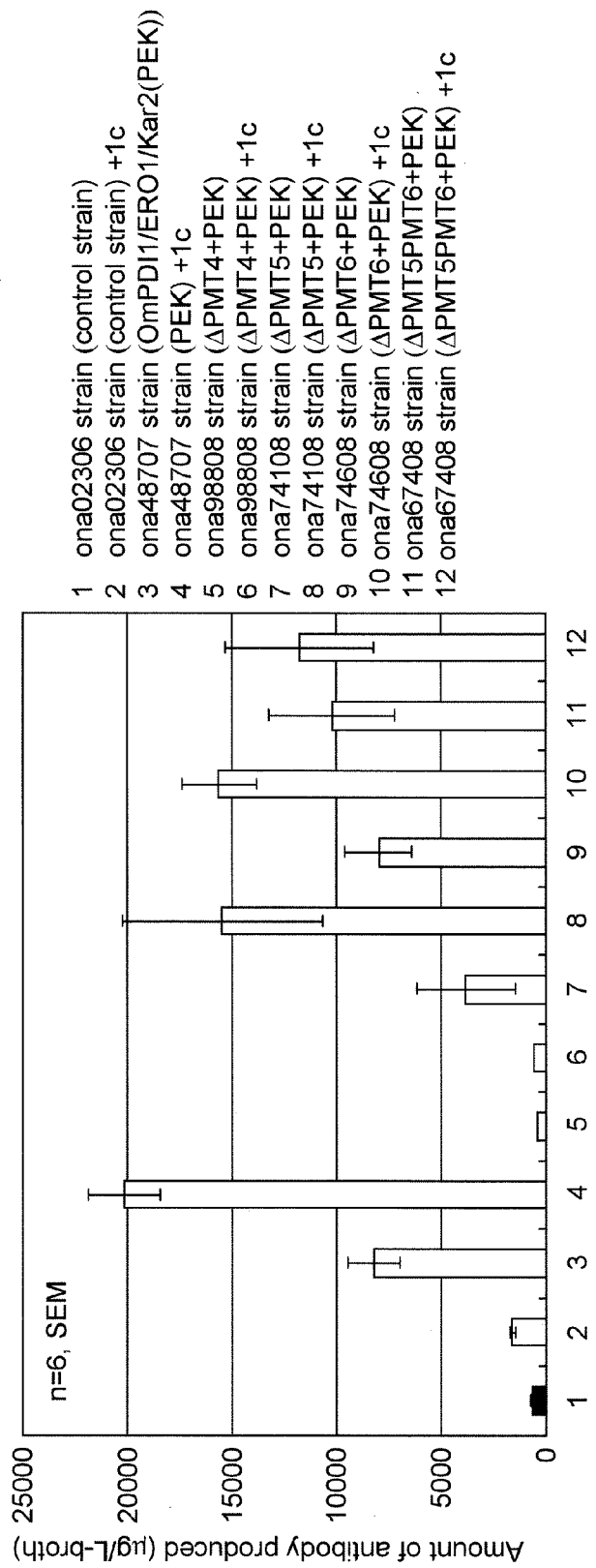
FIG. 23 is a chart showing the results of measuring the amount of secreted antibodies when cultured with or without the addition of an inhibitor of O-mannosylation (rhodanine-3-acetic acid derivative 1c) in strains prepared by introducing coexpression vectors for three types of the *O. minuta*-derived chaperone proteins (OmPDI1, OmERO1, and OmKar2) and an antibody gene into a strain in which the PMT genes had been destroyed.

As shown in FIG. 23, a control strain (i.e., the ona02306 strain) exhibited the amount of antibody secretory production of approximately 0.6 mg/l; the strain constitutively expressing chaperones (OmPDI1/OmERO1/OmKar2) and having the antibody gene introduced therein (i.e., the ona48707 strain) exhibited that of approximately 8.2 mg/l; the *O. minuta* PMT4-deficient strain constitutively expressing chaperones (OmPDI1/OmERO1/OmKar2) and having the antibody gene introduced therein (i.e., the ona98808 strain) exhibited that of approximately 0.4 mg/l; the *O. minuta* PMT5-deficient strain constitutively expressing chaperones (OmPDI1/OmERO1/OmKar2) and having the antibody gene introduced therein (i.e., the ona74108 strain) exhibited that of approximately 3.8 mg/l; the *O. minuta* PMT6-deficient strain constitutively expressing chaperones (OmPDI1/OmERO1/OmKar2) and having the antibody gene introduced therein (i.e., the ona74608 strain) exhibited that of approximately 8 mg/l; and the *O. minuta* PMT5/PMT6 double-deficient strain constitutively expressing chaperones (OmPDI1/OmERO1/OmKar2) and having the gene of an antibody introduced therein (i.e., the ona67408 strain) exhibited that of approximately 8.3 mg/l. Except for the PMT4 gene-deficient strain, enhanced chaperone expression was effective for a single- or double-deficient strain of the PMT gene, and the capacity for antibody secretory production was improved by approximately 5 to 14 times greater than that of a control strain.

Further, addition of PMT inhibitors, rhodanine, to culture resulted in an improvement in the amount of antibody secretory production by approximately 20 times to approximately 33 times in all the antibody-producing strains, as shown in FIG. 23. In the case of the *O. minuta* PMT5-deficient strain constitutively expressing chaperones (OmPDI1/OmERO1/OmKar2) and having the antibody gene introduced therein (i.e., the ona74108 strain) and the *O. minuta* PMT6-deficient strain constitutively expressing chaperones (OmPDI1/OmERO1/OmKar2) and having the antibody gene introduced therein (i.e., the ona74608 strain), the amount of antibody secretory production was reduced to approximately 75% that of the strain constitutively expressing chaperones (OmPDI1/OmERO1/OmKar2) and having the antibody gene introduced therein (i.e., the ona48707 strain). In the case of the *O. minuta* PMT5/PMT6 double-deficient strain constitutively expressing chaperones (OmPDI1/OmERO1/OmKar2) and having the antibody gene introduced therein (i.e., the ona67408 strain), the amount of antibody secretory production thereof was reduced to approximately 60% that of the strain constitutively expressing chaperones (OmPDI1/OmERO1/OmKar2) and having the antibody gene introduced therein (i.e., the ona48707 strain).

Figure 24:
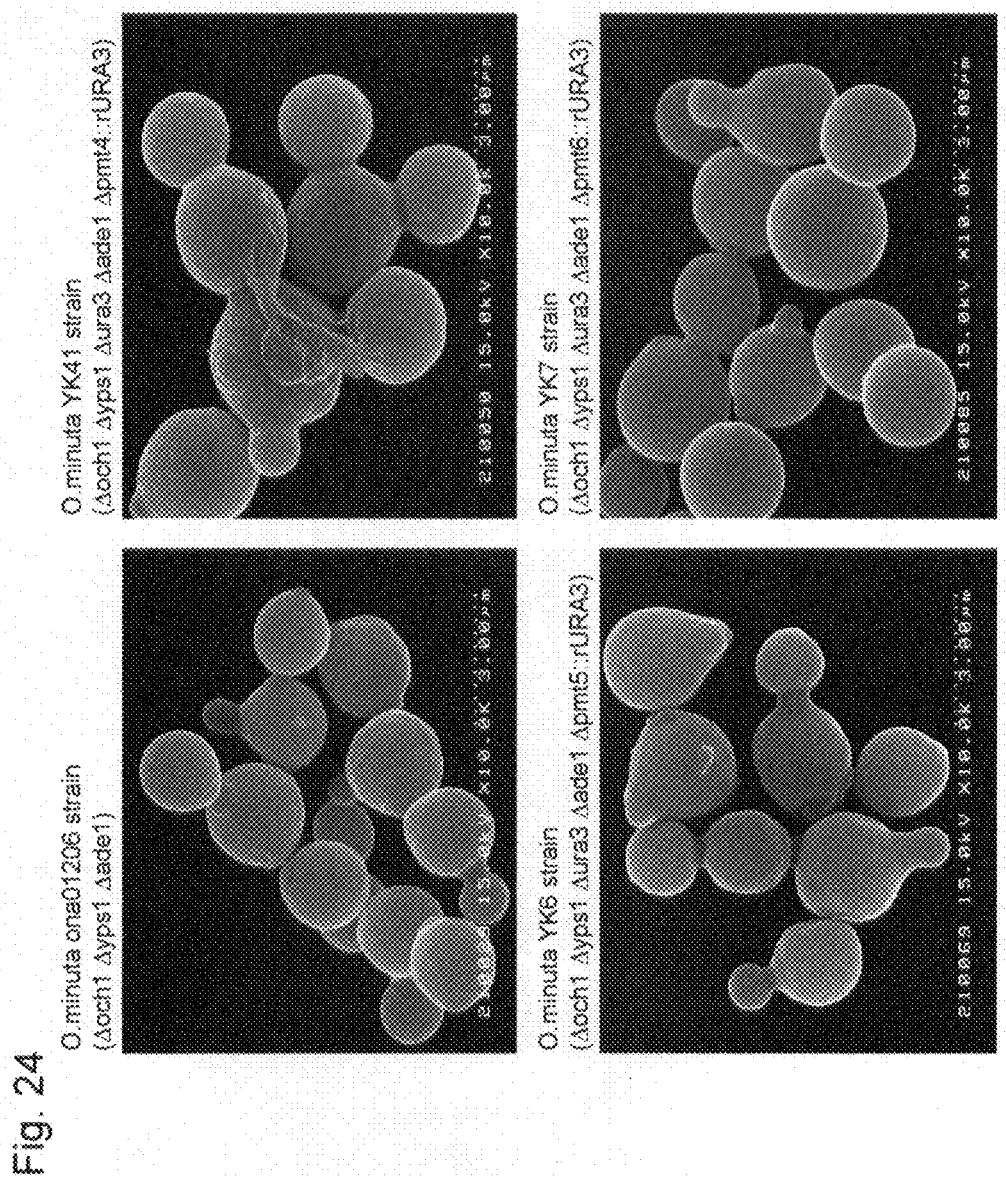
FIG. 24 is a photograph showing the results of scanning electron microscopic observation of the *O. minuta* strain in which the PMT gene had been destroyed.
Figure 25:
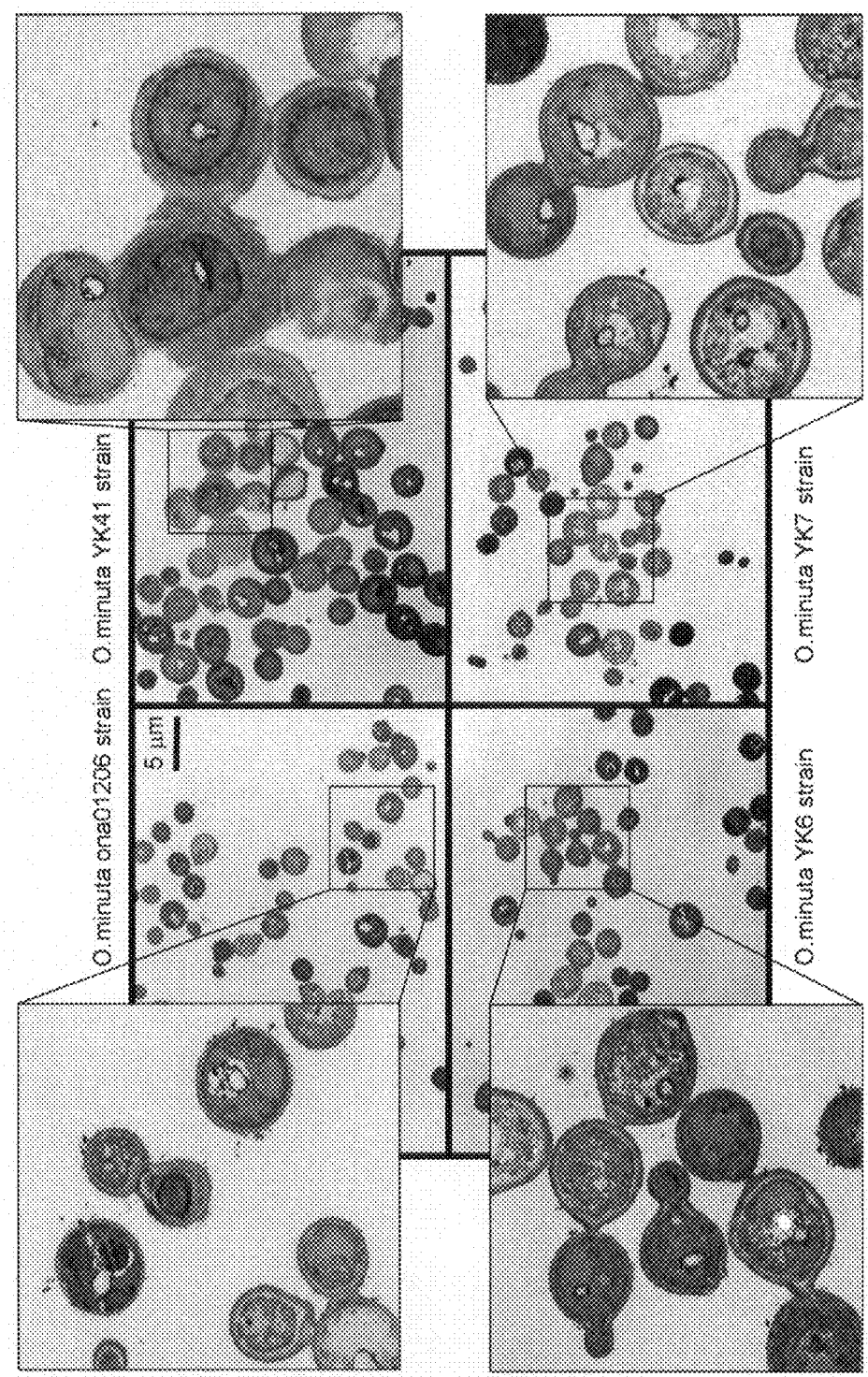
FIG. 25 is a photograph showing the results of transmission electron microscopic observation of the *O. minuta* strain in which the PMT gene had been destroyed.
Figure 26:
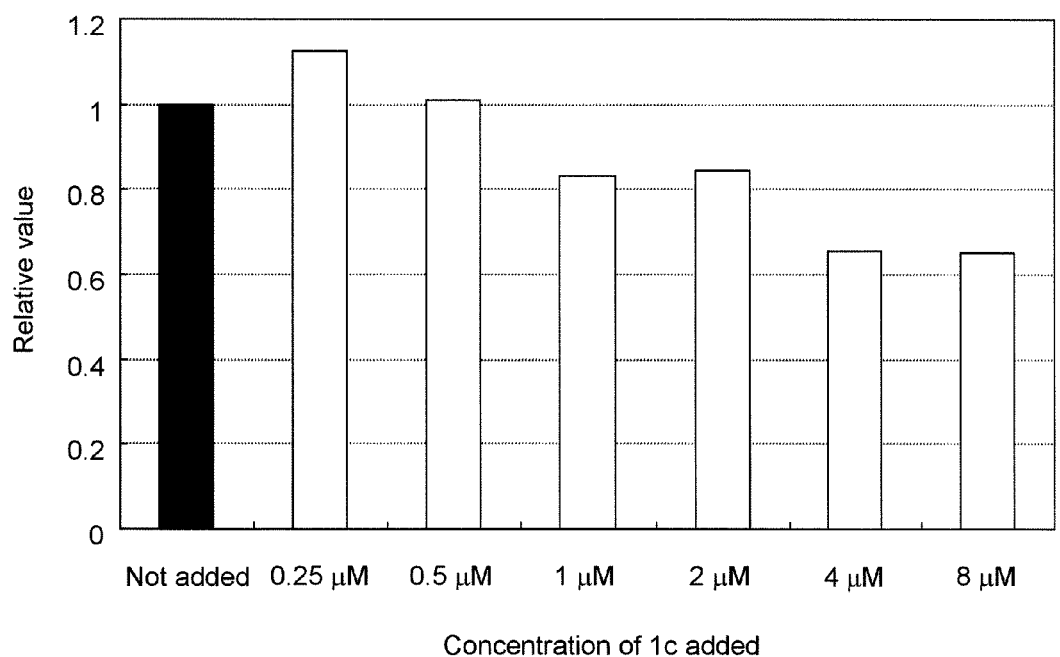
FIG. 26 shows the results of examining concentration of an inhibitor of O-mannosylation (rhodanine-3-acetic acid derivative 1c) that has been added to a strain prepared by introducing coexpression vectors for three types of the *O. minuta*-derived chaperone proteins (OmPDI1, OmERO1, and OmKar2) and an antibody gene into the *O. minuta* strain in which the PMT4 gene had been destroyed.

As described above, the *O. minuta* PMT4-deficient strain constitutively expresses chaperones (OmPDI1/OmERO1/OmKar2) and having the antibody gene introduced therein (i.e., the ona98808 strain), which exhibited the amount of production as low as approximately 0.4 mg/l, underwent abnormal growth and division resulting from PMT4 gene deficiency as shown in FIG. 24 and in FIG. 25. Regarding the *O. minuta* PMT4-deficient strain constitutively expressing chaperones (OmPDI1/OmERO1/OmKar2) and having the antibody gene introduced therein (i.e., the ona98808 strain), the amount of an inhibitor of PMT activity, rhodanine-3-acetic acid derivative 1c added, was examined. Culture was carried out by introducing 800 µl of 2×YP-P6-GG medium to a 96-deep well plate (Greiner, 780271), 100 µl each of medium prepared while adjusting the concentration of the rhodanine-3-acetic acid derivative 1c at 1.25, 2.5, 5, 10, 20, or 40 µM with the aid of 2×YP-P6-GG medium was added 2 and 3 days after the initiation of culture (final concentration: 0.25, 0.5, 1, 2, 4, or 8 µM). As a result, the amount of production was improved by approximately 13% when 2× YP-P6-GG medium containing 0.25 µM 1c (final concentration) was added, as shown in FIG. 26. Concentration of the inhibitor of PMT activity, rhodanine-3-acetic acid derivative 1c, to be added to the *O. minuta* PMT4-deficient strain constitutively expressing chaperones (OmPDI1/OmERO1/OmKar2) and having the antibody gene introduced therein (i.e., the ona98808 strain), was determined to be approximately 1/16 of other strains.

Example 29

Purification of Antibody Produced by Antibody-Producing Yeast Strain (*O. minuta*) Prepared by Introducing the Genes of the *O. minuta*-Derived Chaperone Proteins (PDI1/EPO1/Kar2) into the PMT Gene-Deficient Strain As described in Example 28, it was found that destruction of the PMT gene of *O. minuta* would lower the capacity for antibody secretory production to some extent and would significantly influence the morphology of *O. minuta*. This strongly suggests that suppression of O sugar chain addition via suppression of PMT activity of *O. minuta* significantly influences physiological functions of *O. minuta*. Thus, evaluation of biological activity (i.e., cytotoxic activity) of antibodies produced by such antibody-producing strains is considered to lead to discovery of optimal conditions for combinations of PMT mutation, constitutive expression of chaperone proteins (PDI1/EPO1/Kar2), and addition of an inhibitor of PMT activity (rhodanine-3-acetic acid derivative 1c).

(1) Culture of Antibody-Producing Yeast Strain (*O. minuta*) Prepared by Introducing the Genes of the *O. minuta*-Derived Chaperone Proteins (PDI1/EPO1/Kar2) into the PMT Gene-Deficient Strain The ona02306 strain was selected as a control strain (i.e., a strain into which no chaperones are introduced, but the antibody gene is introduced); the ona48707 strain was selected as a strain constitutively expressing chaperones (OmPDI1/OmERO1/OmKar2) and having the antibody gene introduced therein, the ona98808 strain was selected as the *O. minuta* PMT4-deficient strain constitutively expressing chaperones (OmPDI1/OmERO1/OmKar2) and having the antibody gene introduced therein, the ona74108 strain was selected as the *O. minuta* PMT5-deficient strain constitutively expressing chaperones (OmPDI1/OmERO1/OmKar2) and having the antibody gene introduced therein, the ona74608 strain was selected as the *O. minuta* PMT6-deficient strain constitutively expressing chaperones (OmPDI1/OmERO1/OmKar2) and having the antibody gene introduced therein, and the ona67408 strain was selected as the *O. minuta* PMT5/PMT6 double-deficient strain constitutively expressing chaperones (OmPDI1/OmERO1/OmKar2) and having the antibody gene introduced therein.

A 100-ml Erlenmeyer flask comprising 20 ml of Casamino-U-A medium prepared by adding Zeocin™ (Invitrogen, R250-01) at a concentration of 50 µg/ml to Casamino-U-A medium (6.7 g/l of Yeast Nitrogen Base without amino acids, 0.5 g/l of casamino acid, 20 g/l of glucose, and 20 mg/l of L-tryptophan) was subjected to seed culture at an agitation speed of 210 rpm, an amplitude of 75 mm, at 30° C. for 2 days. Subsequently, 20 to 30 ml of the seed culture solution was introduced into a 2-1 Erlenmeyer flask containing 400 ml of 2×YP-P6-GG medium (the medium was prepared by dissolving 20 g of Difco yeast extract and 40 g of Bacto peptone in 900 ml of pure water, sterilizing the solution via steaming under pressure, and adding 100 ml of separately sterilized 10× phosphate buffer (pH 6.0) (1M $KH_2PO_4$, 0.15M $(NH_4)_2SO_4$, 0.375N KOH), 10 ml of a separately sterilized 50% glucose solution, and 25 ml of separately sterilized 80% glycerine), and culture was carried out at an agitation speed of 210 rpm, an amplitude of 75 mm, at 30° C. After the OD 600 value exceeded 10, an inhibitor of PMT activity (rhodanine-3-acetic acid derivative 1c) (stock solution concentration: 40 mM) was added in amounts of 0.2 µM each as the OD600 value increased by 1. Only in the case of the *O. minuta* PMT4-deficient strain constitutively expressing chaperones (OmPDI1/OmERO1/OmKar2) and having the antibody gene introduced therein (i.e., the ona98808 strain), the inhibitor of PMT activity was added in amounts of 0.0125 µM each.

(2) Purification of Antibody Produced from *O. minuta*

Figure 27:
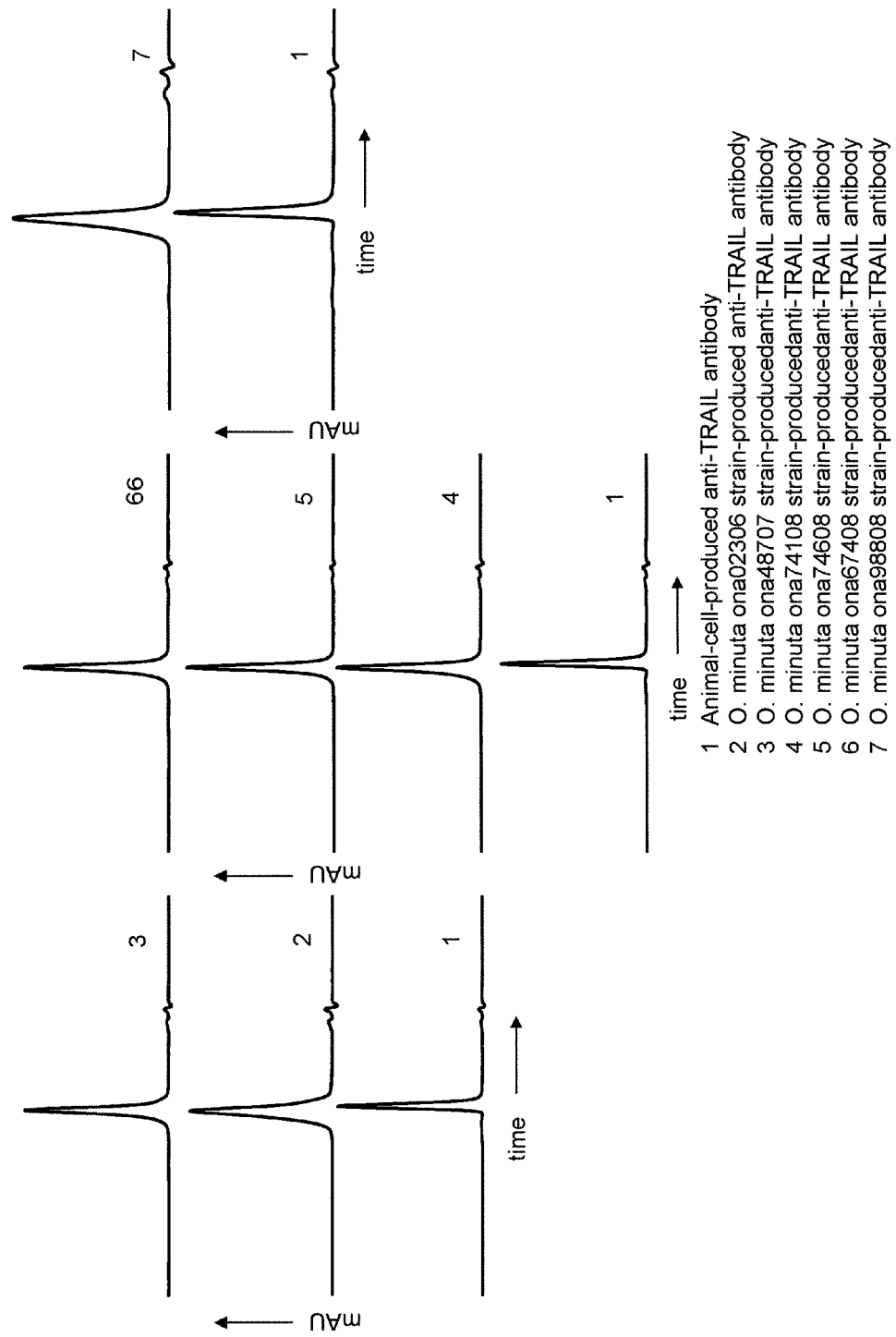
FIG. 27 shows elution patterns of size exclusion chromatography (SEC)-HPLC of various purified antibodies produced from *O. minuta*.

Yeast cells were removed from the culture solution via centrifugation at 13,000×g, 4° C., for 30 minutes, and the culture supernatant was designated as a sample of secreted antibody. The sample was concentrated using Pall Filtron Centrimate™ (10K Omega Centrimate medium screen, Pall) and then purified with the use of the AKTA purifier (GE). At the outset, the concentrated antibody sample was adsorbed to the HiTrap Mabselect SuRe (GE, 11-0034-94), which had been equilibrated with sodium phosphate buffer (20 mM sodium phosphate, 300 mM sodium chloride, pH 7.2), and the sample was eluted with the use of ImmunoPure IgG Elution Buffer (Pierce, 21009). The eluted fraction was immediately neutralized with the addition of 1M Tris-HCl buffer (pH 9) in an amount of one tenth of the elution fraction, and an equivalent amount of sodium phosphate buffer (100 mM sodium phosphate, 150 mM sodium chloride, pH 7.2) was then added. Subsequently, the fraction eluted with the use of HiTrap Mabselect SuRe was adsorbed to Protein L Cartridge (Pierce, #89929), which had been equilibrated with sodium phosphate buffer (100 mM sodium phosphate, 150 mM sodium chloride, pH 7.2), and the sample was eluted with the use of ImmunoPure IgG Elution Buffer (Pierce, 21009). The eluted Protein L Cartridge-purified fraction was subjected to gel filtration with the use of Superdex200 10/30 GL (GE, 17-5175-01), which had been equilibrated with sodium phosphate buffer (10 mM sodium phosphate, 150 mM sodium chloride, pH 7.2) to purify various antibodies produced from *O. minuta*. The purified antibodies were analyzed via size exclusion chromatography (SEC)-HPLC using PROTEIN KW403-4F (4.6 (i.d.)×300 mm) (Showa Denko K.K., F6989202). Sodium phosphate buffer (30 mM sodium phosphate, 300 mM sodium chloride, pH 6.7) was used as a mobile phase. FIG. 27 shows a pattern of elution via SEC-HPLC of the purified antibodies. While the ona02306 strain (the control strain containing no chaperones and having the antibody gene introduced therein) and the PMT4-deficient strain constitutively expressing chaperones (OmPDI1/OmERO1/OmKar2) and having antibody gene introduced therein (i.e., the ona98808) produced broad chromatograms, the strain constitutively expressing chaperones (OmPDI1/OmERO1/OmKar2) and having the antibody gene introduced therein (i.e., the ona48707 strain), the PMT5-deficient strain constitutively expressing chaperones (OmPDI1/OmERO1/OmKar2) and having the antibody gene introduced therein (i.e., the ona74108 strain), the PMT6-deficient strain constitutively expressing chaperones (OmPDI1/OmERO1/OmKar2) and having the antibody gene introduced therein (i.e., the ona74608 strain), and the PMT5/PMT6 double-deficient strain constitutively expressing chaperones (OmPDI1/OmERO1/OmKar2) and having the antibody gene introduced therein (i.e., the ona67408 strain) produced sharp chromatograms.

Figure 28:
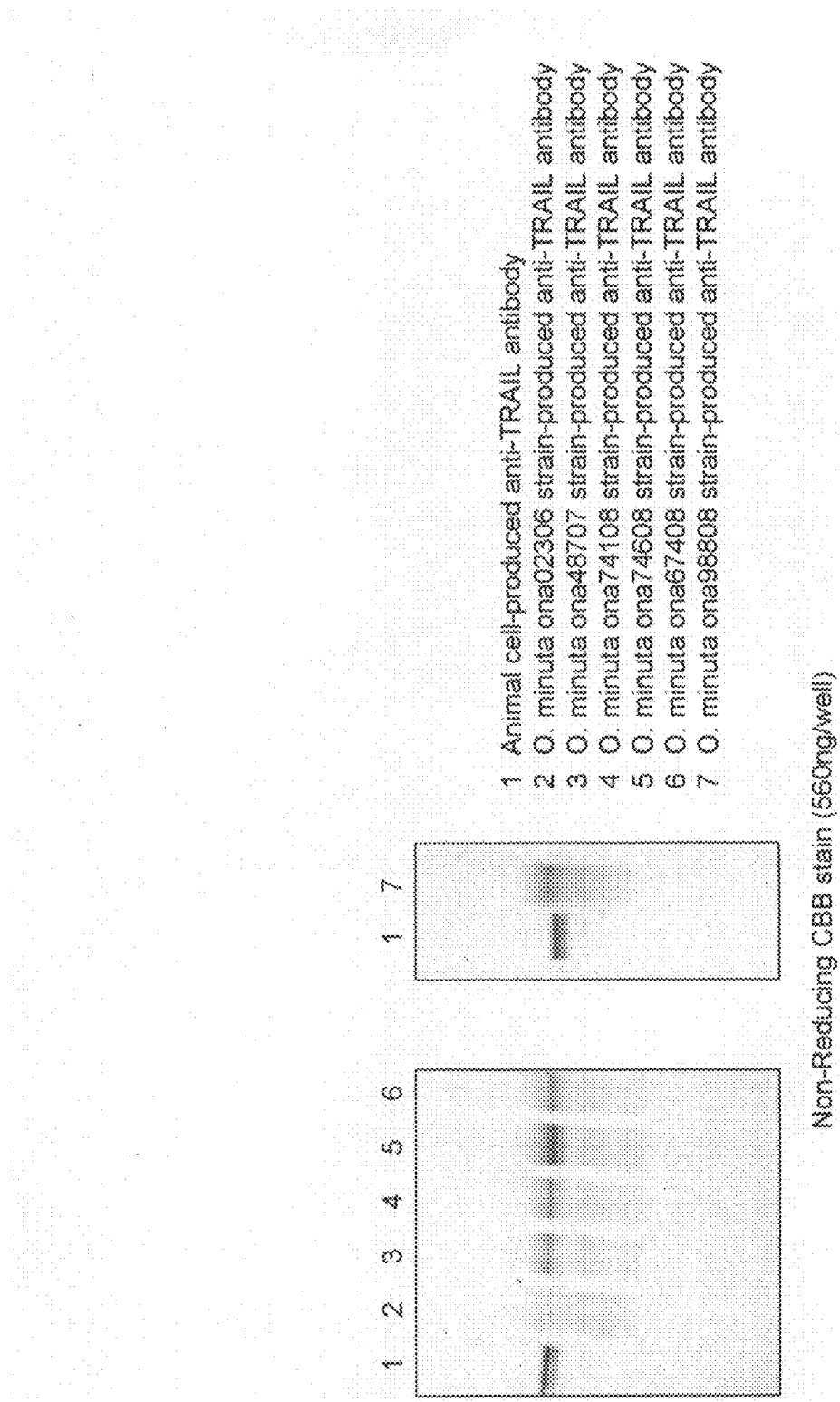
FIG. 28 shows the results of Western blot analysis after non-reducing electrophoresis of various purified antibodies produced from *O. minuta*.

The results of reducing/non-reducing SDS-PAGE followed by Western blot analysis demonstrate that the heterotetramer of the antibody heavy chain and light chain was not clearly detected in the ona02306 strain (the control strain containing no chaperones and having the antibody gene introduced therein) and the PMT4-deficient strain constitutively expressing chaperones (OmPDI1/OmERO1/OmKar2) and having antibody gene introduced therein (i.e., the ona98808) under non-reducing conditions as shown in FIG. 28. On the other hand, the heterotetramer of the antibody heavy chain and light chain was clearly detected in the strain constitutively expressing chaperones (OmPDI1/OmERO1/OmKar2) and having the antibody gene introduced therein (i.e., the ona48707 strain), the PMT5-deficient strain constitutively expressing chaperones (OmPDI1/OmERO1/OmKar2) and having the antibody gene introduced therein (i.e., the ona74108 strain), the PMT6-deficient strain constitutively expressing chaperones (OmPDI1/OmERO1/OmKar2) and having the antibody gene introduced therein (i.e., the ona74608 strain), and the PMT5/PMT6 double-deficient strain constitutively expressing chaperones (OmPDI1/OmERO1/OmKar2) and having the antibody gene introduced therein (i.e., the ona67408 strain). Enhancement of chaperone (OmPDI1/OmERO1/OmKar2) expression was found to accelerate formation of an assembly; i.e., the heterotetramer of the antibody heavy chain and light chain.

(3) Cytotoxic Activity of Antibodies Produced from *O. minuta*

(3-1) Measurement of Amount of Purified Antibody Protein

The amount of the purified antibody protein was measured by employing bovine serum albumin as the standard and using the DC protein assay kit II (Bio-Rad, 500-0112JA).

(3-2) Measurement of Cytotoxic Activity of Purified Antibody

Figure 29:
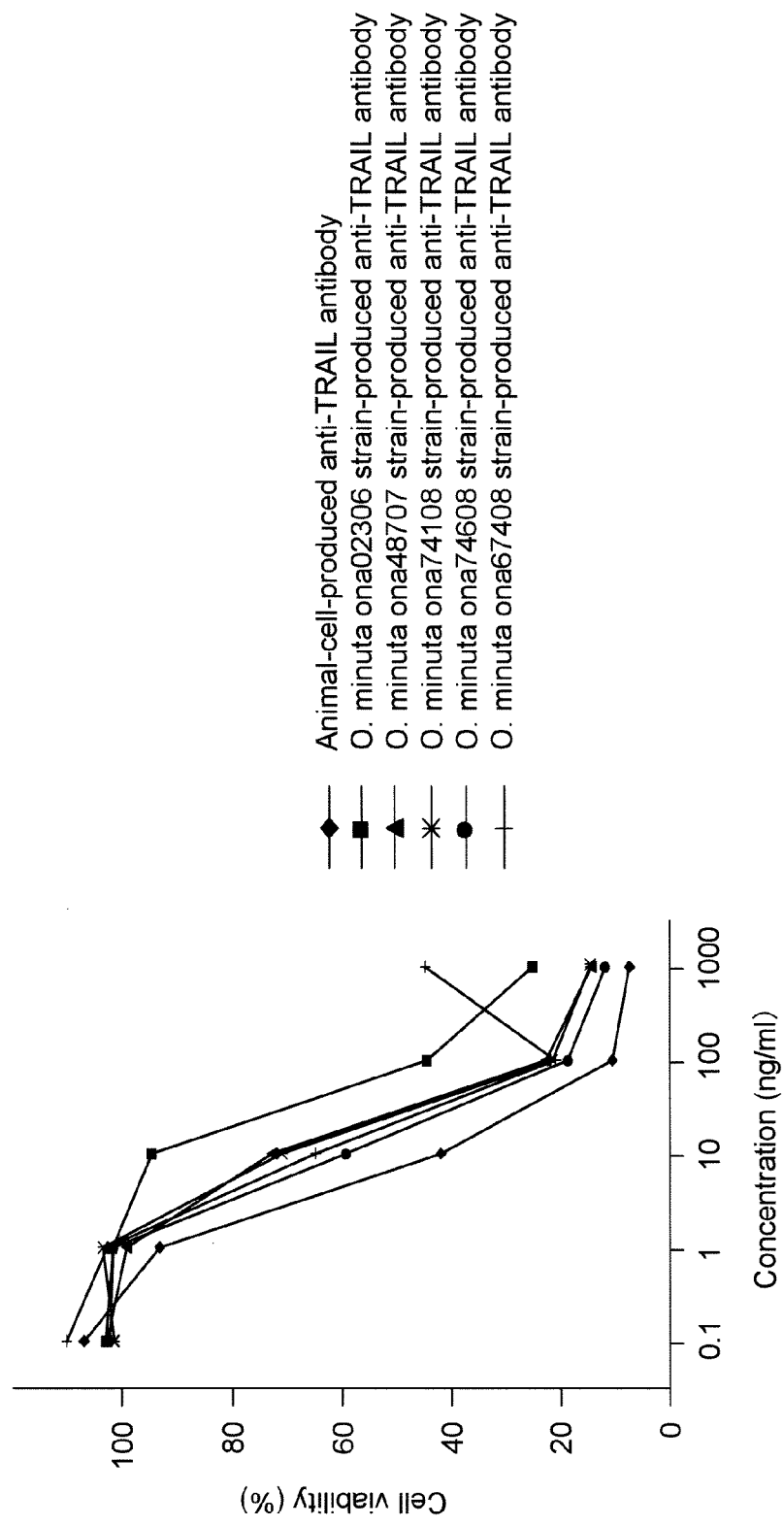
FIG. 29 is a chart showing the results of measuring cytotoxic activity of various purified antibodies produced from *O. minuta*.
Figure 30:
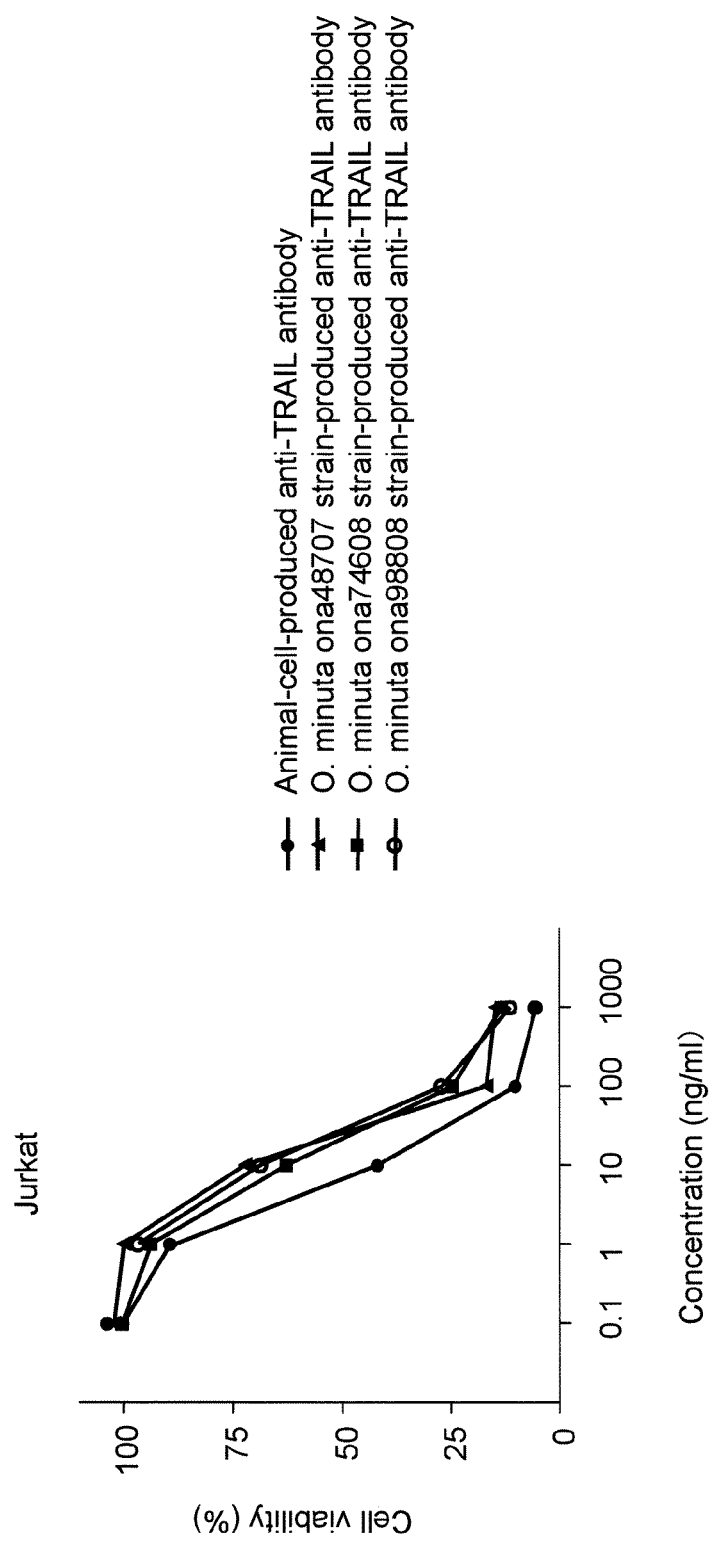
FIG. 30 is a chart showing the results of measuring cytotoxic activity of various purified antibodies produced from *O. minuta*.

Cytotoxic activity of the anti-TRAIL receptor antibody was measured by the cross-link method using secondary antibodies as described below. An anti-TRAIL receptor antibody produced with the use of a mammalian cell was used as a control sample. The goat affinity purified antibody to human IgG Fc (MP Biomedicals, #55071) was used as a secondary antibody. The concentration of the secondary antibody was adjusted at 1 mg/ml with the use of cell culture medium (RPMI 1640 medium containing 10% serum, GIBCO, 11875), and the cell culture medium containing the secondary antibody thus prepared was used to prepare a specimen at a concentration of 2,000 ng/ml. Further, a dilution series of the prepared specimen was prepared (200 ng/ml, 20 ng/ml, 2 ng/ml, and 0.2 ng/ml; 10-fold diluted) and fractionated on the Corning 96 well plate (costar, #3598) at 50 µl/well. A Jurkat cell suspension ($1 \times 10^5$ cells/ml) was sowed on the plate to which the specimen had been added at 50 µl/well. ATP derived from cells having metabolic activity was quantified 72 hours after the initiation of culture with the use of the ATP detection kit (CellTiter-Glo™ Luminescent Cell Viability Assay, Promega, #G7571), cell survival of the untreated group was designated as 100%, and the viable cell count in each treated group was determined. As shown in FIG. 29, whereas the anti-TRAIL antibody produced from animal cells exhibited IC50 of 7 ng/ml, the antibody produced from the ona02306 strain (the control strain containing no chaperones and having the antibody gene introduced therein) exhibited IC50 of 77.3 ng/ml; the antibody produced from the ona48707 strain constitutively expressing chaperones (OmPDI1/OmERO1/OmKar2) and having the antibody gene introduced therein exhibited IC50 of 28.5 ng/ml; the antibody produced from the ona74108 strain (the PMT5-deficient strain constitutively expressing chaperones (OmPDI1/OmERO1/OmKar2) and having the antibody gene introduced therein) exhibited IC50 of 26.6 ng/ml; the antibody produced from the ona74608 (the PMT6-deficient strain constitutively expressing chaperones (OmPDI1/OmERO1/OmKar2) and having the antibody gene introduced therein) exhibited IC50 of 16.8 ng/ml; the antibody produced from the ona67408 strain (the PMT5/PMT6 double-deficient strain constitutively expressing chaperones (OmPDI1/OmERO1/OmKar2) and having the antibody gene introduced therein) exhibited IC50 of 21.8 ng/ml. As shown in FIG. 30, whereas the anti-TRAIL antibody produced from animal cells exhibited IC50 of 6.7 ng/ml, the antibody produced from the ona48707 strain constitutively expressing chaperones (OmPDI1/OmERO1/OmKar2) and having the antibody gene introduced therein exhibited IC50 of 25.3 ng/ml; the antibody produced from the ona74608 (the PMT6-deficient strain constitutively expressing chaperones (OmPDI1/OmERO1/OmKar2) and having the antibody gene introduced therein) exhibited IC50 of 21.6 ng/ml; the antibody produced from the ona98808 strain (the PMT4-deficient strain constitutively expressing chaperones (OmPDI1/OmERO1/OmKar2) and having the antibody gene introduced therein) exhibited IC50 of 28.2 ng/ml.

Cytotoxic activity of the antibody produced from the ona02306 strain (the control strain containing no chaperones and having the antibody gene introduced therein) was as small as one eleventh that of the anti-TRAIL receptor antibody produced from animal cells. The antibody produced by the ona48707 strain constitutively expressing chaperones (OmPDI1/OmERO1/OmKar2) and having the antibody gene introduced therein exhibited cytotoxic activity of 1/4.1 times that of the anti-TRAIL receptor antibody produced from animal cells and 2.7 times that of the control strain. While all of the PMT-deficient strains constitutively expressing chaperones (OmPDI1/OmERO1/OmKar2) and having the antibody gene introduced therein exhibited higher cytotoxic activity than that of the control strain, the antibody produced from the PMT6-deficient strain constitutively expressing chaperones (OmPDI1/OmERO1/OmKar2) and having the antibody gene introduced therein (i.e., the ona74608 strain) exhibited the highest cytotoxic activity, which was 1/2.4 times that of the anti-TRAIL receptor antibody produced from animal cells and 4.6 times higher than that of the control strain. The results demonstrate that an antibody produced by introducing chaperones (OmPDI1/OmERO1/OmKar2) into the PMT6 gene-deficient strain of *O. minuta* with the addition of the PMT inhibitors (i.e., the rhodanine-3-acetic acid derivative 1c) exhibited the highest biological activity.

All publications, patents, and patent applications cited herein are incorporated herein by reference in their entirety.

INDUSTRIAL APPLICABILITY

According to the present invention, introduction of chaperone genes into host cells enables high-level secretion and production of proteins having complicated structures (e.g., antibodies) that are correctly folded in host cells, as well as normal proteins. By employing chaperone gene introduction in combination with suppression of O sugar chain addition inherent to yeast, synergetic effects can be attained regarding high-level secretion and production of proteins.

The invention claimed is:

1. A transformed host cell which is transformed with a nucleic acid comprising an isolated polynucleotide encoding a protein disulfide isomerase (PDI), wherein said isolated polynucleotide is selected from the group consisting of (a) and (b):
   (a) an isolated polynucleotide comprising the nucleotide sequence of SEQ ID NO: 1; and
   (b) an isolated polynucleotide comprising a nucleotide sequence having at least 95% nucleotide sequence identity to the nucleotide sequence of SEQ ID NO: 1, wherein said nucleotide sequence having at least 95% nucleotide sequence identity to the nucleotide sequence of SEQ ID NO: 1 encodes a protein having an activity of accelerating increasing secretion of a foreign protein.

2. The transformed host cell of claim 1, wherein said transformed host cell further comprises an isolated polynucleotide selected from (i) and (ii):
   (i) an isolated polynucleotide comprising the nucleotide sequence of any one of SEQ ID NOs: 3, 5, 7, 9, 11 and 13; and
   (ii) an isolated polynucleotide comprising a nucleotide sequence having at least 95% nucleotide sequence identity to the nucleotide sequence of any one of SEQ ID NOs: 3, 5, 7, 9, 11 and 13, wherein said nucleotide sequence having at least 95% nucleotide sequence identity to the nucleotide sequence of any one of SEQ ID NOs: 3, 5, 7, 9, 11 and 13 encodes a protein having an activity of increasing secretion of a foreign protein.

3. A transformed host cell which is transformed with a nucleic acid comprising an isolated polynucleotide encoding a protein disulfide isomerase (PDI), wherein said isolated polynucleotide encodes a polypeptide selected from the group consisting of (a) and (b):
   (a) a polypeptide comprising the amino acid sequence of SEQ ID NO: 2; and
   (b) a polypeptide comprising an amino acid sequence having at least 95% amino acid sequence identity to the amino acid sequence of SEQ ID NO: 2, wherein said polypeptide comprising an amino acid sequence having at least 95% amino acid sequence identity to the amino acid sequence of SEQ ID NO: 2 has an activity of increasing secretion of a foreign protein.

4. The transformed host cell of claim 3, wherein said transformed host cell further comprises an isolated polynucleotide encoding a polypeptide selected from (i) and (ii):
   (i) a polypeptide comprising the amino acid sequence of any one of SEQ ID NOs: 4, 6, 8, 10, 12 and 14; and
   (ii) a polypeptide comprising an amino acid sequence having at least 95% amino acid sequence identity to the amino acid sequence of any one of SEQ ID NOs: 4, 6, 8, 10, 12 and 14, wherein said polypeptide comprising an amino acid sequence having at least 95% amino acid sequence identity to the amino acid sequence of any one of SEQ ID NOs: 4, 6, 8, 10, 12 and 14 has an activity of increasing secretion of a foreign protein.

5. The transformed host cell of claim 1 or 3, wherein said transformed host cell further comprises an isolated polynucleotide selected from the group consisting of (i) and (ii);
   (i) an isolated polynucleotide encoding MPD1, SCJ1, ERO1, FKB2, JEM1, LHS1, MPD2, ERJ5, or EUG1 from *S. cerevisiae*; and
   (ii) an isolated polynucleotide encoding ERO1-Lα, ERO1-Lβ, or GRP78 from a human.

6. The transformed host cell of claim 1 or 3, wherein said transformed host cell further comprises a polynucleotide selected from (i) to (vi):
   (i) a polynucleotide encoding ERO1 from *O. minuta;*
   (ii) a polynucleotide encoding ERO1 from a human;
   (iii) a polynucleotide encoding Kar2 from *O. minuta;*
   (iv) a polynucleotide encoding ERO1 from *O. minuta*, and a polynucleotide encoding Kar2 from *O. minuta;*
   (v) a polynucleotide encoding ERO1-Lβ from a human, and a polynucleotide encoding GRP78 from a human; and
   (vi) a polynucleotide encoding ERO1 from *O. minuta*, and a polynucleotide encoding GRP78 from a human.

7. The transformed host cell according to claim 1 or 3, wherein the host cell is a eukaryotic cell.

8. The transformed host cell according to claim 7, wherein the eukaryotic cell is a yeast cell.

9. The transformed host cell according to claim 8, wherein the yeast cell is a methanol-assimilating yeast cell.

10. The transformed host cell according to claim 9, wherein the methanol-assimilating yeast cell is *Ogataea minuta*.

11. The transformed host cell according to claim 8, wherein the yeast cell is *Saccharomyces cerevisiae*.

12. The transformed host cell of claim 1 or 3, wherein said transformed host cell further comprises a polynucleotide encoding a foreign protein.

13. The transformed host cell according to claim 12, wherein the foreign protein is a multimeric protein.

14. The transformed host cell according to claim 13, wherein the multimeric protein is a heteromultimer.

15. The transformed host cell according to claim 14, wherein the heteromultimer is an antibody or a functional fragment thereof.

16. The transformed host cell according to claim 12, wherein the foreign protein is a glycosyltransferase.

17. A method for producing a foreign protein, comprising culturing the transformed host cell according to claim 12 in a culture medium to express the foreign protein, and isolating the produced foreign protein from the culture medium.

18. The method according to claim 17, wherein the culturing step is conducted under conditions in which protein O-mannosyltransferase (PMT) activity is inhibited.

19. The method according to claim 18, wherein said transferase activity is inhibited by addition of an inhibitor of said transferase activity to the culture medium.

20. The method according to claim 19, wherein said inhibitor is 5-[[3,4-(1-phenylmethoxy)phenyl]methylene]-4-oxo-2-thioxo-3-thiazolidineacetic acid.

21. The method according to claim 18, wherein said transferase activity is inhibited by disrupting said PMT gene.

22. The method according to claim 21, wherein said disruption is disruption of either the PMT5 gene, the PMT6 gene, or both.

23. The method according to claim 18, wherein said transferase activity is inhibited by disrupting said PMT gene and by adding an inhibitor of said transferase activity to the medium.

24. The method according to claim 23, wherein said inhibitor is 5-[[3,4-(1-phenylmethoxy)phenyl]methylene]-4-oxo-2-thioxo-3-thiazolidineacetic acid.

25. An isolated polynucleotide encoding a protein disulfide isomerase (PDI), wherein said isolated polynucleotide is selected from the group consisting of (a) and (b):
  (a) an isolated polynucleotide comprising the nucleotide sequence of SEQ ID NO: 1; and
  (b) an isolated polynucleotide comprising a nucleotide sequence having at least 95% nucleotide sequence identity to the nucleotide sequence of SEQ ID NO: 1, wherein said nucleotide sequence having at least 95% nucleotide sequence identity to the nucleotide sequence of SEQ ID NO: 1 encodes a protein having an activity of increasing secretion of a foreign protein in a recombinant host cell.

26. An isolated polynucleotide encoding a protein disulfide isomerase (PDI), wherein said isolated polynucleotide encodes a polypeptide selected from the group consisting of (a) and (b):
  (a) a polypeptide comprising the amino acid sequence of SEQ ID NO: 2; and
  (b) a polypeptide comprising an amino acid sequence having at least 95% amino acid sequence identity to the amino acid sequence of SEQ ID NO: 2, wherein said polypeptide comprising an amino acid sequence having at least 95% amino acid sequence identity to the amino acid sequence of SEQ ID NO: 2 has an activity of increasing secretion of a foreign protein in a recombinant host cell.

27. An expression vector comprising the polynucleotide according to claim 25 or 26.

* * * * *